United States Patent
Miyazaki et al.

(10) Patent No.: US 10,087,178 B2
(45) Date of Patent: Oct. 2, 2018

(54) SUBSTITUTED SPIROPYRIDO[1,2-A]PYRAZINE DERIVATIVE AND MEDICINAL USE THEREOF AS HIV INTEGRASE INHIBITOR

(71) Applicant: JAPAN TOBACCO INC., Tokyo (JP)

(72) Inventors: Susumu Miyazaki, Osaka (JP); Hirotaka Isoshima, Osaka (JP); Kengo Oshita, Osaka (JP); Seiji Kawashita, Osaka (JP); Noboru Nagahashi, Osaka (JP); Masakazu Terashita, Osaka (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 14/758,082

(22) PCT Filed: Dec. 27, 2013

(86) PCT No.: PCT/JP2013/085059
§ 371 (c)(1),
(2) Date: Oct. 28, 2016

(87) PCT Pub. No.: WO2014/104279
PCT Pub. Date: Jul. 3, 2014

(65) Prior Publication Data
US 2017/0044156 A1    Feb. 16, 2017

Related U.S. Application Data

(60) Provisional application No. 61/746,457, filed on Dec. 27, 2012.

(30) Foreign Application Priority Data

Dec. 27, 2012 (JP) .................. 2012-284827

(51) Int. Cl.
| | | |
|---|---|---|
| C07D 471/04 | (2006.01) | |
| C07D 487/10 | (2006.01) | |
| C07D 471/10 | (2006.01) | |
| A61K 31/499 | (2006.01) | |
| A61K 45/06 | (2006.01) | |

(52) U.S. Cl.
CPC .......... *C07D 471/04* (2013.01); *A61K 31/499* (2013.01); *A61K 45/06* (2013.01); *C07D 471/10* (2013.01); *C07D 487/10* (2013.01)

(58) Field of Classification Search
CPC ............................ A61K 31/499; A61K 45/06
See application file for complete search history.

(56) References Cited

U.S. PATENT DOCUMENTS

| 7,211,572 B2 | 5/2007 | Miyazaki et al. |
| 7,273,859 B2 | 9/2007 | Naidu |
| 7,419,969 B2 | 9/2008 | Naidu et al. |
| 7,858,788 B2 | 12/2010 | Yoshida et al. |
| 8,129,385 B2 | 3/2012 | Johns et al. |
| 8,188,271 B2 | 5/2012 | Yoshida et al. |
| 8,410,103 B2 | 4/2013 | Johns et al. |
| 8,778,943 B2 | 7/2014 | Johns et al. |
| 9,051,337 B2 | 6/2015 | Johns et al. |

(Continued)

FOREIGN PATENT DOCUMENTS

| AU | 2006307101 A1 | 5/2007 |
| CA | 2 577 239 | 2/2005 |

(Continued)

OTHER PUBLICATIONS

Vippagunta, Sudha R., et al., "Crystalline Solids", Advanced Drug Delivery Reviews 48 (2001) 3-26.

(Continued)

*Primary Examiner* — Erich A Leeser
(74) *Attorney, Agent, or Firm* — Finnegan, Henderson, Farabow, Garrett & Dunner, LLP

(57) ABSTRACT

Provided is a substituted spiropyrido[1,2-a]pyrazine derivative or a pharmaceutically acceptable salt thereof, which is useful as an anti-HIV agent. The present invention relates to a compound represented by the following formula [I] or [II] or a pharmaceutically acceptable salt thereof:

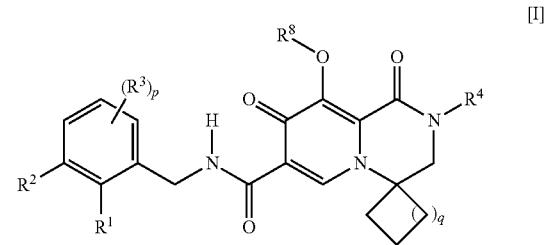

[I]

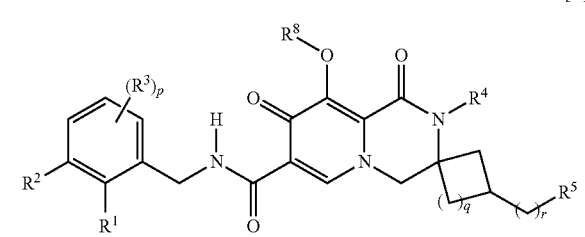

[II]

wherein each symbol is as defined in the specification.

34 Claims, No Drawings

Specification includes a Sequence Listing.

(56) References Cited

U.S. PATENT DOCUMENTS

| | | |
|---|---|---|
| 9,273,065 B2 | 3/2016 | Johns et al. |
| 2005/0054645 A1 | 3/2005 | Miyazaki et al. |
| 2005/0256109 A1 | 11/2005 | Naidu |
| 2006/0052361 A1 | 3/2006 | Miyazaki et al. |
| 2006/0106007 A1 | 5/2006 | Naidu et al. |
| 2008/0161271 A1 | 7/2008 | Yoshida et al. |
| 2008/0161311 A1 | 7/2008 | Miyazaki et al. |
| 2009/0143356 A1 | 6/2009 | Yoshida et al. |
| 2009/0318421 A1 | 12/2009 | Johns et al. |
| 2012/0108564 A1 | 5/2012 | Miyazaki et al. |
| 2012/0115875 A1 | 5/2012 | Johns et al. |
| 2012/0208998 A1 | 8/2012 | Yoshida et al. |
| 2013/0172559 A1 | 7/2013 | Johns et al. |
| 2014/0200209 A1 | 7/2014 | Johns et al. |
| 2014/0221378 A1* | 8/2014 | Miyazaki ............ A61K 31/499 514/249 |
| 2014/0221380 A1 | 8/2014 | Miyazaki et al. |
| 2015/0232479 A1 | 8/2015 | Johns et al. |
| 2015/0329539 A1 | 11/2015 | Embrey et al. |
| 2016/0046641 A1 | 2/2016 | Miyazaki et al. |
| 2016/0137666 A1 | 5/2016 | Johns et al. |
| 2016/0207939 A1 | 7/2016 | Johns et al. |
| 2016/0304535 A1 | 10/2016 | Johns et al. |

FOREIGN PATENT DOCUMENTS

| | | | |
|---|---|---|---|
| CA | 2 789 457 | 9/2011 | |
| CL | 2005001128 | 4/2016 | |
| EP | 1 852 434 A1 | 11/2007 | |
| WO | WO 2005/016927 * | 2/2005 | ........... C07D 471/04 |
| WO | WO 2005/016927 A1 | 2/2005 | |
| WO | WO 2005/113562 A1 | 12/2005 | |
| WO | WO 2006/088173 A1 | 8/2006 | |
| WO | WO 2006/116764 A1 | 11/2006 | |
| WO | WO 2007/049675 A1 | 5/2007 | |
| WO | WO 2011/105590 A1 | 9/2011 | |
| WO | WO 2014/099586 A1 | 6/2014 | |

OTHER PUBLICATIONS

Cardo, D. M., et al., "A Case-Control Study of HIV Seroconversion in Health Care Workers After Percutaneous Exposure," The New England Journal of Medicine, vol. 337, No. 21, pp. 1485-1490 (Nov. 20, 1997).

Choopanya, K. et al., "Antiretroviral Prophylaxis for HIV Infection in Injecting Drug Users in Bangkok, Thailand: (the Bangkok Tenofovir Study): a Randomised, Double-blind Placebo-controlled Phase 3 Trial," The Lancet, vol. 381, pp. 2083-2090 (Jun. 15, 2013).

Extended European Search Report for EP Application No. 13/868,769 dated Jul. 16, 2016.

Hackam, D.G. et al., "Translation of Research Evidence from Animals to Humans," JAMA, vol. 296, No. 14, pp. 1731-1732 (Oct. 11, 2006).

International Search Report for corresponding International Application No. PCT/JP2013/085059, dated Mar. 11, 2014, (3 pages).

Jordan, V.C. et al., "Tamoxifen: A Most Unlikely Pioneering Medicine," Nature Reviews: Drug Discovery, vol. 2, pp. 205-213 (Mar. 2003).

Sperling, R. S. et al., "Maternal Viral Load, Zidovudine Treatment, and the Risk of Transmission of Human Immunodeficiency Virus Type 1 from Mother to Infant," The New England Journal of Medicine, vol. 335, No. 22, pp. 1621-1629 (Nov. 28, 1996).

* cited by examiner

SUBSTITUTED SPIROPYRIDO[1,2-A]PYRAZINE DERIVATIVE AND MEDICINAL USE THEREOF AS HIV INTEGRASE INHIBITOR

TECHNICAL FIELD OF THE INVENTION

The present invention relates to a substituted spiropyrido [1,2-a]pyrazine derivative useful as an anti-HIV agent and a pharmaceutically acceptable salt thereof. In addition, the present invention relates to a pharmaceutical composition comprising the derivative or a pharmaceutically acceptable salt thereof, and a pharmaceutically acceptable carrier; an anti-HIV agent, an HIV integrase inhibitor and the like, comprising the derivative or a pharmaceutically acceptable salt thereof as an active ingredient; an anti-HIV agent comprising a combination of the derivative or a pharmaceutically acceptable salt thereof, and one or more kinds of other anti-HIV active substances; and the like.

BACKGROUND ART

HIV (Human Immunodeficiency Virus (type 1)) belonging to retrovirus is a causative virus of AIDS (Acquired Immunodeficiency Syndrome).

HIV targets CD4 positive cell groups such as helper T cell, macrophage and dendritic cell and destroys these immunocompetent cells to cause immunodeficiency.

Accordingly, a medicament that eradicates HIV in a living organism or suppresses its growth is effective for the prophylaxis or treatment of AIDS.

HIV possesses a bimolecular RNA gene in a shell, which is covered with an envelope protein. The RNA codes for several enzymes (protease, reverse transcriptase, integrase) characteristic of the virus and the like. Translated reverse transcriptase and integrase are present in the shell, and protease is present inside and outside the shell.

HIV contacts and invades a host cell, causes uncoating, and releases a complex of RNA and integrase and the like into the cytoplasm. From the RNA, DNA is transcribed by reverse transcriptase, and a full length double stranded DNA is produced. The DNA moves into the nucleus of the host cell and is incorporated by integrase into the DNA of the host cell. The incorporated DNA is converted to an mRNA by polymerase of the host cell, from which mRNA various proteins necessary for forming a virus are synthesized by HIV protease and the like, and a virus particle is finally formed, which then undergoes budding and its release.

These virus specific enzymes are considered to be essential for the growth of HIV. These enzymes are drawing attention as the target of the development of antiviral agents, and several anti-HIV agents have been already developed.

For example, tenofovir, abacavir, emtricitabine, lamivudine and the like have been already on the market as nucleoside reverse transcriptase inhibitors, efavirenze, nevirapine and the like as non-nucleoside reverse transcriptase inhibitor, and atazanavir, darunavir and the like as protease inhibitors.

In addition, a multiple drug combination therapy using these medicaments in combination (to be also referred to as cART (combination antiretroviral therapy)) is also used. For example, 3 agent combination therapy using two agents from nucleoside reverse transcriptase inhibitors (tenofovir and emtricitabine, or abacavir and lamivudine), and a non-nucleoside reverse transcriptase inhibitor (efavirenz), or a protease inhibitor (atazanavir or darunavir) in combination with ritonavir, and the like is used in clinical practice, and such cART is becoming the mainstream of the AIDS treatment.

However, some of these medicaments are known to cause side effects such as liver function failure, central nervous disorders (e.g., vertigo), and the like. In addition, acquisition of resistance to a medicament causes a problem. Even worse, emergence of an HIV that shows multiple drug resistance in a cART has been known.

Under the circumstances, a further development of a novel medicament, particularly a development of an anti-HIV agent based on a new mechanism, has been desired, wherein a development of an anti-HIV agent having an integrase inhibitory activity is expected, because the integrase that is a feature of retrovirus is an essential enzyme for the growth of HIV.

SUMMARY OF THE INVENTION

Problems to be Solved by the Invention

From the findings obtained from pharmacological studies and clinical results heretofore, an anti-HIV agent is effective for the prophylaxis or treatment of AIDS, and particularly a compound having an integrase inhibitory activity can be an effective anti-HIV agent.

Therefore, the present invention aims at provision of a compound having an anti-HIV activity, particularly a compound having an integrase inhibitory activity.

Means of Solving the Problems

The present inventors have conducted intensive studies in an attempt to find a compound having an anti-HIV action, particularly a compound having the integrase inhibitory action, and completed the present invention.

More specifically, the present invention provides the following.

[1] A compound represented by the following formula [I] or [II] or a pharmaceutically acceptable salt thereof:

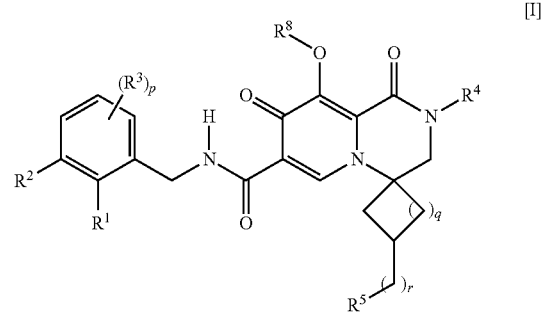

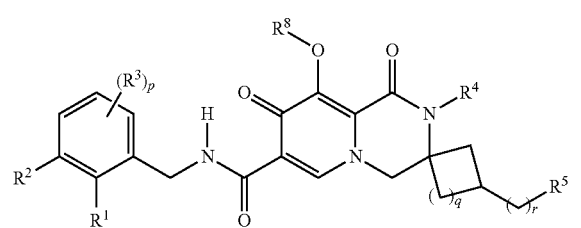

wherein
R¹ is halogen atom,
R² is hydrogen atom, halogen atom or trifluoromethyl group,
R³ is
  (1) halogen atom,
  (2) $C_{1-6}$ alkoxy group, or
  (3) 2-oxopyrrolidinyl group,
when p is 2 or 3, R³ are the same or different,
R⁴ is $C_{1-6}$ alkyl group or cyclopropyl group,
R⁵ is
  (1) hydroxy group,
  (2) $C_{1-6}$ alkoxy group,
  (3) benzyloxy group,
  (4) $C_{1-6}$ alkoxy $C_{2-6}$ alkyleneoxy group,
  (5) carboxy group,
  (6) —CO—$NR^{6a}R^{6b}$
    wherein $R^{6a}$ and $R^{6b}$ are the same or different and each is
      (i) hydrogen atom, or
      (ii) $C_{1-6}$ alkyl group,
  (7) —$NR^{7a}COR^{7b}$
    wherein $R^{7a}$ and $R^{7b}$ are the same or different and each is
      (i) hydrogen atom, or
      (ii) $C_{1-6}$ alkyl group,
  (8) methanesulfonyl group, or
  (9) methanesulfonyloxy group,
R⁸ is
  (1) hydrogen atom,
  (2) acetyl group,
  (3) propionyl group,
  (4) isobutyryl group,
  (5) pivaloyl group,
  (6) palmitoyl group,
  (7) benzoyl group,
  (8) 4-methylbenzoyl group,
  (9) dimethylcarbamoyl group,
  (10) dimethylaminomethylcarbonyl group,
  (11) fumaryl group, or
  (12) 3-carboxybenzoyl group,
p is an integer of 0 to 3,
q is 0 or 1, and
r is 0 or 1.
[2] The compound of the above-mentioned [1], wherein q is 1 or a pharmaceutically acceptable salt thereof.
[3] The compound of the above-mentioned [1], wherein q is 0 or a pharmaceutically acceptable salt thereof.
[4] The compound of the above-mentioned [1], wherein p is 0 or 1, or a pharmaceutically acceptable salt thereof.
[5] The compound of any one of the above-mentioned [1] to [4], wherein r is 1, or a pharmaceutically acceptable salt thereof.
[6] The compound of any one of the above-mentioned [1] to [4], wherein r is 0, or a pharmaceutically acceptable salt thereof.
[7] The compound of any one of the above-mentioned [1] to [4], wherein R² is halogen atom, or a pharmaceutically acceptable salt thereof.
[8] The compound of any one of the above-mentioned [1] to [4], wherein R⁴ is $C_{1-6}$ alkyl group, or a pharmaceutically acceptable salt thereof.
[9] The compound of any one of the above-mentioned [1] to [4], wherein R⁵ is
  (1) hydroxy group,
  (2) $C_{1-6}$ alkoxy group,
  (3) benzyloxy group,
  (4) $C_{1-6}$ alkoxy $C_{2-6}$ alkyleneoxy group, or
  (5) —CO—$NR^{6a}R^{6b}$
    wherein $R^{6a}$ and $R^{6b}$ are the same or different and each is
      (i) hydrogen atom, or
      (ii) $C_{1-6}$ alkyl group,
or a pharmaceutically acceptable salt thereof.
[10] The compound of any one of the above-mentioned [1] to [4], wherein R⁵ is
  (1) hydroxy group,
  (2) $C_{1-6}$ alkoxy group, or
  (3) —CO—$NR^{6a}R^{6b}$
    wherein $R^{6a}$ and $R^{6b}$ are the same or different and each is
      (i) hydrogen atom, or
      (ii) $C_{1-6}$ alkyl group,
or a pharmaceutically acceptable salt thereof.
[11] A compound represented by the formula [I'] or [II'], or a pharmaceutically acceptable salt thereof:

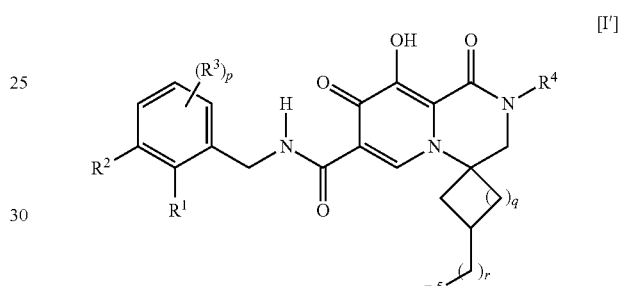

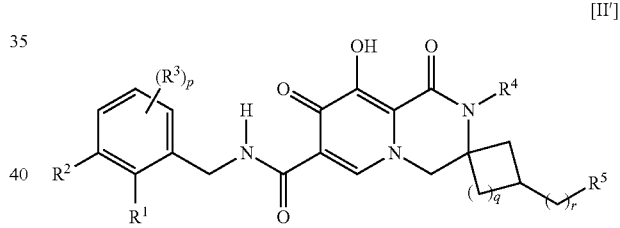

wherein
R¹ is halogen atom,
R² is hydrogen atom, halogen atom or trifluoromethyl group,
R³ is the same or different and each is
  (1) halogen atom,
  (2) $C_{1-6}$ alkoxy group, or
  (3) 2-oxopyrrolidinyl group,
R⁴ is $C_{1-6}$ alkyl group or cyclopropyl group,
R⁵ is
  (1) hydroxy group,
  (2) $C_{1-6}$ alkoxy group,
  (3) benzyloxy group,
  (4) $C_{1-6}$ alkoxy $C_{2-6}$ alkyleneoxy group,
  (5) carboxy group,
  (6) —CO—$NR^{6a}R^{6b}$
    wherein $R^{6a}$ and $R^{6b}$ are the same or different and each is
      (i) hydrogen atom, or
      (ii) $C_{1-6}$ alkyl group,
  (7) —$NR^{7a}COR^{7b}$
    wherein $R^{7a}$ and $R^{7b}$ are the same or different and each is
      (i) hydrogen atom, or
      (ii) $C_{1-6}$ alkyl group, (8) methanesulfonyl group, or
(9) methanesulfonyloxy group,
p is an integer of 0 to 3,
q is 0 or 1, and
r is 0 or 1.
[12] A pharmaceutical composition comprising the compound of any one of the above-mentioned [1] to [11] or a pharmaceutically acceptable salt thereof, and a pharmaceutically acceptable carrier.
[13] An anti-HIV agent comprising the compound of any one of the above-mentioned [1] to [11] or a pharmaceutically acceptable salt thereof, as an active ingredient.
[14] An HIV integrase inhibitor comprising the compound of any one of the above-mentioned [1] to [11] or a pharmaceutically acceptable salt thereof, as an active ingredient.
[15] An anti-HIV agent comprising the compound of any one of the above-mentioned [1] to [11] or a pharmaceutically acceptable salt thereof, in combination with one or more other kinds of anti-HIV active substances.
[16] Use of the compound of any one of the above-mentioned [1] to [11] or a pharmaceutically acceptable salt thereof, for the production of an anti-HIV agent.
[17] Use of the compound of any one of the above-mentioned [1] to [11] or a pharmaceutically acceptable salt thereof, for the production of an HIV integrase inhibitor.
[18] A method for the prophylaxis or treatment of an HIV infection in a mammal, comprising administering an effective amount of the compound of any one of the above-mentioned [1] to [11] or a pharmaceutically acceptable salt thereof, to the mammal.
[19] The method of the above-mentioned [18], further comprising administering an effective amount of one or more other kinds of anti-HIV active substances to the mammal.
[20] A method for inhibiting HIV integrase in a mammal, comprising administering an effective amount of the compound of any one of the above-mentioned [1] to [11] or a pharmaceutically acceptable salt thereof, to the mammal.
[13'] A pharmaceutical composition comprising a compound having an anti-HIV action and a pharmaceutically acceptable carrier, wherein the compound having an anti-HIV action is a compound of any one of the above-mentioned [1] to [11] or a pharmaceutically acceptable salt thereof alone.
[1A] A compound represented by the formula [I'] or [II'] or a pharmaceutically acceptable salt thereof:

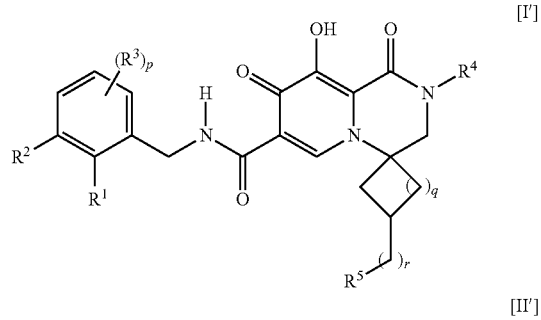

[I']

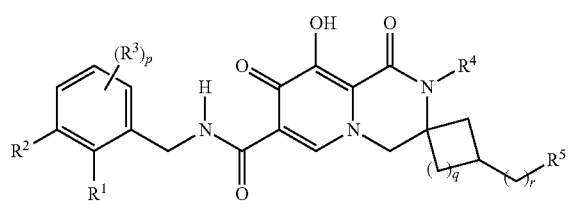

[II']

wherein
$R^1$ is halogen atom,
$R^2$ is hydrogen atom, halogen atom or trifluoromethyl group,
$R^3$ is the same or different and each is
(1) halogen atom,
(2) $C_{1-6}$ alkoxy group, or
(3) 2-oxopyrrolidinyl group,
$R^4$ is $C_{1-6}$ alkyl group or cyclopropyl group,
$R^5$ is
(1) hydroxy group,
(2) $C_{1-6}$ alkoxy group,
(3) benzyloxy group,
(4) $C_{1-6}$ alkoxy $C_{2-6}$ alkyleneoxy group,
(5) carboxy group,
(6) —CO—$NR^{6a}R^{6b}$
    wherein $R^{6a}$ and R are the same or different and each is
    (i) hydrogen atom, or
    (ii) $C_{1-6}$ alkyl group,
(7) —$NR^{7a}COR^{7b}$
    wherein $R^{7a}$ and $R^{7b}$ are the same or different and each is
    (i) hydrogen atom, or
    (ii) $C_{1-6}$ alkyl group,
(8) methanesulfonyl group, or
(9) methanesulfonyloxy group,
p is an integer of 0 to 3,
q is 0 or 1, and
r is 0 or 1.
[2A] The compound of the above-mentioned [1A], wherein q is 1, or a pharmaceutically acceptable salt thereof.
[3A] The compound of the above-mentioned [1A], wherein q is 0, or a pharmaceutically acceptable salt thereof.
[4A] The compound of the above-mentioned [A], wherein p is 0 or 1, or a pharmaceutically acceptable salt thereof.
[5A] The compound of any one of the above-mentioned [1A] to [4A], wherein r is 1, or a pharmaceutically acceptable salt thereof.
[6A] The compound of any one of the above-mentioned [1A] to [4A], wherein r is 0, or a pharmaceutically acceptable salt thereof.
[7A] The compound of any one of the above-mentioned [1A] to [4A], wherein $R^2$ is halogen atom, or a pharmaceutically acceptable salt thereof.
[8A] The compound of any one of the above-mentioned [1A] to [4A], wherein $R^4$ is $C_{1-6}$ alkyl group, or a pharmaceutically acceptable salt thereof.
[9A] The compound of any one of the above-mentioned [1A] to [4A], wherein $R^5$ is
(1) hydroxy group,
(2) $C_{1-6}$ alkoxy group,
(3) benzyloxy group,
(4) $C_{1-6}$ alkoxy $C_{2-6}$ alkyleneoxy group,
(5) carboxy group, or
(6) —CO—$NR^{6a}R^{6b}$
    wherein $R^{6a}$ and $R^{6b}$ are the same or different and each is
    (i) hydrogen atom, or
    (ii) $C_{1-6}$ alkyl group,
or a pharmaceutically acceptable salt thereof.
[10A] The compound of the above-mentioned [9A], wherein $R^5$ is
(1) hydroxy group,
(2) $C_{1-6}$ alkoxy group, or
(3) —CO—$NR^{6a}R^{6b}$
    wherein $R^{6a}$ and $R^{6b}$ are the same or different and each is (i) hydrogen atom, or
(ii) $C_{1-6}$ alkyl group,
or a pharmaceutically acceptable salt thereof.

[11A] A pharmaceutical composition comprising the compound of any one of the above-mentioned [1A] to [10A] or a pharmaceutically acceptable salt thereof, and a pharmaceutically acceptable carrier.

[12A] An anti-HIV agent comprising the compound of any one of the above-mentioned [1A] to [10A] or a pharmaceutically acceptable salt thereof, as an active ingredient.

[13A] An HIV integrase inhibitor comprising the compound of any one of the above-mentioned [1A] to [10A] or a pharmaceutically acceptable salt thereof, as an active ingredient.

[14A] An anti-HIV agent comprising the compound of any one of the above-mentioned [1A] to [10A] or a pharmaceutically acceptable salt thereof, in combination with one or more kinds of other anti-HIV active substances.

[15A] Use of the compound of any one of the above-mentioned ([A] to [10A] or a pharmaceutically acceptable salt thereof, for the production of an anti-HIV agent.

[16A] Use of the compound of any one of the above-mentioned [1A] to [10A] or a pharmaceutically acceptable salt thereof, for the production of an HIV integrase inhibitor.

[17A] A method for prophylaxis or treatment of HIV infection in a mammal, comprising administering an effective amount of the compound of any one of the above-mentioned [1A] to [10A] or a pharmaceutically acceptable salt thereof, to the mammal.

[18A] The method of the above-mentioned [17A], further comprising administering an effective amount of one or more other kinds of anti-HIV active substances to the mammal.

[19A] A method for inhibiting HIV integrase in a mammal, comprising administering an effective amount of the compound of any one of the above-mentioned [1A] to [10A] or a pharmaceutically acceptable salt thereof, to the mammal.

Effect of the Invention

The compound of the present invention can be medicaments effective for the prophylaxis or treatment of HIV infections or AIDS, as anti-HIV agents, having an HIV integrase inhibitory activity. In addition, by a combined use with other anti-HIV agent(s) such as protease inhibitor, reverse transcriptase inhibitor and the like, they can be more effective anti-HIV agents. Furthermore, having high inhibitory activity specific for integrase, they can be medicaments safe for human body with a fewer side effects.

DESCRIPTION OF EMBODIMENTS

The definitions of respective substituents and terms in respective moieties used in the present specification are as follows unless other different description is found. The phrases and terms not particularly defined herein are used in the meanings generally understood by those of ordinary skill in the art.

The "halogen atom" is fluorine atom, chlorine atom, bromine atom or iodine atom. It is preferably fluorine atom or chlorine atom.

The "$C_{1-6}$ alkyl group" is a straight chain or branched chain alkyl group having 1 to 6 carbon atoms, preferably a straight chain or branched chain alkyl group having 1 to 4 carbon atoms. Specific examples include methyl group, ethyl group, propyl group, isopropyl group, butyl group, isobutyl group, sec-butyl group, tert-butyl group, pentyl group, isopentyl group, 1,1-dimethylpropyl group, 1,2-dimethylpropyl group, 2,2-dimethylpropyl group, l-ethylpropyl group, hexyl group and the like, and methyl group, ethyl group, propyl group, isopropyl group, butyl group, isobutyl group, sec-butyl group or tert-butyl group is preferable.

The "$C_{1-6}$ alkoxy group" is a straight chain or branched chain alkoxy group having 1 to 6 carbon atoms, preferably a straight chain or branched chain alkoxy group having 1 to 4 carbon atoms. Specific examples include methoxy group, ethoxy group, propoxy group, isopropoxy group, butoxy group, isobutyloxy group, tert-butyloxy group, pentyloxy group, hexyloxy group and the like, more preferably, methoxy group, ethoxy group, propoxy group, isopropoxy group, butoxy group, isobutyloxy group or tert-butyloxy group.

The "$C_{1-6}$ alkoxy $C_{2-6}$ alkyleneoxy group" is alkoxyalkyleneoxy group wherein the alkoxy moiety is the above-defined "$C_{1-6}$ alkoxy group" and the alkyleneoxy moiety is a straight chain or branched chain alkyleneoxy group having 2 to 6 carbon atoms. It is preferably alkoxyalkyleneoxy group wherein the alkoxy moiety is a straight chain or branched chain alkoxy group having 1 to 4 carbon atoms and the alkyleneoxy moiety is a straight chain or branched chain alkyleneoxy group having 2 to 4 carbon atoms. For example, methoxyethoxy group, methoxypropoxy group, methoxybutoxy group, methoxypentyloxy group, methoxyhexyloxy group, ethoxyethoxy group, ethoxypropoxy group, ethoxybutoxy group, ethoxypentyloxy group, ethoxyhexyloxy group, propoxyethoxy group, propoxypropoxy group, propoxybutoxy group, propoxypentyloxy group, propoxyhexyloxy group, butoxyethoxy group, butoxypropoxy group, butoxybutoxy group, butoxypentyloxy group, butoxyhexyloxy group, pentyloxyethoxy group, pentyloxypropoxy group, pentyloxybutoxy group, pentyloxypentyloxy group, pentyloxyhexyloxy group, hexyloxyethoxy group, hexyloxypropoxy group, hexyloxybutoxy group, hexyloxypentyloxy group, hexyloxyhexyloxy group and the like can be mentioned, with preference given to methoxyethoxy group and methoxypropoxy group.

In the compounds represented by the formula [I] or [II], preferable embodiments are as described below.

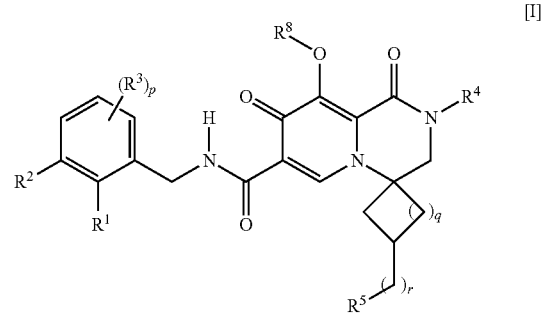

[I]

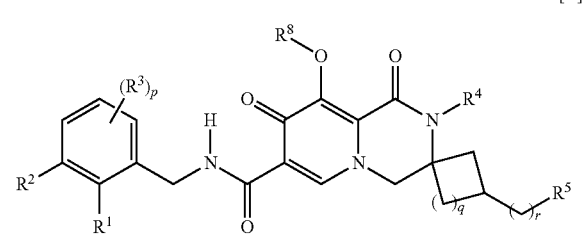

[II]

A preferable embodiment of $R^1$ is fluorine atom.

A preferable embodiment of $R^2$ is hydrogen atom, chlorine atom or trifluoromethyl group. A more preferable embodiment of $R^2$ is hydrogen atom or chlorine atom.

One of the preferable embodiments of $R^3$ is halogen atom or $C_{1-6}$ alkoxy group.

One of the preferable embodiments of $R^3$ is fluorine atom, methoxy group, ethoxy group, isopropoxy group or 2-oxopyrrolidinyl group. A more preferable embodiment of $R^3$ is fluorine atom, methoxy group, ethoxy group or isopropoxy group.

A preferable embodiment of p is 0 or 1. A more preferable embodiment of p is 0.

In a preferable embodiment of a combination of $R^2$ and p, $R^2$ is halogen atom and p is 0. In a more preferable embodiment of a combination of $R^2$ and p, $R^2$ is chlorine atom and p is 0.

In a preferable embodiment of a combination of $R^2$, $R^3$ and p, $R^2$ is hydrogen atom, $R^3$ is halogen atom, and p is 1. More preferably, $R^2$ is hydrogen atom, $R^3$ is fluorine atom, and p is 1.

A preferable embodiment of $R^4$ is methyl group, ethyl group, isopropyl group or cyclopropyl group. A more preferable embodiment of $R^4$ is methyl group, ethyl group or isopropyl group.

One of the preferable embodiments of $R^5$ is hydroxy group, $C_{1-6}$ alkoxy group or —CO—$NR^{6a}R^{6b}$. A more preferable embodiment of $R^5$ is hydroxy group. A more preferable embodiment of $R^5$ is $C_{1-6}$ alkoxy group. A more preferable embodiment of $R^5$ is —CO—$NR^{6a}R^{6b}$.

One of the preferable embodiments of $R^5$ is hydroxy group, methoxy group, ethoxy group, propoxy group, isopropoxy group, benzyloxy group, 2-methoxyethoxy group, carboxy group, methylcarbamoyl group, dimethylcarbamoyl group, acetylamino group, N-acetyl-N-methylamino group, methanesulfonyl group or methanesulfonyloxy group. A more preferable embodiment of $R^5$ is hydroxy group. A more preferable embodiment of $R^5$ is methoxy group, ethoxy group, propoxy group or isopropoxy group. A more preferable embodiment of $R^5$ is methylcarbamoyl group or dimethylcarbamoyl group.

A preferable embodiment of $R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
a more preferable embodiment is
(1) hydrogen atom, or
(2) acetyl group.

A preferable embodiment of a compound represented by the formula [I] or [III], wherein q is 1, is as described below.
$R^1$ is halogen atom,
$R^2$ is hydrogen atom or halogen atom,
$R^3$ is
(1) halogen atom, or
(2) $C_{1-6}$ alkoxy group,
$R^4$ is $C_{1-6}$ alkyl group,
$R^5$ is
(1) hydroxy group,
(2) $C_{1-6}$ alkoxy group,
(3) benzyloxy group,
(4) $C_{1-6}$ alkoxy $C_{2-6}$ alkyleneoxy group,
(5) —CO—$NR^{6a}R^{6b}$
  wherein $R^{6a}$ and $R^{6b}$ are the same or different and each is
  (i) hydrogen atom, or
  (ii) $C_{1-6}$ alkyl group,
(6) —$NR^{7a}COR^{7b}$
  wherein $R^{7a}$ and $R^{7b}$ are the same or different and each is
  (i) hydrogen atom, or
  (ii) $C_{1-6}$ alkyl group, or
(7) methanesulfonyloxy group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0 or 1.

A preferable embodiment of $R^1$ is fluorine atom.
A preferable embodiment of $R^2$ is hydrogen atom or chlorine atom.
A preferable embodiment of $R^3$ is fluorine atom or methoxy group.
A preferable embodiment of $R^4$ is methyl group, ethyl group or isopropyl group.

One of the preferable embodiments of $R^5$ is hydroxy group, $C_{1-6}$ alkoxy group or —CO—$NR^{6a}R^{6b}$. A more preferable embodiment of $R^5$ is hydroxy group. A more preferable embodiment of $R^5$ is $C_{1-6}$ alkoxy group. A more preferable embodiment of $R^5$ is —CO—$NR^{6a}R^{6b}$.

One of the preferable embodiments of $R^5$ is hydroxy group, methoxy group, ethoxy group, propoxy group, isopropoxy group, benzyloxy group, 2-methoxyethoxy group, methylcarbamoyl group, dimethylcarbamoyl group, acetylamino group, N-acetyl-N-methylamino group or methanesulfonyloxy group. A more preferable embodiment of $R^5$ is hydroxy group. A more preferable embodiment of $R^5$ is methoxy group, ethoxy group, propoxy group or isopropoxy group. A more preferable embodiment of $R^5$ is methylcarbamoyl group or dimethylcarbamoyl group.

A preferable embodiment of $R^8$ is
(1) hydrogen atom, or
(2) acetyl group.

A preferable embodiment of p is 0.

A preferable embodiment of a compound represented by the formula [I] or [III], wherein q is 1 and r is 1, is as described below.
$R^1$ is halogen atom,
$R^2$ is hydrogen atom or halogen atom,
$R^3$ is
(1) halogen atom, or
(2) $C_{1-6}$ alkoxy group,
$R^4$ is $C_{1-6}$ alkyl group,
$R^5$ is
(1) hydroxy group,
(2) $C_{1-6}$ alkoxy group, or
(3) —$NR^{7a}COR^{7b}$
  wherein $R^{7a}$ and $R^{7b}$ are the same or different and each is
  (i) hydrogen atom, or
  (ii) $C_{1-6}$ alkyl group, $R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0 or 1.

A preferable embodiment of $R^1$ is fluorine atom.

A preferable embodiment of $R^2$ is hydrogen atom or chlorine atom.

A preferable embodiment of $R^3$ is fluorine atom or methoxy group.

A preferable embodiment of $R^4$ is methyl group, ethyl group or isopropyl group.

One of the preferable embodiments of $R^5$ is hydroxy group or $C_{1-6}$ alkoxy group.

One of the preferable embodiments of $R^5$ is hydroxy group, methoxy group, ethoxy group or acetylamino group. A more preferable embodiment of $R^5$ is hydroxy group. A more preferable embodiment of $R^5$ is methoxy group or ethoxy group.

A preferable embodiment of $R^8$ is
(1) hydrogen atom, or
(2) acetyl group.

A preferable embodiment of p is 0.

A preferable embodiment of a compound represented by the formula [I] or [II], wherein q is 1 and r is 0, is as described below.

$R^1$ is halogen atom,
$R^2$ is hydrogen atom or halogen atom,
$R^3$ is halogen atom or $C_{1-6}$ alkoxy group,
$R^4$ is $C_{1-6}$ alkyl group,
$R^5$ is
(1) hydroxy group,
(2) $C_{1-6}$ alkoxy group,
(3) benzyloxy group,
(4) $C_{1-6}$ alkoxy $C_{2-6}$ alkyleneoxy group,
(5) —CO—$NR^{6a}R^{6b}$
    wherein $R^{6a}$ and $R^{6b}$ are the same or different and each is
    (i) hydrogen atom, or
    (ii) $C_{1-6}$ alkyl group,
(6) —$NR^{7a}COR^{7b}$
    wherein $R^{7a}$ and $R^{7b}$ are the same or different and each is
    (i) hydrogen atom, or
    (ii) $C_{1-6}$ alkyl group, or
(7) methanesulfonyloxy group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0 or 1.

A preferable embodiment of $R^1$ is fluorine atom.

A preferable embodiment of $R^2$ is hydrogen atom or chlorine atom.

A preferable embodiment of $R^3$ is fluorine atom or methoxy group.

A preferable embodiment of $R^4$ is methyl group, ethyl group or isopropyl group.

One of the preferable embodiments of $R^5$ is hydroxy group, $C_{1-6}$ alkoxy group or —CO—$NR^{6a}R^{6b}$. A more preferable embodiment of $R^5$ is hydroxy group. A more preferable embodiment of $R^5$ is $C_{1-6}$ alkoxy group. A more preferable embodiment of $R^5$ is —CO—$NR^{6a}R^{6b}$.

One of the preferable embodiments of $R^5$ is hydroxy group, methoxy group, ethoxy group, propoxy group, isopropoxy group, benzyloxy group, 2-methoxyethoxy group, methylcarbamoyl group, dimethylcarbamoyl group, N-acetyl-N-methylamino group or methanesulfonyloxy group. A more preferable embodiment of $R^5$ is hydroxy group. A more preferable embodiment of $R^5$ is methoxy group, ethoxy group, propoxy group or isopropoxy group. A more preferable embodiment of $R^5$ is methylcarbamoyl group or dimethylcarbamoyl group.

A preferable embodiment of $R^8$ is
(1) hydrogen atom, or
(2) acetyl group.

A preferable embodiment of p is 0.

A preferable embodiment of a compound represented by the formula [I] or [II], wherein q is 0, is as described below.

$R^1$ is halogen atom,
$R^2$ is hydrogen atom, halogen atom or trifluoromethyl group,
$R^3$ is
(1) halogen atom,
(2) $C_{1-6}$ alkoxy group, or
(3) 2-oxopyrrolidinyl group,
$R^4$ is $C_{1-6}$ alkyl group or cyclopropyl group,
$R^5$ is
(1) hydroxy group,
(2) $C_{1-6}$ alkoxy group,
(3) carboxy group,
(4) —CO—$NR^{6a}R^{6b}$
    wherein $R^{6a}$ and $R^{6b}$ are the same or different and each is
    (i) hydrogen atom, or
    (ii) $C_{1-6}$ alkyl group, or
(5) methanesulfonyl group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0 or 1.

A preferable embodiment of $R^1$ is fluorine atom.

A preferable embodiment of $R^2$ is hydrogen atom, chlorine atom or trifluoromethyl group. A more preferable embodiment of $R^2$ is hydrogen atom. A more preferable embodiment of $R^2$ is chlorine atom.

One of the preferable embodiments of $R^3$ is halogen atom or $C_{1-6}$ alkoxy group.

One of the preferable embodiments of $R^3$ is fluorine atom, methoxy group, ethoxy group, isopropoxy group or 2-oxopyrrolidinyl group. A more preferable embodiment of $R^3$ is fluorine atom. A more preferable embodiment of $R^3$ is methoxy group, ethoxy group or isopropoxy group.

A preferable embodiment of $R^4$ is methyl group, ethyl group, isopropyl group or cyclopropyl group. A preferable embodiment of $R^4$ is methyl group, ethyl group or isopropyl group.

One of the preferable embodiments of $R^5$ is hydroxy group, $C_{1-6}$ alkoxy group or —CO—$NR^{6a}R^{6b}$. A more preferable embodiment of $R^5$ is hydroxy group. A more preferable embodiment of $R^5$ is $C_{1-6}$ alkoxy group. A more preferable embodiment of $R^5$ is —CO—$NR^{6a}R^{6b}$.

One of the preferable embodiments of $R^5$ is hydroxy group, methoxy group, ethoxy group, carboxy group, methylcarbamoyl group, dimethylcarbamoyl group or methanesulfonyl group. A more preferable embodiment of $R^5$ is hydroxy group. A more preferable embodiment of $R^5$ is methoxy group or ethoxy group. A more preferable embodiment of $R^5$ is methylcarbamoyl group or dimethylcarbamoyl group.

A preferable embodiment of $R^8$ is
(1) hydrogen atom, or
(2) acetyl group, and
a further preferable embodiment is
hydrogen atom.

A preferable embodiment of p is 0.

A preferable embodiment of a compound represented by the formula [I] or [II], wherein q is 0 and r is 1, is as described below.

$R^1$ is halogen atom,
$R^2$ is hydrogen atom, halogen atom or trifluoromethyl group,
$R^3$ is
(1) halogen atom,
(2) $C_{1-6}$ alkoxy group, or
(3) 2-oxopyrrolidinyl group,
$R^4$ is $C_{1-6}$ alkyl group,
$R^5$ is
(1) hydroxy group,
(2) $C_{1-6}$ alkoxy group, or
(3) methanesulfonyl group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group,
p is 0 or 1.

A preferable embodiment of $R^1$ is fluorine atom.

A preferable embodiment of $R^2$ is hydrogen atom, chlorine atom or trifluoromethyl group. A more preferable embodiment of $R^2$ is hydrogen atom. A more preferable embodiment of $R^2$ is chlorine atom.

One of the preferable embodiments of $R^3$ is halogen atom or $C_{1-6}$ alkoxy group.

One of the preferable embodiments of $R^3$ is fluorine atom, methoxy group, ethoxy group, isopropoxy group or 2-oxopyrrolidinyl group. A more preferable embodiment of $R^3$ is fluorine atom. A more preferable embodiment of $R^3$ is methoxy group, ethoxy group or isopropoxy group.

A preferable embodiment of $R^4$ is methyl group, ethyl group or isopropyl group.

One of the preferable embodiments of $R^5$ is hydroxy group or $C_{1-6}$ alkoxy group.

One of the preferable embodiments of $R^5$ is hydroxy group, methoxy group, ethoxy group or methanesulfonyl group. A more preferable embodiment of $R^5$ is hydroxy group. A more preferable embodiment of $R^5$ is methoxy group or ethoxy group.

A preferable embodiment of $R^8$ is
(1) hydrogen atom, or
(2) acetyl group, and
a further preferable embodiment is
hydrogen atom.

A preferable embodiment of p is 0.

A preferable embodiment of a compound represented by the formula [I] or [II], wherein q is 0 and r is 0, is as described below.

$R^1$ is halogen atom,
$R^2$ is hydrogen atom or halogen atom,
$R^3$ is halogen atom or $C_{1-6}$ alkoxy group,
$R^4$ is $C_{1-6}$ alkyl group or cyclopropyl group,
$R^5$ is
(1) carboxy group, or
(2) —CO—$NR^{6a}R^{6b}$
wherein $R^{6a}$ and $R^{6b}$ are the same or different and each is
(i) hydrogen atom, or
(ii) $C_{1-6}$ alkyl group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0 or 1.

A preferable embodiment of $R^1$ is fluorine atom.

A preferable embodiment of $R^2$ is hydrogen atom or chlorine atom.

A preferable embodiment of $R^3$ is fluorine atom.

A preferable embodiment of $R^4$ is ethyl group, isopropyl group or cyclopropyl group. A more preferable embodiment of $R^4$ is ethyl group or isopropyl group.

A preferable embodiment of $R^5$ is carboxy group, methylcarbamoyl group or dimethylcarbamoyl group.

A preferable embodiment of $R^8$ is
(1) hydrogen atom, or
(2) acetyl group, and
a further preferable embodiment is
hydrogen atom.

A preferable embodiment of p is 0.

A compound represented by the following formula [I'] or [II'], which is a compound represented by the formula [I] or [II] wherein $R^8$ is hydrogen atom, is a preferable embodiment.

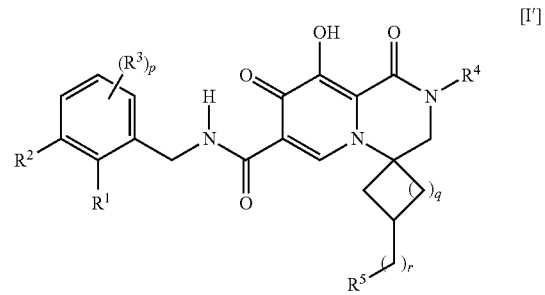

[I']

-continued

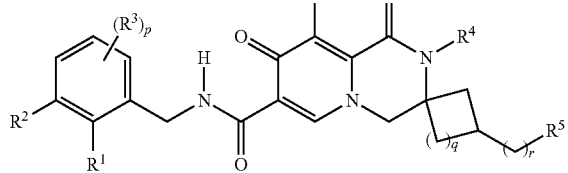
[II']

wherein each symbol is as mentioned above.

A preferable embodiment of $R^1$, $R^2$, $R^3$, $R^4$, $R^5$, p, q and r in the formula [I'] or [II'] is the same as that of $R^1$, $R^2$, $R^3$, $R^4$, $R^5$, p, q and r in the formula [I] or [II].

One of the preferable embodiments of a compound represented by the formula [I]

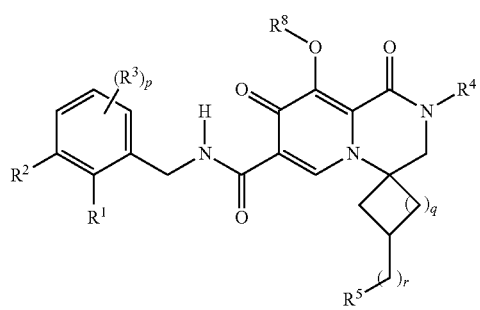
[I]

wherein
$R^1$ is halogen atom,
$R^2$ is hydrogen atom, halogen atom or trifluoromethyl group,
$R^3$ is
 (1) halogen atom,
 (2) $C_{1-6}$ alkoxy group, or
 (3) 2-oxopyrrolidinyl group,
when p is 2 or 3, $R^3$ are the same or different,
$R^4$ is $C_{1-6}$ alkyl group or cyclopropyl group,
$R^5$ is
 (1) hydroxy group,
 (2) $C_{1-6}$ alkoxy group,
 (3) benzyloxy group,
 (4) $C_{1-6}$ alkoxy $C_{2-6}$ alkyleneoxy group,
 (5) carboxy group,
 (6) —CO—$NR^{6a}R^{6b}$
  wherein $R^{6a}$ and $R^{6b}$ are the same or different and each is
   (i) hydrogen atom, or
   (ii) $C_{1-6}$ alkyl group,
 (7) —$NR^{7a}COR^{7b}$
  wherein $R^{7a}$ and $R^{7b}$ are the same or different and each is
   (i) hydrogen atom, or
   (ii) $C_{1-6}$ alkyl group,
 (8) methanesulfonyl group, or
 (9) methanesulfonyloxy group,
$R^8$ is
 (1) hydrogen atom,
 (2) acetyl group,
 (3) propionyl group,
 (4) isobutyryl group,
 (5) pivaloyl group,
 (6) palmitoyl group,
 (7) benzoyl group,
 (8) 4-methylbenzoyl group,
 (9) dimethylcarbamoyl group,
 (10) dimethylaminomethylcarbonyl group,
 (11) fumaryl group, or
 (12) 3-carboxybenzoyl group,
p is an integer of 0 to 3,
q is 0 or 1, and
r is 0 or 1,
or a pharmaceutically acceptable salt thereof, is a compound wherein q is 1.

One of the preferable embodiments of a compound represented by the formula [I], wherein q is 1, is a compound wherein r is 1.

A preferable embodiment of a compound represented by the formula [I], wherein q is 1 and r is 1, is as described below.
$R^1$ is halogen atom,
$R^2$ is hydrogen atom or halogen atom,
$R^3$ is
 (1) halogen atom, or
 (2) $C_{1-6}$ alkoxy group,
$R^4$ is $C_{1-6}$ alkyl group,
$R^5$ is
 (1) hydroxy group,
 (2) $C_{1-6}$ alkoxy group, or
 (3) —$NR^{7a}COR^{7b}$
  wherein $R^{7a}$ and $R^{7b}$ are the same or different and each is
   (i) hydrogen atom, or
   (ii) $C_{1-6}$ alkyl group,
$R^8$ is
 (1) hydrogen atom,
 (2) acetyl group,
 (3) propionyl group,
 (4) isobutyryl group,
 (5) pivaloyl group,
 (6) palmitoyl group,
 (7) benzoyl group,
 (8) 4-methylbenzoyl group, or
 (9) dimethylcarbamoyl group, and
p is 0 or 1.

A preferable embodiment of $R^1$ is fluorine atom.
A preferable embodiment of $R^2$ is hydrogen atom or chlorine atom.
A preferable embodiment of $R^3$ is fluorine atom or methoxy group.
A preferable embodiment of $R^4$ is methyl group, ethyl group or isopropyl group.
A preferable embodiment of $R^5$ is hydroxy group, methoxy group, ethoxy group or acetylamino group.
A preferable embodiment of $R^8$ is
 (1) hydrogen atom, or
 (2) acetyl group.

One of the preferable embodiments of a compound represented by the formula [II] wherein q is 1 is a compound wherein r is 0.

A preferable embodiment of a compound represented by the formula [I], wherein q is 1 and r is 0, is as described below.
$R^1$ is halogen atom,
$R^2$ is hydrogen atom or halogen atom,
$R^3$ is halogen atom,
$R^4$ is $C_{1-6}$ alkyl group,
$R^5$ is
 (1) hydroxy group,
 (2) $C_{1-6}$ alkoxy group, (3) benzyloxy group,
(4) $C_{1-6}$ alkoxy $C_{2-6}$ alkyleneoxy group,
(5) —CO—NR$^{6a}$R$^{6b}$
wherein R$^{6a}$ and R$^{6b}$ are the same or different and each is
(i) hydrogen atom, or
(ii) $C_{1-6}$ alkyl group,
(6) —NR$^{7a}$COR$^{7b}$
wherein R$^{7a}$ and R$^{7b}$ are the same or different and each is
(i) hydrogen atom, or
(ii) $C_{1-6}$ alkyl group, or
(7) methanesulfonyloxy group,
R$^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0 or 1.

A preferable embodiment of R$^1$ is fluorine atom.
A preferable embodiment of R$^2$ is hydrogen atom or chlorine atom.
A preferable embodiment of R$^3$ is fluorine atom.
A preferable embodiment of R$^4$ is methyl group, ethyl group or isopropyl group.
A preferable embodiment of R$^5$ is hydroxy group, methoxy group, ethoxy group, propoxy group, isopropoxy group, benzyloxy group, 2-methoxyethoxy group, methylcarbamoyl group, dimethylcarbamoyl group, N-acetyl-N-methylamino group or methanesulfonyloxy group,
A preferable embodiment of R$^8$ is
(1) hydrogen atom, or
(2) acetyl group.

One of the preferable embodiments of a compound represented by the formula [I] is a compound wherein q is 0.
One of the preferable embodiments of a compound represented by the formula [I] wherein q is 0 is a compound wherein r is 1.
A preferable embodiment of a compound represented by the formula [I], wherein q is 0 and r is 1, is as described below.
R$^1$ is halogen atom,
R$^2$ is hydrogen atom, halogen atom or trifluoromethyl group,
R$^3$ is
(1) halogen atom,
(2) $C_{1-6}$ alkoxy group, or
(3) 2-oxopyrrolidinyl group,
R$^4$ is $C_{1-6}$ alkyl group,
R$^5$ is
(1) hydroxy group,
(2) $C_{1-6}$ alkoxy group, or
(3) methanesulfonyl group,
R$^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group,
a preferable embodiment of R$^8$ is
(1) hydrogen atom, or
(2) acetyl group, and
a further preferable embodiment is
hydrogen atom,
p is 0 or 1.
A preferable embodiment of R$^1$ is fluorine atom.
A preferable embodiment of R$^2$ is hydrogen atom, chlorine atom or trifluoromethyl group.
A preferable embodiment of R$^3$ is fluorine atom, methoxy group, ethoxy group, isopropoxy group or 2-oxopyrrolidinyl group.
A preferable embodiment of R$^4$ is methyl group, ethyl group or isopropyl group.
A preferable embodiment of R$^5$ is hydroxy group, methoxy group, ethoxy group or methanesulfonyl group.

One of the preferable embodiments of a compound represented by the formula [I] wherein q is 0 is a compound wherein r is 0.
A preferable embodiment of a compound represented by the formula [I], wherein q is 0 and r is 0, is as described below.
R$^1$ is halogen atom,
R$^2$ is hydrogen atom or halogen atom,
R$^3$ is halogen atom,
R$^4$ is $C_{1-6}$ alkyl group or cyclopropyl group,
R$^5$ is
(1) carboxy group, or
(2) —CO—NR$^{6a}$R$^{6b}$
wherein R$^{6a}$ and R$^{6b}$ are the same or different and each is
(i) hydrogen atom, or
(ii) $C_{1-6}$ alkyl group,
R$^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0 or 1.
A preferable embodiment of R$^1$ is fluorine atom.
A preferable embodiment of R$^2$ is hydrogen atom or chlorine atom.
A preferable embodiment of R$^3$ is fluorine atom.
A preferable embodiment of R$^4$ is ethyl group, isopropyl group or cyclopropyl group.
A preferable embodiment of R$^5$ is carboxy group, methylcarbamoyl group or dimethylcarbamoyl group,
a preferable embodiment of R$^8$ is
(1) hydrogen atom, or
(2) acetyl group, and
a further preferable embodiment is
hydrogen atom.

A compound represented by the following formula [I'], which is a compound represented by the formula [I] wherein R$^8$ is hydrogen atom, is a preferable embodiment.

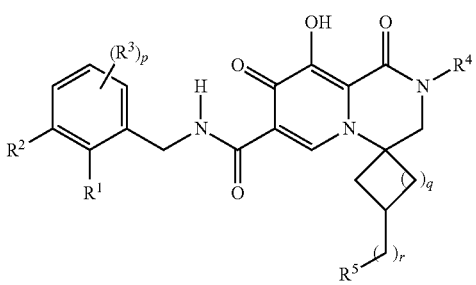

wherein each symbol is as mentioned above.

A preferable embodiment of $R^1$, $R^2$, $R^3$, $R^4$, $R^5$, p, q and r in the formula [I'] is the same as that of $R^1$, $R^2$, $R^3$, $R^4$, $R^5$, p, q and r in the formula [I].

One of the preferable embodiments of a compound represented by the formula [I] is a compound wherein p is 0 or 1.

One of the preferable embodiments of a compound represented by the formula [I] wherein p is 0 or 1 is a compound wherein q is 1.

One of the preferable embodiments of a compound represented by the formula [I], wherein p is 0 or 1 and q is 1, is a compound represented by the formula [I-1] or a pharmaceutically acceptable salt thereof.

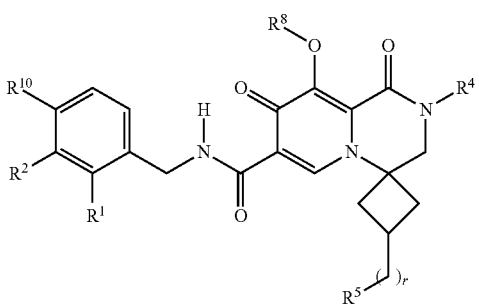

wherein $R^{10}$ is hydrogen atom, halogen atom or $C_{1-6}$ alkoxy group, and $R^1$, $R^2$, $R^4$, $R^5$, $R^8$ and r are as defined in the formula [I].

One of the preferable embodiments of a compound represented by the formula [I-1] is as described below.

$R^1$ is halogen atom,
$R^2$ is hydrogen atom or halogen atom,
$R^{10}$ is
(1) hydrogen atom,
(2) halogen atom, or
(3) $C_{1-6}$ alkoxy group,
$R^4$ is $C_{1-6}$ alkyl group,
$R^5$ is
(1) hydroxy group,
(2) $C_{1-6}$ alkoxy group,
(3) benzyloxy group,
(4) $C_{1-6}$ alkoxy $C_{2-6}$ alkyleneoxy group,
(5) —CO—$NR^{6a}R^{6b}$
wherein $R^{6a}$ and $R^{6b}$ are the same or different and each is
(i) hydrogen atom, or
(ii) $C_{1-6}$ alkyl group,
(6) —$NR^{7a}COR^{7b}$
wherein $R^{7a}$ and $R^{7b}$ are the same or different and each is
(i) hydrogen atom, or
(ii) $C_{1-6}$ alkyl group, or
(7) methanesulfonyloxy group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
r is 0 or 1.

A preferable embodiment of $R^1$ is fluorine atom.

A preferable embodiment of $R^2$ is hydrogen atom or chlorine atom.

A preferable embodiment of $R^{10}$ is hydrogen atom, fluorine atom or methoxy group.

A preferable embodiment of $R^4$ is methyl group, ethyl group or isopropyl group.

One of the preferable embodiments of $R^5$ is hydroxy group, $C_{1-6}$ alkoxy group or —CO—$NR^{6a}R^{6b}$. A more preferable embodiment of $R^5$ is hydroxy group. A more preferable embodiment of $R^5$ is $C_{1-6}$ alkoxy group. A more preferable embodiment of $R^5$ is —CO—$NR^{6a}R^{6b}$.

One of the preferable embodiments of $R^5$ is hydroxy group, methoxy group, ethoxy group, propoxy group, isopropoxy group, benzyloxy group, 2-methoxyethoxy group, methylcarbamoyl group, dimethylcarbamoyl group, acetylamino group, N-acetyl-N-methylamino group or methanesulfonyloxy group.

A more preferable embodiment of $R^5$ is hydroxy group. A more preferable embodiment of $R^5$ is methoxy group, ethoxy group, propoxy group or isopropoxy group. A more preferable embodiment of $R^5$ is methylcarbamoyl group or dimethylcarbamoyl group, A preferable embodiment of $R^8$ is
(1) hydrogen atom, or
(2) acetyl group.

One of the preferable embodiments of a compound represented by the formula [I-1] is a compound represented by the formula [I-1a] or a pharmaceutically acceptable salt thereof.

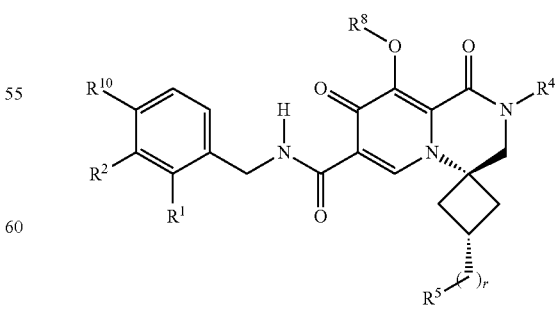

wherein $R^{10}$ is hydrogen atom, halogen atom or $C_{1-6}$ alkoxy group, and $R^1$, $R^2$, $R^4$, $R^5$, $R^8$ and r are as defined in the formula [I-1].

One of the preferable embodiments of a compound represented by the formula [I-1] is a compound represented by the formula [I-1b] or a pharmaceutically acceptable salt thereof.

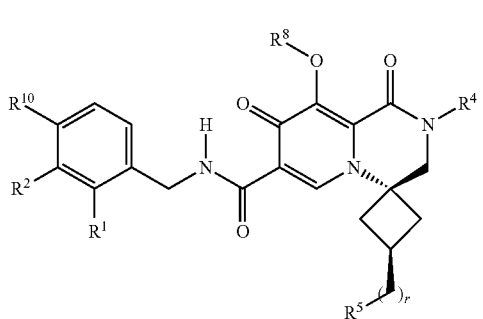

[I-1b]

wherein $R^{10}$ is hydrogen atom, halogen atom or $C_{1-6}$ alkoxy group, and $R^1$, $R^2$, $R^3$, $R^5$, $R^8$ and r are as defined in the formula [I-1].

A compound represented by the following formula [I'-1], which is a compound represented by the formula [I-1] wherein $R^8$ is hydrogen atom, is a preferable embodiment.

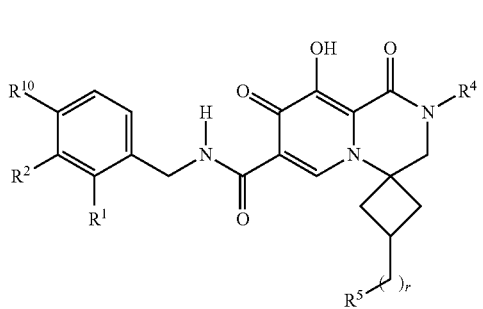

[I'-1]

wherein each symbol is as mentioned above.

A preferable embodiment of $R^1$, $R^2$, $R^4$, $R^5$, $R^{10}$ and r in the formula [I'-1] is the same as that of $R^1$, $R^2$, $R^4$, $R^5$, $R^{10}$ and r in the formula [I-1].

A compound represented by the following formula [I'-1a], which is a compound represented by the formula [I-1a] wherein $R^8$ is hydrogen atom, is a preferable embodiment.

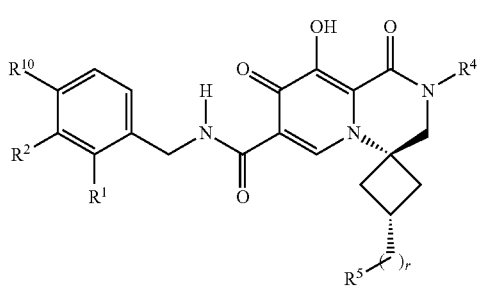

[I'-1a]

wherein each symbol is as mentioned above.

A preferable embodiment of $R^1$, $R^2$, $R^4$, $R^5$, $R^{10}$ and r in the formula [I'-1a] is the same as that of $R^1$, $R^2$, $R^4$, $R^5$, $R^{10}$ and r in the formula [I-1].

A compound represented by the following formula [I'-1b], which is a compound represented by the formula [I-1b] wherein $R^8$ is hydrogen atom, is a preferable embodiment.

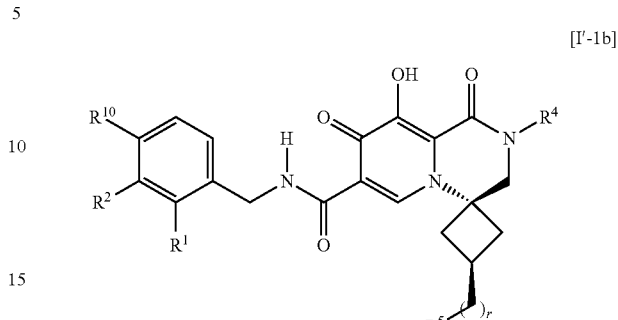

[I'-1b]

wherein each symbol is as mentioned above.

A preferable embodiment of $R^1$, $R^2$, $R^4$, $R^5$, $R^{10}$ and r in the formula [I'-1b] is the same as that of $R^1$, $R^2$, $R^4$, $R^5$, $R^{10}$ and r in the formula [I-1].

A preferable embodiment of $R^1$, $R^2$, $R^{10}$, $R^4$, $R^5$ and $R^8$ in the formula [I-1a] and [I-1b] is the same as that of $R^1$, $R^2$, $R^{10}$, $R^4$, $R^5$ and $R^8$ in the formula [I-1].

One of the preferable embodiments of a compound represented by the formula [I] wherein p is 0 or 1 is a compound wherein q is 0.

A preferable embodiment of a compound represented by the formula [I] wherein p is 0 or 1 and q is 0 is a compound represented by the formula [I-3] or a pharmaceutically acceptable salt thereof.

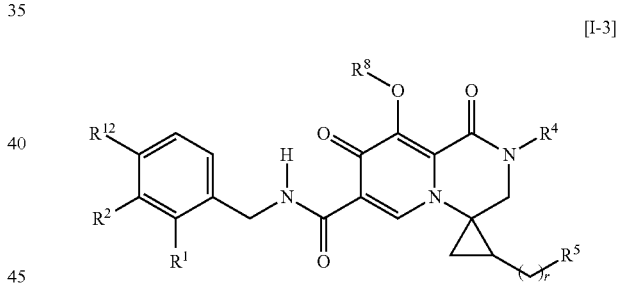

[I-3]

wherein $R^{12}$ is hydrogen atom, halogen atom or $C_{1-6}$ alkoxy group, and $R^1$, $R^2$, $R^4$, $R^5$, $R^8$ and r are as defined in the formula [I].

One of the preferable embodiments of a compound represented by the formula [I-3] is as described below.

$R^1$ is halogen atom, $R^2$ is hydrogen atom, halogen atom or trifluoromethyl group, $R^{12}$ is hydrogen atom, halogen atom or $C_{L-6}$ alkoxy group, $R^4$ is $C_{1-6}$ alkyl group or cyclopropyl group, $R^5$ is (1) hydroxy group, (2) $C_{1-6}$ alkoxy group, (3) carboxy group, (4) —CO—$NR^{6a}R^{6b}$ wherein $R^{6a}$ and $R^{6b}$ are the same or different and each is (i) hydrogen atom, or (ii) $C_{1-6}$ alkyl group, or (5) methanesulfonyl group, R$^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
r is 0 or 1.

A preferable embodiment of R$^1$ is fluorine atom.

A preferable embodiment of R$^2$ is hydrogen atom, chlorine atom or trifluoromethyl group. A more preferable embodiment of R$^2$ is hydrogen atom. A more preferable embodiment of R$^2$ is chlorine atom.

A preferable embodiment of R$^{12}$ is hydrogen atom, fluorine atom, methoxy group or ethoxy group. A more preferable embodiment of R$^{12}$ is fluorine atom. A more preferable embodiment of R$^{12}$ is methoxy group or ethoxy group.

A preferable embodiment of R$^4$ is methyl group, ethyl group, isopropyl group or cyclopropyl group. A more preferable embodiment of R$^4$ is methyl group, ethyl group or isopropyl group.

One of the preferable embodiments of R$^5$ is hydroxy group, C$_{1-6}$ alkoxy group or —CO—NR$^{6a}$R$^{6b}$. A more preferable embodiment of R$^5$ is hydroxy group. A more preferable embodiment of R$^5$ is C$_{1-6}$ alkoxy group. A more preferable embodiment of R$^5$ is —CO—NR$^{6a}$R$^{6b}$.

One of the preferable embodiments of R$^5$ is hydroxy group, methoxy group, ethoxy group, carboxy group, methylcarbamoyl group, dimethylcarbamoyl group or methanesulfonyl group. A more preferable embodiment of R$^5$ is hydroxy group. A more preferable embodiment of R$^5$ is methoxy group or ethoxy group. A more preferable embodiment of R$^5$ is methylcarbamoyl group or dimethylcarbamoyl group.

A preferable embodiment of R$^8$ is
(1) hydrogen atom, or
(2) acetyl group, and
a further preferable embodiment is hydrogen atom.

One of the preferable embodiments of a compound of the formula [I-3] is a compound represented by the formula [I-3a] or a pharmaceutically acceptable salt thereof.

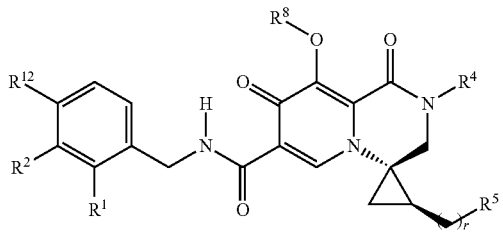

[I-3a]

wherein R$^{12}$ is hydrogen atom, halogen atom or C$_{1-6}$ alkoxy group, and R$^1$, R$^2$, R$^4$, R$^5$, R$^8$ and r are as defined in the formula [I].

One of the preferable embodiments of a compound of the formula [I-3] is a compound represented by the formula [I-3b] or a pharmaceutically acceptable salt thereof.

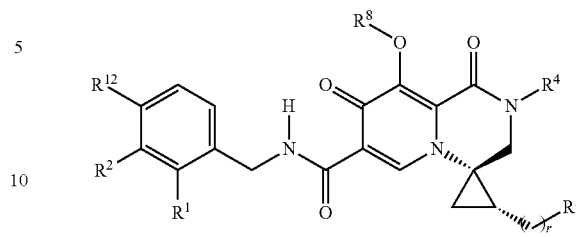

[I-3b]

wherein R$^{12}$ is hydrogen atom, halogen atom or C$_{1-6}$ alkoxy group, and R$^1$, R$^2$, R$^4$, R$^5$, R$^8$ and r are as defined in the formula [I].

One of the preferable embodiments of a compound of the formula [I-3] is a compound represented by the formula [I-3c] or a pharmaceutically acceptable salt thereof.

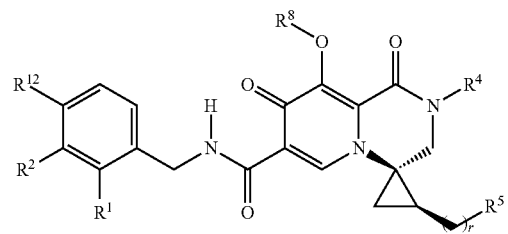

[I-3c]

wherein R$^{12}$ is hydrogen atom, halogen atom or C$_{1-6}$ alkoxy group, and R$^1$, R$^2$, R$^4$, R$^5$, R$^8$ and r are as defined in the formula [I].

One of the preferable embodiments of a compound of the formula [I-3] is a compound represented by the formula [I-3d] or a pharmaceutically acceptable salt thereof.

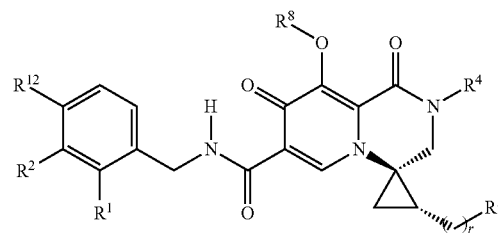

[I-3d]

wherein R$^{12}$ is hydrogen atom, halogen atom or C$_{1-6}$ alkoxy group, and R$^1$, R$^2$, R$^4$, R$^5$, R$^8$ and r are as defined in the formula [I].

A compound represented by the following formula [I'-3], which is a compound represented by the formula [I-3] wherein R$^8$ is hydrogen atom, is a preferable embodiment.

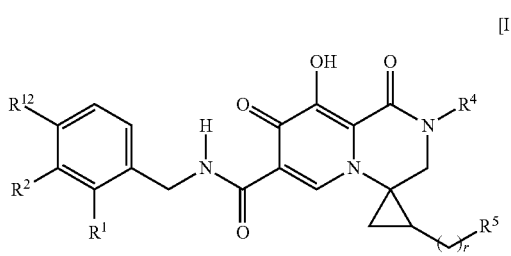

[I'-3]

wherein each symbol is as mentioned above.

A preferable embodiment of $R^1$, $R^2$, $R^4$, $R^5$, $R^{12}$ and r in the formula [I'-3] is the same as that of $R^1$, $R^2$, $R^4$, $R^5$, $R^{12}$ and r in the formula [I-3].

A compound represented by the following formula [I'-3a], which is a compound represented by the formula [I-3a] wherein $R^8$ is hydrogen atom, is a preferable embodiment.

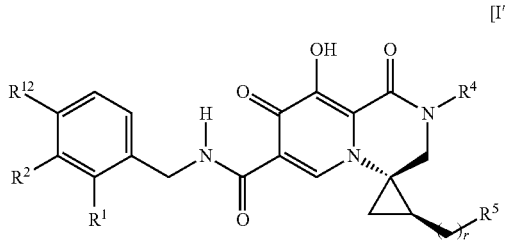

[I'-3a]

wherein each symbol is as mentioned above.

A preferable embodiment of $R^1$, $R^2$, $R^4$, $R^5$, $R^{12}$ and r in the formula [I'-3] is the same as that of $R^1$, $R^2$, $R^4$, $R^5$, $R^{12}$ and r in the formula [I-3].

A compound represented by the following formula [I'-3b], which is a compound represented by the formula [I-3b] wherein $R^8$ is hydrogen atom, is a preferable embodiment.

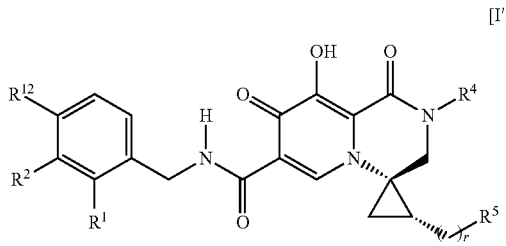

[I'-3b]

wherein each symbol is as mentioned above.

A preferable embodiment of $R^1$, $R^2$, $R^4$, $R^5$, $R^{12}$ and r in the formula [I'-3b] is the same as that of $R^1$, $R^2$, $R^4$, $R^5$, $R^{12}$ and r in the formula [I-3].

A compound represented by the following formula [I'-3c], which is a compound represented by the formula [I-3c] wherein $R^8$ is hydrogen atom, is a preferable embodiment.

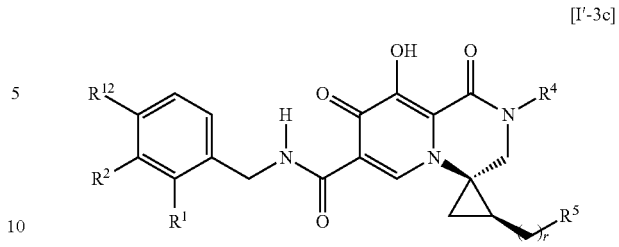

[I'-3c]

wherein each symbol is as mentioned above.

A preferable embodiment of $R^1$, $R^2$, $R^4$, $R^5$, $R^{12}$ and r in the formula [I'-3c] is the same as that of $R^1$, $R^2$, $R^4$, $R^5$, $R^{12}$ and r in the formula [I-3].

A compound represented by the following formula [I'-3d], which is a compound represented by the formula [I-3d] wherein $R^8$ is hydrogen atom, is a preferable embodiment.

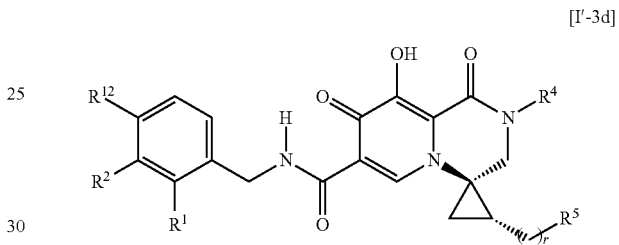

[I'-3d]

wherein each symbol is as mentioned above.

A preferable embodiment of $R^1$, $R^2$, $R^4$, $R^5$, $R^{12}$ and r in the formula [I'-3d] is the same as that of $R^1$, $R^2$, $R^4$, $R^5$, $R^{12}$ and r in the formula [I-3].

A preferable embodiment of $R^1$, $R^2$, $R^{12}$, $R^4$ and $R^5$ in the formula [I-3a], [I-3b], [I-3c] and [I-3d] is the same as that of $R^1$, $R^2$, $R^{12}$, $R^4$ and $R^5$ in the formula [I-3].

One of the preferable embodiments of a compound represented by the formula [I] wherein p is 0 or 1, and q is 0 is a compound represented by the formula [I-4] or a pharmaceutically acceptable salt thereof.

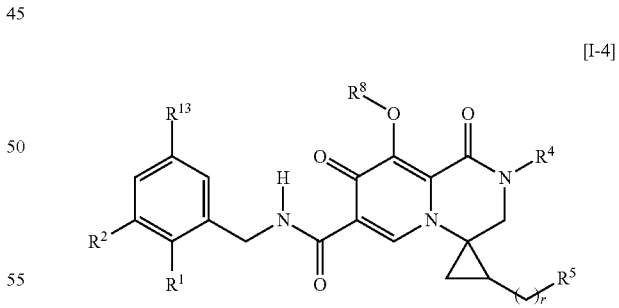

[I-4]

wherein $R^{13}$ is hydrogen atom, $C_{1-6}$ alkoxy group or 2-oxopyrrolidinyl group, and $R^1$, $R^2$, $R^4$, $R^5$, $R^8$ and r are as defined in the formula [I].

One of the preferable embodiments of a compound represented by the formula [I-4] is as described below.

$R^1$ is halogen atom, $R^2$ is halogen atom, $R^{13}$ is hydrogen atom, $C_{1-6}$ alkoxy group or 2-oxopyrrolidinyl group, $R^4$ is $C_{1-6}$ alkyl group,
$R^5$ is $C_{1-6}$ alkoxy group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
r is 0 or 1.

A preferable embodiment of $R^1$ is fluorine atom.
A preferable embodiment of $R^2$ is chlorine atom.
A preferable embodiment of $R^{13}$ is hydrogen atom, methoxy group, ethoxy group, isopropoxy group or 2-oxopyrrolidinyl group. A more preferable embodiment of $R^{13}$ is methoxy group, ethoxy group or isopropoxy group.
A preferable embodiment of $R^4$ is methyl group.
A preferable embodiment of $R^5$ is methoxy group.
A preferable embodiment of $R^8$ is
(1) hydrogen atom, or
(2) acetyl group, and
a further preferable embodiment is
hydrogen atom.

One of the preferable embodiments of a compound represented by the formula [I-4] is a compound represented by the formula [I-4a] or a pharmaceutically acceptable salt thereof.

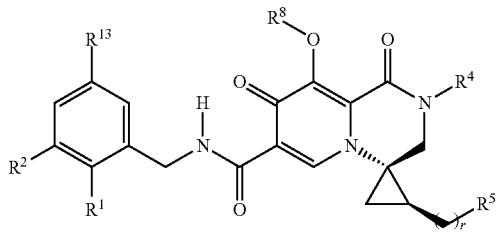

[I-4a]

wherein $R^{13}$ is hydrogen atom, $C_{1-6}$ alkoxy group or 2-oxopyrrolidinyl group, and $R^1$, $R^2$, $R^4$, $R^5$, $R^8$ and r are as defined in the formula [I].

One of the preferable embodiments of a compound represented by the formula [I-4] is a compound represented by the formula [I-4b] or a pharmaceutically acceptable salt thereof.

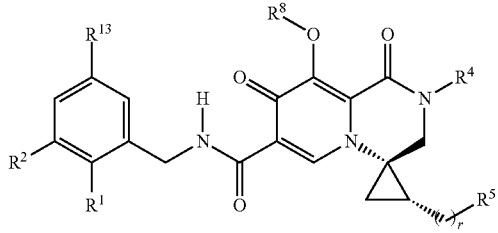

[I-4b]

wherein $R^{13}$ is hydrogen atom, $C_{1-6}$ alkoxy group or 2-oxopyrrolidinyl group, and $R^1$, $R^2$, $R^4$, $R^5$, $R^8$ and r are as defined in the formula [I].

One of the preferable embodiments of a compound represented by the formula [I-4] is a compound represented by the formula [I-4c] or a pharmaceutically acceptable salt thereof.

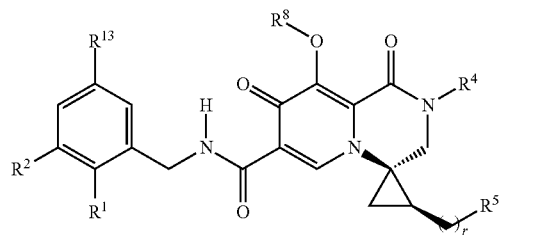

[I-4c]

wherein $R^{13}$ is hydrogen atom, $C_{1-6}$ alkoxy group or 2-oxopyrrolidinyl group, and $R^1$, $R^2$, $R^4$, $R^5$, $R^8$ and r are as defined in the formula [I].

One of the preferable embodiments of a compound represented by the formula [I-4] is a compound represented by the formula [I-4d] or a pharmaceutically acceptable salt thereof.

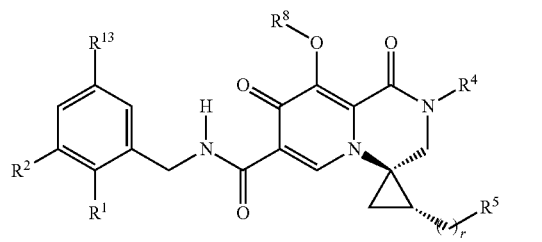

[I-4d]

wherein $R^{13}$ is hydrogen atom, $C_{1-6}$ alkoxy group or 2-oxopyrrolidinyl group, and $R^1$, $R^2$, $R^4$, $R^5$, $R^8$ and r are as defined in the formula [I].

A compound represented by the following formula [I'-4], which is a compound represented by the formula [I-4] wherein $R^8$ is hydrogen atom, is a preferable embodiment.

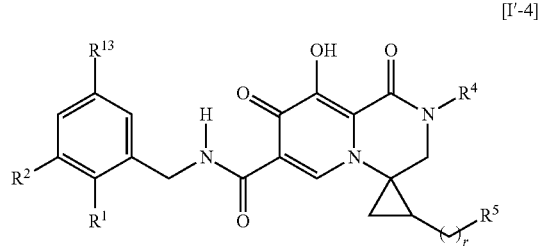

[I'-4]

wherein each symbol is as mentioned above.

A preferable embodiment of $R^1$, $R^2$, $R^4$, $R^5$, $R^{13}$ and r in the formula [I'-4] is the same as that of $R^1$, $R^2$, $R^4$, $R^5$, $R^{13}$ and r in the formula [I-4].

A compound represented by the following formula [I'-4a], which is a compound represented by the formula [I-4a] wherein $R^8$ is hydrogen atom, is a preferable embodiment.

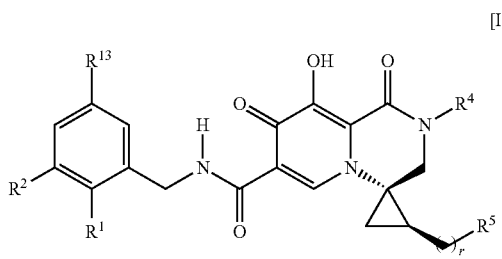

[I'-4a]

wherein each symbol is as mentioned above.

A preferable embodiment of $R^1$, $R^2$, $R^4$, $R^5$, $R^{13}$ and r in the formula [I'-4a] is the same as that of $R^1$, $R^2$, $R^4$, $R^5$, $R^{13}$ and r in the formula [I-4b]

A compound represented by the following formula [I'-4b], which is a compound represented by the formula [I-4b] wherein $R^8$ is hydrogen atom, is a preferable embodiment.

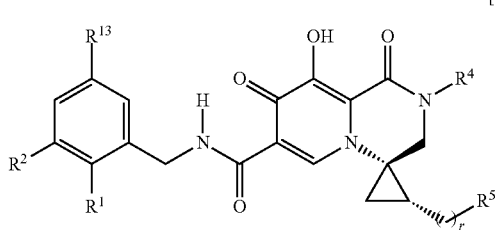

[I'-4b]

wherein each symbol is as mentioned above.

A preferable embodiment of $R^1$, $R^2$, $R^4$, $R^5$, $R^{13}$ and r in the formula [I'-4b] is the same as that of $R^1$, $R^2$, $R^4$, $R^5$, $R^{13}$ and r in the formula [I-4].

A compound represented by the following formula [I'-4c], which is a compound represented by the formula [I-4c] wherein $R^8$ is hydrogen atom, is a preferable embodiment.

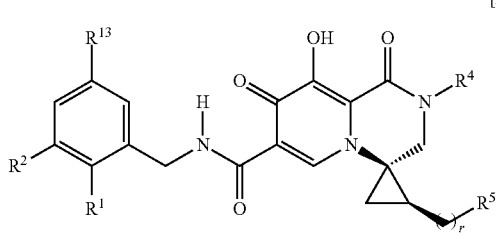

[I'-4c]

wherein each symbol is as mentioned above.

A preferable embodiment of $R^1$, $R^2$, $R^4$, $R^5$, $R^{13}$ and r in the formula [I'-4c] is the same as that of $R^1$, $R^2$, $R^4$, $R^5$, $R^{13}$ and r in the formula [1-4].

A compound represented by the following formula [I'-4d], which is a compound represented by the formula [I-4d] wherein $R^8$ is hydrogen atom, is a preferable embodiment.

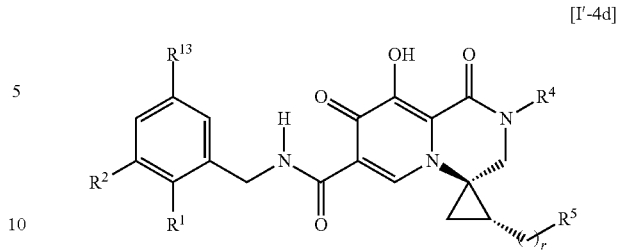

[I'-4d]

wherein each symbol is as mentioned above.

A preferable embodiment of $R^1$, $R^2$, $R^4$, $R^5$, $R^3$ and r in the formula [I'-4d] is the same as that of $R^1$, $R^2$, $R^4$, $R^5$, $R^{13}$ and r in the formula [1-4].

A preferable embodiment of $R^1$, $R^2$, $R^4$, $R^5$, $R^8$ and $R^{13}$ in the formula [I-4a], [I-4b], [I-4c] and [I-4d] is the same as that of $R^1$, $R^2$, $R^4$, $R^5$, $R^8$ and $R^{13}$ in the formula [I-4].

One of the preferable embodiments of a compound represented by the formula [II]

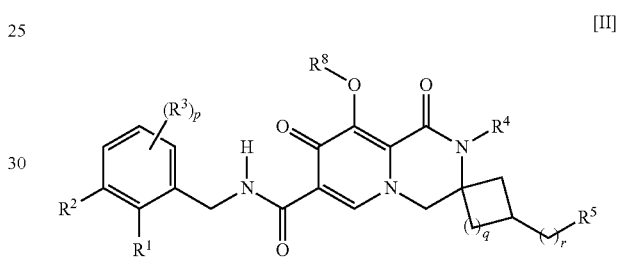

[II]

wherein
$R^1$ is halogen atom,
$R^2$ is hydrogen atom, halogen atom or trifluoromethyl group,
$R^3$ is
(1) halogen atom,
(2) $C_{1-6}$ alkoxy group, or
(3) 2-oxopyrrolidinyl group,
when p is 2 or 3, $R^3$ are the same or different,
$R^4$ is $C_{1-6}$ alkyl group or cyclopropyl group,
$R^5$ is
(1) hydroxy group,
(2) $C_{1-6}$ alkoxy group,
(3) benzyloxy group,
(4) $C_{1-6}$ alkoxy $C_{2-6}$ alkyleneoxy group,
(5) carboxy group,
(6) —CO—$NR^{6a}R^{6b}$
  wherein $R^{6a}$ and $R^{6b}$ are the same or different and each is
  (i) hydrogen atom, or
  (ii) $C_{1-6}$ alkyl group,
(7) —$NR^{7a}COR^{7b}$
  wherein $R^{7a}$ and $R^{7b}$ are the same or different and each is
  (i) hydrogen atom, or
  (ii) $C_{1-6}$ alkyl group,
(8) methanesulfonyl group, or
(9) methanesulfonyloxy group,
$R^8$ is
(1) hydrogen atom,
(2) acetyl group,
(3) propionyl group,
(4) isobutyryl group, (5) pivaloyl group,
(6) palmitoyl group,
(7) benzoyl group,
(8) 4-methylbenzoyl group,
(9) dimethylcarbamoyl group,
(10) dimethylaminomethylcarbonyl group,
(11) fumaryl group, or
(12) 3-carboxybenzoyl group,
p is an integer of 0 to 3,
q is 0 or 1, and
r is 0 or 1,
or a pharmaceutically acceptable salt thereof, is a compound wherein q is 1.

One of the preferable embodiments of a compound represented by the formula [II] wherein q is 1 is a compound wherein r is 1.

A preferable embodiment of a compound represented by the formula [II] wherein q is 1 and r is 1 is as described below.
$R^1$ is halogen atom,
$R^2$ is halogen atom,
$R^4$ is $C_{1-6}$ alkyl group,
$R^5$ is hydroxy group or $C_{1-6}$ alkoxy group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0.

A preferable embodiment of $R^1$ is fluorine atom.
A preferable embodiment of $R^2$ is chlorine atom.
A preferable embodiment of $R^4$ is ethyl group.
A preferable embodiment of $R^5$ is hydroxy group or methoxy group,
A preferable embodiment of $R^8$ is
(1) hydrogen atom, or
(2) acetyl group, and
a further preferable embodiment is
hydrogen atom.

One of the preferable embodiments of a compound represented by the formula [II] wherein q is 1 is a compound wherein r is 0.

A preferable embodiment of a compound represented by the formula [II] wherein q is 1 and r is 0 is as described below.
$R^1$ is halogen atom,
$R^2$ is hydrogen atom or halogen atom,
$R^3$ is halogen atom,
$R^4$ is $C_{1-6}$ alkyl group,
$R^5$ is hydroxy group or $C_{1-6}$ alkoxy group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0 or 1.

A preferable embodiment of $R^1$ is fluorine atom.

A preferable embodiment of $R^2$ is hydrogen atom or chlorine atom.
A preferable embodiment of $R^3$ is fluorine atom.
A preferable embodiment of $R^4$ is methyl group, ethyl group or isopropyl group.
A preferable embodiment of $R^5$ is hydroxy group, methoxy group or ethoxy group.
A preferable embodiment of $R^8$ is
(1) hydrogen atom, or
(2) acetyl group, and
a further preferable embodiment is
hydrogen atom.

One of the preferable embodiments of a compound represented by the formula [II] is a compound wherein q is 0.

One of the preferable embodiments of a compound represented by the formula [II] wherein q is 0 is a compound wherein r is 1.

A preferable embodiment of a compound represented by the formula [II] wherein q is 0 and r is 1 is as described below.
$R^1$ is halogen atom,
$R^2$ is hydrogen atom or halogen atom,
$R^3$ is
(1) halogen atom, or
(2) $C_{1-6}$ alkoxy group,
$R^4$ is $C_{1-6}$ alkyl group,
$R^5$ is hydroxy group or C-s alkoxy group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
p is 0 or 1.

A preferable embodiment of $R^1$ is fluorine atom.
A preferable embodiment of $R^2$ is hydrogen atom or chlorine atom.
A preferable embodiment of $R^3$ is fluorine atom or methoxy group.
A preferable embodiment of $R^4$ is methyl group, ethyl group or isopropyl group.
A preferable embodiment of $R^5$ is hydroxy group, methoxy group or ethoxy group.
A preferable embodiment of $R^8$ is
(1) hydrogen atom, or
(2) acetyl group, and
a further preferable embodiment is
hydrogen atom.

A compound represented by the following formula [II'], which is a compound represented by the formula [II] wherein $R^8$ is hydrogen atom, is a preferable embodiment.

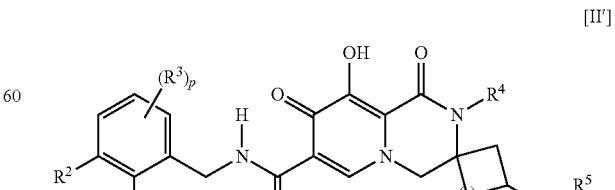

[II']

wherein each symbol is as mentioned above.

A preferable embodiment of $R^1$, $R^2$, $R^3$, $R^4$, $R^5$, p, q and r in the formula [II'] is the same as that of $R^1$, $R^2$, $R^3$, $R^4$, $R^5$, p, q and r in the formula [II].

One of the preferable embodiments of a compound represented by the formula [II] is a compound wherein p is 0 or 1.

One of the preferable embodiments of a compound represented by the formula [II] wherein p is 0 or 1 is a compound wherein q is 1.

One of the preferable embodiments of a compound represented by the formula [II] wherein p is 0 or 1 and q is 1 is a compound represented by the formula [11-1] or a pharmaceutically acceptable salt thereof.

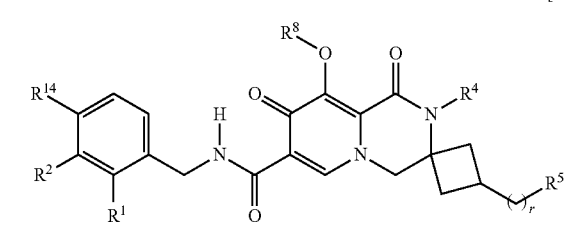

[II-1]

wherein $R^{14}$ is hydrogen atom, halogen atom or $C_{1-6}$ alkoxy group, and $R^1$, $R^2$, $R^4$, $R^5$, $R^8$ and r are as defined in the formula [II].

A preferable embodiment of $R^{14}$ is hydrogen atom or halogen atom.

One of the preferable embodiments of a compound represented by the formula [II-1] is as described below.

$R^1$ is halogen atom,
$R^2$ is hydrogen atom or halogen atom,
$R^{14}$ is hydrogen atom or halogen atom,
$R^4$ is $C_{1-6}$ alkyl group,
$R^5$ is hydroxy group or $C_{3-6}$ alkoxy group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
r is 0 or 1.

A preferable embodiment of $R^1$ is fluorine atom.
A preferable embodiment of $R^2$ is hydrogen atom or chlorine atom.
A preferable embodiment of $R^{14}$ is hydrogen atom or fluorine atom.
A preferable embodiment of $R^4$ is methyl group, ethyl group or isopropyl group.
One of the preferable embodiments of $R^5$ is hydroxy group.
One of the preferable embodiments of $R^5$ is $C_{1-6}$ alkoxy group, more preferably methoxy group or ethoxy group.
A preferable embodiment of $R^8$ is
(1) hydrogen atom, or
(2) acetyl group, and
a further preferable embodiment is
hydrogen atom.

One of the preferable embodiments of a compound represented by the formula [II-1] is a compound represented by the formula [II-1a] or a pharmaceutically acceptable salt thereof.

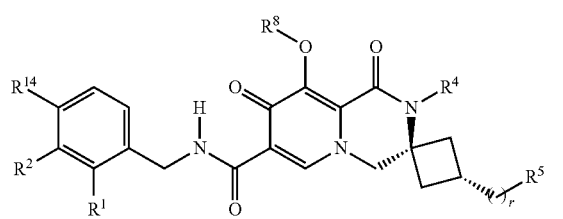

[II-1a]

wherein $R^{14}$ is hydrogen atom, halogen atom or $C_{1-6}$ alkoxy group, and $R^1$, $R^2$, $R^4$, $R^5$, $R^8$ and r are as defined in the formula [II].

One of the preferable embodiments of a compound represented by the formula [II-1] is a compound represented by the formula [II-1b] or a pharmaceutically acceptable salt thereof.

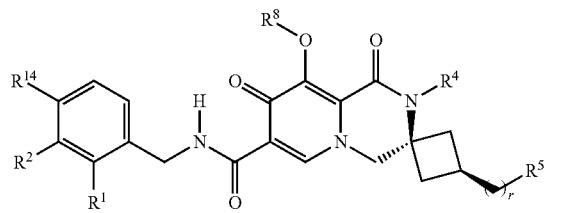

[II-1b]

wherein $R^{14}$ is hydrogen atom, halogen atom or $C_{1-6}$ alkoxy group, and $R^1$, $R^2$, $R^4$, $R^5$, $R^8$ and r are as defined in the formula [II].

A compound represented by the following formula [II'-1], which is a compound represented by the formula [II-1] wherein $R^8$ is hydrogen atom, is a preferable embodiment.

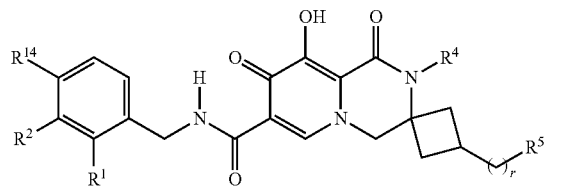

[II'-1]

wherein each symbol is as mentioned above.

A preferable embodiment of $R^1$, $R^2$, $R^4$, $R^5$, $R^{14}$ and r in the formula [II'-1] is the same as that of $R^1$, $R^2$, $R^4$, $R^5$, $R^{14}$ and r in the formula [II-1].

A compound represented by the following formula [II'-1a], which is a compound represented by the formula [II-1a] wherein $R^8$ is hydrogen atom, is a preferable embodiment.

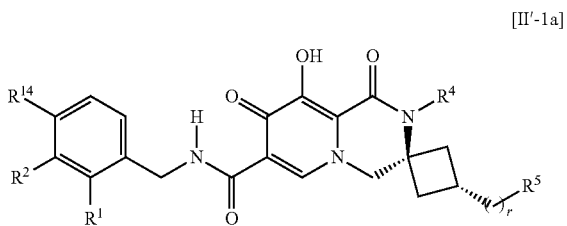

wherein each symbol is as mentioned above.

A preferable embodiment of $R^1$, $R^2$, $R^4$, $R^5$, $R^1$ and r in the formula [II'-1a] is the same as that of $R^1$, $R^2$, $R^4$, $R^5$, $R^{14}$ and r in the formula [II-1].

A compound represented by the following formula [II'-1b], which is a compound represented by the formula [II-1b] wherein $R^8$ is hydrogen atom, is a preferable embodiment.

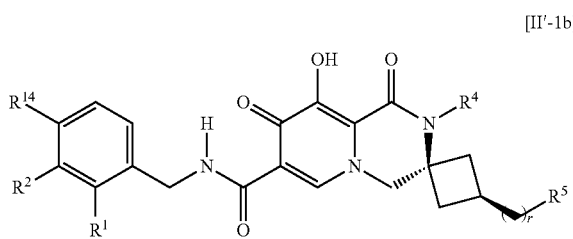

wherein each symbol is as mentioned above.

A preferable embodiment of $R^1$, $R^2$, $R^4$, $R^5$, $R^{14}$ and r in the formula [II'-1b] is the same as that of $R^1$, $R^2$, $R^4$, $R^5$, $R^{14}$ and r in the formula [II-1].

A preferable embodiment of $R^1$, $R^2$, $R^{14}$, $R^4$, $R^5$, $R^8$ and r in the formula [II-1a] and [II-1b] is the same as that of $R^1$, $R^2$, $R^{14}$, $R^4$, $R^5$, $R^8$ and r in the formula [II-1].

One of the preferable embodiments of a compound represented by the formula [II] is a compound wherein q is 0.

One of the preferable embodiments of a compound represented by the formula [II] wherein q is 0 is a compound wherein p is 0 or 1.

One of the preferable embodiments of a compound of the formula [II] wherein p is 0 or 1 and q is 0 is a compound represented by the following formula [II-3] or a pharmaceutically acceptable salt thereof.

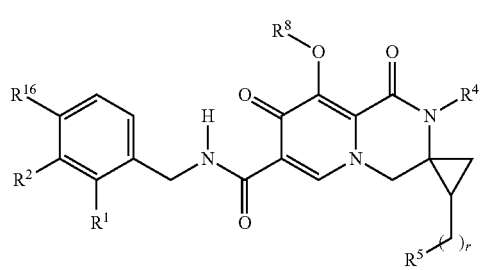

wherein $R^{16}$ is hydrogen atom, halogen atom or $C_{1-6}$ alkoxy group, and $R^1$, $R^2$, $R^4$, $R^5$, $R^8$ and r are as defined in the formula [II].

One of the preferable embodiments of a compound represented by the formula [II-3] is as described below.

$R^1$ is halogen atom,
$R^2$ is hydrogen atom or halogen atom,
$R^{16}$ is hydrogen atom, halogen atom or $C_{1-6}$ alkoxy group,
$R^4$ is $C_{1-6}$ alkyl group,
$R^5$ is hydroxy group or $C_{1-6}$ alkoxy group,
$R^8$ is
(1) hydrogen atom,
(2) acetyl group,
(3) propionyl group,
(4) isobutyryl group,
(5) pivaloyl group,
(6) palmitoyl group,
(7) benzoyl group,
(8) 4-methylbenzoyl group, or
(9) dimethylcarbamoyl group, and
r is 0 or 1.

A preferable embodiment of $R^1$ is fluorine atom.

A preferable embodiment of $R^2$ is hydrogen atom or chlorine atom. One of the more preferable embodiments of $R^2$ is hydrogen atom. One of the more preferable embodiments of $R^2$ is chlorine atom.

A preferable embodiment of $R^{16}$ is hydrogen atom, fluorine atom or methoxy group. One of the more preferable embodiments of $R^{16}$ is fluorine atom. One of the more preferable embodiments of $R^{16}$ is methoxy group.

A preferable embodiment of $R^4$ is methyl group, ethyl group or isopropyl group.

One of the preferable embodiments of $R^5$ is hydroxy group.

One of the preferable embodiments of $R^5$ is $C_{1-6}$ alkoxy group, more preferably methoxy group or ethoxy group.

One of the preferable embodiments of $R^5$ is hydroxy group, methoxy group or ethoxy group.

A preferable embodiment of $R^8$ is
(1) hydrogen atom, or
(2) acetyl group, and
a further preferable embodiment is
hydrogen atom.

One of the preferable embodiments of the compound of the formula [II-3] is a compound represented by the following formula [II-3a] or a pharmaceutically acceptable salt thereof.

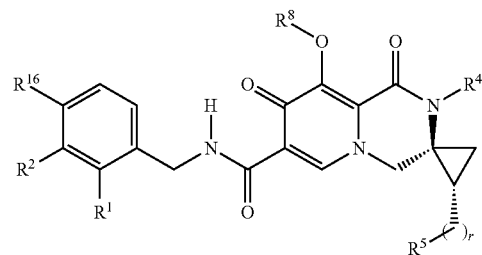

wherein $R^{16}$ is hydrogen atom, halogen atom or $C_{1-6}$ alkoxy group, and $R^1$, $R^2$, $R^4$, $R^5$, $R^8$ and r are as defined in the formula [II].

One of the preferable embodiments of the compound of the formula [II-3] is a compound represented by the following formula [II-3b] or a pharmaceutically acceptable salt thereof.

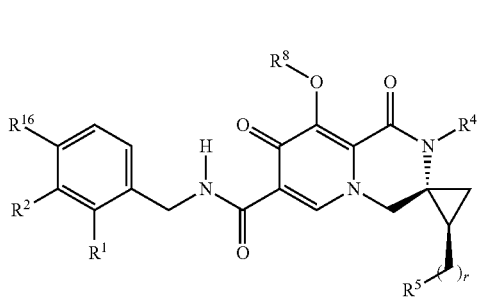

[II-3b]

wherein $R^{16}$ is hydrogen atom, halogen atom or $C_{1-6}$ alkoxy group, and $R^1$, $R^2$, $R^4$, $R^5$, $R^8$ and r are as defined in the formula [II].

A compound represented by the following formula [II'-3], which is a compound represented by the following formula [II-3] wherein $R^8$ is hydrogen atom, is a preferable embodiment.

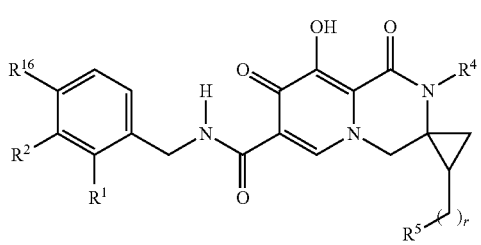

[II'-3]

wherein each symbol is as mentioned above.

A preferable embodiment of $R^1$, $R^2$, $R^4$, $R^5$, $R^{16}$ and r in the formula [II'-3a] is the same as that of $R^1$, $R^2$, $R^4$, $R^5$, $R^{16}$ and r in the formula [II-3].

A compound represented by the following formula [II'-3a], which is a compound represented by the following formula [II-3a] wherein $R^8$ is hydrogen atom, is a preferable embodiment.

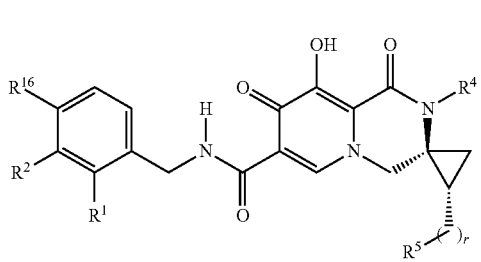

[II'-3a]

wherein each symbol is as mentioned above.

A preferable embodiment of $R^1$, $R^2$, $R^4$, $R^5$, $R^{16}$ and r in the formula [II'-3] is the same as that of $R^1$, $R^2$, $R^4$, $R^5$, $R^{16}$ and r in the formula [II-3].

A compound represented by the following formula [II'-3b], which is a compound represented by the following formula [II-3b] wherein $R^8$ is hydrogen atom, is a preferable embodiment.

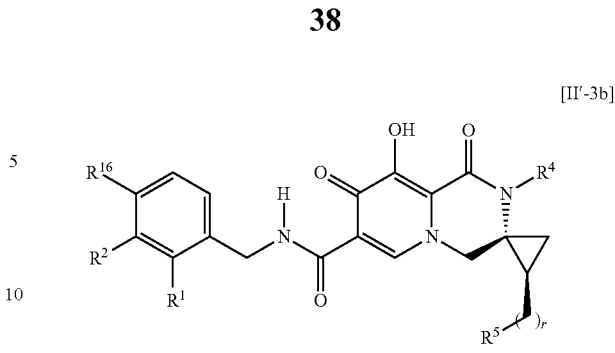

[II'-3b]

wherein each symbol is as mentioned above.

A preferable embodiment of $R^1$, $R^2$, $R^4$, $R^5$, $R^{16}$ and r in the formula [II'-3b] is the same as that of $R^1$, $R^2$, $R^4$, $R^5$, $R^{16}$ and r in the formula [II-3].

A preferable embodiment of $R^1$, $R^2$, $R^{16}$, $R^4$, $R^8$ and $R^5$ in the formula [II-3a] and [II-3b] is the same as that of $R^1$, $R^2$, $R^{16}$, $R^4$, $R^8$ and $R^5$ in the formula [11-3].

In the above-mentioned formulae [I-1a], [I-3b], [I-3d], [I-4b], [I-4d], [II-1a] and [II-3a], wherein r is 0, the steric configuration of $R^5$ is the steric configuration shown in the following partial structural formula.

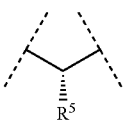

In the above-mentioned formulae [I-1b], [I-3a], [I-3c], [I-4a], [I-4c], [II-1b] and [II-3b], wherein r is 0, the steric configuration of $R^5$ is the steric configuration shown in the following partial structural formula.

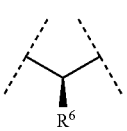

As the "compound represented by the above-mentioned formula [I], [II], [I-1], [I-1a], [I-1b], [I-3], [I-3a], [I-3b], [I-3c], [I-3d], [I-4], [I-4a], [I-4b], [I-4c], [I-4d], [II-1], [II-1a], [II-1b], [II-3], [II-3a] or [II-3b]" (hereinafter to be also referred to as the compound of the present invention), a compound represented by the following formula, or a pharmaceutically acceptable salt thereof is preferable.

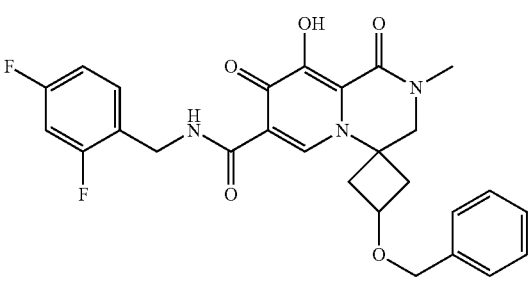

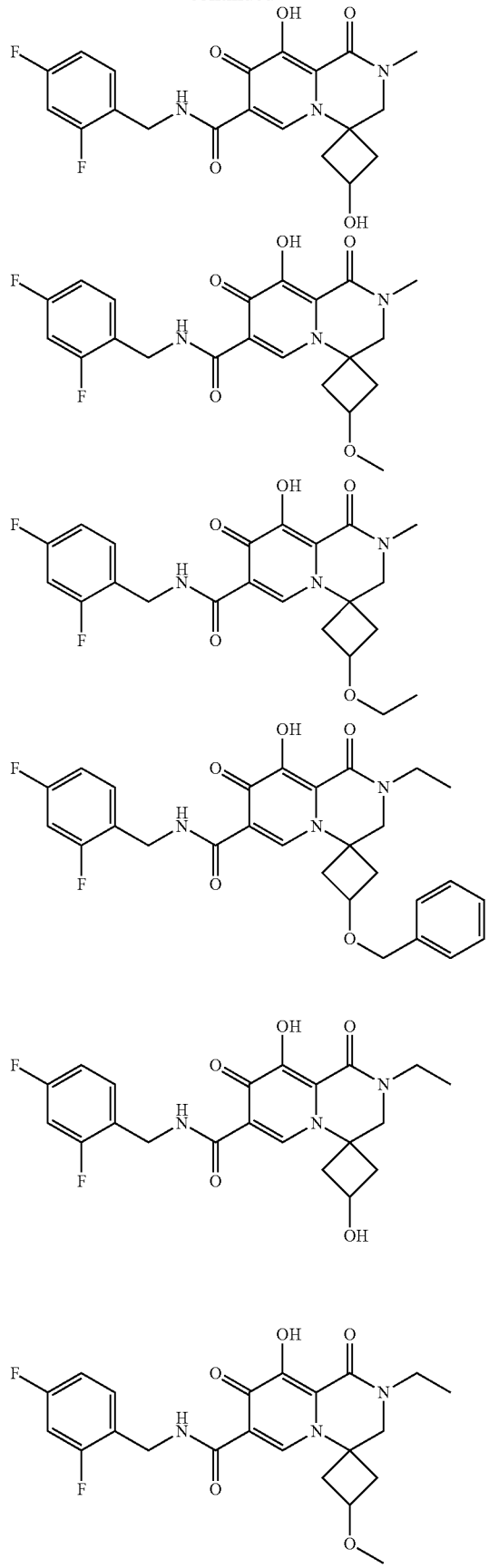
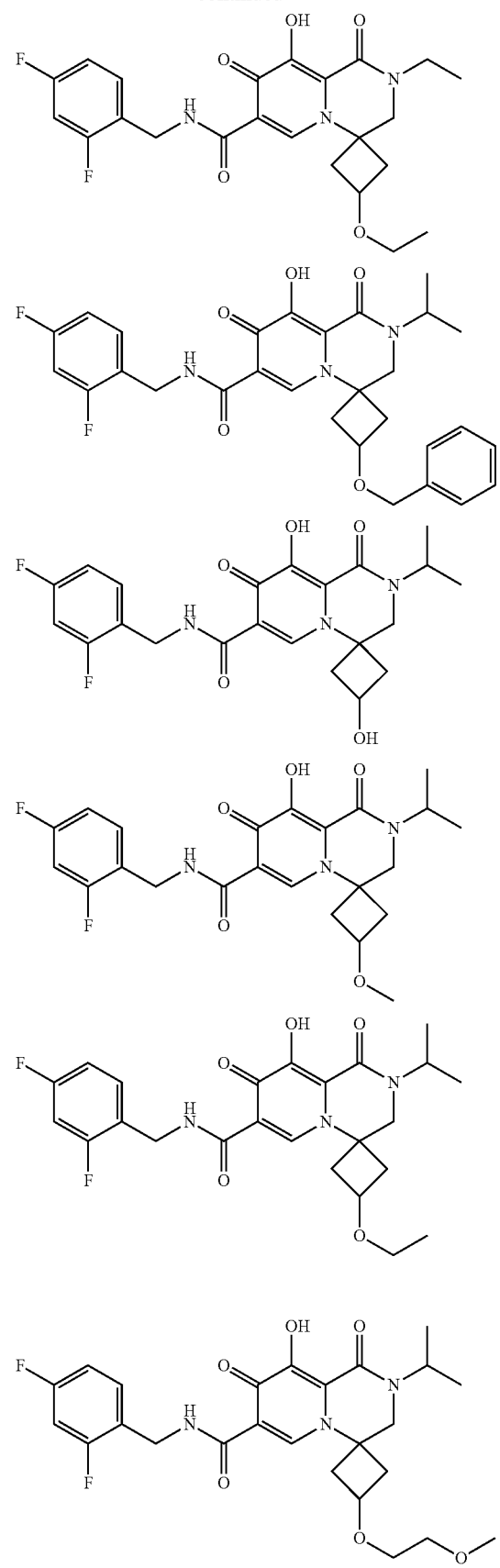

-continued
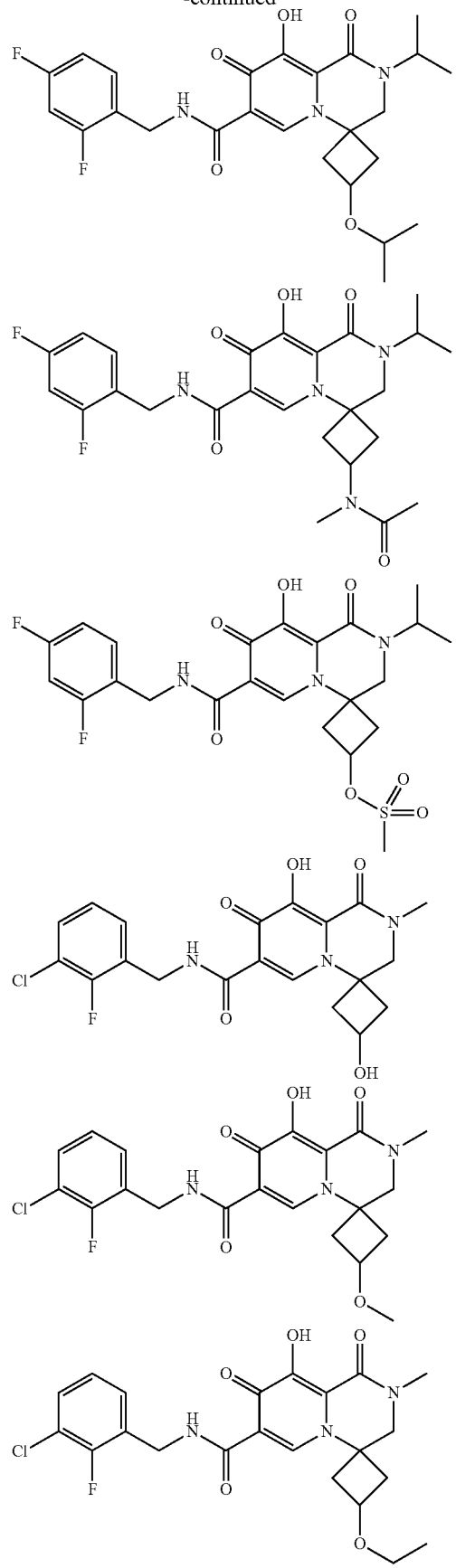
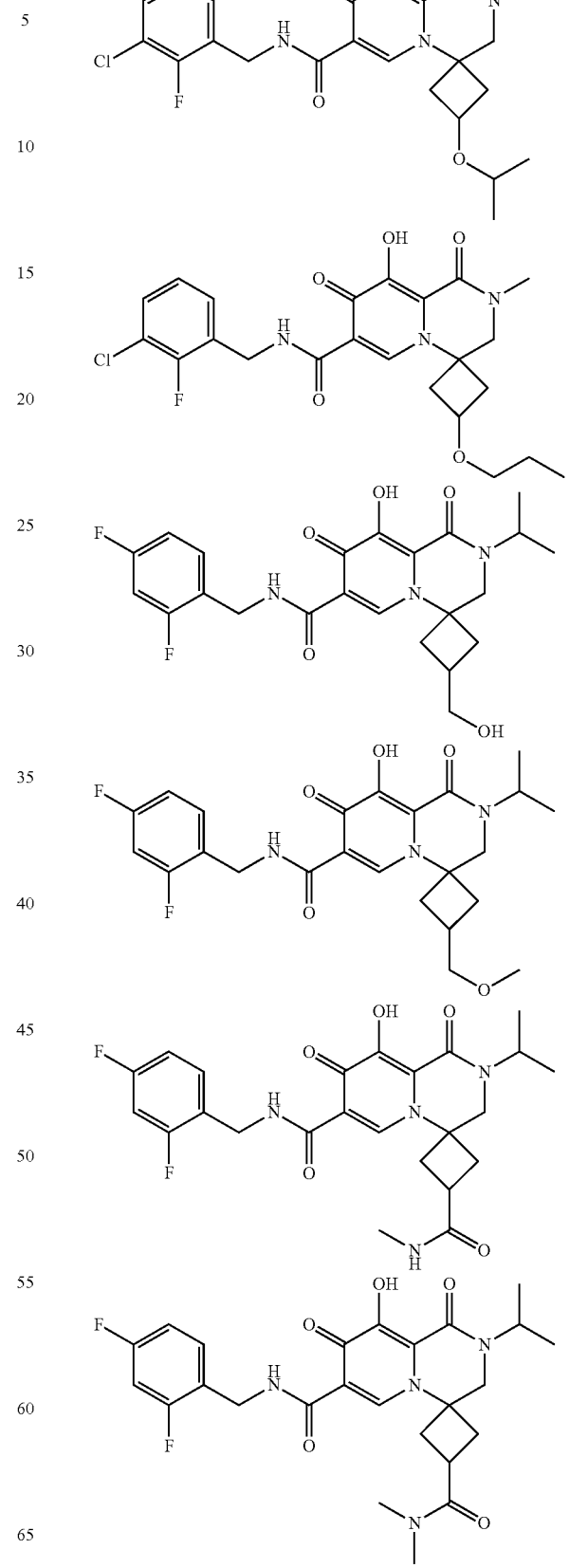

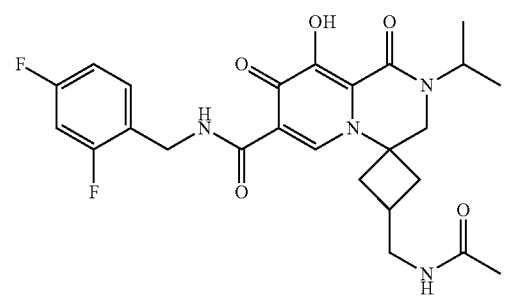
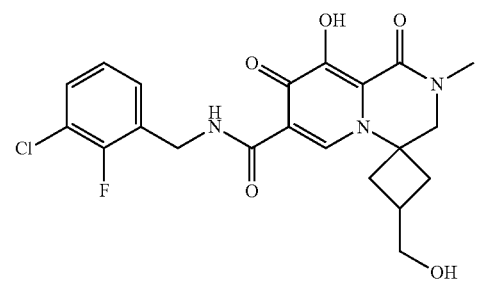
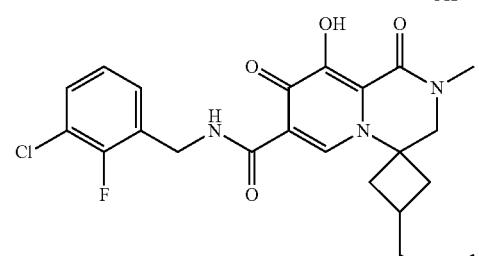
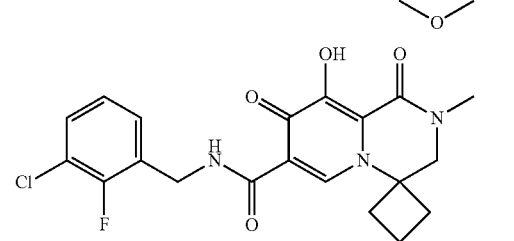
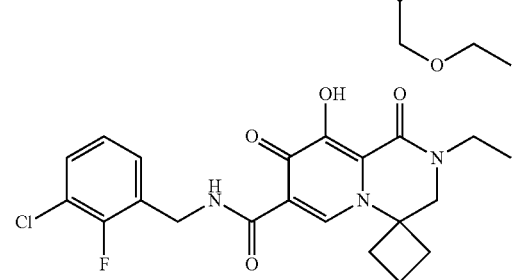
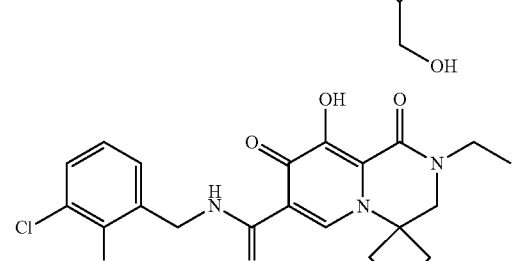
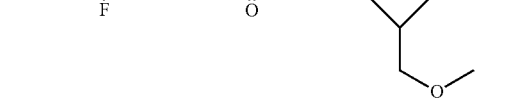
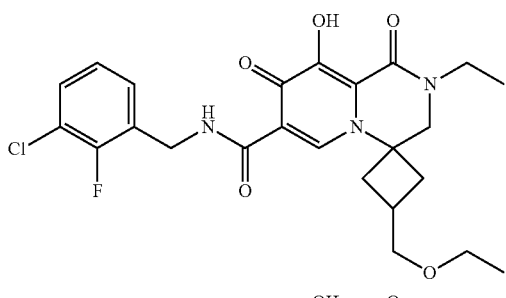
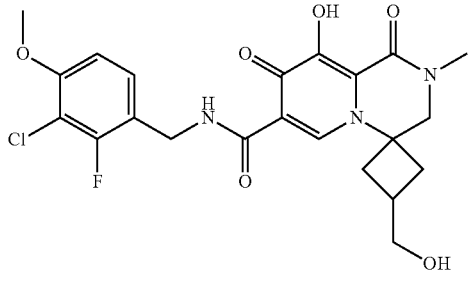
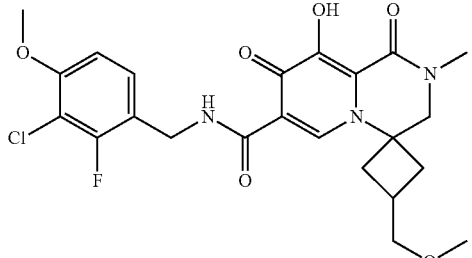
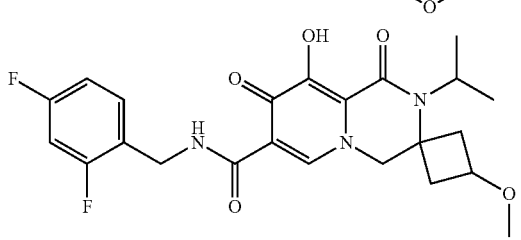
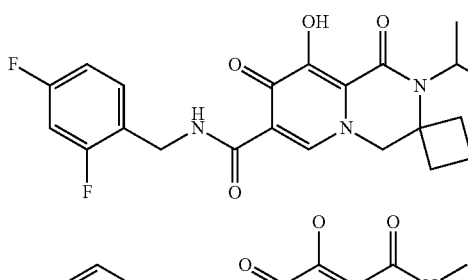
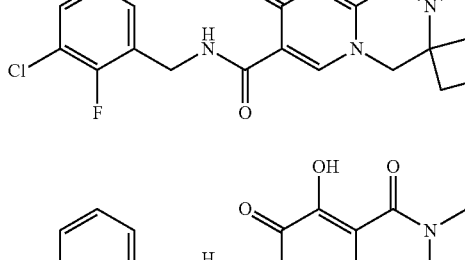
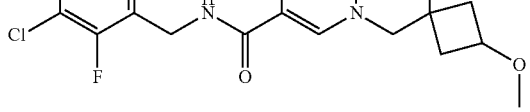

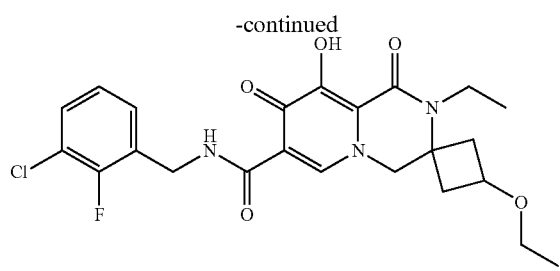
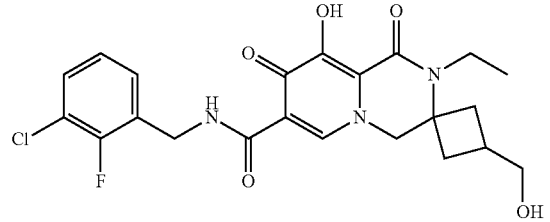
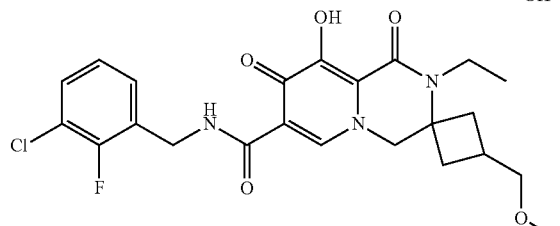
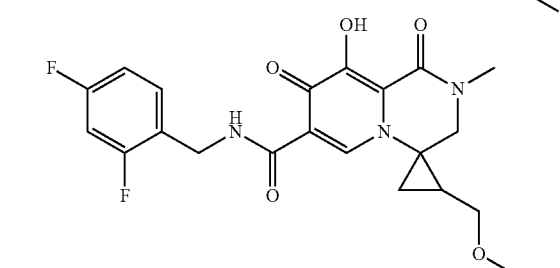
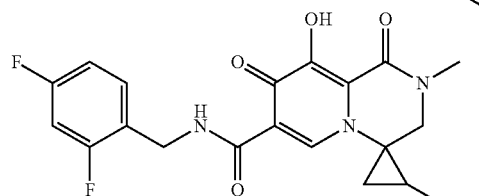
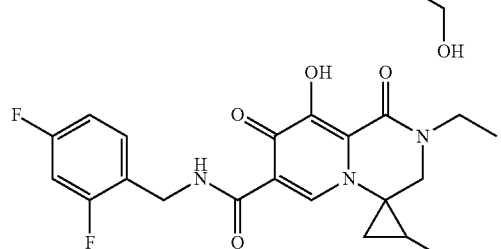
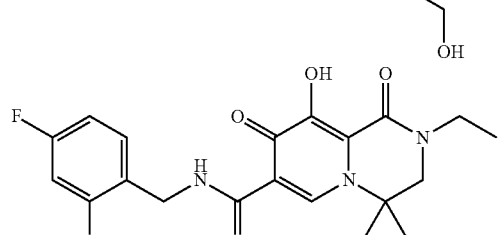
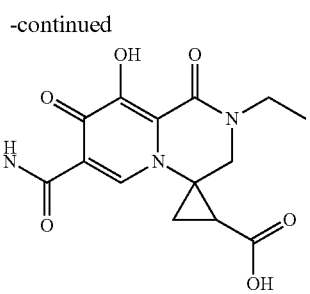
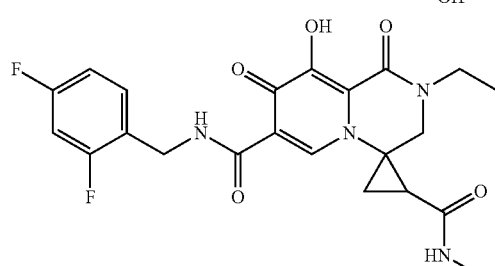
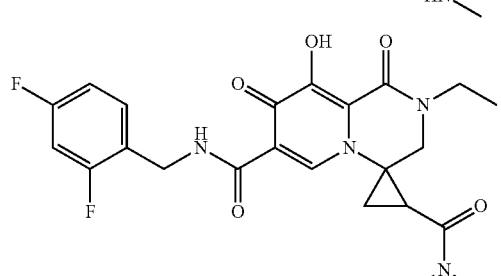
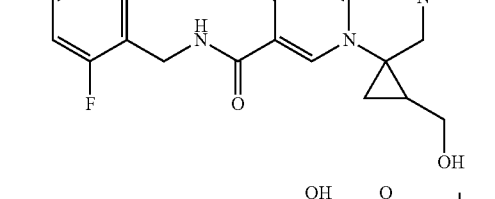
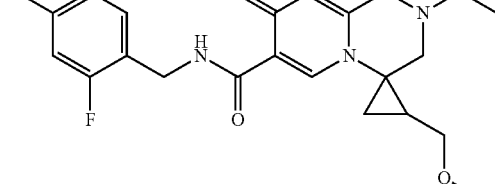
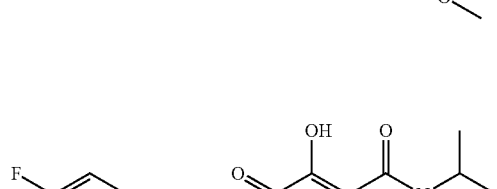
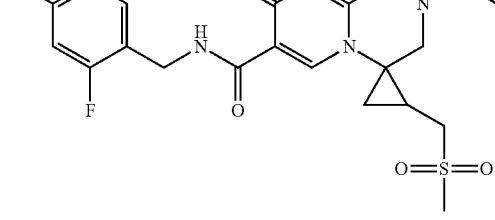

47
-continued
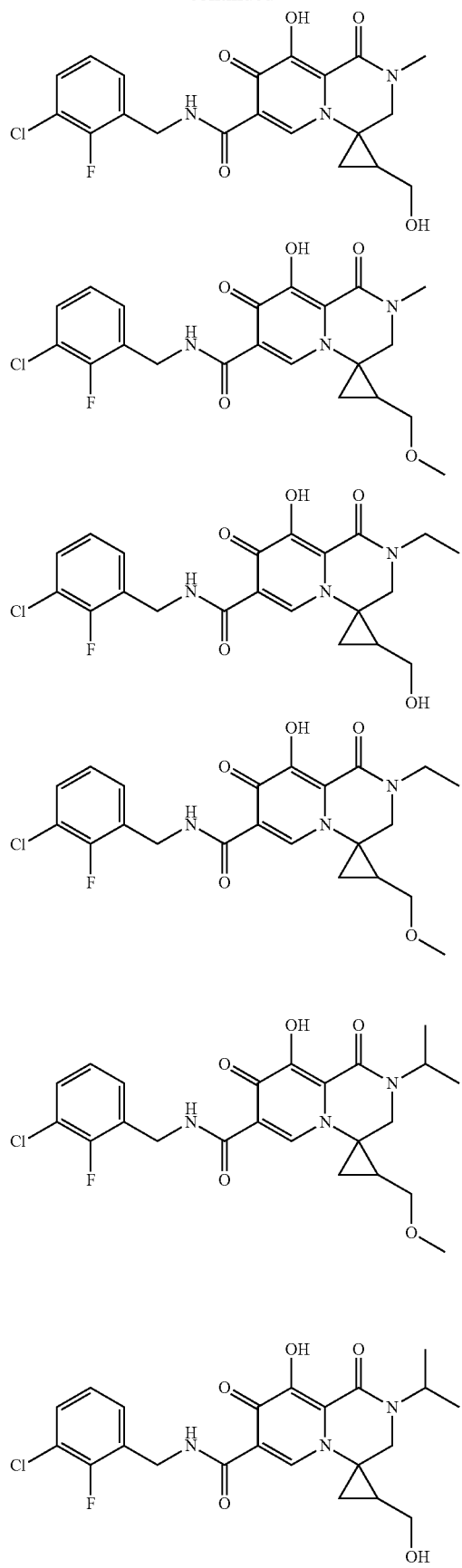
48
-continued
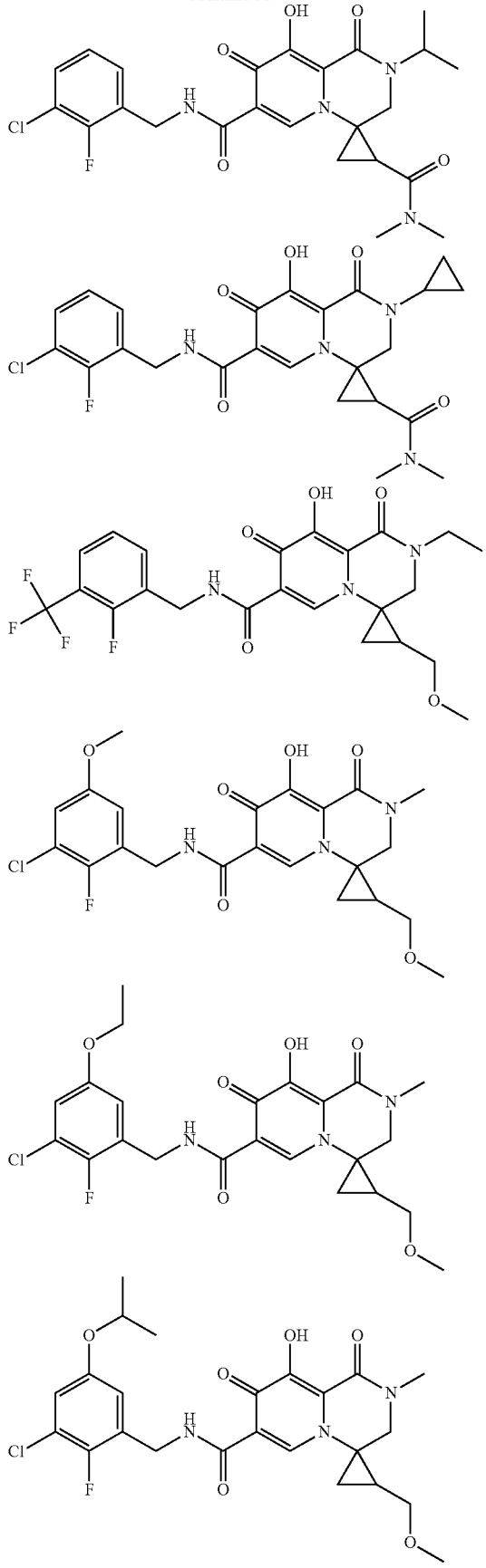

49
-continued
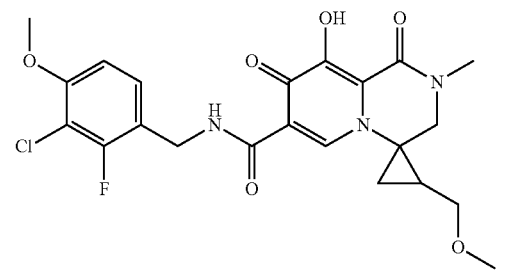
50
-continued
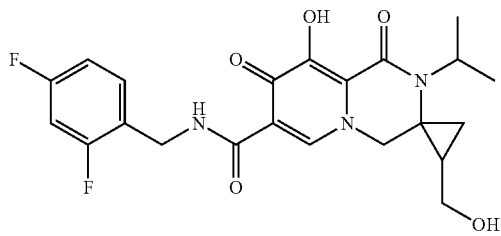
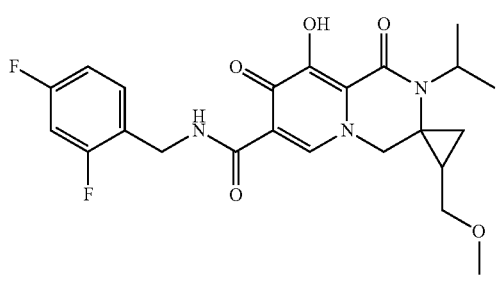
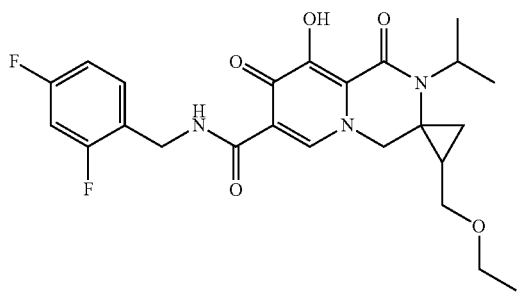
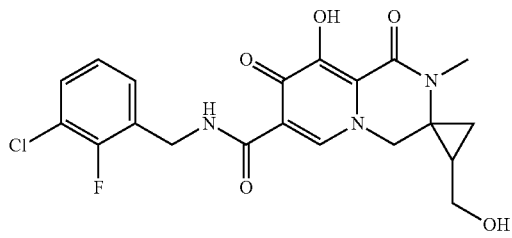
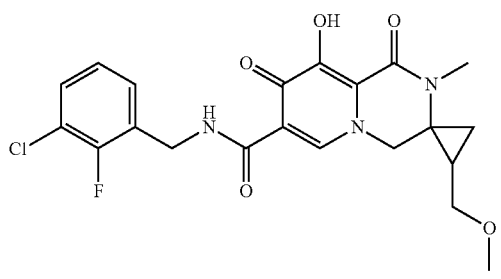
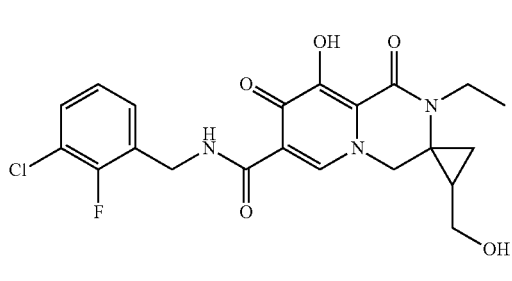

51
-continued
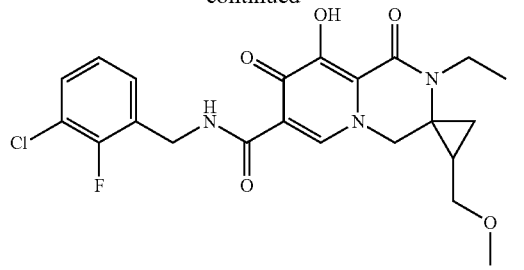
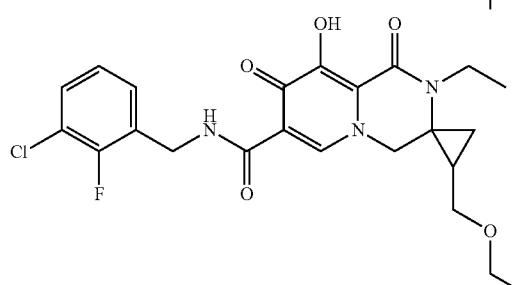
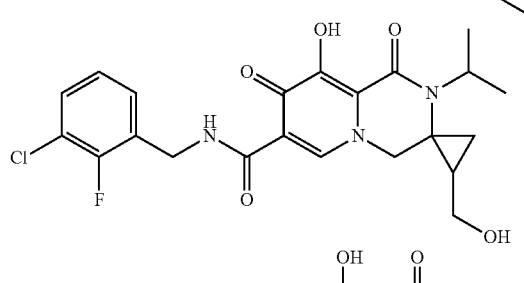
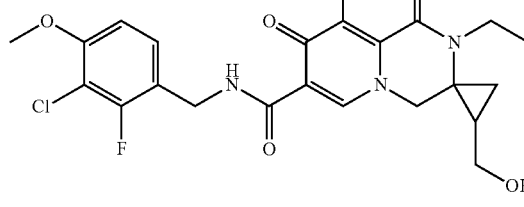
Compounds represented by the following formulae, or pharmaceutically acceptable salts thereof are more preferable embodiments.
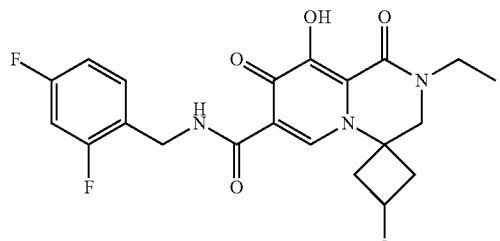
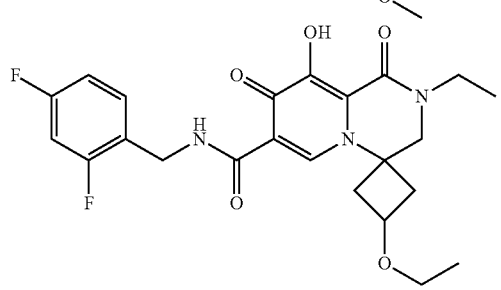
52
-continued
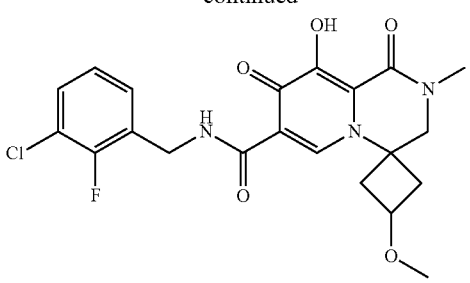
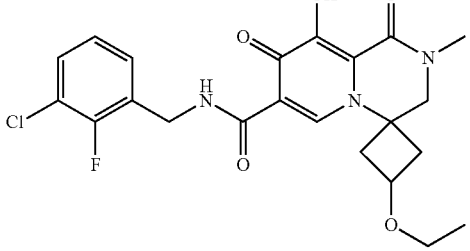
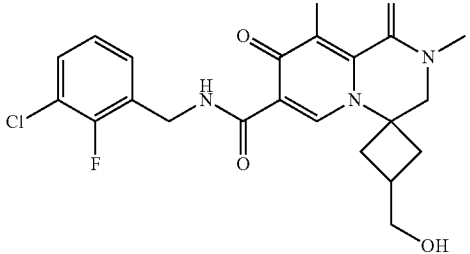
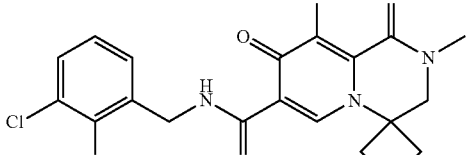
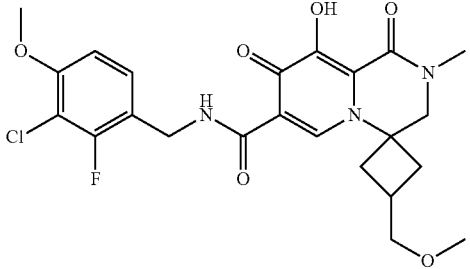
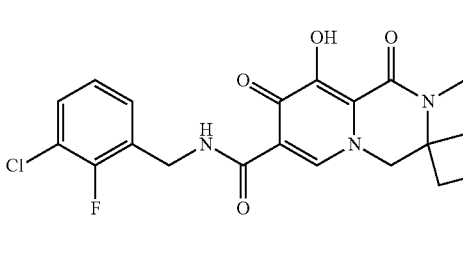

-continued

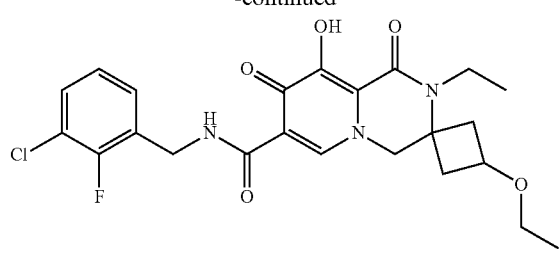

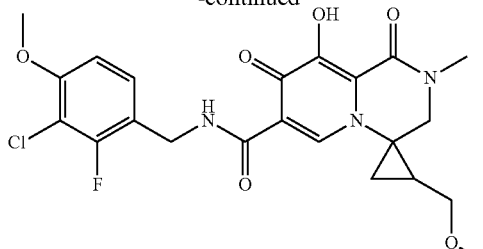

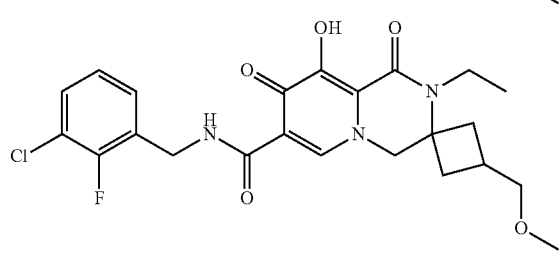

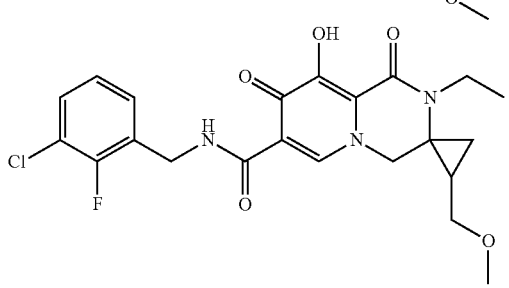

Compounds represented by the following formulae, or pharmaceutically acceptable salts thereof are more preferable embodiments.

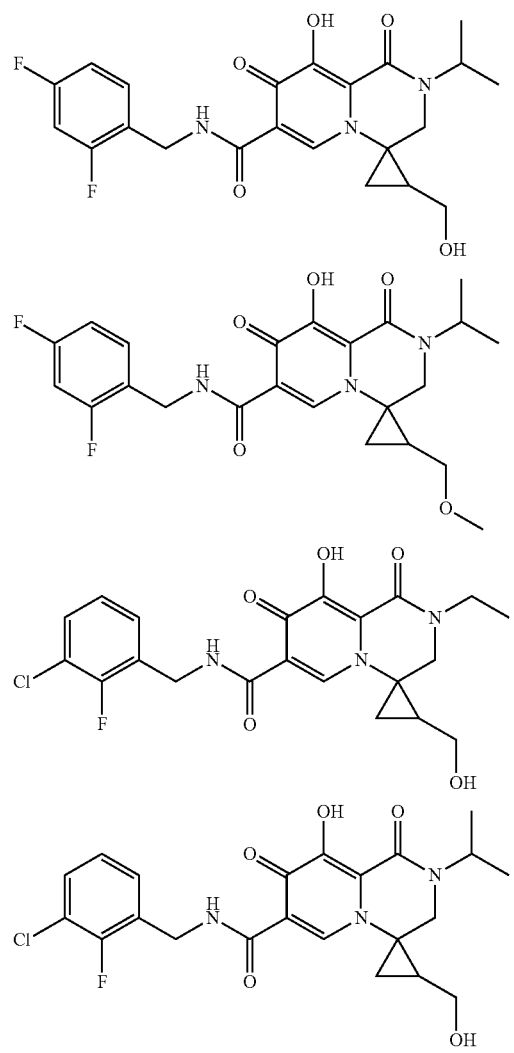

A pharmaceutically acceptable salt of the compound of the present invention may be any salt as long as it forms an atoxic salt with the compound of the present invention. Examples thereof include a salt with an inorganic acid, a salt with an organic acid, a salt with an inorganic base, a salt with an organic base, a salt with an amino acid and the like.

Examples of the salt with an inorganic acid include salts with hydrochloric acid, nitric acid, sulfuric acid, phosphoric acid, hydrobromic acid and the like.

Examples of the salt with an organic acid include salts with oxalic acid, malonic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salt with an inorganic base include sodium salt, potassium salt, calcium salt, magnesium salt, ammonium salt and the like.

Examples of the salt with an organic base include salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like.

Examples of the salt with an amino acid include salts with lysine, arginine, aspartic acid, glutamic acid and the like.

Such salts can be obtained by reacting the compound of the present invention with an inorganic base, an organic base, an inorganic acid, an organic acid or an amino acid according to a method known per se.

In the present invention, as the pharmaceutically acceptable salt of the compound of the present invention, salts with hydrochloric acid (e.g., monohydrochloride, dihydrochloride), salts with hydrobromic acid (e.g., monohydrobromide, dihydrobromide), salts with sulfuric acid, salts with p-toluenesulfonic acid, sodium salt, potassium salt and calcium salt are preferred embodiments.

The compound of the present invention or a pharmaceutically acceptable salt thereof may exist as a solvate.

The "solvate" is the compound of the present invention or a pharmaceutically acceptable salt thereof, with which a molecule of a solvent is coordinated, and also encompasses hydrate (also referred to as water-containing compound).

The solvate is, for example, a pharmaceutically acceptable solvate, such as from 0.4 to 0.8 hydrate, a monohydrate, a hemihydrate, a dihydrate, from 0.4 to 0.8 hydrate of sodium salt, a monohydrate of sodium salt, a monomethanolate, a monoethanolate, a monoacetonitrilate, a ⅔ ethanolate of dihydrochloride of the compound of the present invention and the like. Preferable embodiments of the solvate of the compound of the present invention include from 0.5 to 0.7 hydrate, a monohydrate, a hemihydrate, a 0.6 hydrate, a dihydrate, from 0.5 to 0.7 hydrate of sodium salt, a monohydrate of sodium salt, a 0.6 hydrate of sodium salt, a hemihydrate of sodium salt, and a dihydrate of sodium salt.

A solvate of the compound of the present invention or a pharmaceutically acceptable salt thereof can be obtained according to a method known in the art.

The compound of the present invention may exist as a tautomer. In this case, the compound of the present invention can be a single tautomer or a mixture of individual tautomers.

The compound of the present invention may have a carbon double bond. In this case, the compound of the present invention can be present as E form, Z form, or a mixture of E form and Z form.

The compound of the present invention may contain a stereoisomer that should be recognized as a cis/trans isomer. In this case, the compound of the present invention can be present as a cis form, a trans form, or mixture of a cis form and a trans form.

The compound of the present invention may contain one or more asymmetric carbons. In this case, the compound of the present invention may be present as a single enantiomer, a single diastereomer, a mixture of enantiomers or a mixture of diastereomers.

The compound of the present invention may be present as an atropisomer. In this case, the compound of the present invention may be present as an individual atropisomer or a mixture of atropisomers.

The compound of the present invention may simultaneously contain plural structural characteristics that produce the above-mentioned isomers. Moreover, the compound of the present invention may contain the above-mentioned isomers at any ratio.

In the absence of other reference such as annotation and the like, the formulae, chemical structures and compound names indicated in the present specification without specifying the so stereochemistry thereof encompass all the above-mentioned isomers that may exist.

A diastereomeric mixture can be separated into each diastereomer by conventional methods such as chromatography, crystallization and the like. In addition, each diastereomer can also be formed by using a stereochemically single starting material, or by a synthesis method using a stereoselective reaction.

An enantiomeric mixture can be separated into each single enantiomer by a method well known in the pertinent field.

For example, when an enantiomeric mixture has a functional group, a diastereomeric mixture can be prepared by reacting the enantiomeric mixture with a substantially pure enantiomer that is known as a chiral auxiliary. The diastereomeric mixture can be separated into each diastereomer mentioned above. The separated diastereomer can be converted to a desired enantiomer by removing the added chiral auxiliary by cleavage.

In addition, a mixture of enantiomers of a compound can also be directly separated by a chromatography method using a chiral solid phase well known in the pertinent field.

Alternatively, one of the enantiomers of a compound can also be obtained by using a substantially pure optically active starting material or stereoselective synthesis (asymmetric induction) of a prochiral intermediate using a chiral auxiliary and an asymmetric catalyst.

The absolute steric configuration can be determined based on the X-ray crystal analysis of the resultant crystalline product or intermediate. In this case, a resultant crystalline product or intermediate derivatized with a reagent having an asymmetric center with a known steric configuration may be used where necessary.

In one embodiment of the present invention, the compound may be crystal or amorphous.

In one embodiment of the present invention, the compound may be labeled with an isotope (e.g., $^3$H, $^{14}$C, $^{35}$S etc.).

One preferred embodiment of the compound of the present invention or a pharmaceutically acceptable salt thereof is the substantially purified compound of the present invention or a pharmaceutically acceptable salt thereof. More preferred embodiment is the compound of the present invention or a pharmaceutically acceptable salt thereof which has been purified to a purity of not less than 80%.

In the present invention, a prodrug of the compound of the present invention can also be a useful medicament.

A "prodrug" is a derivative of the compound of the present invention, which has a chemically or metabolically decomposable group and which restores to the original compound to show its inherent efficacy after administration to the body by, for example, hydrolysis, solvolysis or decomposition under physiological conditions.

The prodrug is utilized, for example, for improving absorption by oral administration or targeting of a target site.

Examples of the site to be modified include highly reactive functional groups in the compound of the present invention, such as hydroxy group, carboxyl group, amino group and the like.

Examples of the hydroxy-modifying group include acetyl group, propionyl group, isobutyryl group, pivaloyl group, palmitoyl group, benzoyl group, 4-methylbenzoyl group, dimethylcarbamoyl group, dimethylaminomethylcarbonyl group, sulfo group, alanyl group, fumaryl group and the like. In addition, a sodium salt of 3-carboxybenzoyl group, 2-carboxyethylcarbonyl group and the like can also be used.

Examples of the carboxy-modifying group include methyl group, ethyl group, propyl group, isopropyl group, butyl group, isobutyl group, tert-butyl group, pivaloyloxymethyl group, carboxymethyl group, dimethylaminomethyl group, 1-(acetyloxy)ethyl group, 1-(ethoxycarbonyloxy)ethyl group, 1-(isopropoxycarbonyloxy)ethyl group, 1-(cyclohexyloxycarbonyloxy)ethyl group, (5-methyl-2-oxo-1,3-dioxol-4-yl)methyl group, benzyl group, phenyl group, o-tolyl group, morpholinoethyl group, N,N-diethylcarbamoylmethyl group, phthalidyl group and the like.

Examples of the amino-modifying group include hexylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group and the like.

Examples of the "pharmaceutical composition" include oral preparations such as tablet, capsule, granule, powder, troche, syrup, emulsion, suspension and the like, and parenteral agents such as external preparation, suppository, injection, eye drop, transnasal agent, pulmonary preparation and the like.

The pharmaceutical composition of the present invention (e.g., an anti-HIV composition, a pharmaceutical composition for HIV integrase inhibitory etc.) is produced by appropriately admixing a suitable amount of a compound of the present invention or a salt thereof with at least one kind of a pharmaceutically acceptable carrier according to a method known in the technical field of pharmaceutical preparations. The content of the compound of the present invention or a salt thereof in the pharmaceutical composition varies depending on the dosage form, the dose and the like, and the like. It is, for example, 0.1 to 100 wt % of the whole composition.

Examples of the "pharmaceutically acceptable carrier" include various organic or inorganic carrier substances conventionally used as preparation materials such as excipient, disintegrant, binder, glidant, lubricant and the like for solid preparations, and solvent, solubilizing agent, suspending agent, isotonic agent, buffering agent, soothing agent and the like for liquid preparations. Where necessary, additives such as preservative, antioxidant, colorant, sweetening agent and the like are used.

Examples of the "excipient" include lactose, sucrose, D-mannitol, D-solbitol, cornstarch, dextrin, crystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "glidant" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agent" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonic agent" include glucose, D-sorbitol, sodium chloride, D-mannitol and the like.

Examples of the "buffering agent" include sodium hydrogen phosphate, sodium acetate, sodium carbonate, sodium citrate and the like.

Examples of the "soothing agent" include benzyl alcohol and the like.

Examples of the "preservative" include ethyl parahydroxybenzoate, chlorobutanol, benzyl alcohol, sodium dehydroacetate, sorbic acid and the like.

Examples of the "antioxidant" include sodium sulfite, ascorbic acid and the like.

Examples of the "colorant" include food colors (e.g., Food Color Red No. 2 or 3, Food Color yellow 4 or 5 etc.), 3-carotene and the like.

Examples of the "sweetening agent" include saccharin sodium, dipotassium glycyrrhizinate, aspartame and the like.

The pharmaceutical composition of the present invention can be administered not only to human but also to mammals other than human (e.g., mouse, rat, hamster, guinea pig, rabbit, cat, dog, swine, bovine, horse, sheep, monkey etc.) orally or parenterally (e.g., topical, rectal, intravenous administration etc.). While the dose varies depending on the subject of administration, disease, symptom, dosage form, administration route and the like, for example, the dose for oral administration to an adult patient (body weight: about 60 kg) is generally within the scope of about 1 mg to 1 g per day, based on the compound of the present invention as an active ingredient. The amount can be administered in one to several portions.

The compound of the present invention or a pharmaceutically acceptable salt thereof inhibits HIV integrase, and can be used as an active ingredient of a therapeutic agent or prophylactic agent for HIV infection.

To "inhibit HIV integrase" means to specifically inhibit the function as HIV integrase to eliminate or attenuate the activity thereof. In one aspect, the compound of the present invention or a pharmaceutically acceptable salt thereof may be used to inhibit HIV integrase in the medical treatment of a human patient. In another aspect, the compound of the present invention or a pharmaceutically acceptable salt thereof may be used in a biological test to specifically inhibit the function of HIV integrase under the conditions of the below-mentioned Experimental Example 1. As the "inhibition of HIV integrase", preferred is "inhibition of human HIV integrase". As the "HIV integrase inhibitor", preferred is a "human HIV integrase inhibitor".

The compound of the present invention or a pharmaceutically acceptable salt thereof can be used in combination with other single or plural medicaments (hereinafter to be also referred to as a concomitant drug) by a conventional method generally employed in the medicament field (hereinafter to be referred to as combination use).

In the combination use, the timing of administration of the compound of present invention including its pharmaceutically acceptable salts and the concomitant drug is not limited, and they may be administered as a combined agent to the subject of administration, or the two may be administered simultaneously or at certain time intervals. In addition, they may be used as a medicament in the form of a kit containing the pharmaceutical composition of the present invention and a concomitant drug. The dose of the concomitant drug may be determined according to the dosage used clinically, and can be appropriately determined depending on the subject of administration, disease, symptom, dosage form, administration route, administration time, combination and the like. The dosing regimen of the concomitant drug is not particularly limited, and the concomitant drug needs only be combined with the compound of the present invention or a salt thereof.

An anti-HIV agent is generally required to sustain its effect for a long time, so that can be effective not only for temporal suppression of viral growth but also prohibition of viral re-growth. This means that a prolonged administration is necessary and that a high single dose may be frequently inevitable to sustain effect for a longer period through the night. Such prolonged and high dose administration may increase the risk of causing side effects.

In view of this, one of the preferable embodiments of the compound of the present invention is such compound permitting high absorption by oral administration, and such compound capable of maintaining blood concentration of the administered compound for an extended period of time.

One of other preferable embodiments of the compound of the present invention is a compound having fine pharmacological activity (e.g., a compound having strong HIV integrase inhibitory activity, a compound having high anti-HIV activity), a compound having fine bioavailability (e.g., a compound having high cellular membrane permeability, a compound stable to metabolic enzyme, a compound with low binding ability to protein and the like), a compound having an anti-HIV activity against HIV with Q148 mutation, and the like.

One of other preferable embodiments of the compound of the present invention is a compound having high pharmacological activity (concretely, $EC_{50}$ of HIV integrase inhibitory activity is less than 0.1 µM, preferably less than 0.01 µM).

One of other preferable embodiments of the compound of the present invention is a compound having high oral absorption, whose blood concentration is maintained for a long time after administration.

Using the above-mentioned preferable compound, dose and/or frequency of administration of the compound of the present invention to human are/is expected to be decreased. Preferable administration frequency is not more than twice a day, more preferably, not more than once a day (e.g., once a day, once in two days, etc.).

The compound of the present invention can be used for the improvement of viremia due to HIV and/or maintenance of improved condition thereof, prophylaxis and treatment of virus infections, particularly, an HIV infection and/or maintenance of improved condition thereof.

As an index of the "treatment", "improvement" or "effect", a decrease in the virus level or HIV RNA level in the body, particularly in blood, can be used.

The "prophylaxis of HIV infection" includes administration of a medicament to a person with suspected or possible HIV infection (infection due to transfusion, infection from mother to child), and the like.

By the "prophylaxis of AIDS" is meant, for example, administration of a medicament to an individual who tested HIV positive but has not yet developed the disease state of AIDS; administration of a medicament to an individual who shows an improved disease state of AIDS after treatment but who carries HIV still to be eradicated and whose relapse of AIDS is worried; administration of a medicament before infection with HIV out of a fear of possible infection; and the like.

Examples of the "other anti-HIV agents" and "other anti-HIV active substances" to be used for a multiple drug combination therapy include an anti-HIV antibody or other antibody, an HIV vaccine or other vaccine, immunostimulants such as interferon, interferon agonist and the like, a ribozyme against HIV, an HIV antisense drug, an HIV reverse transcriptase inhibitor, an HIV protease inhibitor, an HIV integrase inhibitor, an inhibitor of attachment between a receptor (CD4, CXCR4, CCR5 and the like) of a host cell recognized by virus and the virus (CCR5 antagonist and the like), a DNA polymerase inhibitor or DNA synthesis inhibitor, a medicament acting on HIVp24, an HIV fusion inhibitor, an IL-2 agonist or antagonist, a TNF-α antagonist, an α-glucosidase inhibitor, a purine nucleoside phosphorylase inhibitor, an apoptosis agonist or inhibitor, a cholinesterase inhibitor, an immunomodulator and the like.

Specific examples of the HIV reverse transcriptase inhibitor include Retrovir® (zidovudine), Epivir® (lamivudine), Zerit® (sanilvudine), Videx® (didanosine), Hivid® (zalcitabine), Ziagen® (abacavir sulfate), Viramune® (nevirapine), Stocrin® (efavirenz), Rescriptor® (delavirdine mesylate), Combivir® (zidovudine+lamivudine), Trizivir® (abacavir sulfate+lamivudine+zidovudine), Coactinon® (emivirine), Phosphonovir®, Coviracil®, alovudine (3'-fluoro-3'-deoxythymidine), Thiovir® (thiophosphonoformic acid), capravirin (5-[(3,5-dichlorophenyl)thio]-4-isopropyl-1-(4-pyridylmethyl) imidazole-2-methanol carbamic acid), tenofovir disoproxil fumarate ((R)-[[2-(6-amino-9H-purin-9-yl)-1-methylethoxy]methyl]phosphonic acid bis(isopropoxycarbonyloxymethyl)ester fumarate), tenofovir alafenamide fumarate, tenofovir alafenamide hemifumarate, DPC-083 ((4S)-6-chloro-4-[(1E)-cyclopropylethenyl]-3,4-dihydro-4-trifluoromethyl-2(1H)-quinazolinone), DPC-961 ((4S)-6-chloro-4-(cyclopropylethynyl)-3,4-dihydro-4-(trifluoromethyl)-2 (1H)-quinazolinone), DAPD ((-)-β-D-2,6-diaminopurine dioxolane), Immunocal®, MSK-055, MSA-254, MSH-143, NV-01, TMC-120, DPC-817, GS-7340, TMC-125, SPD-754, D-A4FC, capravirine, UC-781, emtricitabine, alovudine, Phosphazid, BCH-10618, DPC-083, Etravirine, BCH-13520, MIV-210, Abacavir sulfate/lamivudine, GS-7340, GW-5634, GW-695634, TMC-278 and the like, wherein ® means a registered trademark and the names of medicaments without ® are generic names (ex. INN) or code number named by company (hereinafter the same).

Specific examples of the HIV protease inhibitor include Crixivan® (indinavir sulfate ethanolate), saquinavir, Invirase® (saquinavir mesylate), Norvir® (ritonavir), Viracept® (nelfinavir mesylate), lopinavir, Prozei® (amprenavir), Kaletra® (ritonavir+lopinavir), mozenavir dimesylate ([4R-(4α,5α,6β)]-1,3-bis[(3-aminophenyl)methyl]-hexahydro-5,6-dihydroxy-4,7-bis(phenylmethyl)-2H-1,3-diazepin-2-one dimethanesulfonate), tipranavir (3'-[(1R)-1-[(6R)-5,6-dihydro-4-hydroxy-2-oxo-6-phenylethyl-6-propyl-2H-pyran-3-yl]propyl]-5-(trifluoromethyl)-2-pyridinesulfonamide), lasinavir (N-[5(S)-(tert-butoxycarbonylamino)-4(S)-hydroxy-6-phenyl-2(R)-(2,3,4-trimethoxybenzyl)hexanoyl]-L-valine 2-methoxyethylenamide), KNI-272 ((R)—N-tert-butyl-3-[(2S,3S)-2-hydroxy-3-N—[(R)-2-N-(isoquinolin-5-yloxyacetyl)amino-3-methylthiopropanoyl]amino-4-phenylbutanoyl]-5,5-dimethyl-1,3-thiazolidine-4-carboxamide), GW-433908, TMC-126, DPC-681, buckminsterfullerene, MK-944A (MK944 (N-(2(R)-hydroxy-1(S)-indanyl)-2(R)-phenylmethyl-4(S)-hydroxy-5-[4-(2-benzo[b]furanylmethyl)-2(S)-(tert-butylcarbamoyl) piperazin-1-yl]pentanamide)+indinavir sulfate), JE-2147 ([2 (S)-oxo-4-phenylmethyl-3(S)-[(2-methyl-3-oxy) phenylcarbonylamino]-1-oxabutyl]-4-[(2-methylphenyl) methylamino]carbonyl-4 (R)-5,5-dimethyl-1,3-thiazole), BMS-232632 (dimethyl(3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedicarboxylate), DMP-850 ((4R,5S,6S,7R)-1-(3-amino-1H-indazol-5-ylmethyl)-4,7-dibenzyl-3-butyl-5,6-dihydroxyperhydro-1,3-diazepin-2-one), DMP-851, RO-0334649, Nar-DG-35, R-944, VX-385, TMC-114, Tipranavir, Fosamprenavir sodium, Fosamprenavir calcium, Darunavir, GW-0385, R-944, RO-033-4649, AG-1859 and the like.

The HIV integrase inhibitor is exemplified by S-1360, L-870810, ISENTRESS® (Raltegravir), JTK-303 (Elvitegravir), S/GSK1 349572 (Doltegravir) and the like, the DNA polymerase inhibitor or DNA synthesis inhibitor is exemplified by Foscavir®, ACH-126443 (L-2',3'-didehydro-dideoxy-5-fluorocytidine), entecavir ((1S,3S,4S)-9-[4-hydroxy-3-(hydroxymethyl)-2-methylenecyclopentyl]guanine), calanolide A ([10R-(10α,11β,12α)]-11,12-dihydro-12-hydroxy-6,6,10,11-tetramethyl-4-propyl-2H,6H,10H-benzo[1,2-b:3,4-b':5,6-b"]tripyran-2-one), calanolide B, NSC-674447 (1,1'-azobisformamide), Iscador (viscum alubm extract), Rubitecan and the like, the HIV antisense drug is exemplified by HGTV-43, GEM-92 and the like, the anti- HIV antibody or other antibody is exemplified by NM-01, PRO-367, KD-247, Cytolin®, TNX-355 (CD4 antibody), AGT-1, PRO-140 (CCR5 antibody), Anti-CTLA-4MAb and the like, the HIV vaccine or other vaccine is exemplified by ALVAC®, AIDSVAX®, Remune®, HIV gp41 vaccine, HIV gp120 vaccine, HIV gp140 vaccine, HIV gp160 vaccine, HIV p17 vaccine, HIV p24 vaccine, HIV p55 vaccine, AlphaVax Vector System, canarypox gp160 vaccine, Anti-Tat, MVA-F6 Nef vaccine, HIV rev vaccine, C4-V3 peptide, p2249f, VIR-201, HGP-30W, TBC-3B, PARTICLE-3B, Antiferon (interferon-α vaccine) and the like, the interferon or interferon agonist is exemplified by Sumiferon®, Multi-Feron®, interferon-τ, Reticulose, human leukocyte interferon α and the like, the CCR5 antagonist is exemplified by SCH-351125 and the like, the medicament acting on HIV p24 is exemplified by GPG-NH2 (glycyl-prolyl-glycinamide) and the like, the HIV fusion inhibitor is exemplified by FP-21399 (1,4-bis[3-[(2,4-dichlorophenyl)carbonylamino]-2-oxo-5,8-disodium sulfonyl]naphthyl-2,5-dimethoxyphenyl-1,4-dihydrazone), T-1249, Synthetic Polymeric Construction No3, pentafuside, FP-21399, PRO-542, Enfuvirtide and the like, the IL-2 agonist or antagonist is exemplified by interleukin-2, Imunace®, Proleukin®, Multikine®, Ontak® and the like, the TNF-α antagonist is exemplified by Thalomid® (thalidomide), Remicade® (infliximab), curdlan sulfate and the like, the α-glucosidase inhibitor is exemplified by Bucast® and the like, the purine nucleoside phosphorylase inhibitor is exemplified by peldesine (2-amino-4-oxo-3H,5H-7-[(3-pyridyl)methyl]pyrrolo[3,2-d]pyrimidine) and the like, the apoptosis agonist or inhibitor is exemplified by Arkin Z®, Panavir®, Coenzyme Q10 (2-deca(3-methyl-2-butenylene)-5,6-dimethoxy-3-methyl-β-benzoquinone) and the like, the cholinesterase inhibitor is exemplified by Cognex® and the like, and the immunomodulator is exemplified by Imunox®, Prokine®, Met-enkephalin (6-de-L-arginine-7-de-L-arginine-8-de-L-valinamide-adrenorphin), WF-10 (10-fold dilute tetrachlorodecaoxide solution), Perthon, PRO-542, SCH-D, UK-427857, AMD-070, AK-602 and the like.

In addition, Neurotropin®, Lidakol®, Ancer 20®, Ampligen®, Anticort®, Inactivin®, PRO-2000, Rev M10 gene, HIV specific cytotoxic T cell (CTL immunotherapy, ACTG protocol 080 therapy, CD4-gene therapy), SCA binding protein, RBC-CD4 complex, Motexafin gadolinium, GEM-92, CNI-1493, (±)-FTC, Ushercell, D2S, BufferGel®, Viva-Gel®, Glyminox vaginal gel, sodium lauryl sulfate, 2F5, 2F5/2G12, VRX-496, Ad5gag2, BG-777, IGIV-C, BILR-255 and the like are exemplified.

The compound of the present invention can be combined with one or more (e.g., 1 or 2) kinds of other anti-HIV active substances (to be also referred to as other anti-HIV agents), and used as an anti-HIV agent and the like for the prophylaxis or treatment of HIV infection. As the "other anti-HIV agents" and "other anti-HIV active substances" to be used for a multiple drug combination therapy with the compound of the present invention, preferred are an HIV reverse transcriptase inhibitor and an HIV protease inhibitor. Two or three, or even a greater number of medicaments can be used in combination or processed into a combination drug, wherein a combination of medicaments having different action mechanisms is one of the preferable embodiments. In addition, selection of medicaments free of side effect duplication is preferable.

Specific examples of the combination of medicaments include a combination of a group consisting of efavirenz, tenofovir, emtricitabine, indinavir, nelfinavir, atazanavir, ritonavir+indinavir, ritonavir+lopinavir, ritonavir+saquinavir, didanosine+lamivudine, zidovudine+didanosine, stavudine+didanosine, zidovudine+lamivudine, stavudine+lamivudine and tenofovir+emtricitabine, and the compound of the present invention (Guidelines for the Use of Antiretroviral Agents in HIV-Infected Adults and Adolescents. Aug. 13, 2001 etc.). Furthermore, a combination of a group consisting of atazanavir+ritonavir, darunavir, darunavir+ritonavir, maraviroc and the compound of the present invention can be mentioned. Particularly preferred is a combined use of two agents with efavirenz, indinavir, nelfinavir, tenofovir, emtricitabine, zidovudine or lamivudine, and a combined use of three agents with zidovudine+lamivudine, tenofovir+lamivudine, tenofovir+zidovudine, tenofovir+efavirenz, tenofovir+nelfinavir, tenofovir+indinavir, tenofovir+emtricitabine, emtricitabine+lamivudine, emtricitabine+zidovudine, emtricitabine+efavirenz, emtricitabine+nelfinavir, emtricitabine+indinavir, nelfinavir+lamivudine, nelfinavir+zidovudine, nelfinavir+efavirenz, nelfinavir+indinavir, efavirenz+lamivudine, efavirenz+zidovudine, efavirenz+indinavir, tenofovir disoproxil fumarate+emtricitabine, darunavir+emtricitabine, abacavir+3TC, CMX157+tenofovir disoproxil fumarate, CMX157+emtricitabine, CMX157+tenofovir alafenamide fumarate, CMX157+tenofovir alafenamide hemifumarate, CMX157+lamivudine (3TC), CMX157+abacavir sulfate (ABC), 4'-C-ethynyl-2'-deoxy-fluoroadenosine (EFdA)+tenofovir disoproxil fumarate, 4'-C-ethynyl-2'-deoxy-fluoroadenosine (EFdA)+emtricitabine, 4'-C-ethynyl-2'-deoxy-fluoroadenosine (EFdA)+tenofovir alafenamide fumarate, 4'-C-ethynyl-2'-deoxy-fluoroadenosine (EFdA)+tenofovir alafenamide hemifumarate, 4'-C-ethynyl-2'-deoxy-fluoroadenosine (EFdA)+lamivudine (3TC), 4'-C-ethynyl-2'-deoxy-fluoroadenosine (EFdA)+abacavir sulfate (ABC), Festinavir® (BMS-986001)+tenofovir disoproxil fumarate, Festinavir® (BMS-986001)+emtricitabine, Festinavir® (BMS-986001)+tenofovir alafenamide fumarate, Festinavir® (BMS-986001)+tenofovir alafenamide hemifumarate, Festinavir® (BMS-986001)+lamivudine (3TC), emtricitabine+tenofovir alafenamide fumarate, emtricitabine+tenofovir alafenamide hemifumarate, Festinavir® (BMS-986001)+abacavir sulfate (ABC) or a combined use thereof with a combination drug. To these combinations, a CYP inhibitor that inhibits metabolizing enzymes can also be further added. Examples of the CYP inhibitor include ritonavir and cobicistat. Ritonavir can also be used as a CYP inhibitor, or as other anti-HIV agent. Here, "+" means a combined use of the described medicaments.

In the case of combined administration, the compound of the present invention can be administered simultaneously with a medicament to be used in combination (hereinafter concomitant drug) or administered at certain time intervals. In the case of combined administration, a pharmaceutical composition comprising the compound of the present invention and a concomitant drug can be administered. Alternatively, a pharmaceutical composition comprising the compound of the present invention and a pharmaceutical composition comprising a concomitant drug may be administered separately. The administration route of the compound of the present invention and that of the concomitant drug may be the same or different.

In the case of a combined administration, the compound of the present invention can be administered once a day or several times a day in a single dose of 0.01 mg to 1 g, or may be administered at a smaller dose. The concomitant drug can be administered at a dose generally used for the prevention or treatment of an HIV infection, for example, at a single dose of 0.01 mg to 0.3 g. Alternatively, it may be administered in a smaller dose.

Now, production methods of the compound of the present invention are specifically explained. However, the present invention is not limited to these production methods. For production of the compound of the present invention, the order of reactions can be appropriate. The reactions may be performed from a reasonable step or a reasonable substitution moiety. In addition, an appropriate substituent conversion (conversion or further modification of substituent) step may be inserted between respective steps. When a reactive functional group is present, protection and deprotection may be appropriately performed. Furthermore, to promote the progress of reactions, reagents other than those exemplified below may be used as appropriate. The starting compounds whose production methods are not described are commercially available or can be easily prepared by a combination of known synthesis reactions. The compound obtained in each step can be purified by conventional methods such as distillation, recrystallization, column chromatography and the like. In some cases, the next step may be performed without isolation and purification.

In the following Production methods, the "room temperature" means 1 to 40° C.

A compound represented by the formula [I] or [II]

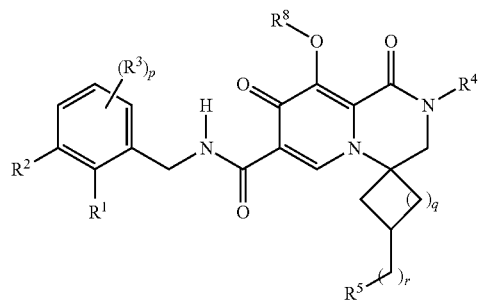

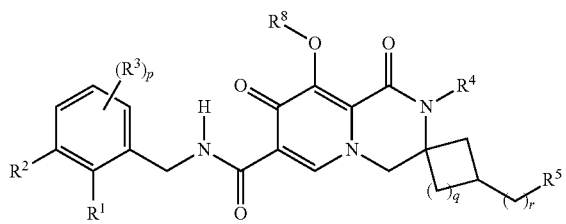

wherein each symbol is as mentioned above,
or a pharmaceutically acceptable salt thereof, or a solvate thereof, can be produced by the following Production method 1 or
Production Method 2.
Production Method 1

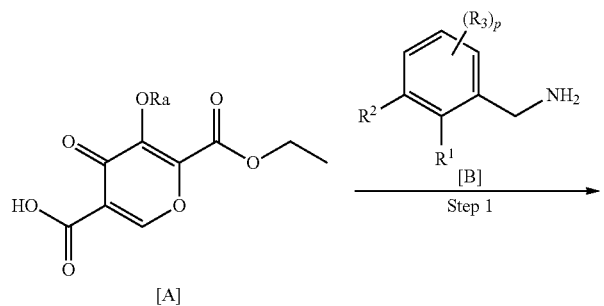

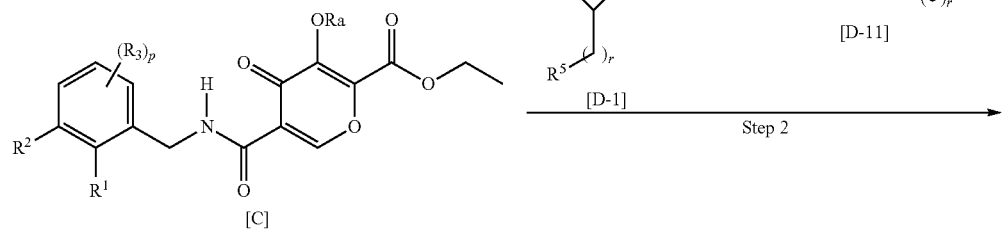

-continued

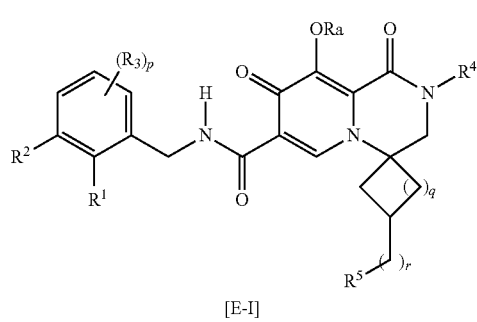

[E-I]

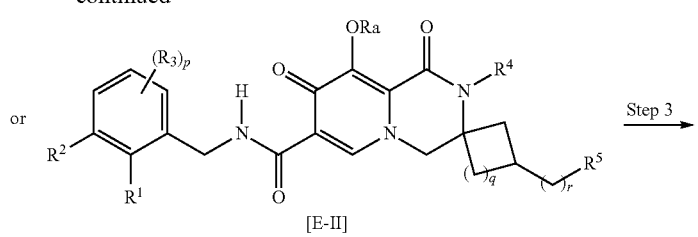

[E-II]

Step 3

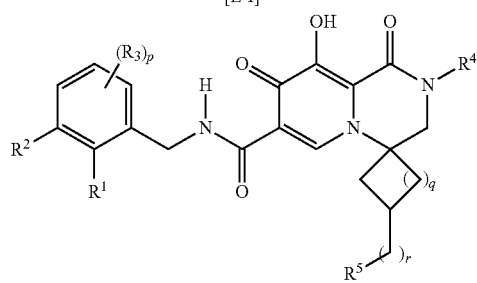

[I']

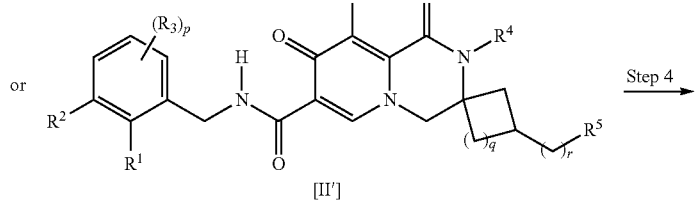

[II']

Step 4

[I]
or
[II]

wherein Ra is hydroxy-protecting group such as benzyl group, tert-butyl group, trimethylsilyl group, triethylsilyl group, tert-butyldimethylsilyl group, triisopropylsilyl group, tert-butyldiphenylsilyl group and the like, and other symbols are as mentioned above.

Step 1

A compound of the formula [C] can be produced by reacting a compound of the formula [B] and a compound of an acid chloride which can be produced by reacting a compound of the formula [A] and a chlorinating agent.

The reaction of a compound of the formula [A] and a chlorinating agent is performed in the presence of, where necessary, a catalyst.

Examples of the solvent include a single or mixed solvent of chloroform, methylene chloride, ethyl acetate, toluene, 1,2-dimethoxyethane, 1,4-dioxane, tetrahydrofuran (THF) and the like.

Examples of the chlorinating agent include oxalyl dichloride, thionyl chloride, phosphorus trichloride and the like.

Examples of the catalyst include N,N-dimethylformamide (DMF) and the like.

The reaction temperature is preferably under ice-cooling to room temperature.

The reaction of the acid chloride and a compound of the formula [B] is generally performed in the presence of a base.

Examples of the solvent include a single or mixed solvent of chloroform, methylene chloride, ethyl acetate, toluene, 1,2-dimethoxyethane, 1,4-dioxane, THF and the like.

Examples of the base include triethylamine, diisopropylethylamine, pyridine and the like.

The reaction temperature is preferably −78° C. to room temperature.

Step 2

A compound of the formula [E-I] or a compound of the formula [E-II] can be produced by reacting a compound of the formula [C] and the corresponding compound of the formula [D-I] or the formula [D-II] in a solvent.

The reaction of a compound of the formula [C] and the corresponding compound of the formula [D-I] or the formula [D-II] is generally performed in the presence of a base. An additive may be used where necessary.

Examples of the solvent include a single or mixed solvent of chloroform, dichloromethane, DMF, N,N-dimethylacetamide (DMA), dimethyl sulfoxide (DMSO), acetonitrile, 1,2-dimethoxyethane, 1,4-dioxane, THF, toluene, water and the like.

Examples of the base include triethylamine, diisopropylethylamine, diazabicycloundecene, sodium carbonate, potassium carbonate, sodium hydrogen carbonate and the like.

Examples of the additive include acetic acid, p-toluenesulfonic acid, methanesulfonic acid and the like.

The reaction temperature is preferably from room temperature to under heating.

Step 3

A compound of the formula [I'] or the formula [II'] can be produced by deprotecting hydroxy-protecting group Ra of a compound of the formula [E-I] or a compound of the formula [E-II] in a solvent. For example, when the hydroxy-protecting group is benzyl group, the deprotection is generally performed under acidic conditions.

Examples of the solvent include a single or mixed solvent of chloroform, methylene chloride, ethyl acetate, toluene, methanol, ethanol, 2-propanol, THF, 1,4-dioxane, acetonitrile, water and the like.

Examples of the acid include hydrochloric acid, sulfuric acid, hydrogen bromide, phosphoric acid, acetic acid, trifluoroacetic acid and the like.

The reaction temperature is preferably under ice-cooling to room temperature.

Step 4

A compound of the formula [I] or the formula [II] can be produced by reacting a compound of the formula [I'] or a compound of the formula [II'] with an acylating agent or carbamic acid chloride in a solvent.

The reaction of a compound of the formula [I'] or the formula [II'] and an acylating agent is generally performed in the presence of a base. A catalyst may be added where necessary.

Examples of the solvent include a single or mixed solvent of chloroform, methylene chloride, tetrahydrofuran (THF) and the like.

Examples of the acylating agent include acid halides such as acetyl chloride, fumaryl dichloride and the like, acid anhydrides such as acetic anhydride, palmitic anhydride and the like, mixed anhydride prepared from acetic acid and isobutyl chlorocarbonate and the like.

As the base, an organic base is preferable, and examples thereof include triethylamine, diisopropylethylamine, pyridine and the like.

Examples of the catalyst include N,N'-dimethylaminopyridine (DMAP) and the like.

The reaction temperature is preferably under ice-cooling to under heating.

A compound of the formula [I] or the formula [II], wherein $R^8$ is dimethylcarbamoyl group, can also be produced by reacting a compound of the formula [I'] or a compound of the formula [II'] with triphosgene and dimethylamine or dimethylamine hydrochloride in a solvent. The reaction is generally performed in the presence of a base. A catalyst may be added where necessary.

Examples of the solvent include a single or mixed solvent of chloroform, methylene chloride, tetrahydrofuran (THF) and the like.

As the base, an organic base is preferable, and examples thereof include triethylamine, diisopropylethylamine, pyridine and the like.

Examples of the catalyst include N,N'-dimethylaminopyridine (DMAP) and the like.

The reaction temperature is preferably under ice-cooling to under heating.

When a compound of the formula [I], a compound of the formula [II], a compound of the formula [E-I] or a compound of the formula [E-II] is a mixture of stereoisomers, the compounds can be separated into each single compound by silica gel column chromatography, high performance liquid chromatography (HPLC) and the like.

Production Method 2

A compound represented by the formula [I] or [II] or a pharmaceutically acceptable salt thereof, or a solvate thereof can be produced from a compound of the formula [E-Ia] or a compound of the formula [E-IIa], which is a compound of the formula [E-I] or [E-II] wherein $R^5$ is hydroxy group in Production method 1, via a compound represented by the formula [I'] or [II'], according to the following method. In this Production method 2, when the compound obtained from a compound of the formula [E-Ia] or a compound of the formula [E-IIa] is a mixture of stereoisomers, the compounds can be separated into each single compound by silica gel column chromatography, HPLC and the like.

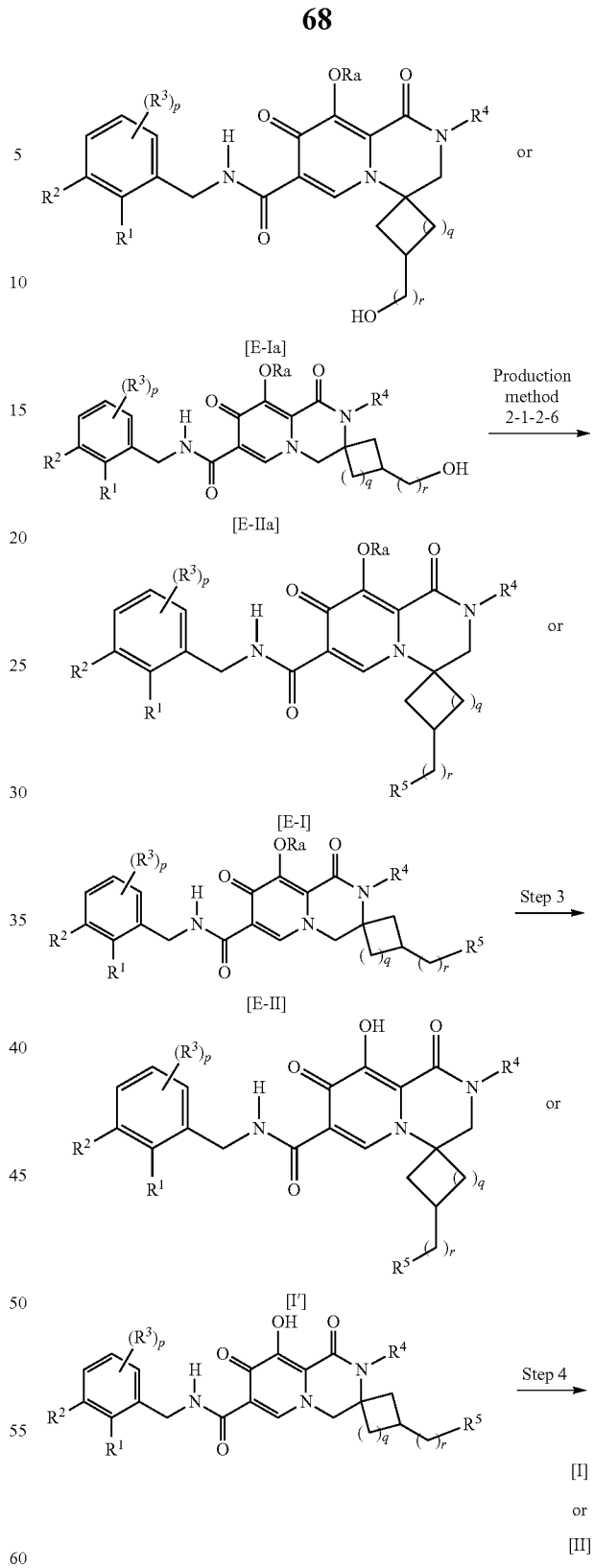

wherein each symbol is as mentioned above, and step 3 and step 4 are step 3 and step 4 in Production method Step Production Method 2-1

A compound of the formula [E-I] or a compound of the formula [E-II] wherein $R^5$ is $C_{1-6}$ alkoxy group or benzyloxy group can be produced by reacting a compound of the formula [E-Ia] or a compound of the formula [E-IIa] with a $C_{1-6}$ alkylating agent, benzyl bromide or benzyl chloride in a solvent. A compound of the formula [E-Ia] or a compound of the formula [E-IIa] and a $C_{1-6}$ alkylating agent are generally reacted in the presence of a base. A catalyst may be added where necessary.

Examples of the solvent include a single or mixed solvent of toluene, methylene chloride, 1,2-dimethoxyethane, 1,4-dioxane, THF, DMF, DMA, acetonitrile, water and the like.

As the $C_{1-6}$ alkylating agent, $C_{1-6}$ alkyl halide such as iodomethane, iodoethane and the like, or dialkyl sulfate such as dimethyl sulfate, diethyl sulfate and the like is preferable.

Examples of the base include sodium hydride, potassium tert-butoxide, potassium carbonate, sodium hydroxide and the like.

Examples of the catalyst include tetrabutylammonium hydrogen sulfate salt and the like.

The reaction temperature is preferably from under ice-cooling to under heating.

Production Method 2-2

A compound of the formula [E-I] or a compound of the formula [E-II] wherein $R^5$ is $C_{1-6}$ alkoxy $C_{2-6}$ alkyleneoxy group can be produced by reacting a compound of the formula [E-Ia] or a compound of the formula [E-IIa] with $C_{1-6}$ alkoxy $C_{2-6}$ alkylating agent in a solvent. A compound of the formula [E-Ia] or a compound of the formula [E-IIa] and $C_{1-6}$ alkoxy $C_{2-6}$ alkylating agent are generally reacted in the presence of a base. A catalyst may be added where necessary.

Examples of the solvent include a single or mixed solvent of toluene, methylene chloride, 1,2-dimethoxyethane, 1,4-dioxane, THF, DMF, DMA, acetonitrile, water and the like.

As the $C_{1-6}$ alkoxy $C_{2-6}$ alkylating agent, $C_{1-6}$ alkoxy $C_{2-6}$ alkyl halide such as 1-bromo-2-methoxyethane, 1-bromo-3-methoxypropane and the like is preferable.

Examples of the base include sodium hydride, potassium tert-butoxide, potassium carbonate, sodium hydroxide and the like.

Examples of the catalyst include tetrabutylammonium hydrogen sulfate and the like.

The reaction temperature is preferably from under ice-cooling to under heating.

Production Method 2-3
Production Method 2-3-1

A compound of the formula [E-I] or a compound of the formula [E-II] wherein r is 0 and $R^5$ is carboxy group can be produced by reacting a compound of the formula [E-Ia] or a compound of the formula [E-IIa] wherein r is 1 with an oxidizing agent, in the presence of a catalyst where necessary, in a solvent.

Examples of the solvent include a single or mixed solvent of acetone, carbon tetrachloride, DMF, DMA, acetonitrile, water and the like.

As the oxidizing agent, sodium hypochlorite, sodium chlorite, potassium permanganate and the like are preferably used alone or in combination.

As the catalyst, 2,2,6,6-tetramethylpiperidin-1-oxyl is preferable.

The reaction temperature is preferably under ice-cooling to room temperature.

Production Method 2-3-2

A compound of the formula [E-I] or a compound of the formula [E-II] wherein r is 1 and $R^5$ is carboxy group can be produced from a compound of the formula [E-Ia] or a compound of the formula [E-IIa] wherein r is 1, via a compound of the formula [E-I] or a compound of the formula [E-II] wherein $R^5$ is methanesulfonyloxy group, and a cyano intermediate, in a solvent.

A compound of the formula [E-I] or a compound of the formula [E-II] wherein $R^5$ is methanesulfonyloxy group can be produced by reacting a compound of the formula [E-Ia] or a compound of the formula [E-IIa] wherein r is 1 with methanesulfonyl chloride in a solvent. The reaction of a compound of the formula [E-Ia] or a compound of the formula [E-IIa] and methanesulfonyl chloride is generally performed in the presence of a base.

Examples of the solvent include a single or mixed solvent of toluene, methylene chloride, chloroform, 1,2-dimethoxyethane, 1,4-dioxane, THF, pyridine and the like.

Examples of the base include triethylamine, diisopropylethylamine, pyridine and the like.

The reaction temperature is preferably under ice-cooling to room temperature.

The cyano intermediate can be produced by reacting a compound of the formula [E-I] or a compound of the formula [E-II] wherein $R^5$ is methanesulfonyloxy group with KCN or NaCN in a solvent.

Examples of the solvent include a single or mixed solvent of 1,2-dimethoxyethane, 1,4-dioxane, THF, DMF, DMA, DMSO, acetonitrile, water and the like.

The reaction temperature is preferably from under ice-cooling to under heating.

A compound of the formula [E-I] or a compound of the formula [E-II] wherein $R^5$ is carboxy group can be produced by hydrolyzing a cyano intermediate in a solvent. The cyano intermediate is generally hydrolyzed in the presence of a base.

Examples of the solvent include a single or mixed solvent of 1,2-dimethoxyethane, 1,4-dioxane, THF, ethanol, ethylene glycol, DMF, DMA, DMSO, water and the like.

Examples of the base include potassium hydroxide, sodium hydroxide and the like.

The reaction temperature is preferably under heating.

Production Method 2-4

A compound of the formula [E-I] or a compound of the formula [E-II] wherein $R^5$ is —CO—$NR^{6a}R^{6b}$ can be produced by reacting a compound of the formula [E-I] or a compound of the formula [E-II] obtained in Production method 2-3-1 or 2-3-2, wherein $R^5$ is carboxy group, with $HNR^{6a}R^{6b}$ and a condensing agent in a solvent.

Examples of the solvent include DMF, DMA, acetonitrile and the like.

Examples of the condensing agent include N,N'-dicyclohexylcarbodiimide (DCC), 1-ethyl-3-(3-dimethylaminopropyl)carbodiimide (EDC) hydrochloride and the like.

The reaction temperature is preferably room temperature.

Production Method 2-5

A compound of the formula [E-I] or a compound of the formula [E-II] wherein $R^5$ is —$NR^{7a}COR^{7b}$ can be produced from a compound of the formula [E-Ia] or a compound of the formula [E-IIa], via ketone intermediate 1 or aldehyde intermediate 1 and amine intermediate 1.

The ketone intermediate 1 or aldehyde intermediate 1 can be produced by reacting a compound of the formula [E-Ia] or a compound of the formula [E-IIa] with an oxidizing agent.

Examples of the solvent include methylene chloride, chloroform, acetonitrile and the like.

Examples of the oxidizing agent include 1,1,1-triacetoxy-1,1-dihydro-1,2-benziodoxol-3 (1H)-one (Dess-Martin reagent), tetrapropylammnonium perruthenate, chlorochromic acid, pyridinium dichromate and the like.

The reaction temperature is preferably under ice-cooling to room temperature.

The amine intermediate 1 can be produced by reacting ketone intermediate 1 or aldehyde intermediate 1, $R^{7a}NH_2$ and a reducing agent.

Examples of the solvent include methylene chloride, chloroform and the like.

Examples of the reducing agent include sodium triacetoxyborohydride and the like.

The reaction temperature is preferably under ice-cooling to room temperature.

A compound of the formula [E-I] or a compound of the formula [E-II] wherein $R^5$ is —$NR^{7a}COR^{7b}$ can be produced by reacting amine intermediate 1 with an acylating agent.

The amine intermediate 1 and the acylating agent are generally reacted in the presence of a base.

Examples of the solvent include methylene chloride, chloroform, 1,2-dimethoxyethane, 1,4-dioxane, THF, pyridine and the like.

Examples of the acylating agent include $R^{7b}COCl$, $(R^{7b}CO)_2O$ and the like.

Examples of the base include triethylamine, diisopropylethylamine, pyridine and the like.

The reaction temperature is preferably under ice-cooling to room temperature.

Production Method 2-6

A compound of the formula [E-I] or a compound of the formula [E-II] wherein $R^5$ is methanesulfonyl group can be produced by reacting a compound of the formula [E-I] or the formula [E-II] wherein $R^5$ is methanesulfonyloxy group with sodium methanesulfinate in a solvent.

Examples of the solvent include DMF, DMA and the like.

The reaction temperature is preferably under heating.

Alternatively, a compound of the formula [E-I] or a compound of the formula [E-II] wherein $R^5$ is methanesulfonyl group can be produced from a compound of the formula [E-Ia] or a compound of the formula [E-IIa], via halo intermediate 1.

The halo intermediate 1 can be produced by reacting a compound of the formula [E-Ia] or a compound of the formula [E-IIa] with a halogenating agent.

Examples of the solvent include methylene chloride, chloroform, carbon tetrachloride and the like.

Examples of the halogenating agent include thionyl chloride, phosphorus oxychloride, phosphorus oxybromide, oxalyl dichloride and the like.

The reaction temperature is preferably from room temperature to under heating.

A compound of the formula [E-I] or a compound of the formula [E-II] wherein $R^5$ is methanesulfonyl group can be produced by reacting halo intermediate 1 with sodium methanesulfinate.

Examples of the solvent include DMF, DMA and the like.

The reaction temperature is preferably under heating.

Production Method 3

Production Method of a Compound of the Formula [A] in Production Method 1

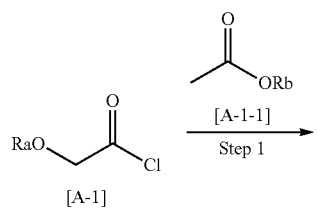

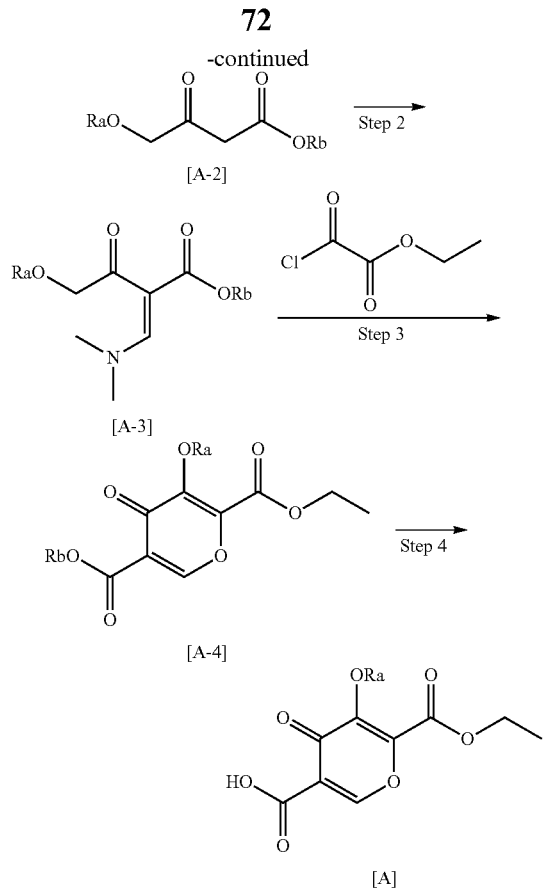

wherein Rb is carboxy-protecting group such as methyl group, ethyl group, benzyl group, tert-butyl group and the like, and other symbols are as mentioned above.

Step 1

A compound of the formula [A-2] can be produced by reacting a compound of the formula [A-1] with a compound of the formula [A-1-1] in a solvent.

The reaction of a compound of the formula [A-1] and a compound of the formula [A-1-1] is generally performed in the presence of a base.

Examples of the solvent include DMF, DMA, DMSO, THF, toluene and the like.

Examples of the base include sodium hydride, lithium diisopropylamide (LDA), lithium hexamethyldisilazide (LHMDS) and the like.

The reaction temperature is preferably −78° C. to room temperature.

Step 2

A compound of the formula [A-3] can be produced by reacting a compound of the formula [A-2] with N,N-dimethylformamide dimethyl acetal in a solvent.

Examples of the solvent include DMF, acetonitrile, THF, chloroform, ethyl acetate, methylene chloride, toluene and the like.

The reaction temperature is preferably from room temperature to under heating.

Step 3

A compound of the formula [A-4] can be produced by reacting a compound of the formula [A-3] with ethyl chloroglyoxylate.

The reaction of a compound of the formula [A-3] and ethyl chloroglyoxylate is generally performed in the presence of a base.

Examples of the solvent include DMF, DMA, DMSO, THF, toluene and the like.

Examples of the base include sodium hydride, LDA, LHMDS and the like. It is preferable to further treat with triethylamine, diisopropylethylamine and the like after reacting with a compound.

The reaction temperature is preferably −78° C. to room temperature.

Step 4

A compound of the formula [A] can be produced by deprotecting the carboxy-protecting group Rb of a compound of the formula [A-4] in a solvent. The carboxy-protecting group Rb is deprotected by a known method.

For example, when the protecting group is tert-butyl group, the deprotection is performed under acidic conditions.

Examples of the solvent include a single or mixed solvent of hexane, chloroform, methylene chloride, ethyl acetate, toluene, 1,2-dimethoxyethane, 1,4-dioxane, THF, methanol, ethanol, 2-propanol, DMSO, DMF, DMA, acetonitrile, water and the like.

Examples of the acid include p-toluenesulfonic acid, methanesulfonic acid, boron trifluoride, boron trichloride, boron tribromide, aluminum trichloride, hydrochloric acid, hydrogen bromide, phosphoric acid, sulfuric acid, acetic acid, trifluoroacetic acid and the like.

The reaction temperature is preferably from under ice-cooling to under heating.

Production Method 4

Production Method of a Compound of the Formula [B] in Production Method 1

Compound [B] may be a commercially available compound, or can also be produced from a commercially available compound by a known method.

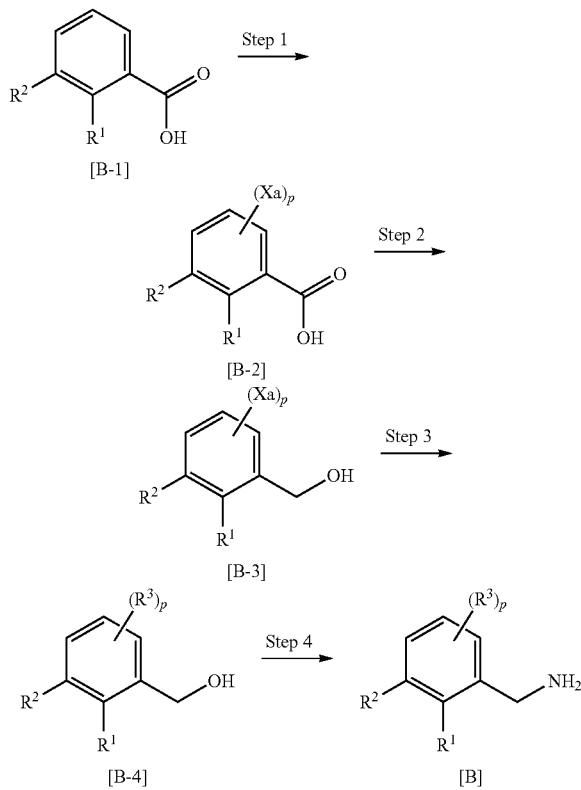

wherein Xa is halogen atom, and other symbols are as mentioned above.

Step 1

A compound of the formula [B-2] can be produced by reacting a compound of the formula [B-1] with a halogenating agent.

Examples of the solvent include hexane, methylene chloride, chloroform, carbon tetrachloride, concentrated sulfuric acid, acetic acid and the like.

Examples of the halogenating agent include N-iodosuccinimide, N-bromosuccinimide, bromine, iodine and the like.

The reaction temperature is preferably from under ice-cooling to under heating.

Step 2

A compound of the formula [B-3] can be produced by reacting a compound of the formula [B-2] with a reducing agent.

Examples of the solvent include hexane, toluene, 1,2-dimethoxyethane, 1,4-dioxane, THF and the like.

As the reducing agent, borane-THF complex are preferable.

The reaction temperature is preferably from under ice-cooling to under heating.

Alternatively, a compound of the formula [B-3] can be produced by reacting a compound of the formula [B-2] with ethyl chlorocarbonate and the like to convert the compound into an active ester, and reacting same with a reducing agent.

Examples of the solvent include solvents such as 1,2-dimethoxyethane, 1,4-dioxane, THF, water and the like and a mixed solvent thereof.

As the reducing agent, sodium borohydride is preferable.

The reaction temperature is preferably under ice-cooling to room temperature.

Step 3

A compound of the formula [B-4] can be produced by reacting a compound of the formula [B-3] with a compound represented by the formula $R^3$—H. Here, H of $R^3$—H means hydrogen atom bonded to a hetero atom for $R^3$.

The reaction of a compound of the formula [B-3] and the compound represented by the formula $R^3$—H is generally performed in the presence of a base, by adding a catalyst and a ligand where necessary.

Examples of the solvent include a single or mixed solvent of toluene, 1,2-dimethoxyethane, 1,4-dioxane, THF, methanol, ethanol, 2-propanol, DMSO, DMF, DMA, acetonitrile, water and the like.

Examples of the base include sodium methoxide, potassium tert-butoxide, potassium carbonate, cesium carbonate, potassium phosphate and the like.

Examples of the catalyst include copper(I) iodide, palladium(II) acetate, tris(dibenzylideneacetone)dipalladium(0) and the like.

Examples of the ligand include 1,10-phenanthroline, 4,5'-bis(diphenylphosphino)-9,9'-dimethylxanthene and the like.

The reaction temperature is preferably from under ice-cooling to under heating.

When $R^3$ is $C_{1-5}$ alkoxy group, a compound of the formula [B-4] can also be produced from a compound of the formula [B-3], via hydroxy intermediate 1.

The hydroxy intermediate 1 can be produced by reacting a compound of the formula [B-3] with water.

The reaction of a compound of the formula [B-3] and water is generally performed in the presence of a base, by adding a catalyst and a ligand where necessary.

Examples of the solvent include a single or mixed solvent of 1,2-dimethoxyethane, 1,4-dioxane, THF, methanol, ethanol, 2-propanol, DMSO, DMF, DMA, acetonitrile, water and the like.

Examples of the base include potassium hydroxide, sodium hydroxide and the like.

As the catalyst, copper(I) iodide is preferable.

As the ligand, 1,10-phenanthroline is preferable.

The reaction temperature is preferably from room temperature to under heating.

A compound of the formula [B-4] can be produced by reacting hydroxy intermediate 1 with a $C_{1-6}$ alkylating agent.

The reaction of hydroxy intermediate 1 and a $C_{1-6}$ alkylating agent is generally performed in the presence of a base.

Examples of the solvent include a single or mixed solvent of 1,2-dimethoxyethane, 1,4-dioxane, THF, DMSO, DMF, DMA, acetonitrile and the like.

As the $C_{1-6}$ alkylating agent, $C_{1-6}$ alkyl halide such as iodomethane, iodoethane and the like or dialkyl sulfate such as dimethyl sulfate, diethyl sulfate and the like is preferable.

Examples of the base include potassium tert-butoxide, potassium carbonate, cesium carbonate, sodium hydrogen carbonate, potassium phosphate and the like.

The reaction temperature is preferably from under ice-cooling to under heating.

Step 4

A compound of the formula [B] can be produced from a compound of the formula [B-4], via phthalimide intermediate 1.

The phthalimide intermediate 1 can be produced by reacting a compound of the formula [B-4], phthalimide, an azo compound and an additive in a solvent.

Examples of the solvent include a single or mixed solvent of THF, methylene chloride, chloroform, DMF, ethyl acetate, toluene and the like.

Examples of the azo compound include diisopropyl azodicarboxylate, diethyl azodicarboxylate, N,N,N',N'-tetramethylazodicarboxamide, 1,1'-(azodicarbonyl)dipiperidine and the like.

Examples of the additive include phosphorus reagents such as triphenylphosphine, diphenyl(2-pyridyl)phosphine, tributylphosphine, tri-tert-butylphosphine etc., and the like.

The reaction temperature is preferably under ice-cooling to room temperature.

A compound of the formula [B] can be produced by reacting phthalimide intermediate 1 with hydrazine in a solvent.

Examples of the solvent include a single or mixed solvent of methanol, ethanol, toluene and the like.

The reaction temperature is preferably under heating.

Production Method 5

Production Method of a Compound of the Formula [D-I] in Production Method 1

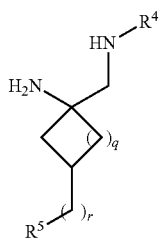

wherein each symbol is as mentioned above.

Production Method 5-1

A compound of the formula [D-I] wherein q is 1 (hereinafter to be referred to as a compound of the formula [D-Ia]) can be produced by the following Production methods 5-1-1 to 5-1-3.

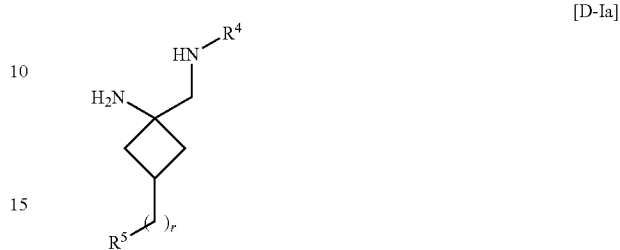

wherein each symbol is as mentioned above.

Production Method 5-1-1

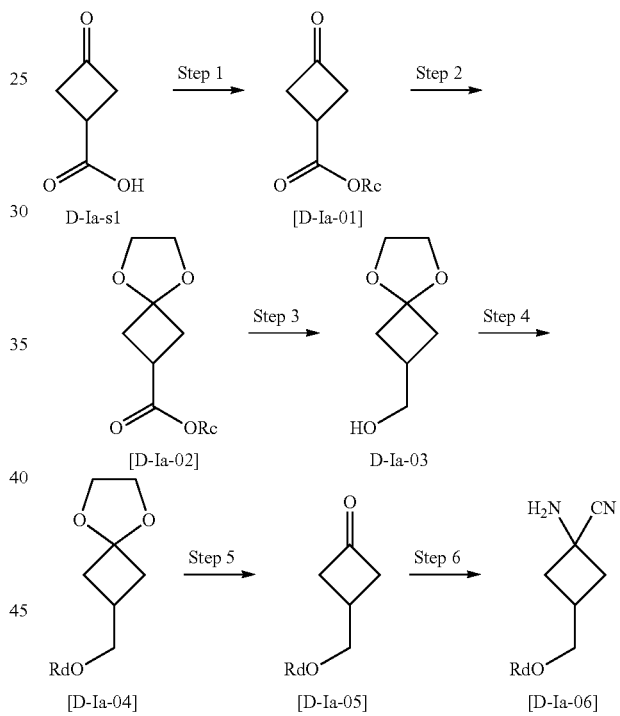

wherein Rc is carboxy-protecting group such as methyl group, ethyl group, benzyl group, tert-butyl group and the like, Rd is hydroxy-protecting group such as $C_{1-6}$ alkyl group, or $C_{1-6}$ alkoxy $C_{2-6}$ alkylene group, benzyl group, tert-butyidimethylsilyl group, triisopropylsilyl group, tert-butyldiphenylsilyl group and the like, and other symbols are as mentioned above.

Step 1

A compound of the formula [D-Ia-01] can be produced by esterifying commercially available 3-oxocyclobutanecarboxylic acid D-Ia-s1 by a known method. For example, when Rc is benzyl group, a compound of the formula [D-Ia-01] can be produced by reacting 3-oxocyclobutanecarboxylic acid with benzyl chloride or benzyl bromide in a solvent. The reaction of 3-oxocyclobutanecarboxylic acid and benzyl chloride or benzyl bromide is generally performed in the presence of a base.

Examples of the solvent include toluene, 1,2-dimethoxyethane, 1,4-dioxane, THF, DMF, DMA, acetonitrile and the like.

Examples of the base include sodium hydride, potassium carbonate and the like.

The reaction temperature is preferably room temperature.

Step 2

A compound of the formula [D-Ia-02] can be produced by ketalizing compound [D-Ia-01] with ethylene glycol and an additive in a solvent by a known method.

Examples of the solvent include toluene, 1,2-dimethoxyethane, 1,4-dioxane, chloroform, methylene chloride and the like.

Examples of the additive include pyridinium p-toluenesulfonate, p-toluenesulfonic acid, camphorsulfonic acid and the like.

The reaction temperature is preferably from room temperature to under heating.

Step 3

The compound D-Ia-03 can be produced by reacting a compound of the formula [D-Ia-02] with a reducing agent in a solvent.

Examples of the solvent include THF, 1,2-dimethoxyethane, 1,4-dioxane and the like ether solvents As the reducing agent, diisobutylaluminum hydride, lithium aluminum hydride are preferable.

The reaction temperature is preferably under ice-cooling to room temperature.

Step 4

A compound of the formula [D-Ia-04] can be produced from the compound D-Ia-03 in the same manner as in Production method 2-1 or 2-2 in a solvent, or by protecting the hydroxy group of the compound D-Ia-03. The hydroxy group of the compound D-Ia-03 may be protected by a known method. For example, when Rd is tert-butyldiphenylsilyl group, a compound of the formula [D-Ia-04] can be produced by reacting the compound D-Ia-03 with tert-butyldiphenylsilyl chloride in a solvent.

The reaction of compound D-Ia-03 and tert-butyldiphenylsilyl chloride is generally performed in the presence of a base.

Examples of the solvent include toluene, 1,2-dimethoxyethane, 1,4-dioxane, THF, DMF, DMA, acetonitrile and the like.

Examples of the base include triethylamine, imidazole and the like.

The reaction temperature is preferably room temperature.

Step 5

A compound of the formula [D-Ia-05] can be produced by reacting a compound of the formula [D-Ia-04] with an acid in a solvent.

A compound of the formula [D-Ia-04] and acid may be reacted according to a known method.

Examples of the solvent include a single or mixed solvent of chloroform, methylene chloride, toluene, 1,2-dimethoxyethane, 1,4-dioxane, THF, methanol, ethanol, 2-propanol, water and the like.

As the acid, 1N or 2N aqueous hydrochloric acid solution is preferable.

Step 6

A compound of the formula [D-Ia-06] can be produced by subjecting a compound of the formula [D-Ia-05], aqueous ammonia, potassium cyanide and an additive to Strecker reaction in a solvent.

Examples of the solvent include a single or mixed solvent of water, methanol, ethanol, 2-propanol, 1,4-dioxane, THF and the like.

Examples of the additive include ammonium chloride and the like.

The reaction temperature is preferably under ice-cooling to room temperature.

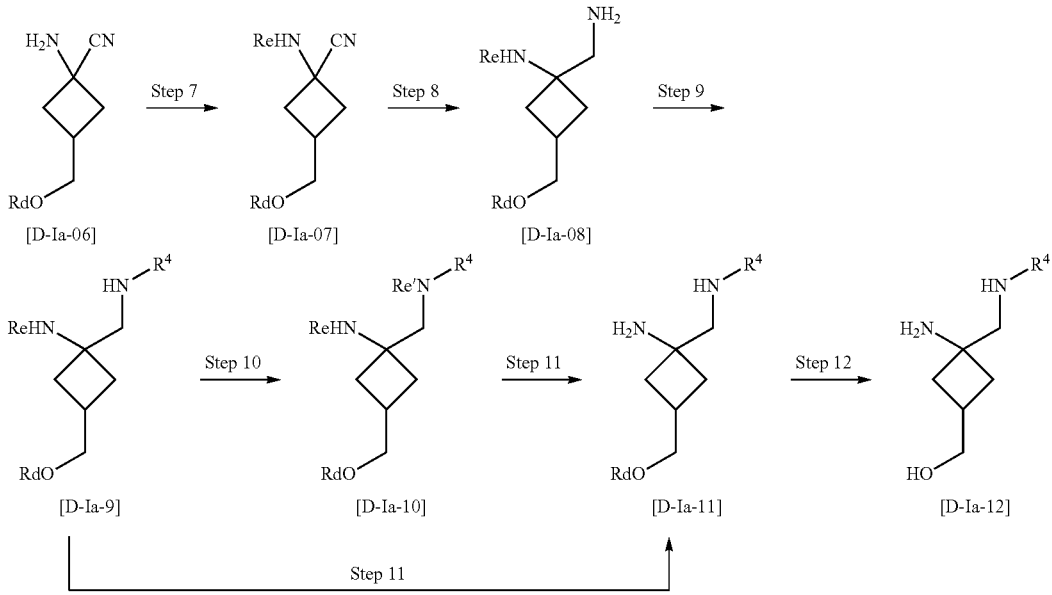

wherein Re and Re' are the same or different and each is amino-protecting group such as tert-butoxycarbonyl group, benzyloxycarbonyl group and the like, and other symbols are as mentioned above.

Step 7

A compound of the formula [D-Ia-07] can be produced by protecting the amino group of a compound of the formula [D-Ia-06].

The amino group may be protected according to a known method.

For example, when Re is tert-butoxycarbonyl group, a compound of the formula [D-Ia-07] can be produced by reacting a compound of the formula [D-Ia-06] with di-tert-butyl dicarbonate in a solvent.

The reaction of a compound of the formula [D-Ia-06] and di-tert-butyl dicarbonate is generally performed in the presence of a base.

Examples of the solvent include a single or mixed solvent of chloroform, methylene chloride, ethyl acetate, toluene, 1,2-dimethoxyethane, 1,4-dioxane, THF, DMF, DMA, acetonitrile, water and the like.

Examples of the base include sodium hydrogen carbonate, triethylamine and the like.

The reaction temperature is preferably room temperature.

Step 8

A compound of the formula [D-Ia-08] can be produced by reacting a compound of the formula [D-Ia-07] with a reducing agent in a solvent.

Examples of the solvent include methanol, ethanol and the like.

As the reducing agent, a complex of sodium borohydride and cobalt(II) chloride hexahydrate is preferable.

The reaction temperature is preferably under ice-cooling to room temperature.

Step 9

A compound of the formula [D-Ia-09] can be produced by reacting a compound of the formula [D-Ia-08] and a ketone compound or an aldehyde compound corresponding to $R^4$ with a reducing agent in a solvent.

Examples of the solvent include DMF, acetonitrile, THF, chloroform, ethyl acetate, methylene chloride, toluene and the like.

The ketone compound corresponding to $R^4$ is, for example, acetone when $R^4$ is isopropyl group, and cyclopropanone when $R^4$ is cyclopropyl group.

The aldehyde compound corresponding to $R^4$ is, for example, formaldehyde when $R^4$ is methyl group, and acetaldehyde when $R^4$ is ethyl group.

Examples of the reducing agent include sodium borohydride, sodium triacetoxyborohydride and the like.

The reaction temperature is preferably under ice-cooling to room temperature.

Step 10

A compound of the formula [D-Ia-10] can be produced by protecting the amino group of a compound of the formula [D-Ia-09].

For example, when Re' is tert-butoxycarbonyl group, a compound of the formula [D-Ia-10] can be produced in the same manner as in the above-mentioned step 7.

Step 11

A compound of the formula [D-Ia-11] can be produced by deprotecting the amino-protecting group of a compound of the formula [D-Ia-09] or a compound of the formula [D-Ia-10]. The amino-protecting group may be deprotected by a known method.

For example, when Re and Re' are tert-butoxycarbonyl groups, the amino-protecting group is deprotected under acidic conditions.

Examples of the solvent include a single or mixed solvent of chloroform, methylene chloride, ethyl acetate, toluene, 1,2-dimethoxyethane, 1,4-dioxane, THF, methanol, ethanol, 2-propanol, DMSO, DMF, DMA, acetonitrile, water and the like.

Examples of the acid include trifluoroacetic acid, hydrochloric acid, hydrogen bromide and the like.

Step 12

A compound of the formula [D-Ia-12] can be produced by deprotecting the hydroxy-protecting group of a compound of the formula [D-Ia-11]. For example, when Rd is benzyl group, the hydroxy-protecting group is deprotected under acidic conditions.

Examples of the solvent include toluene, 1,2-dimethoxyethane, 1,4-dioxane, THF, DMF, DMA, acetonitrile and the like.

Examples of the acid include hydrogen bromide/acetic acid, hydrogen bromide and the like.

The reaction temperature is preferably under ice-cooling to room temperature.

When Rd is tert-butyldiphenylsilyl group, the hydroxy-protecting group is deprotected by reacting with a fluorinating agent such as tetrabutylammonium fluoride and the like.

A compound of the formula [D-Ia-06], a compound of the formula [D-Ia-07], a compound of the formula [D-Ia-08], a compound of the formula [D-Ia-09], a compound of the formula [D-Ia-10], a compound of the formula [D-Ia-11] and a compound of the formula [D-Ia-12] can be each separated into a single compound (cis form or trans form) by silica gel column chromatography, HPLC and the like. The separated each compound can be reacted in the same manner as in the above-mentioned step 7 to step 12.

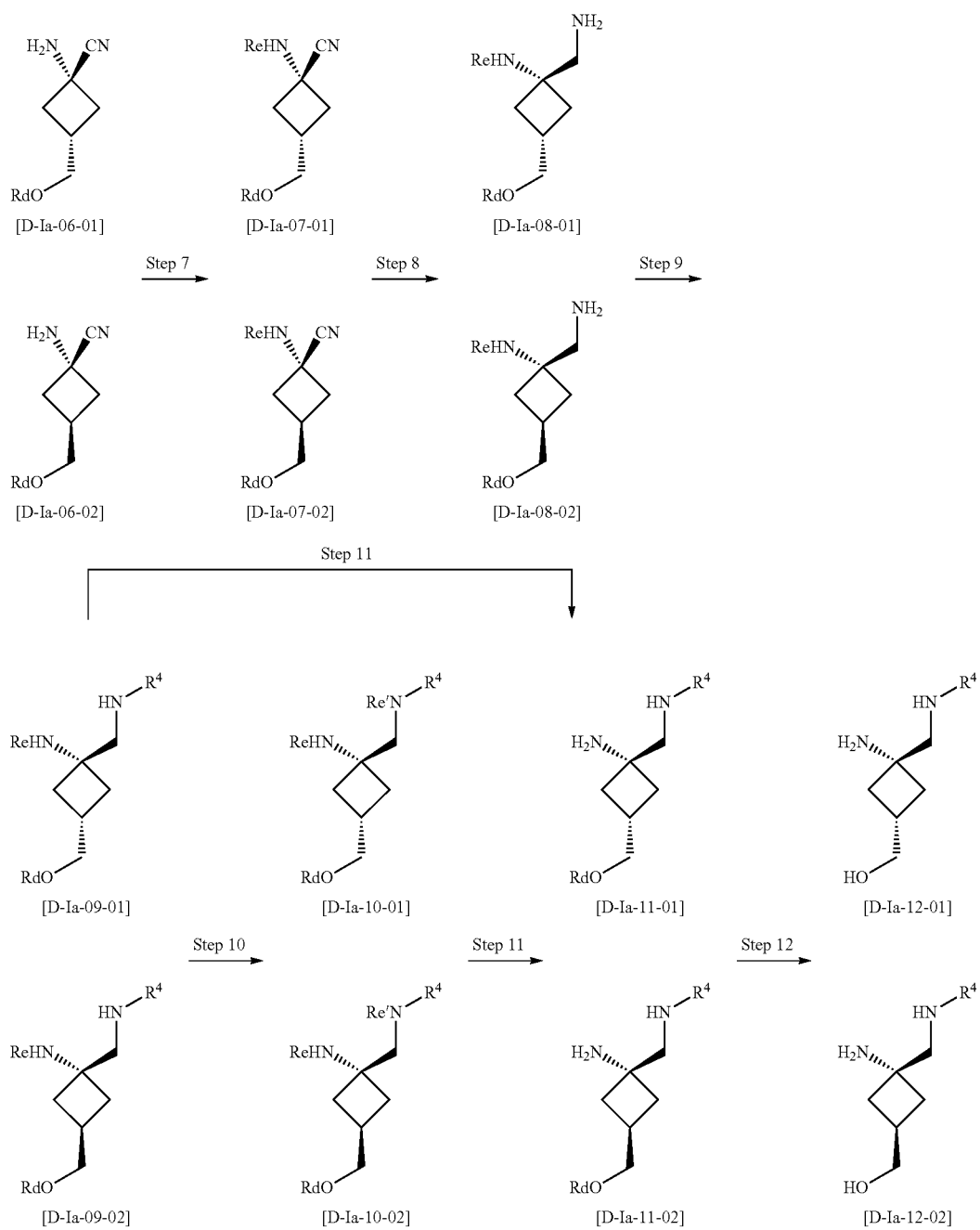
wherein each symbol is as mentioned above.
Production Method 5-1-2
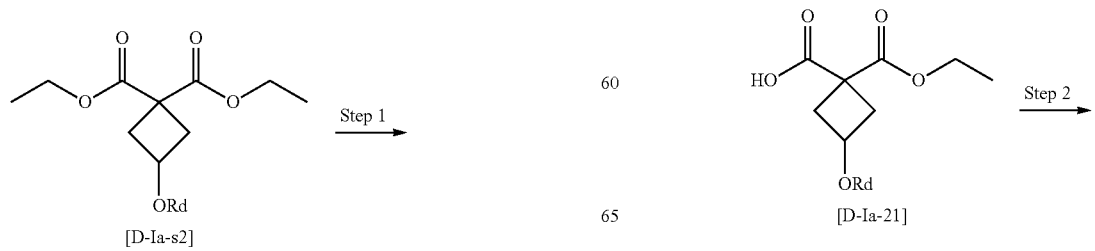

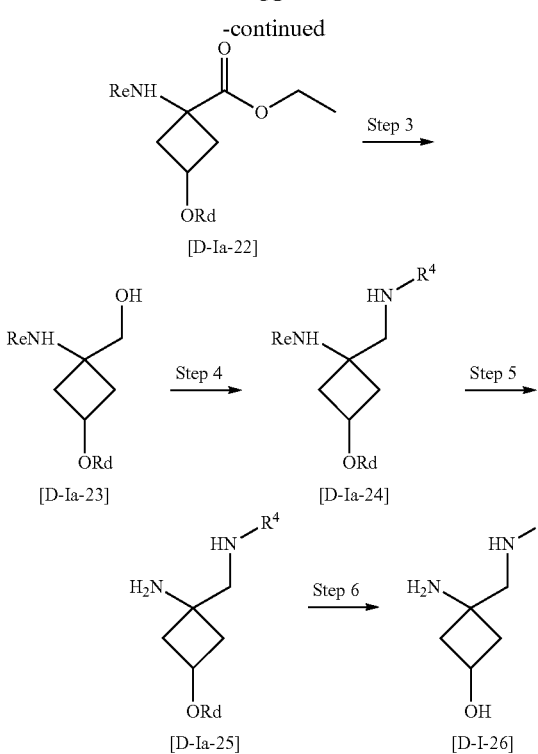

[D-Ia-22]

[D-Ia-23]

[D-Ia-24]

[D-Ia-25]

[D-I-26]

wherein each symbol is as mentioned above.

Step 1

A compound of the formula [D-Ia-21] can be produced by hydrolyzing a compound of the formula [D-Ia-s2] in a solvent.

A compound of the formula [D-Ia-s2] is generally hydrolyzed in the presence of a base.

Examples of the solvent include solvents such as THF, methanol, ethanol, water and the like and a mixed solvent thereof.

Examples of the base include sodium hydroxide, potassium hydroxide and the like.

The reaction temperature is preferably heating under reflux.

A compound of the formula [D-Ia-s2] may be commercially available diethyl 3-benzyloxy-1,1-cyclobutanedicarboxylate, or can be produced from commercially available diethyl 3-hydroxy-1,1-cyclobutanedicarboxylate in the same manner as in Production method 5-1-1, step 4.

Step 2

A compound of the formula [D-Ia-22] can be produced from a compound of the formula [D-Ia-21] via acid azide intermediate 1.

The acid azide intermediate 1 can be produced by reacting a compound of the formula [D-Ia-21] with an azide reagent in a solvent. The reaction of a compound of the formula [D-Ia-21] and an azide reagent is generally performed in the presence of a base.

Examples of the solvent include toluene, tert-butyl alcohol, 1,2-dimethoxyethane, 1,4-dioxane, THF, DMF, acetonitrile and the like solvent and a mixed solvent thereof.

Examples of the base include triethylamine, diisopropylethylamine and the like.

Examples of the azide reagent include diphenylphosphoryl azide (DPPA) and the like.

The reaction temperature is preferably from room temperature to under heating.

Alternatively, the acid azide intermediate 1 can be produced by converting a compound of the formula [D-Ia-21] to an active ester by reacting with ethyl chlorocarbonate and the like in the presence of a base, and reacting the active ester with an azide reagent.

Examples of the solvent include solvents such as toluene, tert-butyl alcohol, 1,2-dimethoxyethane, 1,4-dioxane, THF, DMF, acetonitrile, acetone, water and the like and a mixed solvent thereof.

Examples of the azide reagent include sodium azide and the like.

The reaction temperature is preferably from room temperature to under heating.

A compound of the formula [D-Ia-22] can be produced by subjecting the acid azide intermediate 1 to Curtius rearrangement in a solvent to give an isocyanate, and reacting same with tert-butyl alcohol, benzyl alcohol and the like. The above-mentioned reaction is generally performed in the presence of a base.

Examples of the solvent include solvents such as toluene, tert-butyl alcohol, 1,2-dimethoxyethane, 1,4-dioxane, THF, DMF, acetonitrile, acetone and the like and a mixed solvent thereof.

Examples of the base include triethylamine, diisopropylethylamine and the like.

The reaction temperature is preferably from room temperature to under heating.

Step 3

A compound of the formula [D-Ia-23] can be produced by reacting a compound of the formula [D-Ia-22] with a reducing agent in a solvent.

Examples of the solvent include THF, 1,4-dioxane and the like.

Examples of the reducing agent include lithium aluminum hydride and the like.

The reaction temperature is preferably under ice-cooling to room temperature.

Step 4

A compound of the formula [D-Ia-24] can be produced from a compound of the formula [D-Ia-23] via aldehyde intermediate 2.

The aldehyde intermediate 2 can be produced by reacting a compound of the formula [D-Ia-23] with an oxidizing agent in a solvent.

Examples of the solvent include methylene chloride, chloroform, acetonitrile and the like.

Examples of the oxidizing agent include 1,1,1-triacetoxy-1,1-dihydro-1,2-benziodoxol-3(1H)-one (Dess-Martin reagent), tetrapropylammonium perruthenate, chlorochromic acid, pyridinium dichromate and the like.

The reaction temperature is preferably under ice-cooling to room temperature.

A compound of the formula [D-Ia-24] can be produced by reacting aldehyde intermediate 2, $R^4NH_2$ and a reducing agent in a solvent.

Examples of the solvent include methylene chloride, chloroform and the like.

Examples of the reducing agent include sodium triacetoxyborohydride and the like.

The reaction temperature is preferably under ice-cooling to room temperature.

Step 5

A compound of the formula [D-Ia-25] can be produced by reacting a compound of the formula [D-Ia-24] in the same manner as in Production method 5-1-1, step 11.

Step 6

A compound of the formula [D-Ia-26] can be produced by reacting a compound of the formula [D-Ia-25] in the same manner as in Production method 5-1-1, step 12.

A compound of the formula [D-Ia-21], a compound of the formula [D-Ia-22], a compound of the formula [D-Ia-23], a compound of the formula [D-Ia-24], a compound of the formula [D-Ia-25] and a compound of the formula [D-Ia-26] can be each separated into a single compound (cis form or trans form) by recrystallization, silica gel column chromatography, HPLC and the like. The separated each compound can be reacted in the same manner as in the above-mentioned step 2 to step 6.

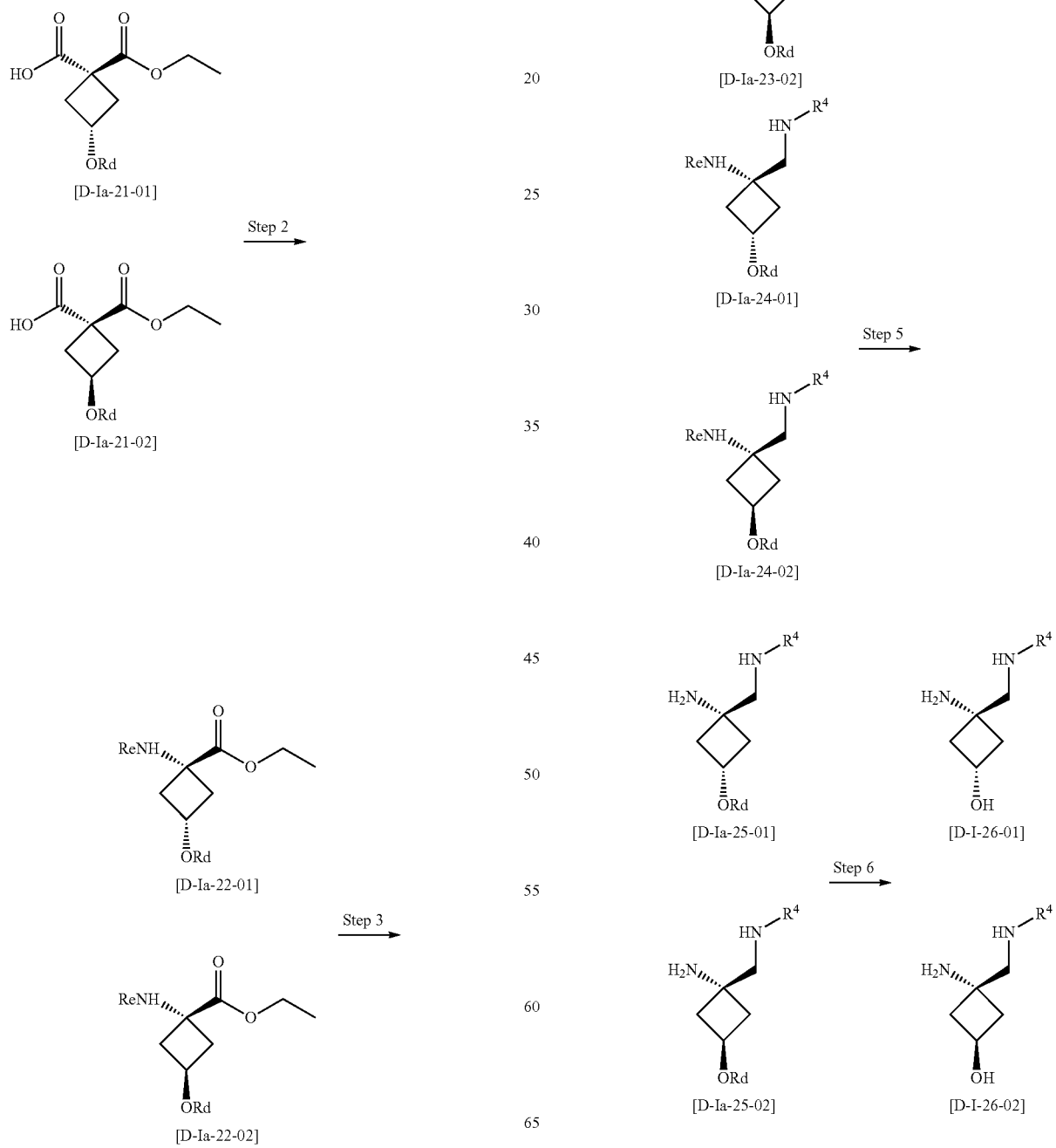

wherein each symbol is as mentioned above.

Production Method 5-1-3

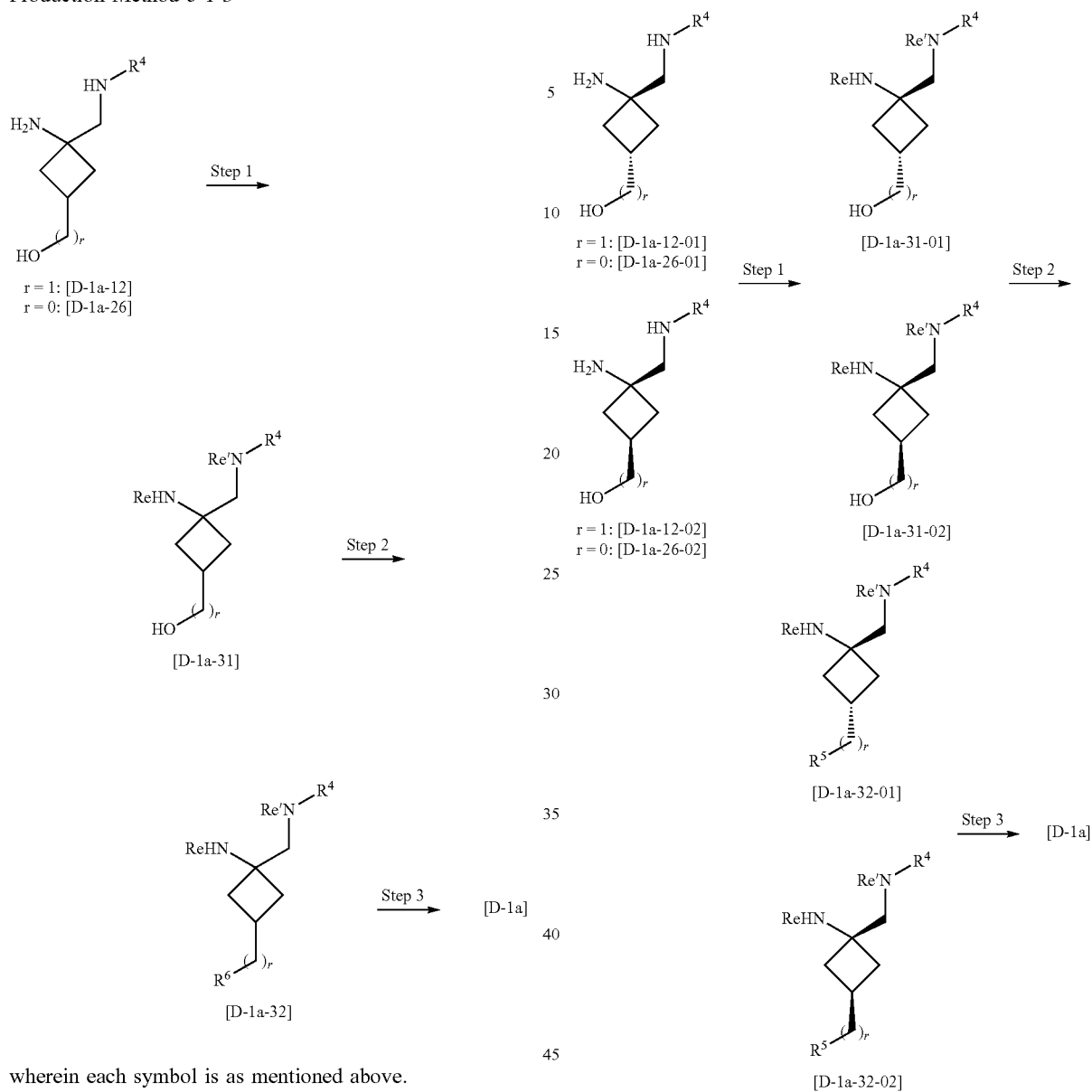

wherein each symbol is as mentioned above.

Step 1

A compound of the formula [D-Ia-31] can be produced by reacting a compound of the formula [D-Ia-12] or a compound of the formula [D-Ia-26] in the same manner as in Production method 5-1-1, step 7.

Step 2

A compound of the formula [D-Ia-32] can be produced by reacting a compound of the formula [D-Ia-31] in the same manner as in Production methods 2-1 to 2-6.

Step 3

A compound of the formula [D-Ia] can be produced by reacting a compound of the formula [D-Ia-32] in the same manner as in Production method 5-1-1, step 11.

The compounds of the formula [D-Ia-12], the formula [D-Ia-26], the formula [D-Ia-31], the formula [D-Ia-32] and the formula [D-Ia] can be each separated into a single compound (cis form or trans form) by silica gel column chromatography, HPLC and the like. The separated each compound can be reacted in the same manner as in the above-mentioned step 1 to step 3.

wherein each symbol is as mentioned above.

Production Method 5-2

A compound of the formula [D-I] wherein q is 0 (hereinafter to be referred to as a compound of the formula [D-Ib]) can be produced by the following Production methods 5-2-1 to 5-2-9.

Production Method 5-2-1

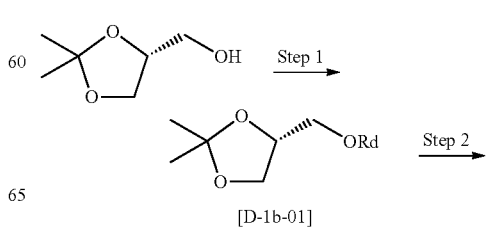

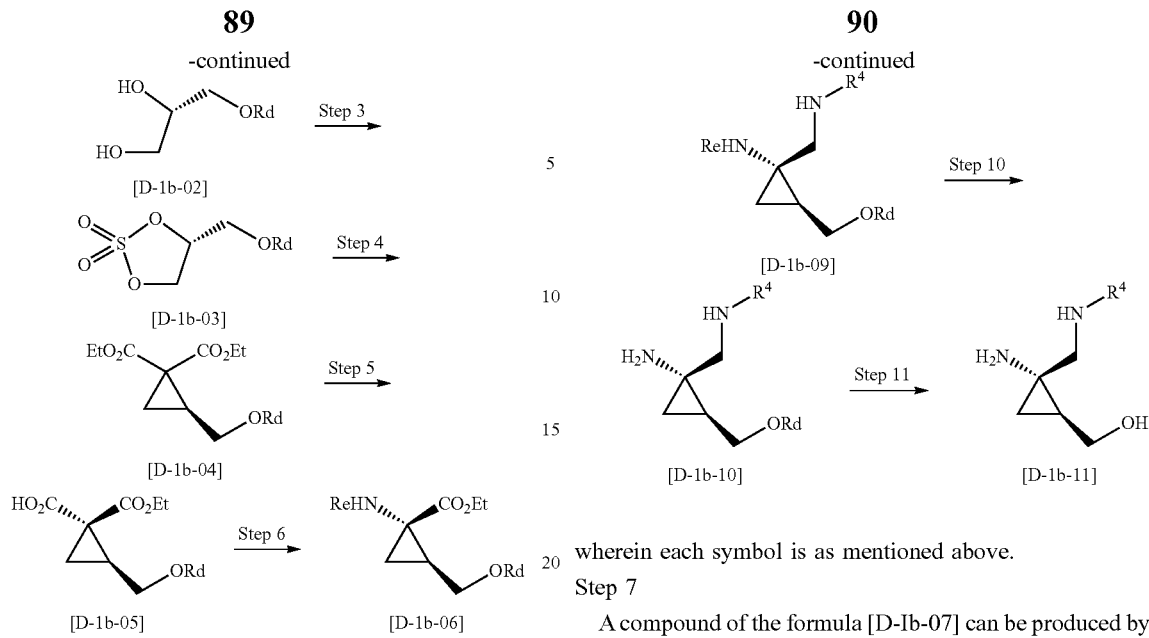

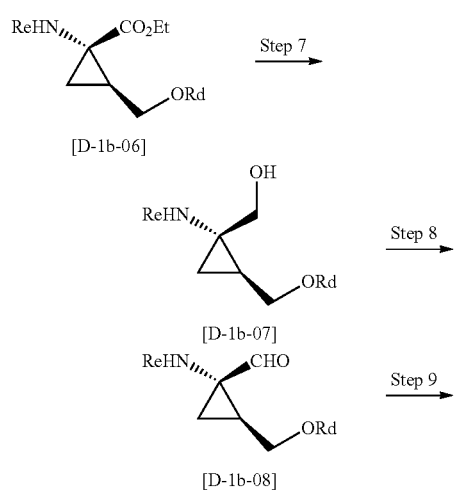

wherein each symbol is as mentioned above.

Step 1

A compound of the formula [D-Ib-01] can be produced by reacting a commercially available compound ((R)-(−)-2,2-dimethyl-1,3-dioxolan-4-methanol, Tokyo Chemical Industry Co., Ltd., specific optical rotation $[\alpha]_D^{20}$ −11.0 to −15.0 deg (neat)) in the same manner as in Production method 5-1-1, step 4.

Step 2

A compound of the formula [D-Ib-02] can be produced by reacting a compound of the formula [D-Ib-01] in the same manner as in Production method 5-1-1, step 5.

Step 3-6

A compound of the formula [D-Ib-05] or a compound of the formula [D-Ib-06] can be produced from a compound of the formula [D-Ib-02] according to the method described in Synthesis, 1996, 1463. When Re of a compound of the formula [D-Ib-06] is benzyloxycarbonyl group, benzyl alcohol may be used instead of tert-butanol.

Step 7

A compound of the formula [D-Ib-07] can be produced by reacting a compound of the formula [D-Ib-06] with a reducing agent.

Examples of the solvent include ether solvents such as tetrahydrofuran, 1,2-dimethoxyethane, 1,4-dioxane and the like.

As the reducing agent, diisobutylaluminum hydride, lithium aluminum hydride are preferable.

The reaction temperature is preferably under ice-cooling to room temperature.

Step 8

A compound of the formula [D-Ib-08] can be produced by reacting a compound of the formula [D-Ib-07] with an oxidizing agent.

Examples of the solvent include methylene chloride, chloroform, acetonitrile and the like.

Examples of the oxidizing agent include 1,1,1-triacetoxy-1,1-dihydro-1,2-benziodoxol-3 (1H)-one (Dess-Martin reagent), tetrapropylammonium perruthenate, chlorochromic acid, pyridinium dichromate and the like.

The reaction temperature is preferably under ice-cooling to room temperature.

Step 9

A compound of the formula [D-Ib-09] can be produced by reacting a compound of the formula [D-Ib-08], $R^4NH_2$ and a reducing agent in a solvent.

Examples of the solvent include methylene chloride, chloroform and the like.

Examples of the reducing agent include sodium triacetoxyborohydride and the like.

The reaction temperature is preferably under ice-cooling to room temperature.

Step 10

A compound of the formula [D-Ib-10] can be produced by reacting a compound of the formula [D-Ib-09] in the same manner as in Production method 5-1-1, step 11.

Step 11

A compound of the formula [D-Ib-11] can be produced by reacting a compound of the formula [D-Ib-10] in the same manner as in Production method 5-1-1, step 12.

Production Method 5-2-2

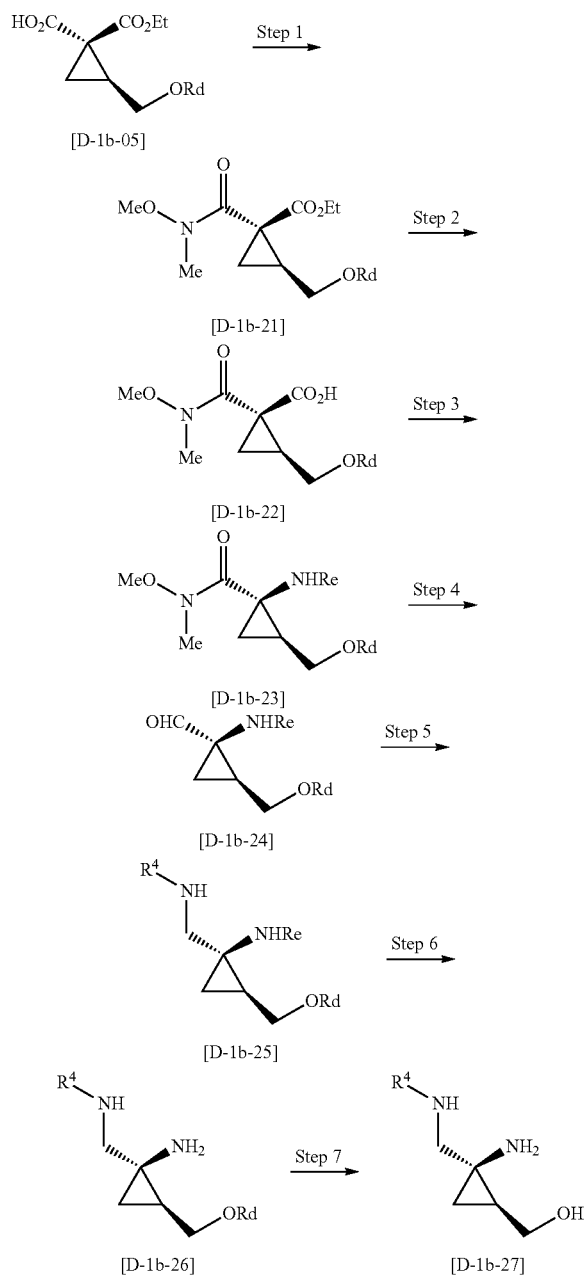

wherein each symbol is as mentioned above.

Step 1

A compound of the formula [D-Ib-21] can be produced by reacting a compound of the formula [D-Ib-05] with N,O-dimethyihydroxylamine hydrochloride in the presence of a base in the same manner as in Production method 2-4.

Step 2

A compound of the formula [D-Ib-22] can be produced by hydrolyzing a compound of the formula [D-Ib-21].

A compound of the formula [D-Ib-21] is generally hydrolyzed in the presence of a base.

Examples of the solvent include solvents such as THF, methanol, ethanol, water and the like and a mixed solvent thereof.

Examples of the base include sodium hydroxide, potassium hydroxide and the like.

The reaction temperature is preferably room temperature.

Step 3

A compound of the formula [D-Ib-23] can be produced by reacting a compound of the formula [D-Ib-22] in the same manner as in Production method 5-2-1, step 6.

Step 4

A compound of the formula [D-Ib-24] can be produced by reacting a compound of the formula [D-Ib-23] with a reducing agent.

Examples of the solvent include ether solvents such as tetrahydrofuran, 1,2-dimethoxyethane, 1,4-dioxane and the like.

As the reducing agent, diisobutylaluminum hydride, lithium aluminum hydride are preferable.

The reaction temperature is preferably under ice-cooling.

Step 5

A compound of the formula [D-Ib-25] can be produced by reacting a compound of the formula [D-Ib-24], $R^4NH_2$ and a reducing agent.

Examples of the solvent include DMF, acetonitrile, THF, chloroform, ethyl acetate, methylene chloride, toluene and the like.

Examples of the reducing agent include sodium triacetoxyborohydride and the like.

The reaction temperature is preferably under ice-cooling to room temperature.

Step 6

A compound of the formula [D-Ib-26] can be produced by reacting a compound of the formula [D-Ib-25] in the same manner as in Production method 5-1-1, step 11.

Step 7

A compound of the formula [D-Ib-27] can be produced by reacting a compound of the formula [D-Ib-26] in the same manner as in Production method 5-1-1, step 12.

Production Method 5-2-3

The following compounds can be produced from a commercially available compound ((S)-(+)-2,2-dimethyl-1,3-dioxolan-4-methanol, Tokyo Chemical Industry Co., Ltd., specific optical rotation $[\alpha]_D^{20}$ +13.5 to +14.5 deg (neat)) in the same manner as in Production method 5-2-1.

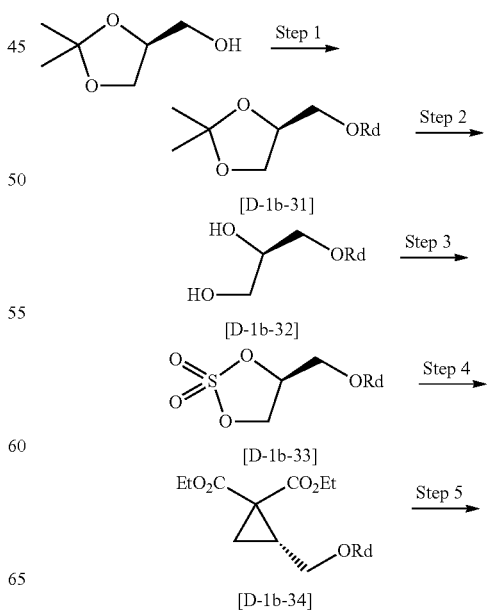

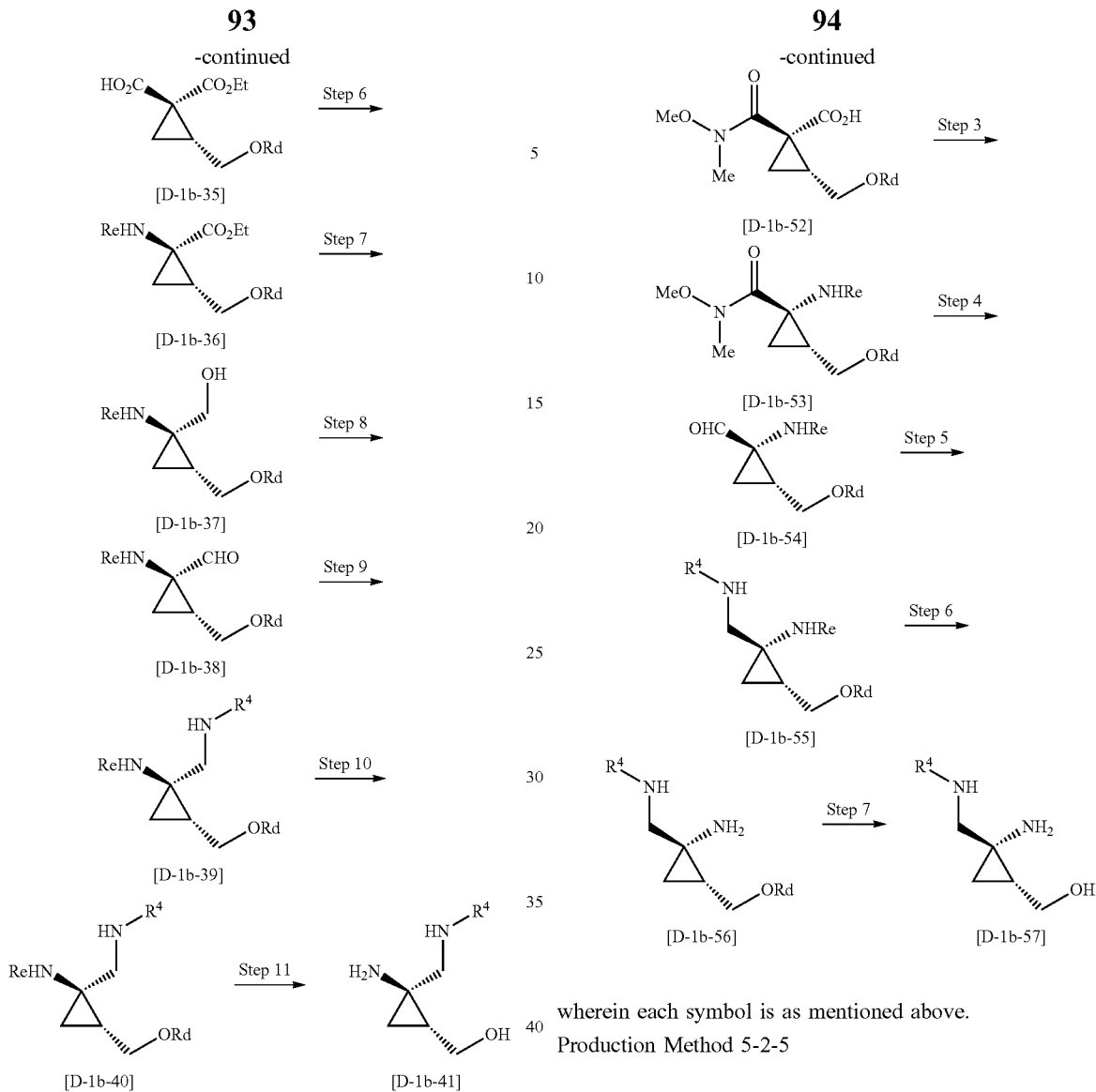
wherein each symbol is as mentioned above.
Production Method 5-2-4
The following compound can be produced from a compound of the formula [D-Ib-35] obtained in Production method 5-2-3, step in the same manner as in Production method 5-2-2.
wherein each symbol is as mentioned above.
Production Method 5-2-5
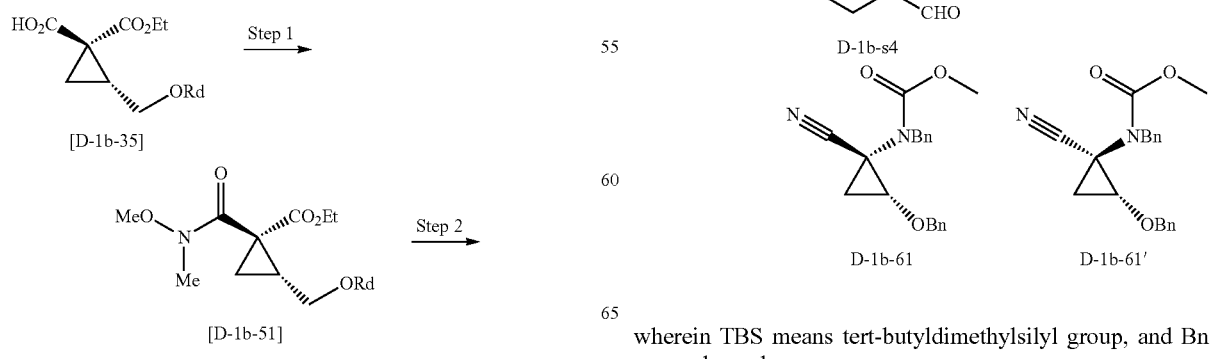
wherein TBS means tert-butyldimethylsilyl group, and Bn means benzyl group.

Step 1

The compound D-Ib-61 or D-Id-61' can be produced from the compound D-Ib-s3 that can be synthesized from 1,3:4,6-di-O-benzylidenemannitol (D form), via the compound D-Ib-s4 according to the method described in Tetrahedron: Asymmetry 11 (2000) 1015-1025, respectively.

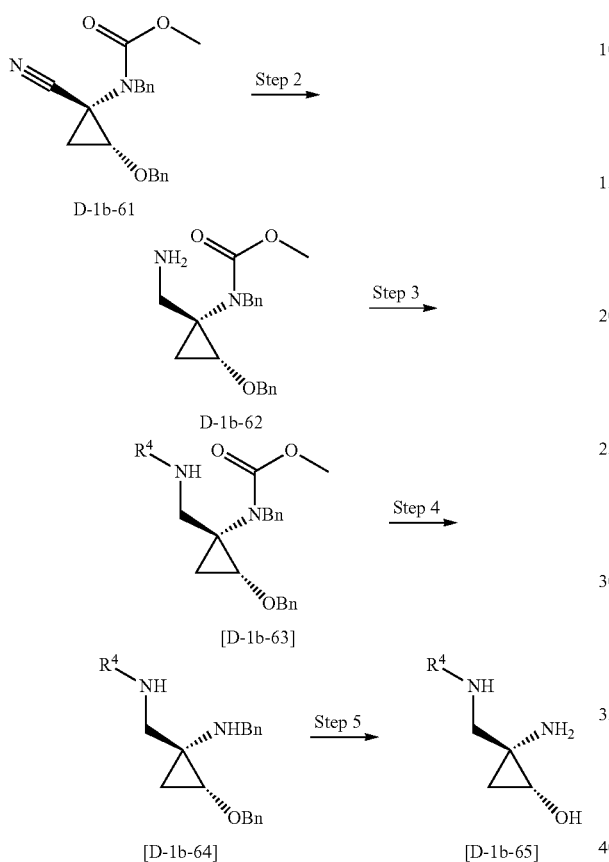

wherein Bn is benzyl group, and other symbols are as mentioned above.

Step 2

The compound D-Ib-62 can be produced by reacting the compound D-Ib-61 in the same manner as in Production method 5-1-1, step 8.

Step 3

A compound of the formula [D-Ib-63] can be produced by reacting the compound D-Ib-62 in the same manner as in Production method 5-1-1, step 9.

Step 4

A compound of the formula [D-Ib-64] can be produced from a compound of the formula [D-Ib-63] by deprotecting methoxycarbonyl group by a known method.

The methoxycarbonyl group is generally deprotected in the presence of a base.

Examples of the solvent include a single or mixed solvent of 1,2-dimethoxyethane, 1,4-dioxane, THF, methanol, ethanol, 2-propanol, water and the like.

Examples of the base include sodium hydroxide, potassium hydroxide, sodium methoxide and the like.

The reaction temperature is preferably from room temperature to under heating.

Step 5

A compound of the formula [D-Ib-65] can be produced from a compound of the formula [D-Ib-64] by deprotecting benzyl group by a known method.

The benzyl group is generally deprotected in the presence of a catalyst under a hydrogen atmosphere.

Examples of the solvent include a single or mixed solvent of ethyl acetate, toluene, 1,2-dimethoxyethane, 1,4-dioxane, THF, methanol, ethanol, 2-propanol, water and the like.

Examples of the catalyst include palladium/carbon, palladium hydroxide and the like.

The reaction temperature is preferably room temperature.

Production Method 5-2-6

A compound of the formula [D-Ib-65'] can be produced by reacting the compound D-Ib-61' obtained in Production method 5-2-5, step 1, in the same manner as in Production method 5-2-5, step 2 to step 5.

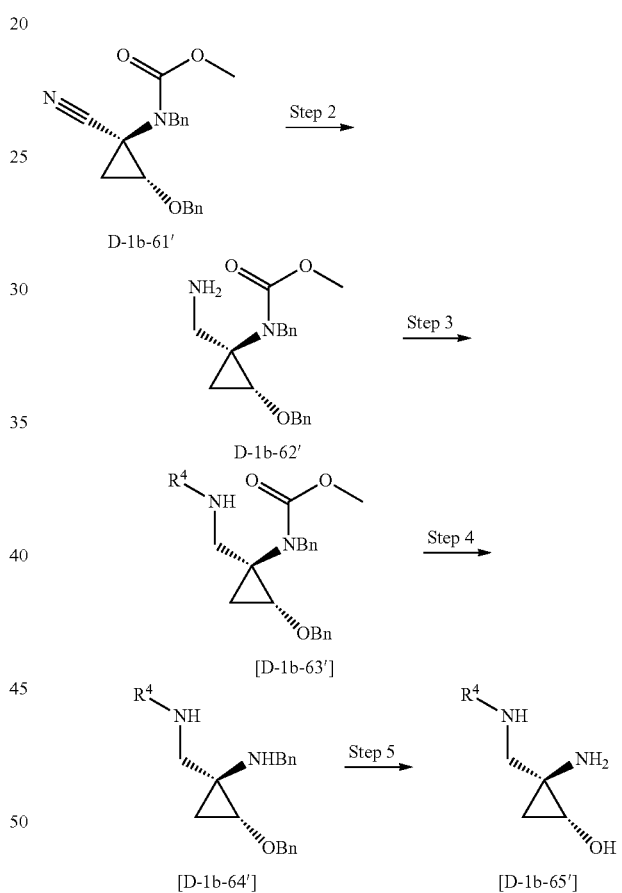

wherein each symbol is as mentioned above.

Production Method 5-2-7

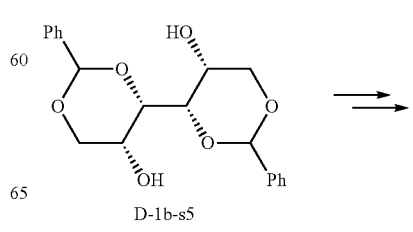

D-Ib-s5

-continued

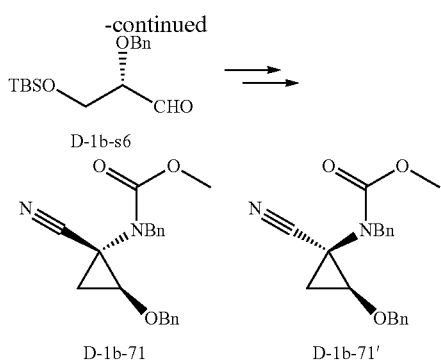

wherein TBS means tert-butyldimethylsilyl group, and Bn means benzyl group.

Step 1

The compound D-Ib-71 or D-Ib-71' can be produced from the compound D-Ib-s5 that can be synthesized from 1,3:4,6-di-O-benzylidenemannitol (L form), via the compound D-Ib-s6 in the same manner as in Production method 5-2-5, step 1.

Step 2-5

A compound of the formula [D-Ib-75] can be produced by reacting the compound D-Ib-71 obtained step 1 in the same manner as in Production method 5-2-5, step 2 to step 5.

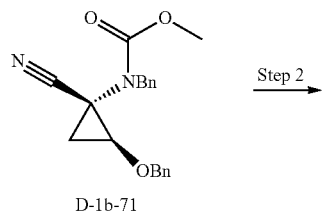

wherein Bn means benzyl group, and other symbols are as mentioned above.

Production Method 5-2-8

A compound of the formula [D-Ib-75'] can be produced by reacting the compound D-Ib-71' obtained in Production method 5-2-7, step 1, in the same manner as in Production method 5-2-5, step 2 to step 5.

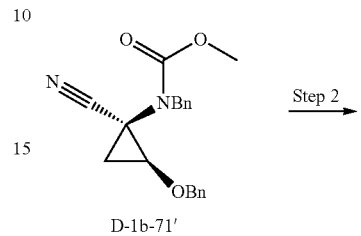

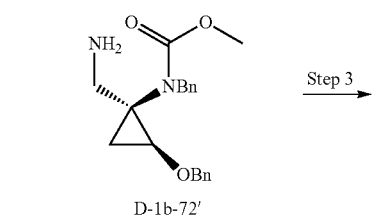

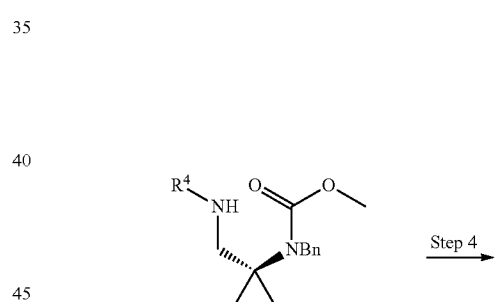

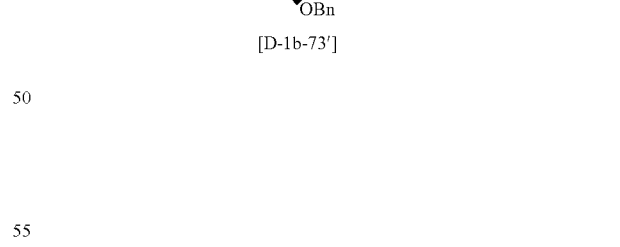

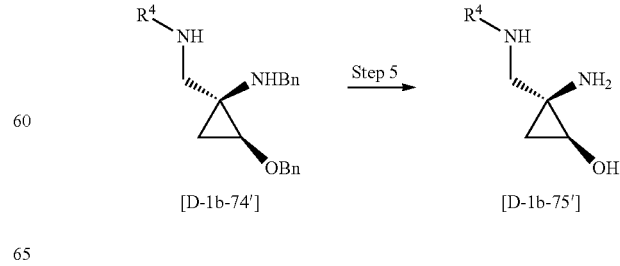

wherein Bn is benzyl group, and other symbols are as mentioned above.

Production Method 5-2-9

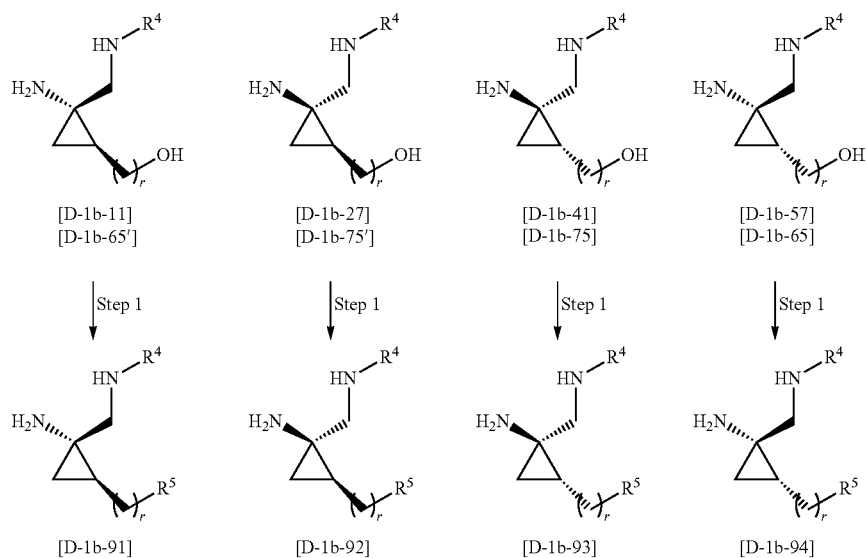

wherein each symbol is as mentioned above.
Step 1
A compound of the formula [D-Ib-91], a compound of the formula [D-Ib-92], a compound of the formula [D-Ib-93] and a compound of the formula [D-Ib-94] can be produced by reacting a compound of the formula [D-Ib-11], a compound of the formula [D-Ib-27], a compound of the formula [D-Ib-41], a compound of the formula [D-Ib-57], a compound of the formula [D-Ib-65], a compound of the formula [D-Ib-65'], a compound of the formula [D-Ib-75] or a compound of the formula [D-Ib-75'] in the same manner as in Production method 5-1-1, step 10, Production methods 2-1 to 2-6, and then Production method 5-1-1, step 11.

Production Method 6
Production Method of a Compound of the Formula [D-II] in Production Method 1

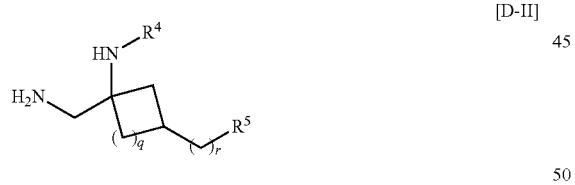
[D-II]

wherein each symbol is as mentioned above.
Production Method 6-1
A compound of the formula [D-II] wherein q is 1 (hereinafter to be referred to as a compound of the formula [D-IIa]) can be produced by the following Production methods 6-1-1 to 6-1-3.

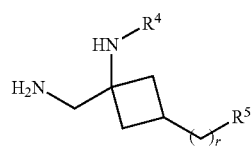
[D-IIa]

wherein each symbol is as mentioned above.

Production Method 6-1-1

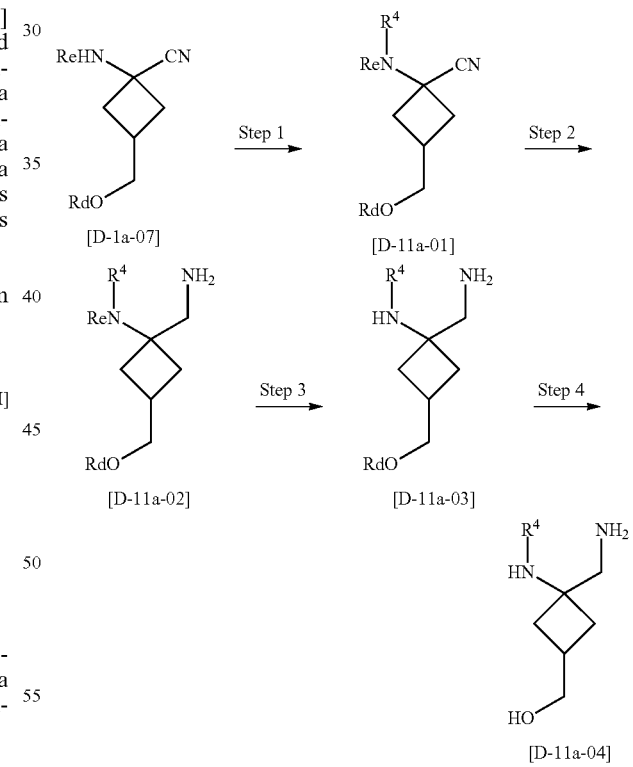

wherein each symbol is as mentioned above.
Step 1
A compound of the formula [D-IIa-01] can be produced by reacting a compound of the formula [D-Ia-07] obtained in Production Method 5-1-1, step 7, with $R^4$—Xb wherein Xb is chlorine atom, bromine atom or iodine atom in a solvent.

The reaction of a compound of the formula [D-Ia-07] and R⁴—Xb is generally performed in the presence of a base.

Examples of the solvent include DMF, acetonitrile, THF, toluene and the like.

Examples of the base include sodium hydride, potassium carbonate and the like.

The reaction temperature is preferably under ice-cooling to room temperature.

Step 2

A compound of the formula [D-IIa-02] can be produced by reacting a compound of the formula [D-IIa-01] in the same manner as in Production method 5-1-1, step 8.

Step 3

A compound of the formula [D-IIa-03] can be produced by reacting a compound of the formula [D-IIa-02] in the same manner as in Production method 5-1-1, step 11.

Step 4

A compound of the formula [D-IIa-01] can be produced by reacting a compound of the formula [D-IIa-03] in the same manner as in Production method 5-1-1, step 12.

A compound of the formula [D-IIa-01], a compound of the formula [D-IIa-02], a compound of the formula [D-IIa-03] and a compound of the formula [D-IIa-04] can be each separated into a single compound (cis form or trans form) by silica gel column chromatography, HPLC and the like. The separated each compound can be reacted in the same manner as in the above-mentioned step 1 to step 4.

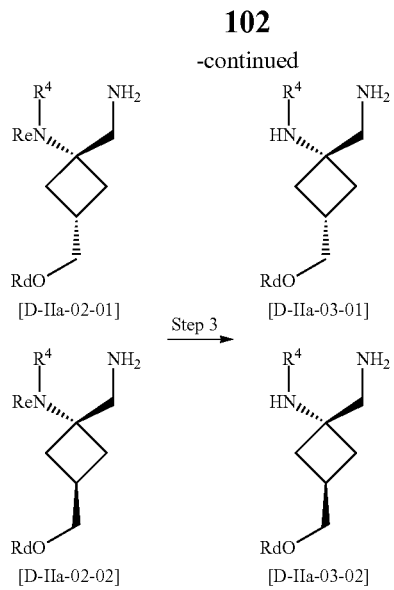

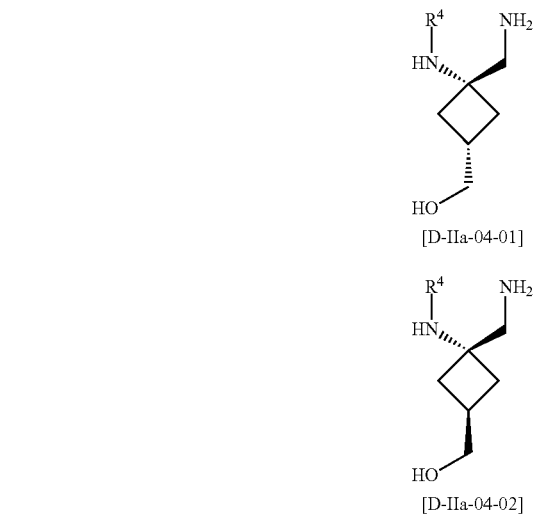

wherein each symbol is as mentioned above.

Production Method 6-1-2

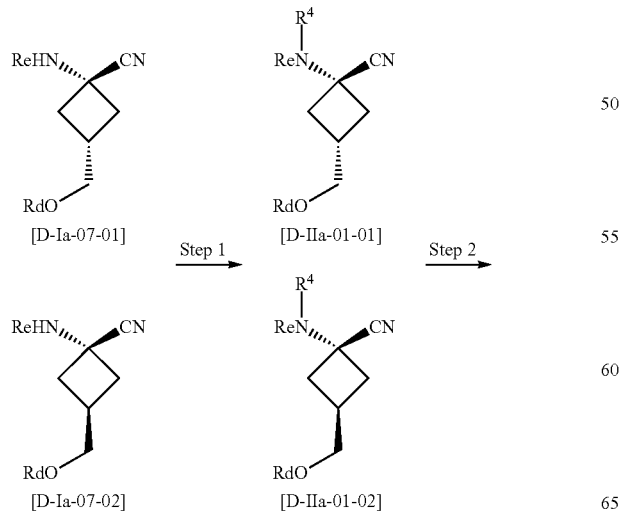

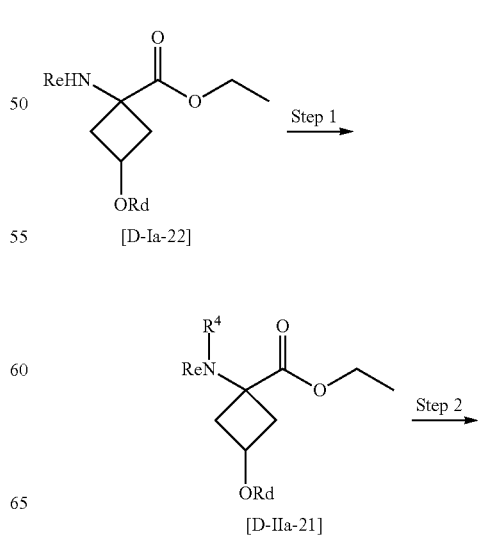

-continued

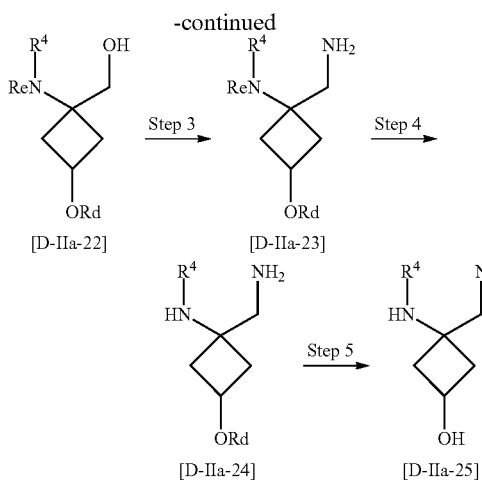

wherein each symbol is as mentioned above.

Step 1

A compound of the formula [D-IIa-21] can be produced by reacting a compound of the formula [D-Ia-22] obtained in Production method 5-1-2, Step 2 in the Same Manner as in Production method 6-1-1, Step 1.

Step 2

A compound of the formula [D-IIa-22] can be produced by reacting a compound of the formula [D-IIa-21] in the same manner as in Production method 5-1-2, step 3.

Step 3

A compound of the formula [D-IIa-23] can be produced from the formula [D-IIa-22] via phthalimide intermediate 2.

The phthalimide intermediate 2 can be produced by reacting a compound of the formula [D-IIa-22], phthalimide, an azo compound and an additive in a solvent.

Examples of the solvent include a single or mixed solvent of THF, methylene chloride, chloroform, DMF, ethyl acetate, toluene and the like.

Examples of the azo compound include diisopropyl azodicarboxylate, diethyl azodicarboxylate, N,N,N',N'-tetramethylazodicarboxamide, 1,1'-(azodicarbonyl)dipiperidine and the like.

Examples of the additive include phosphorus reagents such as triphenylphosphine, diphenyl(2-pyridyl)phosphine, tributylphosphine, tri-tert-butylphosphine, etc., and the like.

The reaction temperature is preferably room temperature.

A compound of the formula [D-IIa-23] can be produced by reacting the phthalimide intermediate 2 with hydrazine in a solvent.

Examples of the solvent include methanol, ethanol and the like.

The reaction temperature is preferably under heating.

Step 4

A compound of the formula [D-IIa-24] can be produced by reacting a compound of the formula [D-IIa-23] in the same manner as in Production method 5-1-1, step 11.

Step 5

A compound of the formula [D-IIa-25] can be produced by reacting a compound of the formula [D-IIa-24] in the same manner as in Production method 5-1-1, step 12.

A compound of the formula [D-Ia-22], a compound of the formula [D-IIa-21], a compound of the formula [D-IIa-22], a compound of the formula [D-IIa-23], a compound of the formula [D-IIa-24] and a compound of the formula [D-IIa-25] can be each separated into a single compound (cis form or trans form) by recrystallization, silica gel column chromatography, HPLC and the like. The separated each compound can be reacted in the same manner as in the above-mentioned step 1 to step 5.

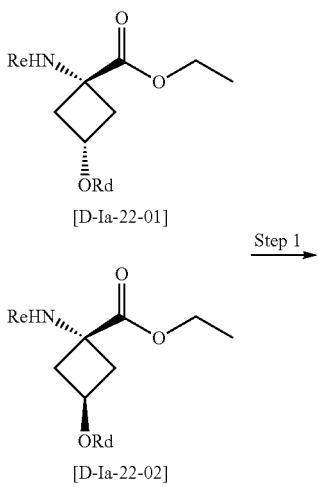

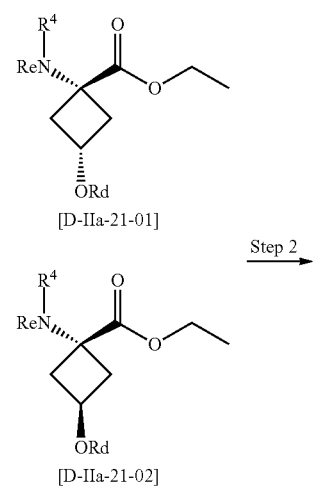

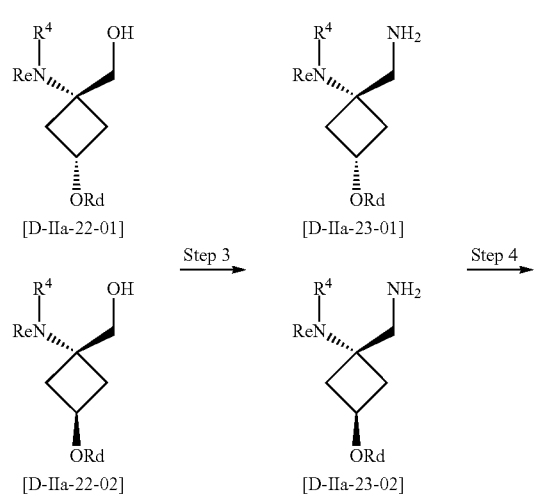

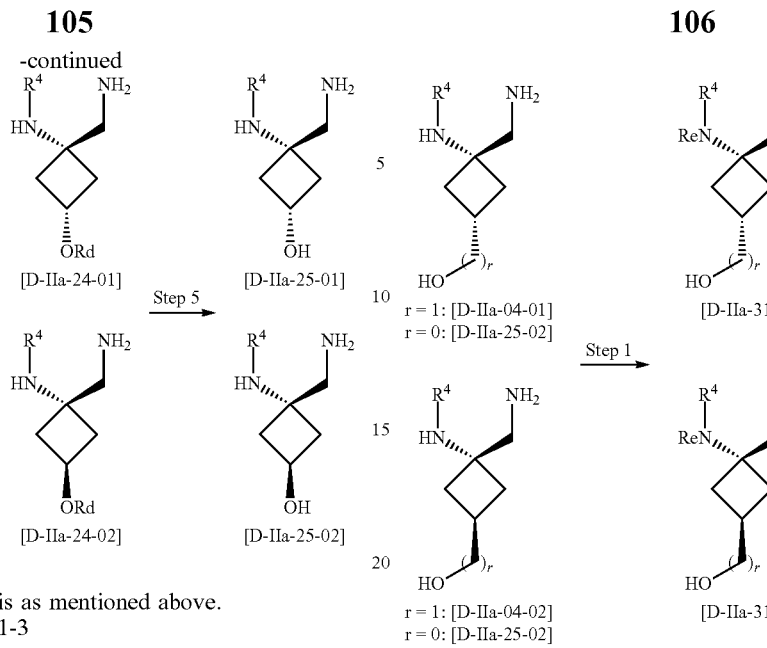

wherein each symbol is as mentioned above.
Production Method 6-1-3

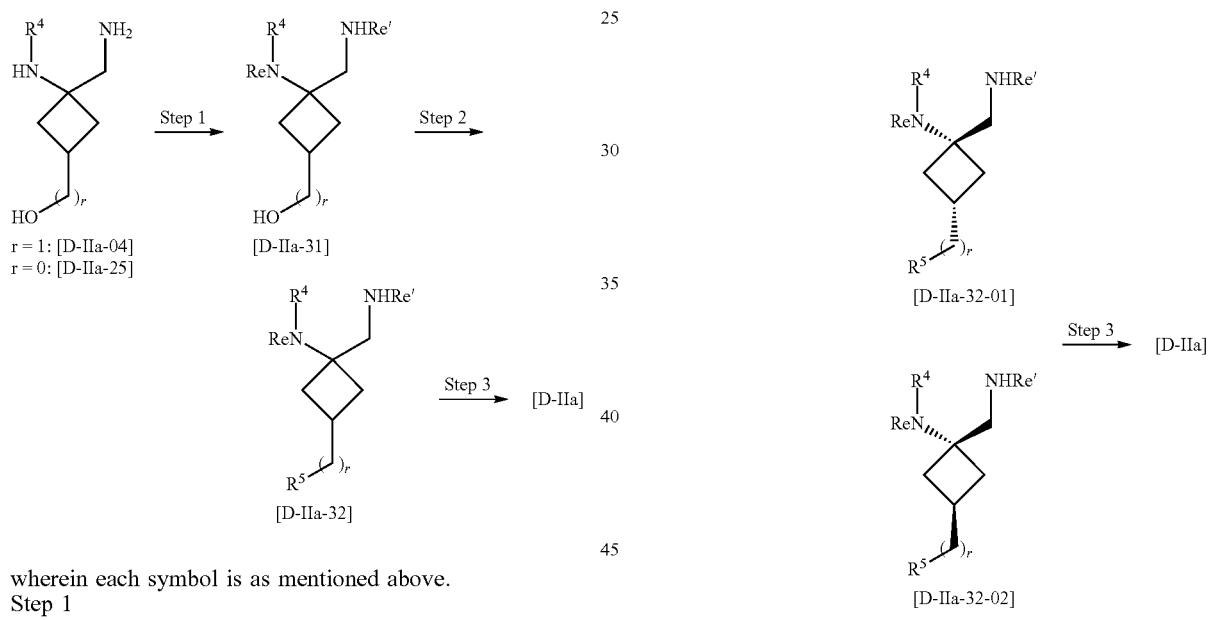

wherein each symbol is as mentioned above.

Step 1

A compound of the formula [D-IIa-31] can be produced by reacting a compound of the formula [D-IIa-04] or a compound of the formula [D-IIa-25] in the same manner as in Production method 5-1-1, step 7.

Step 2

A compound of the formula [D-IIa-32] can be produced by reacting a compound of the formula [D-IIa-31] in the same manner as in Production methods 2-1 to 2-6.

Step 3

A compound of the formula [D-IIa] can be produced by reacting a compound of the formula [D-IIa-32] in the same manner as in Production method 5-1-1, step 11.

The compound of a compound of the formula [D-IIa-04], the formula [D-IIa-25], a compound of the formula [D-IIa-31], a compound of the formula [D-IIa-32] and a compound of the formula [D-IIa] can be each separated into a single compound (cis form or trans form) by silica gel column chromatography, HPLC and the like. The separated each compound can be reacted in the same manner as in the above-mentioned step 1 to step 3.

Production Method 6-2

A compound of the formula [D-II] wherein q is 0 (hereinafter to be referred to as a compound of the formula [D-IIb]) can be produced by the following Production methods 6-2-1 to 6-2-9.

Production Method 6-2-1

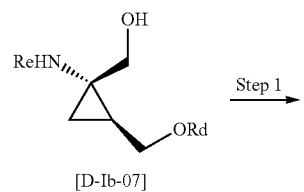

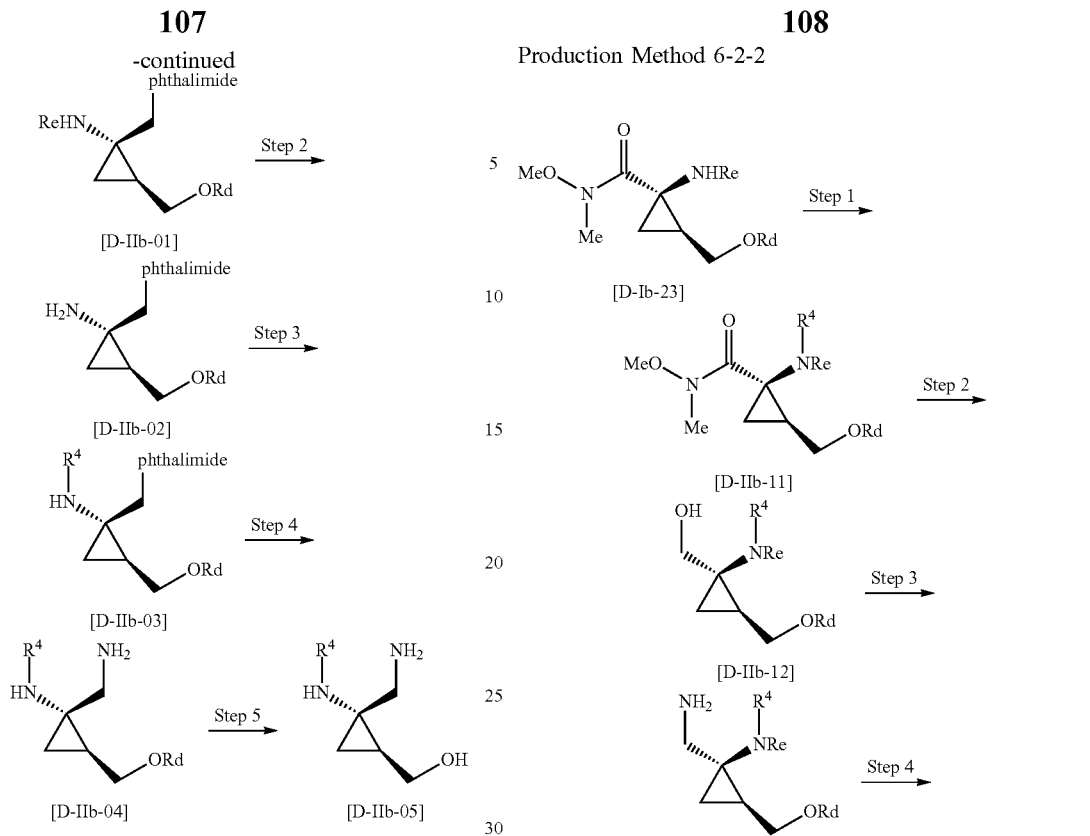

wherein each symbol is as mentioned above.

Step 1

A compound of the formula [D-IIb-01] can be produced by reacting a compound of the formula [D-Ib-07] obtained in Production method 5-2-1, step 7, phthalimide, an azo compound, and an additive in a solvent.

Examples of the solvent include a single or mixed solvent of THF, methylene chloride, chloroform, DMF, ethyl acetate, toluene and the like.

Examples of the azo compound include diisopropyl azodicarboxylate, diethyl azodicarboxylate, N,N,N',N'-tetramethylazodicarboxamide, 1,1'-(azodicarbonyl)dipiperidine and the like.

Examples of the additive include phosphorus reagents such as triphenylphosphine, diphenyl(2-pyridyl)phosphine, tributylphosphine, tri-tert-butylphosphine, etc., and the like.

The reaction temperature is preferably room temperature.

Step 2

A compound of the formula [D-IIb-02] can be produced by reacting a compound of the formula [D-IIb-01] in the same manner as in Production method 5-1-1, step 11.

Step 3

A compound of the formula [D-IIb-03] can be produced by reacting a compound of the formula [D-IIb-02] in the same manner as in Production method 5-1-1, step 9.

Step 4

A compound of the formula [D-IIb-04] can be produced by reacting a compound of the formula [D-IIb-03] with hydrazine in a solvent.

Examples of the solvent include methanol, ethanol and the like.

The reaction temperature is preferably under heating.

Step 5

A compound of the formula [D-IIb-05] can be produced by reacting a compound of the formula [D-IIb-04] in the same manner as in Production method 5-1-1, step 12.

Production Method 6-2-2

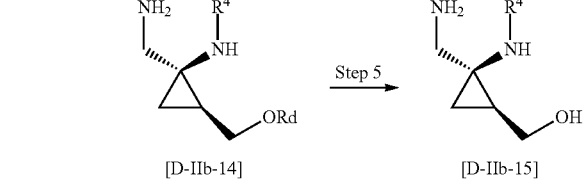

wherein each symbol is as mentioned above.

Step 1

A compound of the formula [D-IIb-11] can be produced from a compound of the formula [D-Ib-23] obtained in Production method 5-2-2, step 3 in the same manner as in Production method 6-1-1, step 1.

Step 2

A compound of the formula [D-IIb-12] can be produced by reacting a compound of the formula [D-IIb-11] with a reducing agent.

Examples of the solvent include ether solvents such as tetrahydrofuran, 1,2-dimethoxyethane, 1,4-dioxane and the like.

As the reducing agent, diisobutylaluminum hydride, lithium aluminum hydride are preferable.

The reaction temperature is preferably under ice-cooling to room temperature.

Step 3

A compound of the formula [D-IIb-13] can be produced from a compound of the formula [D-IIb-12] in the same manner as in Production method 6-1-2, step 3.

Step 4

A compound of the formula [D-IIb-14] can be produced from a compound of the formula [D-IIb-13] in the same manner as in Production method 5-1-1, step 11.

Step 5

A compound of the formula [D-IIb-15] can be produced from a compound of the formula [D-IIb-14] in the same manner as in Production method 5-1-1, step 12.

Production Method 6-2-3

The following compounds can be produced from a compound of the formula [D-Ib-37] obtained in Production method 5-2-3, step 7, and in the same manner as in Production method 6-2-1.

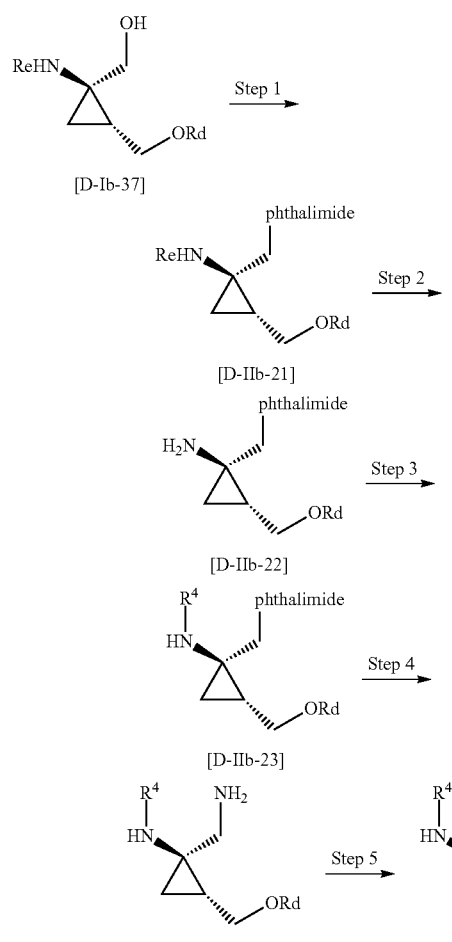

wherein each symbol is as mentioned above.

Production Method 6-2-4

The following compounds can be produced from a compound of the formula [D-Ib-53] obtained in Production method 5-2-4, step 9, and in the same manner as in Production method 6-2-2.

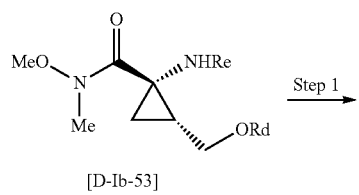

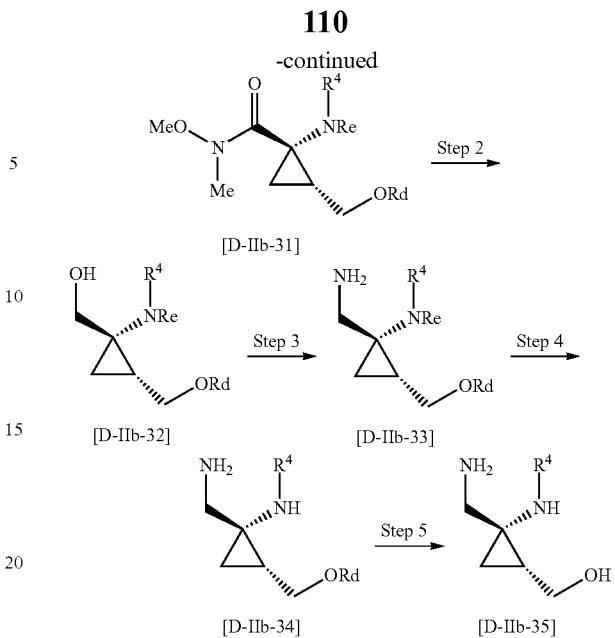

wherein each symbol is as mentioned above.

Production Method 6-2-5 wherein each symbol is as mentioned above.

Step 1

A compound of the formula [D-IIb-41] can be produced by reacting the compound D-Ib-62 obtained in Production method 5-2-5, step 2 in the same manner as in Production method 5-1-1, step 7.

Step 2

A compound of the formula [D-IIb-42] can be produced by reacting a compound of the formula [D-IIb-41] in the same manner as in Production method 5-2-5, step 4.

Step 3

A compound of the formula [D-IIb-43] can be produced by reacting a compound of the formula [D-IIb-42] in the same manner as in Production method 5-1-1, step 9.

Step 4

A compound of the formula [D-IIb-44] can be produced by reacting a compound of the formula [D-IIb-43] in the same manner as in Production method 5-1-1, step 11.

Step 5

A compound of the formula [D-IIb-45] can be produced by reacting a compound of the formula [D-IIb-44] in the same manner as in Production method 5-2-5, step 5.

Production Method 6-2-6

The following compounds can be produced from the compound D-Ib-62' obtained in Production method 5-2-6, step 2, and in the same manner as in Production method 6-2-5.

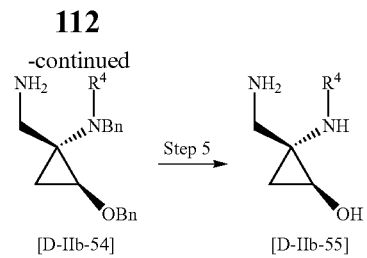

wherein each symbol is as mentioned above.

Production Method 6-2-8

The following compounds can be produced from the compound D-Ib-72' obtained in Production method 5-2-8, step 2, and in the same manner as in Production method 6-2-5.

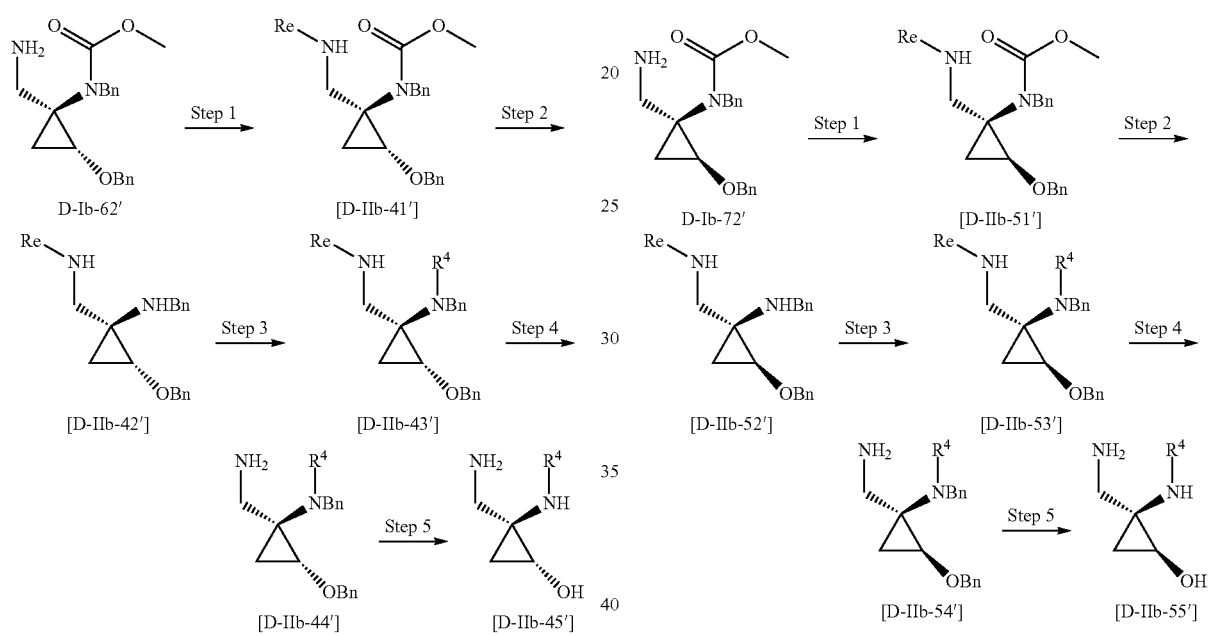

wherein each symbol is as mentioned above.

Production Method 6-2-7

The following compounds can be produced from the compound D-Ib-72 obtained in Production method 5-2-7, step 2 in the same manner as in Production method 6-2-5.

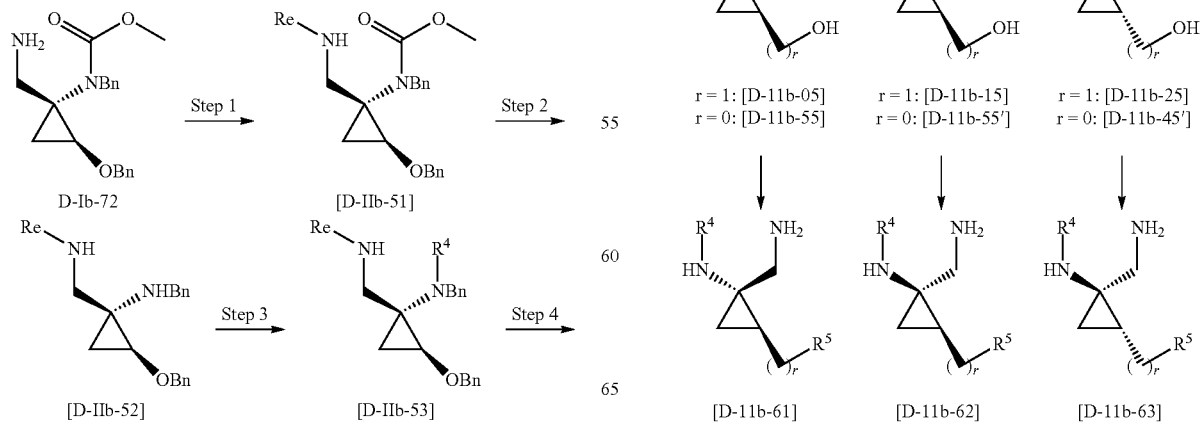

Production Method 6-2-9

113

-continued

R⁴ group structure [D-11b-35] (r=1) and [D-11b-45] (r=0):

$HN(R^4)$—cyclopropane—$CH_2NH_2$, —$(CH_2)_r$—OH r = 1: [D-11b-35]
r = 0: [D-11b-45]

↓

[D-11b-64]:

$HN(R^4)$—cyclopropane—$CH_2NH_2$, —$(CH_2)_r$—$R^5$

[D-11b-64]

wherein each symbol is as mentioned above.

Step 1

A compound of the formula [D-IIb-61], a compound of the formula [D-IIb-62], a compound of the formula [D-IIb-63] and a compound of the formula [D-IIb-64] can be produced by reacting a compound of the formula [D-IIb-05], a compound of the formula [D-IIb-55], a compound of the formula [D-IIb-15], a compound of the formula [D-IIb-55'], a compound of the formula [D-IIb-25], a compound of the formula [D-IIb-45'], a compound of the formula [D-IIb-35] or a compound of the formula [D-IIb-45] in the same manner as in Production method 5-1-1, step 10, Production methods 2-1 to 2-6, and then Production method 5-1-1, step 11.

EXAMPLES

Now, the production methods of the compound of the present invention are specifically explained by referring to Examples, which are not to be construed as limitative.

The abbreviations used in the specification mean the following.

Bn: benzyl group
Boc: tert-butoxycarbonyl group
Et: ethyl group
Me: methyl group
TBS: tert-butyldimethylsilyl group
Z: benzyloxycarbonyl group
THF: tetrahydrofuran
DMF: N,N-dimethyl formamide
DMSO: dimethyl sulfoxide
DME: 1,2-dimethoxyethane
TFA: trifluoroacetic acid
DPPA: diphenylphosphoryl azide
HOBt.H₂O: 1-hydroxybenzotriazole hydrate
EDC: 1-ethyl-3-(3-dimethylaminopropyl)carbodiimide hydrochloride
DIAD: diisopropyl azodicarboxylate
HATU: O-(7-aza-1H-benzotriazol-1-yl)-N,N,N',N'-tetramethyluronium hexafluorophosphate
Dess-Martin reagent: 1,1,1-triacetoxy-1,1-dihydro-1,2-benziodoxol-3 (1H)-one
DBU: diazabicycloundecene In addition, the following ¹H-NMR values were measured by resolution 400 MHz.

114

Reference Example 1 tert-butyl acetate + BnO—CH₂—C(O)—Cl → BnO—CH₂—C(O)—CH₂—C(O)—O-tBu

R1-1

Under nitrogen, a solution of 1M lithium bis(trimethylsilyl)amide-THF/ethylbenzene (100 mL) in THF (100 mL) was cooled to −70° C. and, under stirring, tert-butyl acetate (13.5 mL) was added dropwise. After stirring for 15 min, benzyloxyacetyl chloride (7.52 mL) was added dropwise. After stirring for 1 hr, 2N aqueous hydrochloric acid solution was added until the reaction mixture became pH=3 and the mixture was allowed to warm to room temperature. The mixture was extracted with ethyl acetate, and the organic layer was washed with 2N aqueous hydrochloric acid solution and saturated brine, dried over sodium sulfate and concentrated. The above operation was repeated again, and the both were combined to give compound R1-1 (40.3 g) as a crude product.

Step R1-2

R1-1 →

R1-2 (BnO—CH₂—C(O)—C(=CH—N(CH₃)₂)—C(O)—O-tBu)

To a solution of compound R1-1 (38 g) obtained in step R1-1 in toluene (80 mL) was added dimethylformamide dimethyl acetal (38 mL), and the mixture was stirred at 100° C. for 1 hr. The mixture was allowed to cool, concentrated, and purified by silica gel column chromatography (ethyl acetate:hexane=1:2 to ethyl acetate) to give compound R1-2 (11.3 g).

¹H-NMR (CDCl₃) δ: 7.66 (s, 1H), 7.40-7.13 (m, 5H), 4.60 (s, 2H), 4.42 (s, 2H), 3.40-2.65 (m, 6H), 1.45 (s, 9H).

Step R1-3

R1-2 →

-continued

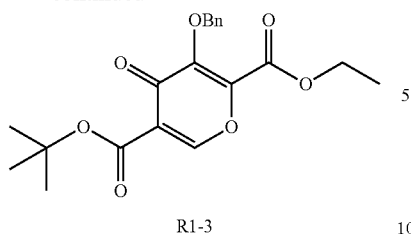

R1-3

Under nitrogen, a solution of 1M lithium bis(trimethylsilyl)amide-THF/ethylbenzene (42.5 mL) in THF (150 mL) was cooled to −70° C. and, under stirring, a solution of compound R1-2 (11.3 g) obtained in step R1-2 in THF (50 mL) was added dropwise over 3 min. After stirring for 20 min, ethyl chloroglyoxylate (4.75 mL) was added at once. After stirring for 25 min, saturated aqueous potassium hydrogen sulfate solution and ethyl acetate were added, and the mixture was allowed to warm to room temperature. The organic layer was separated and washed with saturated brine, dried over sodium sulfate, and concentrated. Toluene was added to the residue, and the mixture was once concentrated. Toluene (100 mL) and triethylamine (10 mL) were added and the mixture was stirred at room temperature. One hour later, the mixture was concentrated and purified by silica gel column chromatography (ethyl acetate:hexane=1:6 to 1:3) to give compound R1-3 (6.03 g).

$^1$H-NMR (CDCl$_3$) δ: 8.39 (s, 1H), 7.51-7.47 (m, 2H), 7.39-7.30 (m, 3H), 5.32 (s, 2H), 4.34 (q, 2H, J=7.2 Hz), 1.57 (s, 9H), 1.31 (t, 3H, J=7.2 Hz).

Step R1-4

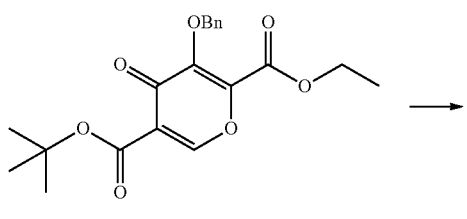

To a solution of compound R1-3 (18.7 g) obtained in step R1-3 in ethyl acetate (20 mL) was added under stirring 4N hydrochloric acid/ethyl acetate (200 mL), and the mixture was stirred at room temperature for 1 hr. Hexane (1 L) was added to the reaction mixture and, after stirring for a while, crystals were collected by filtration, and dried to give compound R1 (11.1 g).

$^1$H-NMR (CDCl$_3$) δ: 13.03 (s, 1H), 8.80 (s, 1H), 7.47-7.43 (m, 2H), 7.41-7.35 (m, 3H), 5.38 (s, 2H), 4.40 (q, 2H, J=7.2 Hz), 1.35 (t, 3H, J=7.2 Hz).

Example 1

Production of N-(3-chloro-2-fluorobenzyl)-9'-hydroxy-cis-3-methoxy-2'-methyl-1',8'-dioxo-1',2',3',8'-tetrahydrospiro[cyclobutane-1,4'-pyrido[1,2-a]pyrazine]-7'-carboxamide hydrochloride Step 1

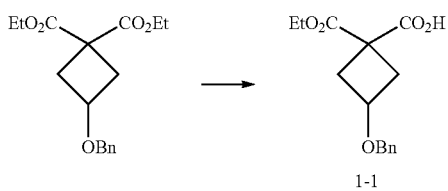 [SMILES: CCOC(=O)C1(C(=O)OCC)CC(OCc2ccccc2)C1 ; CCOC(=O)C1(C(=O)O)CC(OCc2ccccc2)C1]

To a mixed solution of commercially available 3-benzyloxycyclobutane-1,1-dicarboxylic acid diethyl ester (5.00 g) in ethanol-water (42 mL-10.5 mL) was added potassium hydroxide (981 mg, 85%), and the mixture was stirred at 100° C. for 16 hr. The reaction mixture was concentrated, water was added, and the mixture was extracted 3 times with diethyl ether to give organic layer 1-1 and aqueous layer 1-1.

The organic layer 1-1 was dried over magnesium sulfate, and concentrated to give a residue 1-1-1 (949 mg).

To aqueous layer 1-1 was added potassium hydrogen sulfate (7.67 g), and the mixture was extracted 3 times with ethyl acetate. The organic layer was washed with saturated brine, dried over magnesium sulfate, and concentrated. Toluene was added and the mixture was concentrated to give residue 1-1-2.

To the residue 1-1-1 (949 mg) were added ethanol (8 mL), water (2 mL), and potassium hydroxide (194 mg, 85%), and the mixture was stirred at 100° C. for 3.5 hr, and stood at room temperature for 3 days. To the reaction mixture was added aqueous potassium hydrogen sulfate solution, and the mixture was extracted twice with ethyl acetate. The organic layer was washed with saturated brine, dried over magnesium sulfate and concentrated to give a residue 1-1-3.

The residue 1-1-2 and the residue 1-1-3 were combined and so purified by silica gel column chromatography (hexane:ethyl acetate=1:2 to ethyl acetate:acetone=3:1) to give compound 1-1 (4.04 g).

$^1$H-NMR (CDCl$_3$) δ: 7.37-7.14 (m, 5H), 4.44 (s, 2H), 4.27-4.14 (m, 3H), 2.87-2.80 (m, 2H), 2.64-2.57 (m, 2H), 1.31-1.27 (m, 3H).

Step 2

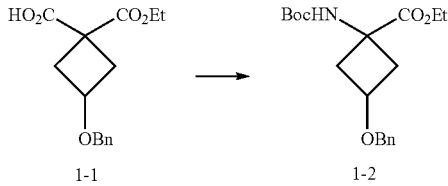 [SMILES: CCOC(=O)C1(C(=O)O)CC(OCc2ccccc2)C1 ; CCOC(=O)C1(NC(=O)OC(C)(C)C)CC(OCc2ccccc2)C1]

To a solution of compound 1-1 (104 mg) obtained in the above-mentioned step in toluene (1 mL) were added triethylamine (104 μL) and DPPA (113 μL) at room temperature under an argon atmosphere, and the mixture was stirred at room temperature for 20 min. tert-Butanol (3 mL) was added, and the mixture was stirred at 110° C. for 4 hr. The reaction mixture was concentrated, toluene was added, and the mixture was concentrated to give a residue 1-2-1. Similarly, to a solution of compound 1-1 (3.91 g) in toluene (40 mL) were added triethylamine (4.00 mL) and DPPA (4.25 mL) at room temperature under an argon atmosphere, and the mixture was stirred at room temperature for 20 min. tert-Butanol (120 mL) was added, and the mixture was stirred at 110° C. for 18 hr. The reaction mixture was concentrated, toluene was added, and the mixture was concentrated to give a residue 1-2-2.

The residue 1-2-1 and the residue 1-2-2 were combined and purified by silica gel column chromatography (hexane:ethyl acetate=10:1 to 5:1) to give compound 1-2 (4.49 g).

$^1$H-NMR (CDCl$_3$) δ: 7.35-7.28 (m, 5H), 5.16-4.86 (br m, 1H), 4.45-4.44 (m, 2H), 4.28-4.20 (m, 1H), 4.22-4.16 (m, 2H), 2.94-2.89 (m, 1H), 2.66-2.61 (m, 1H), 2.51-2.43 (br m, 1H), 2.33-2.25 (br m, 1H), 1.43 (s, 9H), 1.29-1.25 (m, 3H).

Step 3

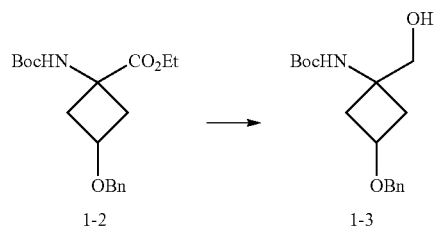 [SMILES: CCOC(=O)C1(NC(=O)OC(C)(C)C)CC(OCc2ccccc2)C1 ; CC(C)(C)OC(=O)NC1(CO)CC(OCc2ccccc2)C1]

To a solution of lithium aluminum hydride (1.00 g) in THF (30 mL) was added dropwise a solution of compound 1-2 (4.49 g) in THF (15 mL) under ice-cooling under a nitrogen atmosphere. The mixture was stirred for 30 min, and at room temperature for 1 hr. The reaction mixture was ice-cooled, water (1.00 mL) and 10% aqueous sodium hydroxide solution (1.00 mL) were successively added, and the mixture was stirred for 3 min. Water (3.01 mL) was added again, and the mixture was stirred at room temperature for 30 min. The solid was filtered off, and washed with THF. The filtrate was concentrated, toluene was added and the mixture was concentrated. The operation of concentration with toluene was performed twice to give compound 1-3 (4.37 g).

$^1$H-NMR (CDCl$_3$) δ: 7.38-7.27 (m, 5.00H), 4.89-4.87 (br m, 0.45H), 4.83-4.80 (br m, 0.55H), 4.42 (s, 0.90H), 4.41 (s, 1.10H), 4.24 (tt, 0.55H, J=7.2, 5.3 Hz), 3.91 (quint, 0.45H, J=7.0 Hz), 3.76-3.75 (m, 1.10H), 3.64-3.61 (m, 0.90H), 2.67-2.62 (m, 0.90H), 2.47-2.42 (m, 1.10H), 2.20-2.14 (m, 1.10H), 2.05-2.00 (m, 0.90H), 1.44 (s, 4.95H), 1.43 (s, 4.05H).

Step 4

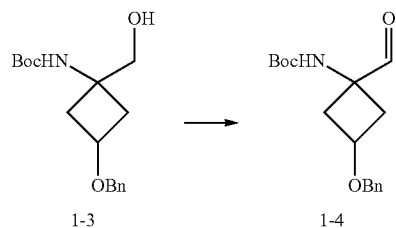 [SMILES: CC(C)(C)OC(=O)NC1(CO)CC(OCc2ccccc2)C1 ; CC(C)(C)OC(=O)NC1(C=O)CC(OCc2ccccc2)C1]

To a solution of compound 1-3 (198 mg) obtained in the above-mentioned step in chloroform (3 mL) was added Dess-Martin reagent (554 mg), and the mixture was stirred at room temperature for 1 hr. To the reaction mixture was added saturated aqueous sodium hydrogen carbonate solution, sodium sulfite was added, and the mixture was extracted twice with ethyl acetate. The organic layer was washed with saturated brine, dried over magnesium sulfate and concentrated to give a crude product of compound 1-4. The obtained crude product of compound 1-4 was directly used in the next step.

Step 5

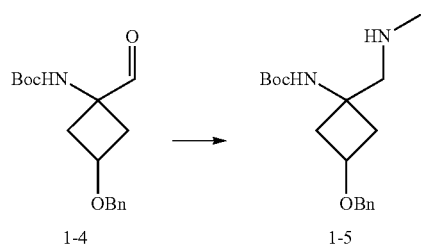 [SMILES: CC(C)(C)OC(=O)NC1(C=O)CC(OCc2ccccc2)C1 ; CNCC1(NC(=O)OC(C)(C)C)CC(OCc2ccccc2)C1]

To a solution of methylamine hydrochloride (285 mg) in chloroform (4 mL) was added triethylamine (577 μL), and the mixture was stirred at room temperature for 16 min. A solution of the crude product of compound 1-4 in chloroform (4 mL) and acetic acid (212 μL) were successively added, and the mixture was stirred at room temperature for 15 min. Sodium triacetoxyborohydride (800 mg) was added, and the mixture was stirred at room temperature for 3 days. To the reaction mixture was added saturated aqueous sodium hydrogen carbonate solution, and the mixture was extracted 3 times with chloroform. The organic layer was dried over magnesium sulfate and concentrated to give a crude product of compound 1-5. The obtained crude product of compound 1-5 was directly used in the next step.

Step 6

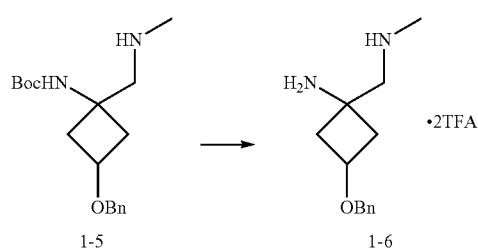 [SMILES: CNCC1(NC(=O)OC(C)(C)C)CC(OCc2ccccc2)C1 ; CNCC1(N)CC(OCc2ccccc2)C1]

To the crude product of compound 1-5 obtained in the above-mentioned step was added TFA (2 mL), and the mixture was stood at room temperature for 20 min. The reaction mixture was concentrated, chloroform was added and the mixture was concentrated again to give a crude product of compound 1-6. The obtained crude product of compound 1-6 was directly used in the next step.

Step 7

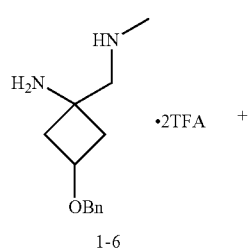

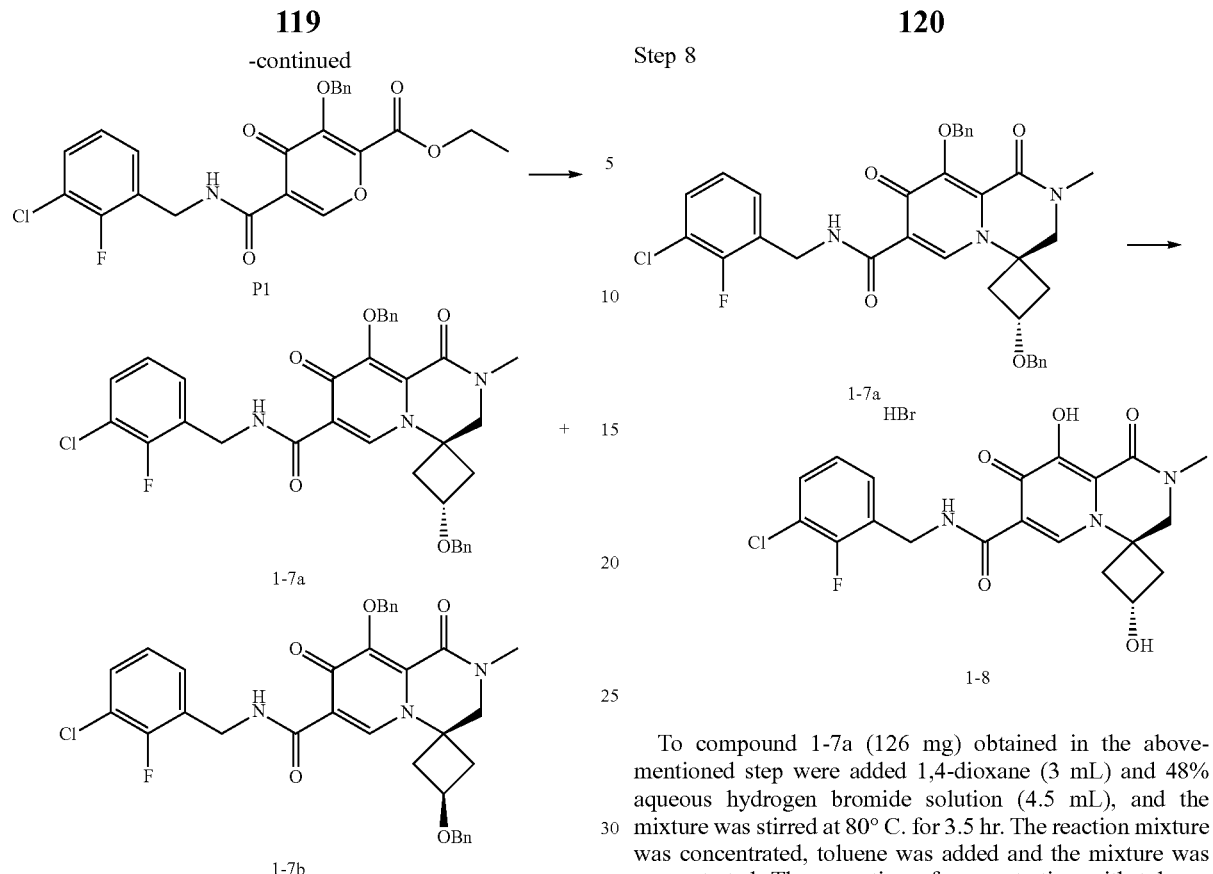

To a solution of the crude product of compound 1-6 obtained in the above-mentioned step in THF (3 mL) were added triethylamine (1 mL) and ethanol (0.5 mL), and a solution of compound P1 (269 mg) obtained in the below-mentioned Preliminary step 1-1 in THF (2 mL) was added. After stirring at room temperature for 30 min, the reaction mixture was concentrated, toluene (15 mL) and DBU (1 mL) were added, and the mixture was stirred at 80° C. for 1 hr. To the reaction mixture was added acetic acid (2 mL), and the mixture was stirred at 100° C. for 1 hr. The reaction mixture was concentrated, ethyl acetate and 10% aqueous potassium hydrogen sulfate solution were added, and the mixture was extracted 3 times with ethyl acetate. The organic layer was washed with saturated brine, dried over magnesium sulfate, and concentrated. The residue was purified by silica gel column chromatography (hexane:ethyl acetate=2:1 to 0:1), and then silica gel thin layer chromatography (ethyl acetate) to give compound 1-7a (126 mg) and compound 1-7b (115 mg).

Compound 1-7a $^1$H-NMR (CDCl$_3$) δ: 10.54 (t, 1H, J=6.0 Hz), 8.76 (s, 1H), 7.61-7.59 (m, 2H), 7.40-7.27 (m, 10H), 7.06-7.02 (m, 1H), 5.30 (s, 2H), 4.71 (d, 2H, J=6.0 Hz), 4.49 (s, 2H), 3.98 (quint, 1H, J=6.6 Hz), 3.40 (s, 2H), 3.15 (s, 3H), 2.62-2.59 (m, 4H).

Compound 1-7b $^1$H-NMR (CDCl$_3$) δ: 10.57-10.54 (br m, 1H), 8.65 (s, 1H), 7.61-7.58 (m, 2H), 7.40-7.27 (m, 10H), 7.06-7.02 (m, 1H), 5.30 (s, 2H), 4.70 (d, 2H, J=6.2 Hz), 4.48 (s, 2H), 4.39-4.34 (m, 1H), 3.72 (s, 2H), 3.15 (s, 3H), 2.87-2.82 (m, 2H), 2.35-2.30 (m, 2H).

Step 8

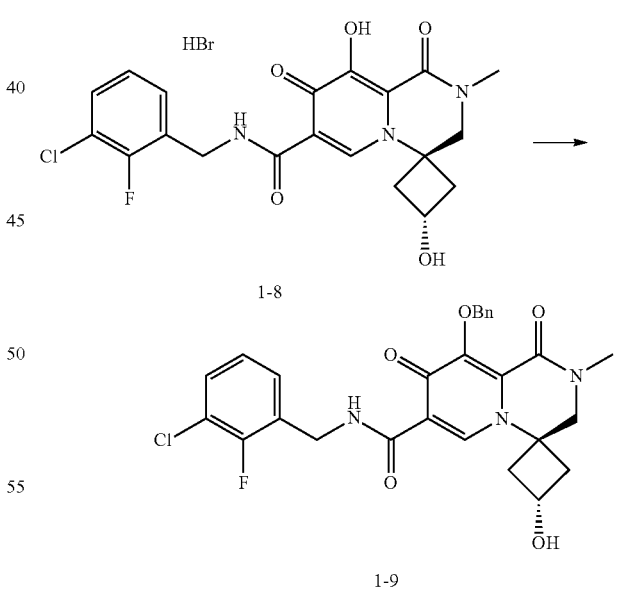

To compound 1-7a (126 mg) obtained in the above-mentioned step were added 1,4-dioxane (3 mL) and 48% aqueous hydrogen bromide solution (4.5 mL), and the mixture was stirred at 80° C. for 3.5 hr. The reaction mixture was concentrated, toluene was added and the mixture was concentrated. The operation of concentration with toluene was performed 3 times to give a crude product of compound 1-8.

Step 9

To the crude product of compound 1-8 obtained in the above-mentioned step were added potassium carbonate (300 mg), DMF (3 mL), and benzyl bromide (80 μL), and the mixture was stirred at room temperature for 8 hr. Potassium carbonate (100 mg) and benzylbromide (30 μL) were added, and the mixture was stirred at room temperature for 1 hr and stood for 3 days. To the reaction mixture was added saturated brine, and the mixture was extracted 3 times with ethyl acetate. The organic layer was washed with saturated brine, dried over magnesium sulfate, concentrated and purified by silica gel thin layer chromatography (chloroform:acetone=1:1) to give compound 1-9 (101 mg).

¹H-NMR (CDCl₃) δ: 10.62-10.59 (br m, 1H), 8.80 (s, 1H), 7.62-7.59 (m, 2H), 7.37-7.27 (m, 5H), 7.06-7.02 (m, 1H), 5.30 (s, 2H), 4.71 (d, 2H, J=6.2 Hz), 4.36-4.31 (m, 1H), 3.43 (s, 2H), 3.18 (s, 3H), 2.85 (d, 1H, J=6.5 Hz), 2.74-2.69 (m, 2H), 2.66-2.61 (m, 2H).

Step 10

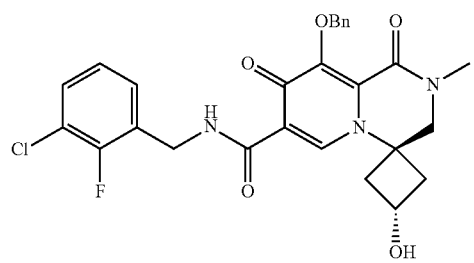

1-9

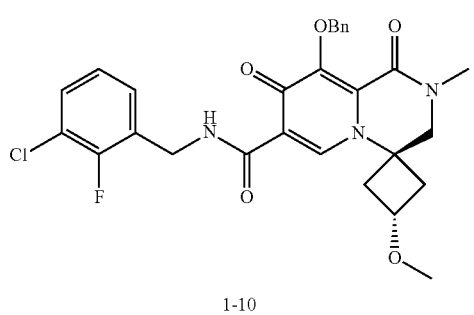

1-10

To a mixed solution of compound 1-9 (27 mg) obtained in the above-mentioned step in toluene-methylene chloride (3 mL-3 mL) were added tetrabutylammonium hydrogen sulfate (30 mg), dimethyl sulfate (33 μL) and 50% aqueous sodium hydroxide solution (48 μL), and the mixture was stirred at room temperature for 20 min. Dimethyl sulfate (33 μL) and 50% aqueous sodium hydroxide solution (48 μL) were added 3 times every 30 min, and the mixture was further stirred at room temperature for 30 min. To the reaction mixture was added triethylamine (0.5 mL) and the mixture was stirred for 50 min. 10% Aqueous potassium hydrogen sulfate solution was added, and the mixture was extracted 3 times with chloroform. The organic layer was dried over magnesium sulfate, concentrated, and purified by silica gel thin layer chromatography (chloroform:acetone=3:2) to give compound 1-10 (24 mg).

¹H-NMR (CDCl₃) δ: 10.54 (t, 1H, J=6.0 Hz), 8.76 (s, 1H), 7.62-7.60 (m, 2H), 7.37-7.27 (m, 5H), 7.06-7.02 (m, 1H), 5.30 (s, 2H), 4.71 (d, 2H, J=6.0 Hz), 3.85 (quint, 1H, J=6.5 Hz), 3.43 (s, 2H), 3.29 (s, 3H), 3.18 (s, 3H), 2.67-2.62 (m, 2H), 2.59-2.54 (m, 2H).

Step 11

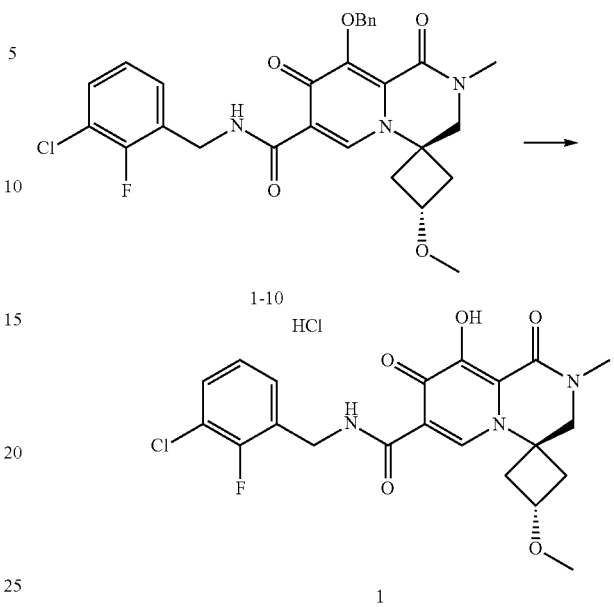

1-10
HCl

1

To compound 1-10 (24 mg) obtained in the above-mentioned step were successively added 4N hydrochloric acid/1,4-dioxane (1 mL) and TFA (3 mL), and the mixture was stood at room temperature for 2 hr. The reaction mixture was concentrated, ethyl acetate was added and the mixture was concentrated again. Ethyl acetate (200 μL), hexane (7.5 mL), and 4N hydrochloric acid/ethyl acetate (100 μL) were added. The mixture was stirred for a while and supernatant liquid was removed by decantation. Ethyl acetate (400 μL), hexane (11.5 mL), and 4N hydrochloric acid/ethyl acetate (100 μL) were added again. The mixture was stirred for a while and supernatant liquid was removed by decantation. The obtained residue was dried under reduced pressure to give the title compound (8.7 mg).

¹H-NMR (DMSO-d₆) δ: 12.83 (br s, 1H), 10.43 (t, 1H, J=6.0 Hz), 8.48 (s, 1H), 7.52-7.47 (m, 1H), 7.35-7.31 (m, 1H), 7.22-7.18 (m, 1H), 4.62 (d, 2H, J=6.0 Hz), 3.97 (quint, 1H, J=6.4 Hz), 3.79 (s, 2H), 3.20 (s, 3H), 3.12 (s, 3H), 2.70-2.65 (m, 2H), 2.42-2.37 (m, 2H).

Preliminary Step 1-1

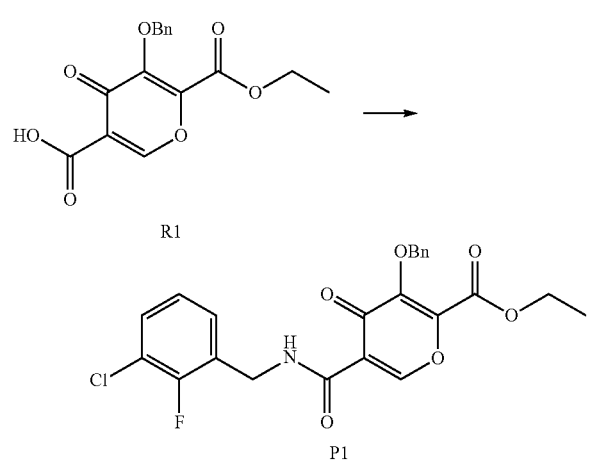

R1

P1

To a solution of compound R1 (504 mg) obtained in Reference Example 1, step R1-4 in chloroform (6 mL) were added oxalyl chloride (276 μL) and a catalytic amount of DMF under ice-cooling, and the mixture was stirred at room temperature for 30 min. The mixture was concentrated, and dissolved in chloroform (6 mL) and a solution of commercially available 3-chloro-2-fluorobenzylamine (215 mg) and triethylamine (441 μL) in chloroform (8 mL) was added dropwise at an outer temperature of −50° C. After the completion of the dropwise addition, the mixture was stirred at room temperature overnight. To the reaction mixture were added ethyl acetate and 0.5N hydrochloric acid and, after partitioning, the organic layer was washed with 0.5N aqueous sodium hydroxide solution and saturated brine. The mixture was dried, concentrated and purified by silica gel column chromatography (hexane:ethyl acetate=20:1 to 2:1) to give compound P1 (581 mg).

$^1$H-NMR (CDCl$_3$) δ: 9.62-9.47 (m, 1H), 8.79 (s, 1H), 7.50-7.43 (m, 2H), 7.40-7.24 (m, 5H), 7.06 (t, 1H, J=7.9 Hz), 5.28 (s, 2H), 4.68 (d, 2H, J=6.2 Hz), 4.37 (q, 2H, J=7.2 Hz), 1.33 (t, 3H, J=7.2 Hz).

Example 2

Production of N-(3-chloro-2-fluorobenzyl)-9'-hydroxy-trans-3-methoxy-2'-methyl-1',8'-dioxo-1',2',3', 8'-tetrahydrospiro[cyclobutane-1,4'-pyrido[1,2-a]pyrazine]-7'-carboxamide hydrochloride Step 1

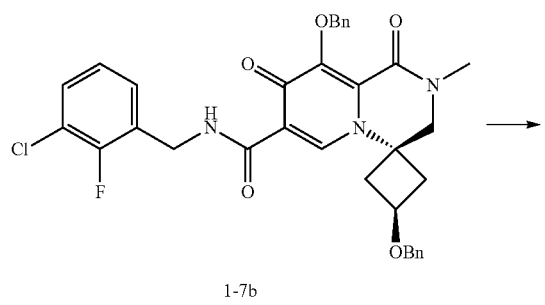

1-7b

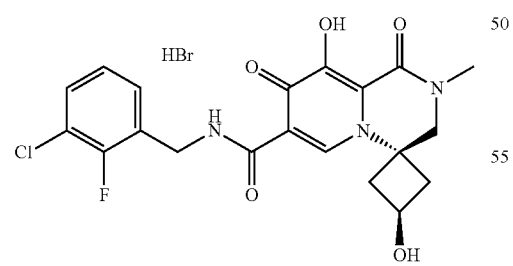

2-1

From compound 1-7b (115 mg) obtained in Example 1, step 7, and by a method similar to that in Example 1, step 8, a crude product of compound 2-1 was obtained. The obtained crude product of compound 2-1 was directly used in the next step.

Step 2

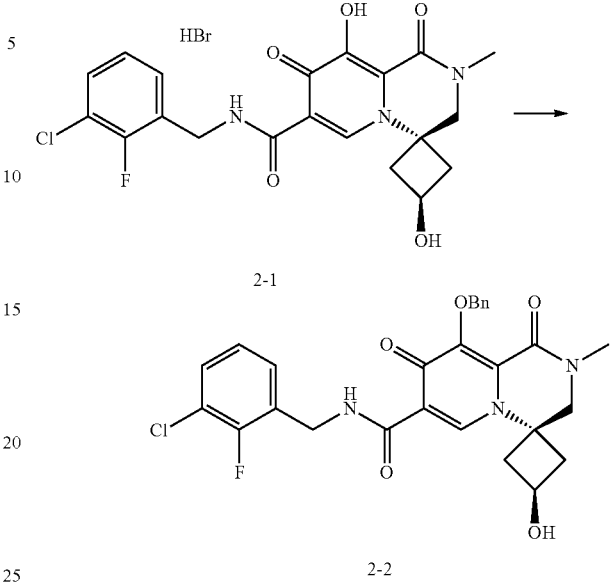

2-1

2-2

From a crude product of compound 2-1 obtained in the above-mentioned step, and by a method similar to that in Example 1, step 9, compound 2-2 (112 mg) was obtained.

$^1$H-NMR (CDCl$_3$) δ: 10.56 (br s, 1H), 8.65 (s, 1H), 7.62-7.59 (m, 2H), 7.37-7.28 (m, 5H), 7.06-7.00 (m, 1H), 5.31 (s, 2H), 4.74-4.70 (m, 3H), 3.79 (s, 2H), 3.20 (s, 3H), 2.95-2.88 (m, 2H), 2.33-2.31 (m, 1H), 2.30-2.28 (m, 1H), 2.17-2.15 (m, 1H).

Step 3

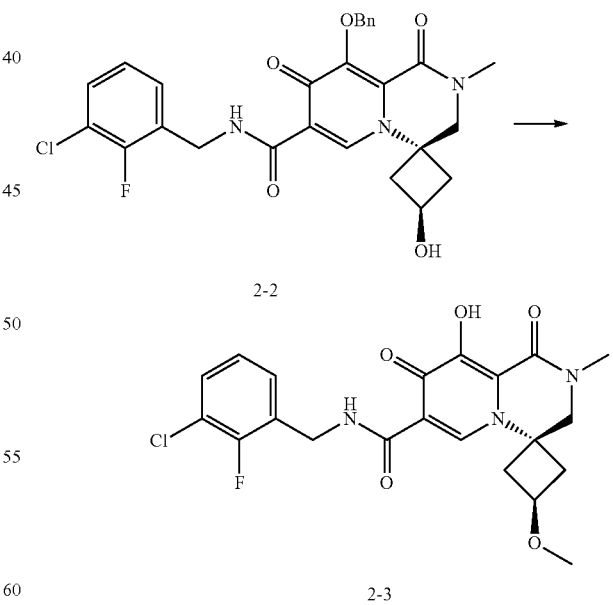

2-2

2-3

From compound 2-2 (24 mg) obtained in the above-mentioned step, and by a method similar to that in Example 1, step 10, compound 2-3 (22 mg) was obtained.

$^1$H-NMR (CDCl$_3$) δ: 10.56 (t, 1H, J=6.2 Hz), 8.67 (s, 1H), 7.62-7.59 (m, 2H), 7.37-7.28 (m, 5H), 7.06-7.02 (m, 1H), 5.31 (s, 2H), 4.71 (d, 2H, J=6.2 Hz), 4.18-4.13 (m, 1H), 3.71 (s, 2H), 3.30 (s, 3H), 3.19 (s, 3H), 2.86-2.81 (m, 2H), 2.33-2.30 (m, 1H), 2.29-2.27 (m, 1H).

Step 4

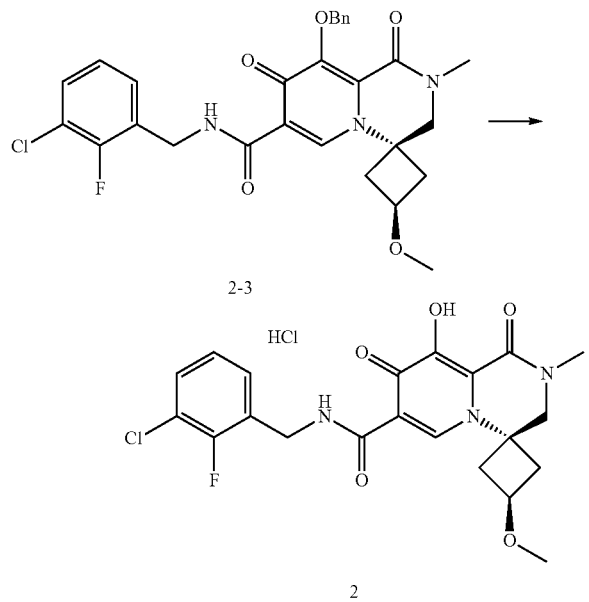

From compound 2-3 (22 mg) obtained in the above-mentioned step, and by a method similar to that in Example 1, step 11, the title compound (15.2 mg) was obtained.

$^1$H-NMR (DMSO-$d_6$) δ: 12.89 (br s, 1H), 10.45 (t, 1H, J=6.1 Hz), 8.48 (s, 1H), 7.52-7.47 (m, 1H), 7.35-7.31 (m, 1H), 7.22-7.18 (m, 1H), 4.62 (d, 2H, J=6.1 Hz), 4.11-4.05 (m, 1H), 3.88 (s, 2H), 3.20 (s, 3H), 3.11 (s, 3H), 2.86-2.81 (m, 2H), 2.35-2.30 (m, 2H).

Example 3

Production of N-(3-chloro-2-fluorobenzyl)-9'-hydroxy-cis-3-(methoxymethyl)-2'-methyl-1',8'-dioxo-1',2',3',8'-tetrahydrospiro[cyclobutane-1,4'-pyrido[1,2-a]pyrazine]-7'-carboxamide hydrochloride Step 1

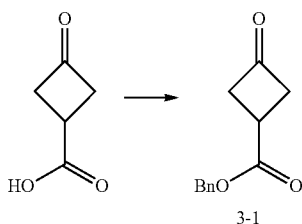 [SMILES: O=C1CC(C(=O)O)C1 ; O=C1CC(C(=O)OCc2ccccc2)C1]

To a solution of commercially available 3-oxocyclobutanecarboxylic acid (14.9 g) in DMF (210 mL) were added potassium carbonate (27.07 g) and benzyl bromide (18.6 mL), and the mixture was stirred at room temperature for 2 hr. To the reaction mixture was added acetic acid (22.4 mL) over 12 min, and the mixture was stirred at room temperature for 10 min. Water (350 mL) was added, and the mixture was extracted 3 times with ethyl acetate. The organic layer was washed 4 times with saturated brine, dried over magnesium sulfate and concentrated. Toluene was added and the mixture was concentrated to give a crude product of compound 3-1. The obtained crude product of compound 3-1 was directly used in the next step.

Step 2

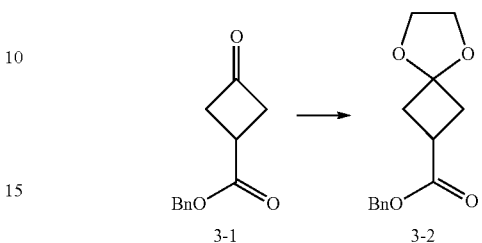

To a solution of a crude product of compound 3-1 obtained in the above-mentioned step in toluene (400 mL) were added pyridinium p-toluenesulfonate (4.91 g) and ethylene glycol (8 mL), and the mixture was stirred under reflux by heating for 2.5 hr. Ethylene glycol (1.5 mL) was added, and the mixture was stirred under reflux by heating for 1.5 hr. Ethylene glycol (2.3 mL) was added again, and the mixture was further stirred under reflux by heating for 2 hr. The reaction mixture was allowed to cool to room temperature, saturated aqueous sodium hydrogen carbonate solution was added, and the mixture was extracted twice with ethyl acetate. The organic layer was washed with saturated brine, dried over magnesium sulfate and concentrated to give a crude product of compound 3-2. The obtained crude product of compound 3-2 was directly used in the next step.

Step 3

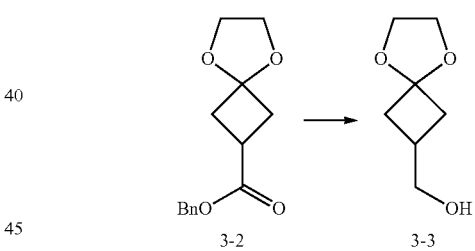

To a solution of lithium aluminum hydride (5.93 g) in THF (150 mL) was added dropwise a solution of the crude product of compound 3-2 obtained in the above-mentioned step in THF (150 mL) over 15 min under ice-cooling under a nitrogen atmosphere. The mixture was stirred at room temperature for 40 min, ice-cooled again, ethyl acetate (36 mL), water (18 mL), 4.0M aqueous sodium hydroxide solution (18 mL), and water (54 mL) were successively added, and the mixture was stirred at room temperature for 1 hr. The reaction mixture was filtered through Celite, and washed with ethyl acetate and water, and the filtrate was concentrated to give residue 3-3.

To the residue 3-3 were added ethyl acetate and water, and the mixture was extracted 9 times with ethyl acetate. The organic layer was washed successively with saturated aqueous sodium hydrogen carbonate solution and saturated brine, dried over sodium sulfate, and concentrated. The residue was purified by silica gel column chromatography (hexane: ethyl acetate=100:0 to 0:100) to give compound 3-3 (15.20 g).

¹H-NMR (CDCl₃) δ: 3.93-3.86 (m, 4H), 3.68 (dd, 2H, J=6.7, 5.5 Hz), 2.47-2.40 (m, 2H), 2.34-2.24 (m, 1H), 2.14-2.07 (m, 2H), 1.41 (t, 1H, J=5.5 Hz).

Step 4

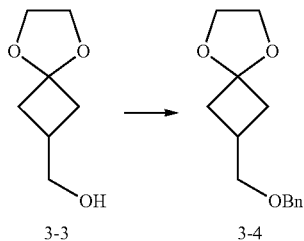 [SMILES: OCC1CC2(C1)OCCO2 ; c1ccc(COCC2CC3(C2)OCCO3)cc1]

To a solution of compound 3-3 (5.00 g) obtained in the above-mentioned step in DMF (25 mL) were added sodium hydride (60% dispersion, 2.77 g) and benzyl bromide (6.19 mL) under ice-cooling, and the mixture was warmed to room temperature and stirred for 2 hr. To the reaction mixture was added under ice-cooling saturated aqueous ammonium chloride solution, and the mixture was extracted with ethyl acetate. The organic layer was washed successively with water and saturated brine, dried over sodium sulfate, and concentrated. The residue was purified by silica gel column chromatography (hexane:ethyl acetate=100:0 to 85:15) to give compound 3-4 (7.23 g).

¹H-NMR (CDCl₃) δ: 7.37-7.27 (m, 5H), 4.52 (s, 2H), 3.91-3.84 (m, 4H), 3.50 (d, 2H, J=6.9 Hz), 2.46-2.30 (m, 3H), 2.13-2.07 (m, 2H).

Step 5

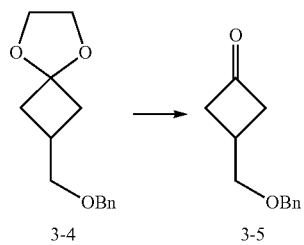 [SMILES: c1ccc(COCC2CC3(C2)OCCO3)cc1 ; O=C1CC(COCc2ccccc2)C1]

To a solution of compound 3-4 (7.21 g) obtained in the above-mentioned step in THF (36 mL) was added 2N hydrochloric acid (15.4 mL) at room temperature, and the mixture was stirred at room temperature overnight. The reaction mixture was extracted with ethyl acetate, and the organic layer was washed successively with water, saturated aqueous sodium hydrogen carbonate solution, water and saturated brine, dried over sodium sulfate, and concentrated to give compound 3-5 (6.32 g).

¹H-NMR (CDCl₃) δ: 7.38-7.27 (m, 5H), 4.56 (s, 2H), 3.60 (d, 2H, J=6.6 Hz), 3.17-3.08 (m, 2H), 2.92-2.84 (m, 2H), 2.75-2.64 (m, 1H).

Step 6

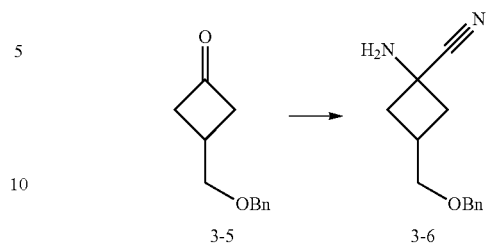

To compound 3-5 (5.09 g) obtained in the above-mentioned step was added under ice-cooling 7N ammonia/methanol (25 mL), and the mixture was stirred at the same temperature for 1 hr to give solution 3-6.

Ammonium chloride (3.58 g) and potassium cyanide (2.27 g) were dissolved in 28% aqueous ammonia (50 mL), and the solution 3-6 was added dropwise. The mixture was stirred at room temperature for 3 days, and extracted with chloroform and the organic layer was washed with saturated brine, dried over sodium sulfate, and concentrated. The residue was purified by silica gel column chromatography (hexane:ethyl acetate=100:0 to 20:80) to give compound 3-6 (major form: 1.89 g, minor form: 861 mg, 63:37 major/minor mixture: 1.68 g).

Major Form

¹H-NMR (CDCl₃) δ: 7.37-7.27 (m, 5H), 4.52 (s, 2H), 3.47 (d, 2H, J=5.3 Hz), 2.76-2.70 (m, 2H), 2.68-2.58 (m, 1H), 2.09-2.03 (m, 2H), 1.85 (br s, 2H).

Minor Form

¹H-NMR (CDCl₃) δ: 7.37-7.27 (m, 5H), 4.53 (s, 2H), 3.49 (d, 2H, J=6.2 Hz), 2.92-2.81 (m, 1H), 2.48-2.43 (m, 2H), 2.20-2.15 (m, 2H), 1.82 (br s, 2H).

Step 7

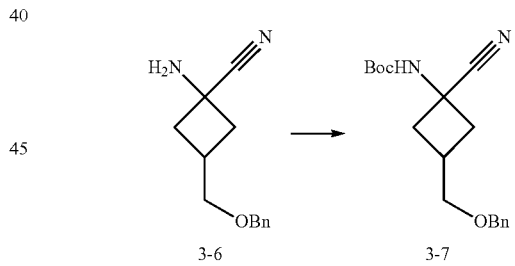

To a solution of compound 3-6 (1.0 g, 63:37 major/minor mixture) obtained in the above-mentioned step in 1,4-dioxane (5 mL) were added saturated aqueous sodium hydrogen carbonate solution (5 mL) and di-tert-butyl dicarbonate (1.21 g), and the mixture was stirred at room temperature overnight. To the reaction mixture was added water, and the mixture was extracted with ethyl acetate. The organic layer was washed with saturated brine, dried over sodium sulfate, and concentrated. The residue was purified by silica gel column chromatography (hexane:ethyl acetate=100:0 to 60:40) to give compound 3-7 (1.54 g).

¹H-NMR (CDCl₃) δ: 7.37-7.27 (m, 5.00H), 4.87 (br s, 1.00H), 4.53 (s, 0.70H), 4.51 (s, 1.30H), 3.51 (d, 0.70H, J=6.2 Hz), 3.44 (d, 1.30H, J=3.5 Hz), 2.83-2.73 (m, 2.30H), 2.60-2.54 (m, 0.70H), 2.43-2.38 (m, 0.70H), 2.22-2.17 (m, 1.30H), 1.48 (s, 3.15H), 1.47 (s, 5.85H).

Step 8

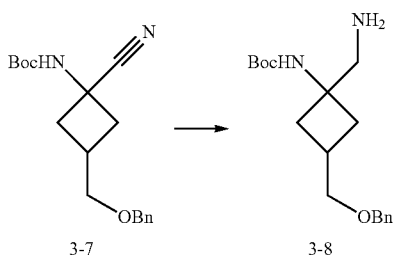 [SMILES: CC(C)(C)OC(=O)NC1(C#N)CC(COCc2ccccc2)C1 ; CC(C)(C)OC(=O)NC1(CN)CC(COCc2ccccc2)C1]

To a solution of compound 3-7 (300 mg) obtained in the above-mentioned step in methanol (9 mL) was added cobalt (II) chloride hexahydrate (226 mg) under ice-cooling. Then, sodium borohydride (179 mg) was added by small portions, and the mixture was stirred at the same temperature for 10 min, and at room temperature overnight. To the reaction mixture were added under ice-cooling saturated aqueous sodium hydrogen carbonate solution and chloroform, and the insoluble material was filtered off through Celite. The filtrate was extracted with chloroform. The organic layer was washed with saturated brine, dried over sodium sulfate, and concentrated to give a crude product of compound 3-8 (339 mg). The obtained crude product of compound 3-8 was directly used in the next step.

Step 9

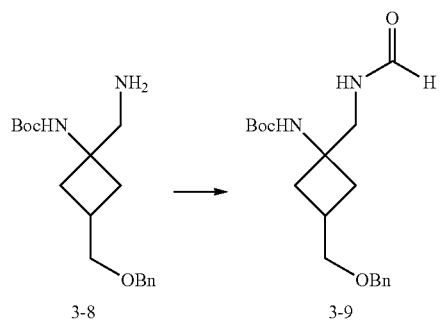 [SMILES: CC(C)(C)OC(=O)NC1(CN)CC(COCc2ccccc2)C1 ; CC(C)(C)OC(=O)NC1(CNC=O)CC(COCc2ccccc2)C1]

To a suspension of 1,1'-carbonyldiimidazole (161 mg) in THF (3 mL) was added formic acid (37.6 μL), and the mixture was stirred at room temperature for 10 min. A solution of the crude product of compound 3-8 (339 mg) obtained in the above-mentioned step in THF (3 mL) was added, and the mixture was stirred at room temperature for 3 hr. To the reaction mixture was added saturated aqueous sodium hydrogen carbonate solution, and the mixture was extracted with ethyl acetate. The organic layer was washed with saturated brine, dried over sodium sulfate, and concentrated to give a crude product of compound 3-9 (341 mg). The obtained crude product of compound 3-9 was directly used in the next step.

Step 10

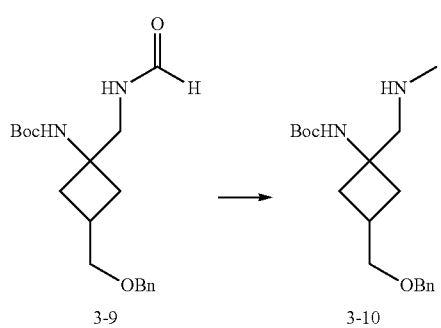 [SMILES: CC(C)(C)OC(=O)NC1(CNC=O)CC(COCc2ccccc2)C1 ; CNCC1(NC(=O)OC(C)(C)C)CC(COCc2ccccc2)C1]

To a solution of a crude product of compound 3-9 (341 mg) obtained in the above-mentioned step in THF. (3 mL) was added borane-THF complex/THF solution (0.9M, 1.5 mL) under ice-cooling, and the mixture was stirred at room temperature for 4 hr. Borane-THF complex/THF solution (0.9M, 1.0 mL) was added under ice-cooling, and the mixture was stirred at room temperature overnight. To the reaction mixture was added saturated aqueous sodium hydrogen carbonate solution, and the mixture was extracted with chloroform. The organic layer was washed with saturated brine, dried over sodium sulfate, and concentrated. The residue was purified by silica gel column chromatography (chloroform:methanol=100:0 to 80:20) to give compound 3-10 (96 mg).

$^1$H-NMR (CDCl$_3$) δ: 7.36-7.27 (m, 5.00H), 5.08 (br s, 1.00H), 4.51 (s, 2.00H), 3.52 (d, 1.30H, J=6.5 Hz), 3.46 (d, 0.70H, J=6.2 Hz), 2.84 (s, 1.30H), 2.80 (s, 0.70H), 2.74-2.72 (br m, 0.35H), 2.49 (s, 1.95H), 2.43 (s, 1.05H), 2.39-2.31 (m, 1.30H), 2.17 (s, 2.35H), 1.94-1.89 (m, 1.00H), 1.45 (s, 3.15H), 1.43 (s, 5.85H).

Step 11

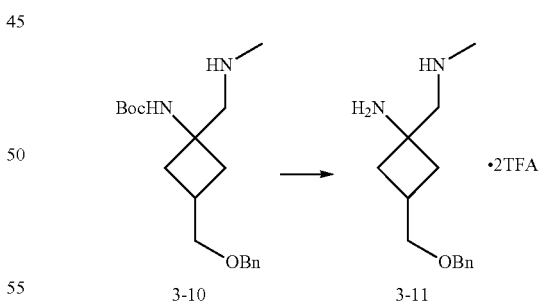

To compound 3-10 (93 mg) obtained in the above-mentioned step was added TFA (0.9 mL), and the mixture was stirred at room temperature for 30 min. The reaction mixture was concentrated to give a crude product of compound 3-11. The obtained crude product of compound 3-11 was directly used in the next step.

Step 12

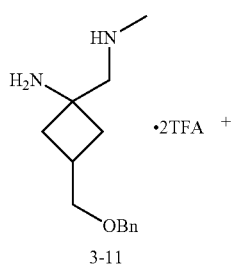

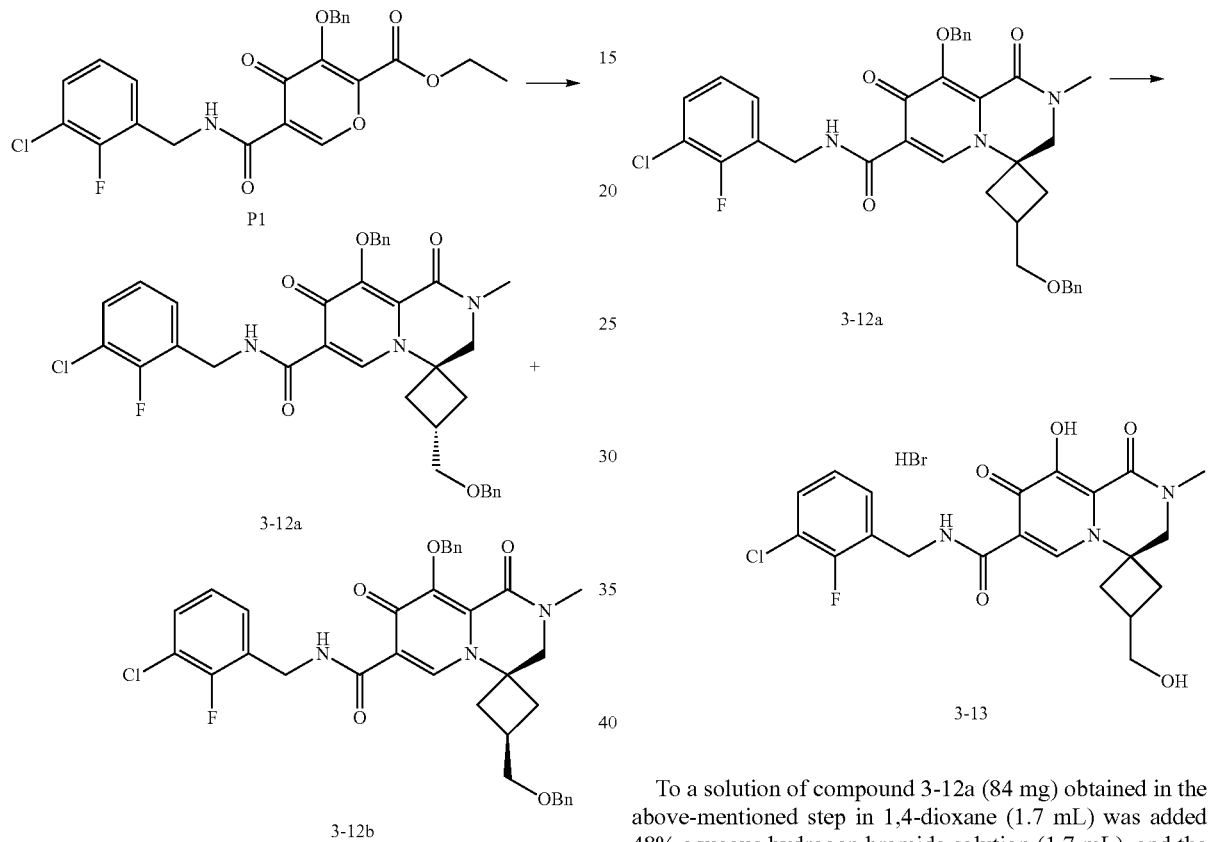

To a solution of the crude product of compound 3-11 obtained in the above-mentioned step in THF (1.9 mL) were successively added under ice-cooling triethylamine (194 μL) and compound P1 (128 mg) obtained in Example 1, Preliminary step 1-1, and the mixture was stirred at room temperature for 2 hr. The reaction mixture was concentrated to give residue 3-12.

To a solution of the residue 3-12 in toluene (1.9 mL) was added DBU (167 μL), and the mixture was stirred at 80° C. for 2 hr. Acetic acid (319 μL) was added, and the mixture was stirred at 110° C. for 2 hr. The reaction mixture was cooled to room temperature, saturated aqueous sodium hydrogen carbonate solution was added, and the mixture was extracted with ethyl acetate. The organic layer was washed successively with water and saturated brine, dried over sodium sulfate, concentrated, and purified by silica gel thin layer chromatography (ethyl Jo acetate) to give compound 3-12a (88 mg) and compound 3-12b (50 mg).

Compound 3-12a $^1$H-NMR (CDCl$_3$) δ: 10.56 (t, 1H, J=6.0 Hz), 8.81 (s, 1H), 7.62-7.60 (m, 2H), 7.37-7.27 (m, 10H), 7.06-7.02 (m, 1H), 5.30 (s, 2H), 4.72 (d, 2H, J=6.0 Hz), 4.57 (s, 2H), 3.54 (s, 2H), 3.51 (d, 2H, J=4.9 Hz), 3.18 (s, 3H), 2.59-2.53 (m, 2H), 2.52-2.44 (m, 1H), 2.32-2.27 (m, 2H).

Compound 3-12b $^1$H-NMR (CDCl$_3$) δ: 10.61 (t, 1H, J=6.0 Hz), 8.80 (s, 1H), 7.62-7.59 (m, 2H), 7.41-7.28 (m, 10H), 7.06-7.01 (m, 1H), 5.30 (s, 2H), 4.71 (d, 2H, J=6.0 Hz), 4.56 (s, 2H), 3.60 (s, 2H), 3.55 (d, 2H, J=3.2 Hz), 2.95 (s, 3H), 2.88-2.82 (m, 1H), 2.67-2.61 (m, 2H), 2.41-2.36 (m, 2H).

Step 13

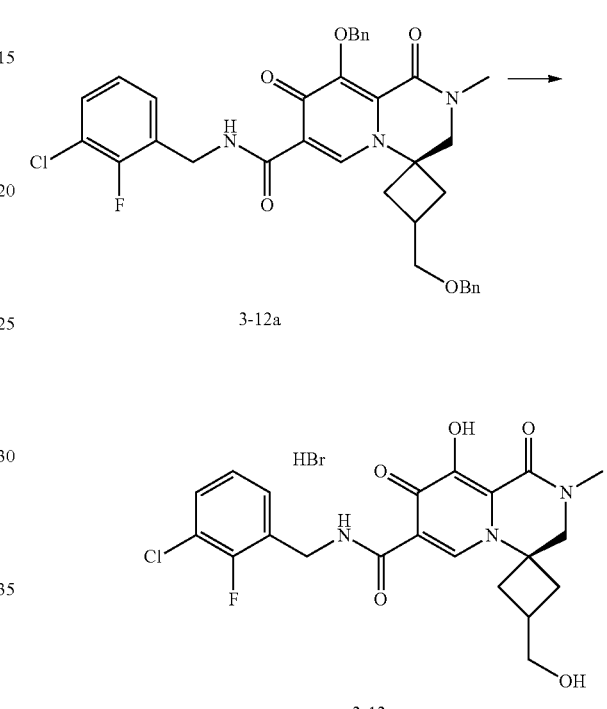

To a solution of compound 3-12a (84 mg) obtained in the above-mentioned step in 1,4-dioxane (1.7 mL) was added 48% aqueous hydrogen bromide solution (1.7 mL), and the mixture was stirred at 80° C. for 3 hr. The reaction mixture was concentrated, toluene and 1,4-dioxane were added and the mixture was concentrated. The operation of concentration with toluene and 1,4-dioxane was performed 3 times to give a crude product of compound 3-13. The obtained crude product of compound 3-13 was directly used in the next step.

Step 14

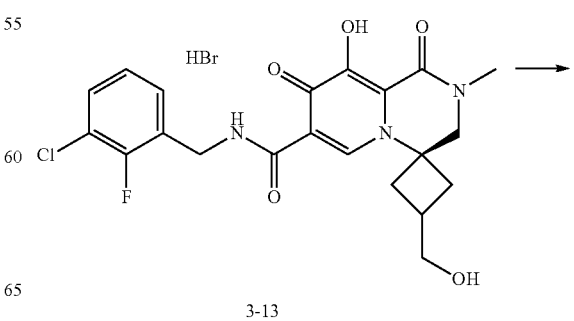

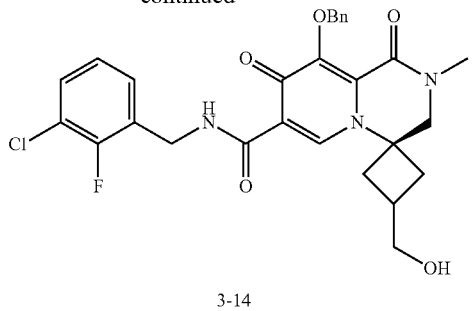

3-14

To a solution of the crude product of compound 3-13 obtained in the above-mentioned step in DMF (1.7 mL) were added potassium carbonate (367 mg) and benzyl bromide (0.79 mL), and the mixture was stirred at 60° C. for 2 hr. The reaction mixture was cooled to room temperature, water was added, and the mixture was extracted with ethyl acetate. The organic layer was washed with water and saturated brine, dried over sodium sulfate, concentrated, and purified by silica gel thin layer chromatography (chloroform:methanol=95:5) to give compound 3-14 (70 mg).

$^1$H-NMR (CDCl$_3$) δ: 10.61 (t, 1H, J=6.0 Hz), 8.84 (s, 1H), 7.63-7.60 (m, 2H), 7.38-7.28 (m, 5H), 7.06-7.01 (m, 1H), 5.30 (s, 2H), 4.71 (d, 2H, J=6.0 Hz), 3.74-3.72 (m, 2H), 3.57 (s, 2H), 3.21 (s, 3H), 2.67-2.62 (m, 2H), 2.49-2.43 (m, 1H), 2.31-2.26 (m, 2H), 2.08 (br s, 1H).

Step 15

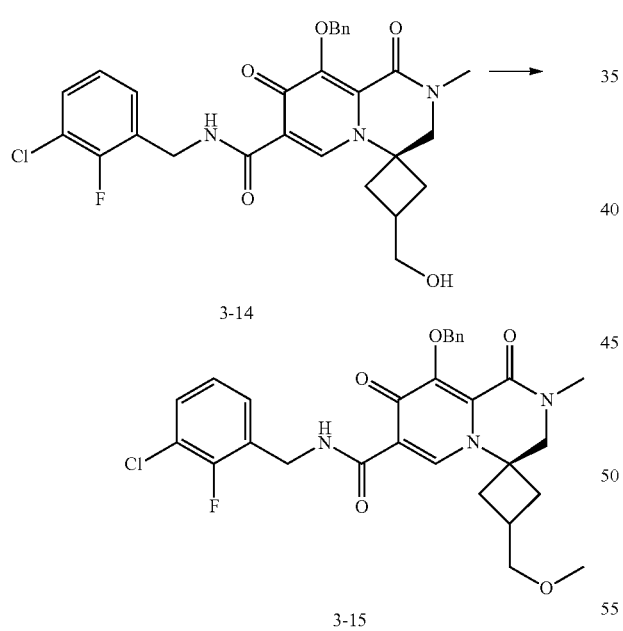

3-14

3-15

To a solution of compound 3-14 (25 mg) obtained in the above-mentioned step in dichloromethane (1.5 mL) were added tetrabutylammonium hydrogen sulfate (15.7 mg), dimethyl sulfate (8.8 μL) and 50% aqueous sodium hydroxide solution (50 μL), and the mixture was stirred at room temperature for 40 min. Dimethyl sulfate (8.8 μL) was added, and the mixture was stirred at room temperature for 40 min. Dimethyl sulfate (17.6 μL) and 50% aqueous sodium hydroxide solution (50 μL) were added 4 times every 30 min, and the mixture was stirred at room temperature for 3 days. To the reaction mixture was added triethylamine (0.3 mL), and the mixture was stirred at room temperature for 30 min. Water was added and the mixture was extracted with chloroform. The organic layer was washed with saturated brine, dried over sodium sulfate, concentrated, and purified by silica gel thin layer chromatography (chloroform:methanol=95:5) to give compound 3-15 (22 mg).

$^1$H-NMR (CDCl$_3$) δ: 10.58 (t, 1H, J=6.0 Hz), 8.82 (s, 1H), 7.63-7.59 (m, 2H), 7.37-7.27 (m, 5H), 7.06-7.02 (m, 1H), 5.30 (s, 2H), 4.72 (d, 2H, J=6.0 Hz), 3.55 (s, 2H), 3.43 (d, 2H, J=4.6 Hz), 3.41 (s, 3H), 3.19 (s, 3H), 2.61-2.55 (m, 2H), 2.51-2.41 (m, 1H), 2.32-2.26 (m, 2H).

Step 16

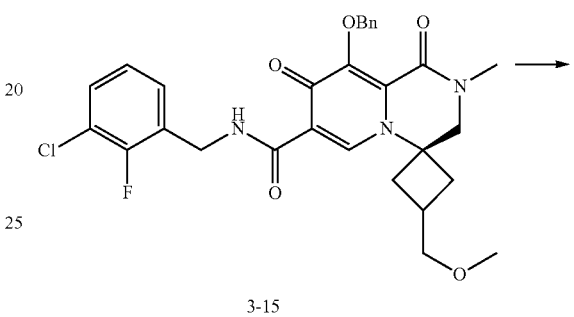

3-15

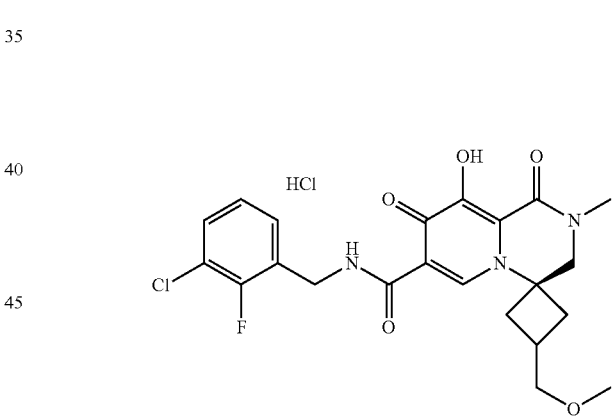

3

To compound 3-15 (21 mg) obtained in the above-mentioned step was added TFA (0.6 mL), and the mixture was stirred at room temperature for 30 min. The reaction mixture was concentrated, toluene was added and the mixture was concentrated. The operation of concentration with toluene was performed 3 times. Ethyl acetate (0.6 mL) and 4N hydrochloric acid/ethyl acetate (63 μL) were added and the mixture was stirred at room temperature for 15 min. The mixture was concentrated again and crystallized from diethyl ether-hexane to give the title compound (15.1 mg).

$^1$H-NMR (DMSO-d$_6$) δ: 12.82 (s, 1H), 10.45 (t, 1H, J=6.0 Hz), 8.53 (s, 1H), 7.52-7.47 (m, 1H), 7.35-7.31 (m, 1H), 7.22-7.18 (m, 1H), 4.62 (d, 2H, J=6.0 Hz), 3.90 (s, 2H), 3.39 (d, 2H, J=5.3 Hz), 3.27 (s, 3H), 3.14 (s, 3H), 2.61-2.54 (m, 1H), 2.37-2.25 (m, 4H).

Example 4

Production of N-(3-chloro-2-fluorobenzyl)-9'-hydroxy-trans-3-(methoxymethyl)-2'-methyl-1',8'-dioxo-1',2',3',8'-tetrahydrospiro[cyclobutane-1,4'-pyrido[1,2-a]pyrazine]-7'-carboxamide hydrochloride

Step 1

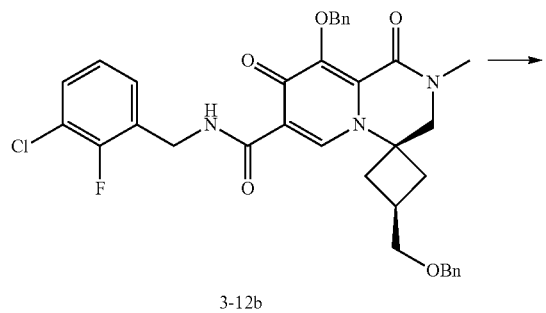

3-12b

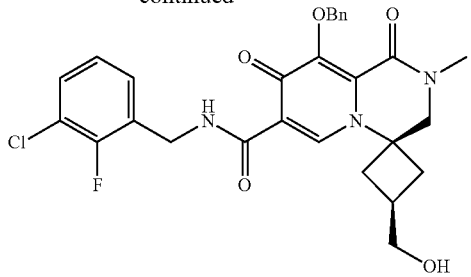

4-2

From a crude product of compound 4-1 obtained in the above-mentioned step, and by a method similar to that in Example 3, step 14, compound 4-2 (34 mg) was obtained.

$^1$H-NMR (CDCl$_3$) δ: 10.61 (t, 1H, J=5.7 Hz), 8.83 (s, 1H), 7.63-7.60 (m, 2H), 7.37-7.28 (m, 5H), 7.06-7.02 (m, 1H), 5.31 (s, 2H), 4.72 (d, 2H, J=5.7 Hz), 3.73 (t, 2H, J=3.5 Hz), 3.65 (s, 2H), 3.17 (s, 3H), 2.88-2.80 (br m, 1H), 2.65-2.59 (m, 2H), 2.44-2.38 (m, 2H), 1.66 (t, 1H, J=3.5 Hz).

Step 3

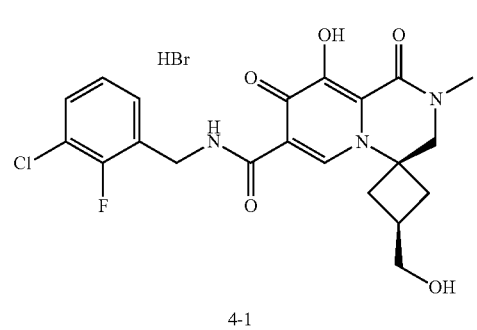

4-1

From compound 3-12b (48 mg) obtained in Example 3, step 12, and by a method similar to that in Example 3, step 13, a crude product of compound 4-1 was obtained. The obtained crude product of compound 4-1 was directly used in the next step.

Step 2

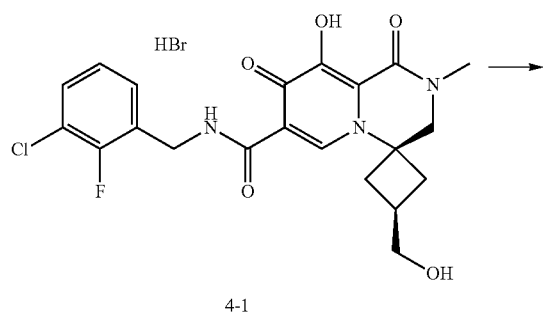

4-1

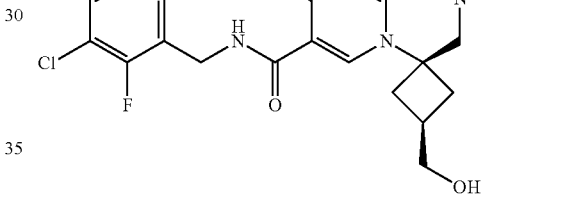

4-2

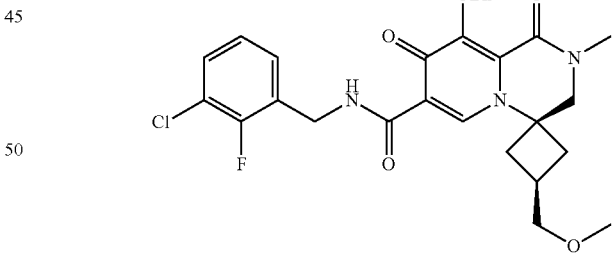

4-3

From compound 4-2 (20 mg) obtained in the above-mentioned step, and by a method similar to that in Example 3, step 15, compound 4-3 was obtained. The total amount of the obtained compound 4-3 was directly used in the next step.

$^1$H-NMR (CDCl$_3$) δ: 10.62 (t, 1H, J=5.8 Hz), 8.81 (s, 1H), 7.62-7.60 (m, 2H), 7.37-7.28 (m, 5H), 7.07-7.02 (m, 1H), 5.30 (s, 2H), 4.71 (d, 2H, J=5.8 Hz), 3.64 (s, 2H), 3.42 (d, 2H, J=3.2 Hz), 3.42 (s, 3H), 3.16 (s, 3H), 2.89-2.78 (m, 1H), 2.64-2.58 (m, 2H), 2.39-2.34 (m, 2H).

Step 4

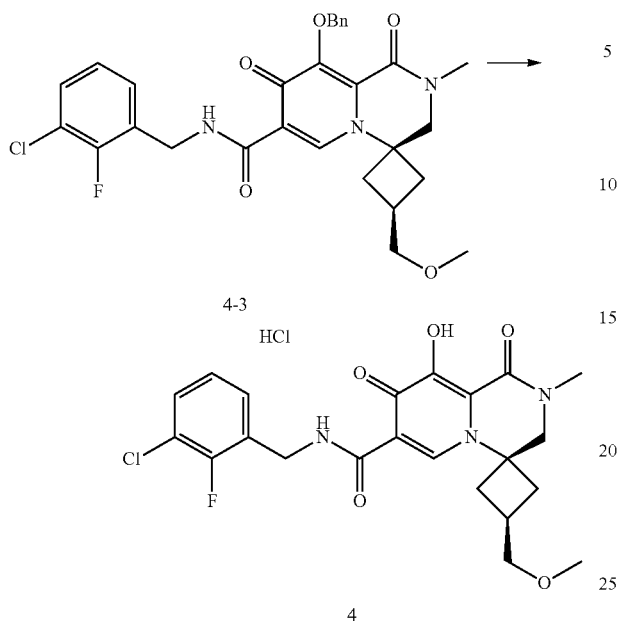

From compound 4-3 obtained in the above-mentioned step, and by a method similar to that in Example 3, step 16, the title compound (15.2 mg) was obtained.

¹H-NMR (DMSO-d₆) δ: 12.95 (br s, 1H), 10.46 (t, 1H, J=6.0 Hz), 8.58 (s, 1H), 7.52-7.48 (m, 1H), 7.36-7.32 (m, 1H), 7.23-7.18 (m, 1H), 4.62 (d, 2H, J=6.0 Hz), 3.82 (s, 2H), 3.42 (d, 2H, J=6.0 Hz), 3.28 (s, 3H), 3.10 (s, 3H), 2.73-2.63 (m, 1H), 2.57-2.51 (m, 2H), 2.25-2.20 (m, 2H).

Example 5

Production of N-(3-chloro-2-fluorobenzyl)-2'-ethyl-9'-hydroxy-trans-3-methoxy-1',8'-dioxo-1',2',4',8'-tetrahydrospiro[cyclobutane-1,3'-pyrido[1,2-a]pyrazine]-7'-carboxamide hydrochloride Step 1

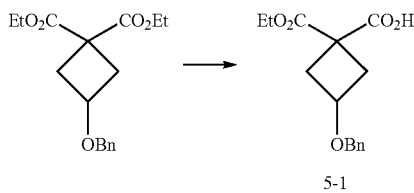 [SMILES: CCOC(=O)C1(C(=O)OCC)CC(OCc2ccccc2)C1 ; CCOC(=O)C1(C(=O)O)CC(OCc2ccccc2)C1]

To a mixed solution of commercially available 3-benzyloxycyclobutane-1,1-dicarboxylic acid diethyl ester (5.00 g) in ethanol-water (42 mL-10.5 mL) was added potassium hydroxide (981 mg, 85%), and the mixture was stirred at 100° C. for 16 hr. The reaction mixture was concentrated, water was added, and the mixture was extracted 3 times with diethyl ether to give an organic layer 5-1 and an aqueous layer 5-1.

The organic layer 5-1 was dried over magnesium sulfate, and concentrated to give residue 5-1-1 (949 mg).

To the aqueous layer 5-1 was added potassium hydrogen sulfate (7.67 g), and the mixture was extracted 3 times with ethyl acetate. The organic layer was washed with saturated brine, dried over magnesium sulfate, and concentrated, toluene was added and the mixture was concentrated to give residue 5-1-2.

To the residue 5-1-1 (949 mg) were added ethanol (8 mL), water (2 mL), and potassium hydroxide (194 mg, 85%), and the mixture was stirred at 100° C. for 3.5 hr and stood at room temperature for 3 days. To the reaction mixture was added aqueous potassium hydrogen sulfate solution, and the mixture was extracted twice with ethyl acetate. The organic layer was washed with saturated brine, dried over magnesium sulfate and concentrated to give residue 5-1-3.

The residue 5-1-2 and the residue 5-1-3 were combined and purified by silica gel column chromatography (hexane:ethyl acetate=1:2 to ethyl acetate:acetone=3:1) to give compound 5-1 (4.04 g).

¹H-NMR (CDCl₃) δ: 7.37-7.14 (m, 5H), 4.44 (s, 2H), 4.27-4.14 (m, 3H), 2.87-2.80 (m, 2H), 2.64-2.57 (m, 2H), 1.31-1.27 (m, 3H).

Step 2

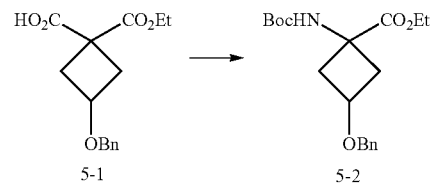 [SMILES: CCOC(=O)C1(C(=O)O)CC(OCc2ccccc2)C1 ; CCOC(=O)C1(NC(=O)OC(C)(C)C)CC(OCc2ccccc2)C1]

To a solution of compound 5-1 (104 mg) obtained in the above-mentioned step in toluene (1 mL) were added triethylamine (104 µL) and DPPA (113 µL) at room temperature under an argon atmosphere, and the mixture was stirred at room temperature for 20 min. tert-Butanol (3 mL) was added, and the mixture was stirred at 110° C. for 4 hr. The reaction mixture was concentrated, toluene was added, and the mixture was concentrated to give residue 5-2-1. Similarly, to a solution of compound 5-1 (3.91 g) in toluene (40 mL) were added triethylamine (4.00 mL) and DPPA (4.25 mL) at room temperature under an argon atmosphere, and the mixture was stirred at room temperature for 20 min. tert-Butanol (120 mL) was added, and the mixture was stirred at 110° C. for 18 hr. The reaction mixture was concentrated, toluene was added, and the mixture was concentrated to give residue 5-2-2.

The residue 5-2-1 and the residue 5-2-2 were combined and purified by silica gel column chromatography (hexane:ethyl acetate=10:1 to 5:1) to give compound 5-2 (4.49 g).

¹H-NMR (CDCl₃) δ: 7.35-7.28 (m, 5H), 5.16-5.08 (br m, 1H), 4.96-4.86 (br m, 1H), 4.45-4.44 (m, 2H), 4.28-4.20 (m, 1H), 4.22-4.16 (m, 2H), 2.94-2.89 (m, 1H), 2.66-2.61 (m, 1H), 2.51-2.43 (br m, 1H), 2.33-2.25 (br m, 1H), 1.43 (s, 9H), 1.29-1.25 (m, 3H).

Step 3

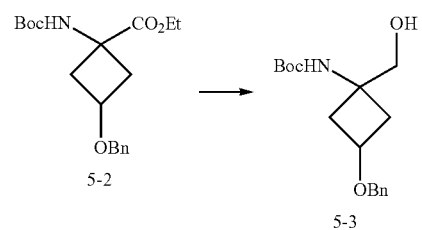 [SMILES: CCOC(=O)C1(NC(=O)OC(C)(C)C)CC(OCc2ccccc2)C1 ; CC(C)(C)OC(=O)NC1(CO)CC(OCc2ccccc2)C1]

To a solution of lithium aluminum hydride (1.00 g) in THF (30 mL) was added dropwise a solution of compound 5-2 (4.49 g) obtained in the above-mentioned step in THF (15 mL) under ice-cooling under a nitrogen atmosphere. The mixture was stirred for 30 min, and at room temperature for 1 hr. The reaction mixture was ice-cooled, water (1.00 mL) and 10% aqueous sodium hydroxide solution (1.00 mL) were successively added, and the mixture was stirred for 3 min. Water (3.01 mL) was added again, and the mixture was stirred at room temperature for 30 min. The solid was filtered off, and washed with THF. The filtrate was concentrated, toluene was added, and the mixture was concentrated. The operation of concentration with toluene was performed twice to give compound 5-3 (4.37 g).

$^1$H-NMR (CDCl$_3$) δ: 7.38-7.27 (m, 5.00H), 4.89-4.87 (br m, 0.45H), 4.83-4.80 (br m, 0.55H), 4.42 (s, 0.90H), 4.41 (s, 1.10H), 4.24 (tt, 0.55H, J=7.2, 5.3 Hz), 3.91 (quint, 0.45H, J=7.0 Hz), 3.76-3.75 (m, 1.10H), 3.64-3.61 (m, 0.90H), 2.67-2.62 (m, 0.90H), 2.47-2.42 (m, 1.10H), 2.20-2.14 (m, 1.10H), 2.05-2.00 (m, 0.90H), 1.44 (s, 4.95H), 1.43 (s, 4.05H).

Step 4

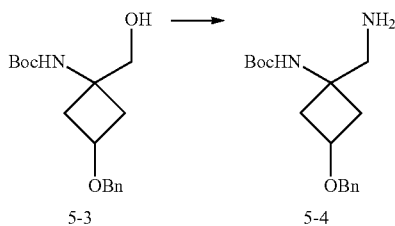 [SMILES: CC(C)(C)OC(=O)NC1(CO)CC(OCc2ccccc2)C1 ; CC(C)(C)OC(=O)NC1(CN)CC(OCc2ccccc2)C1]

To a solution of compound 5-3 (682 mg) obtained in the above-mentioned step, triphenylphosphine (1.76 g) and phthalimide (992 mg) in toluene (20 mL) was added dropwise DIAD (1.31 mL) at room temperature, and the mixture was stirred at the same temperature for 1 hr. Ethanol (2 mL), and hydrazine hydrate (2.5 mL) were added, and the mixture was stirred at 80° C. for 2 hr. The reaction mixture was cooled to room temperature, and the solid was filtered off and washed with an ethanol-toluene (1:10) mixed solution. The filtrate was concentrated, toluene was added and the mixture was concentrated. The operation of concentration with toluene was performed 3 times to give compound 5-4. The obtained compound 5-4 was directly used in the next step.

Step 5

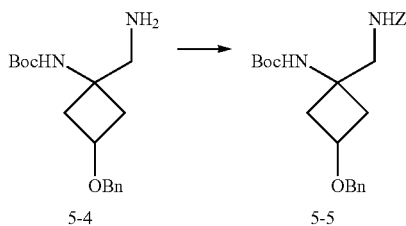

To compound 5-4 obtained in the above-mentioned step were added ethyl acetate (15 mL), sodium hydrogen carbonate (3.02 g), water (15 mL), and benzyl chloroformate (0.75 mL), and the mixture was stirred at room temperature for 15 hr. To the reaction mixture was added isopropylamine (1 mL), and the mixture was stirred at room temperature for 1 hr and extracted 3 times with ethyl acetate. The organic layer was washed successively with saturated brine, 10% aqueous potassium hydrogen sulfate solution and saturated brine, dried over magnesium sulfate and concentrated to give compound 5-5. The obtained compound 5-5 was directly used in the next step.

Step 6

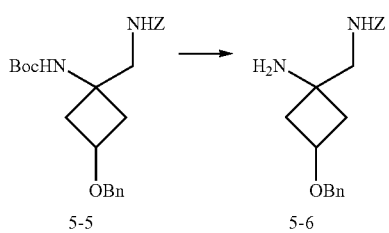

To compound 5-5 obtained in the above-mentioned step was added 4N hydrochloric acid/ethyl acetate (15 mL), and the mixture was stirred at room temperature for 20 min. To the reaction mixture were added hexane (10 mL) and ethyl acetate (5 mL), and the mixture was extracted 4 times with water. The aqueous layers were combined, and washed successively with toluene, and hexane-ethyl acetate (1:2). Under ice-cooling, potassium carbonate (10 g) was added, and the mixture was extracted 4 times with chloroform. The organic layer was dried over magnesium sulfate and concentrated to give compound 5-6 (546 mg).

$^1$H-NMR (CDCl$_3$) δ: 7.38-7.27 (m, 10.00H), 5.26-5.09 (m, 3.00H), 4.42 (s, 0.68H), 4.39 (s, 1.32H), 4.26-4.20 (m, 0.66H), 3.88-3.80 (m, 0.34H), 3.28 (d, 1.32H, J=6.2 Hz), 3.16 (d, 0.68H, J=5.5 Hz), 2.57-1.79 (m, 4.00H).

Step 7

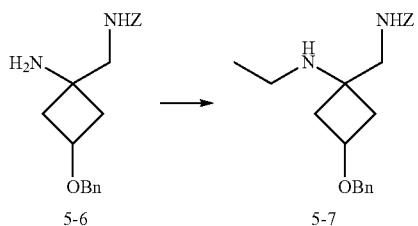

To a solution of compound 5-6 (252 mg) obtained in the above-mentioned step in chloroform (8 mL) were added acetaldehyde (40 μL) and acetic acid (51 μL) under ice-cooling, and the mixture was stirred at room temperature for 40 min. Sodium triacetoxyborohydride (200 mg) was added, and the mixture was stirred at room temperature for 1.5 hr. To the reaction mixture was added saturated aqueous sodium hydrogen carbonate solution, and the mixture was extracted 3 times with chloroform. The organic layer was dried over magnesium sulfate and concentrated to give compound 5-7. The obtained compound 5-7 was directly used in the next step.

Step 8

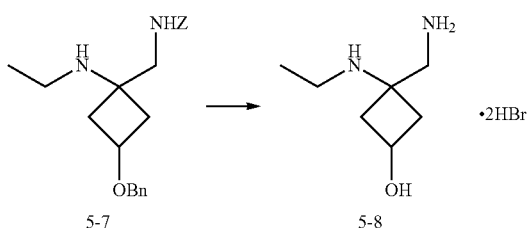

To compound 5-7 obtained in the above-mentioned step was added 48% aqueous hydrogen bromide solution (5 mL), and the mixture was stirred at 80° C. for 4 hr. The reaction mixture was cooled to room temperature, toluene was added, and the mixture was extracted 4 times with water. The obtained aqueous layer was washed with toluene, and concentrated to give residue 5-8.

To the residue 5-8 was added methanol and the mixture was concentrated again to give compound 5-8 (250 mg). The obtained compound 5-8 was directly used in the next step.

Step 9

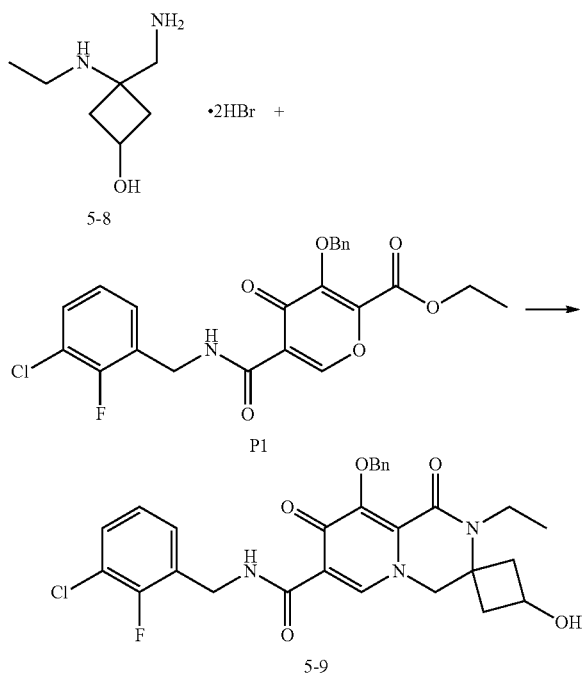

To a solution of compound 5-8 (250 mg) obtained in the above-mentioned step in THF (10 mL) were added ethanol (3 mL), methanol (2 mL), triethylamine (3 mL), and compound P1 (347 mg) obtained in Example 1, Preliminary step 1-1. The mixture was stirred at room temperature for 20 min, and concentrated, toluene (30 mL) and DBU (3 mL) were added, and the mixture was stirred at 80° C. for 6 hr. The reaction mixture was cooled to room temperature, 10% aqueous potassium hydrogen sulfate solution was added and the mixture was extracted 4 times with chloroform. The organic layer was washed with saturated brine, dried over magnesium sulfate, concentrated and purified by silica gel thin layer chromatography (chloroform:acetone=1:1) to give compound 5-9 (224 mg).

$^1$H-NMR (CDCl$_3$) δ: 10.60 (t, 0.68H, J=6.0 Hz), 10.56 (t, 0.32H, J=5.6 Hz), 8.43 (s, 0.68H), 8.34 (s, 0.32H), 7.58-7.54 (m, 2.00H), 7.35-7.28 (m, 5.00H), 7.07-7.02 (m, 1.00H), 5.32 (s, 0.64H), 5.32 (s, 1.36H), 4.71 (d, 2.00H, J=6.0 Hz), 4.56-4.52 (m, 0.68H), 4.40 (s, 1.36H), 4.21-4.18 (m, 0.32H), 3.95 (s, 0.64H), 3.69 (q, 0.64H, J=7.0 Hz), 3.61 (q, 1.36H, J=7.0 Hz), 2.60-2.54 (m, 1.36H), 2.45-2.39 (m, 0.64H), 2.33-2.27 (m, 0.64H), 2.04-2.02 (m, 0.68H), 2.01-1.98 (m, 0.68H), 1.22 (t, 0.96H, J=7.0 Hz), 1.21 (t, 2.04H, J=7.0 Hz).

Step 10

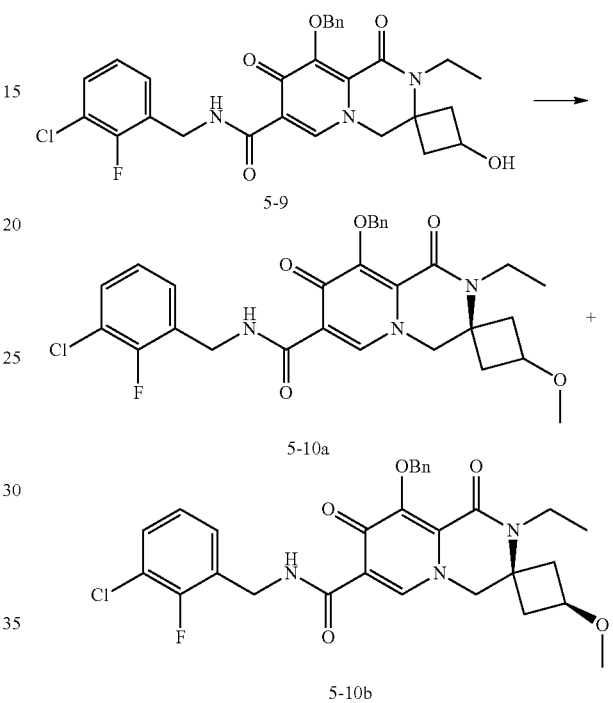

To a solution of compound 5-9 (62 mg) obtained in the above-mentioned step in toluene (1.5 mL) were added tetrabutylammonium hydrogen sulfate (75 mg), dimethyl sulfate (70 μL) and 50% aqueous sodium hydroxide solution (103 μL), and the mixture was stirred at room temperature for 5 min. Dimethyl sulfate (70 μL), and 50% aqueous sodium hydroxide solution (103 μL) were added, and the mixture was stirred at room temperature for 7 min. Dimethyl sulfate (70 μL), and 50% aqueous sodium hydroxide solution (103 μL) were added, and the mixture was stirred at room temperature for 24 min. Dimethyl sulfate (70 μL), and 50% aqueous sodium hydroxide solution (103 μL) were added, and the mixture was further stirred at room temperature for 20 min. To the reaction mixture was added triethylamine (1 mL) and the mixture was stirred for 15 min. 10% Aqueous potassium hydrogen sulfate solution was added and the mixture was extracted 4 times with chloroform. The organic layer was dried over magnesium sulfate, concentrated and purified by silica gel thin layer chromatography (chloroform:acetone=3:1) to give compound 5-10a (36 mg) and compound 5-10b (15 mg).

Compound 5-10a $^1$H-NMR (CDCl$_3$) δ: 10.58 (t, 1H, J=5.8 Hz), 8.40 (s, 1H), 7.59-7.57 (m, 2H), 7.35-7.27 (m, 5H), 7.07-7.02 (m, 1H), 5.32 (s, 2H), 4.72 (d, 2H, J=5.8 Hz), 4.27 (s, 2H), 3.98 (tt, 1H, J=6.9, 1.6 Hz), 3.63 (q, 2H, J=7.0 Hz), 3.24 (s, 3H), 2.52-2.46 (m, 2H), 2.06-2.02 (m, 2H), 1.21 (t, 3H, J=7.0 Hz).

Compound 5-10b

¹H-NMR (CDCl₃) δ: 10.56 (t, 1H, J=5.8 Hz), 8.35 (s, 1H), 7.56-7.53 (m, 2H), 7.35-7.28 (m, 5H), 7.07-7.02 (m, 1H), 5.33 (s, 2H), 4.71 (d, 2H, J=5.8 Hz), 3.96 (s, 2H), 3.69 (quint, 1H, J=6.5 Hz), 3.67 (q, 2H, J=7.1 Hz), 3.25 (s, 3H), 2.40-2.35 (m, 2H), 2.26-2.21 (m, 2H), 1.21 (t, 3H, J=7.1 Hz).

Step 11

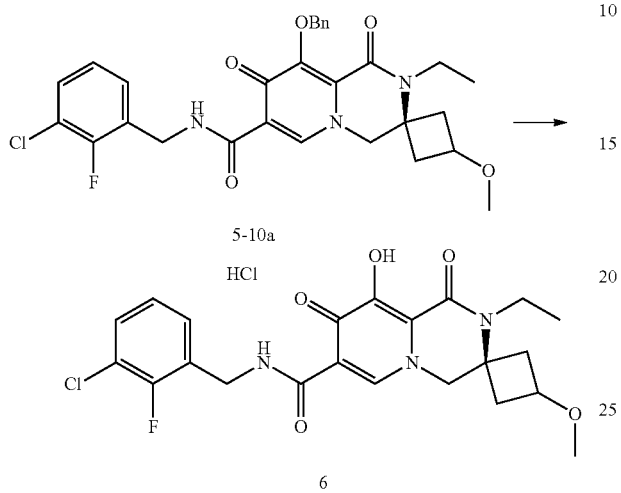

To compound 5-10a (36 mg) obtained in the above-mentioned step were successively added TFA (1 mL), and 4N hydrochloric acid/ethyl acetate (400 μL), and the mixture was stirred at room temperature for 15 min. The reaction mixture was concentrated, ethyl acetate was added and the mixture was concentrated to give residue 5-11.

To the residue 5-11 were added 4N hydrochloric acid/ethyl acetate (200 μL), hexane (8 mL), and ethyl acetate (1.5 mL), and the precipitated solid was collected by filtration to give the title compound (24 mg).

¹H-NMR (DMSO-d₆) δ: 12.39 (br s, 1H), 10.47 (t, 1H, J=5.9 Hz), 8.45 (s, 1H), 7.52-7.47 (m, 1H), 7.35-7.31 (m, 1H), 7.22-7.18 (m, 1H), 4.61 (d, 2H, J=5.9 Hz), 4.46 (s, 2H), 4.09-4.04 (m, 1H), 3.65 (q, 2H, J=6.9 Hz), 3.18 (s, 3H), 2.70-2.64 (m, 2H), 2.20-2.16 (m, 2H), 1.17 (t, 3H, J=6.9 Hz).

Elemental analysis: calcd. C, 52.81; H, 4.83; N, 8.40. found C, 52.57; H, 4.81; N, 8.23.

Example 6

Production of N-(3-chloro-2-fluorobenzyl)-2'-ethyl-9'-hydroxy-cis-3-methoxy-1',8'-dioxo-1',2',4',8'-tetrahydrospiro[cyclobutane-1,3'-pyrido[1,2-a]pyrazine]-7'-carboxamide hydrochloride Step 1

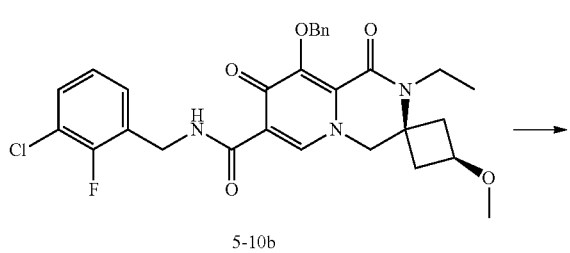

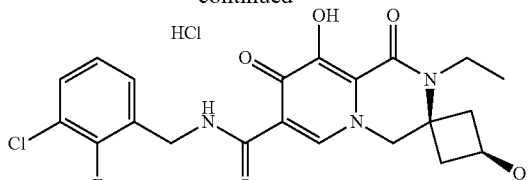

From compound 5-10b (15 mg) obtained in Example 5, step 10, and by a method similar to that in Example 5, step 11, the title compound (8.8 mg) was obtained.

¹H-NMR (DMSO-d₆) δ: 10.46 (t, 1H, J=6.0 Hz), 8.46 (s, 1H), 7.52-7.48 (m, 1H), 7.33 (t, 1H, J=7.4 Hz), 7.20 (t, 1H, J=7.9 Hz), 4.62 (d, 2H, J=6.0 Hz), 4.39 (s, 2H), 3.89 (quint, 1H, J=6.7 Hz), 3.65 (q, 2H, J=7.1 Hz), 3.17 (s, 3H), 2.51-2.48 (m, 2H), 2.30-2.25 (m, 2H), 1.15 (t, 3H, J=7.1 Hz).

Example 7

Production of N-(3-chloro-2-fluoro-4-methoxybenzyl)-9'-hydroxy-trans-3-(methoxymethyl)-2'-methyl-1',8'-dioxo-1',2',3',8'-tetrahydrospiro[cyclobutane-1,4'-pyrido[1,2-a]pyrazine]-7'-carboxamide hydrochloride Step 1

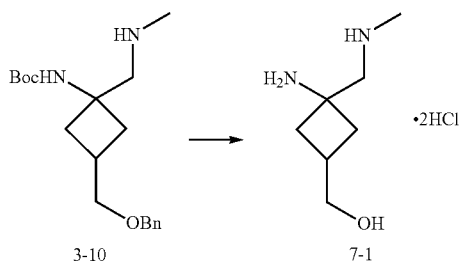

To compound 3-10 (145 mg) obtained in the same manner as in Example 3, step 10 was added TFA (3 mL), and the mixture was stood at room temperature for 15 min. The reaction mixture was concentrated, toluene was added, and the mixture was concentrated to give residue 7-1-1.

To a mixed solution of the residue 7-1-1 in ethanol-acetic acid (1 mL-1 mL) was added palladium-platinum/carbon (ASCA2, manufactured by N.E. CHEMCAT Corporation, 145 mg), and the mixture was stirred overnight under a hydrogen atmosphere at room temperature. The reaction mixture was filtered through Celite, and concentrated, ethanol was added, and the mixture was concentrated. 4N Hydrochloric acid/dioxane was added, and the mixture was concentrated to give residue 7-1-2.

To the residue 7-1-2 was added diisopropyl ether and the supernatant liquid was removed by decantation. This operation was performed twice, and the resulting residue was dried under reduced pressure to give a crude product of compound 7-1. The obtained crude product of compound 7-1 was directly used in the next step.

Step 2

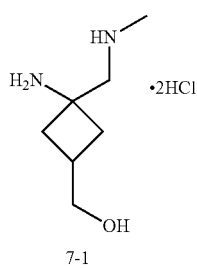
7-1

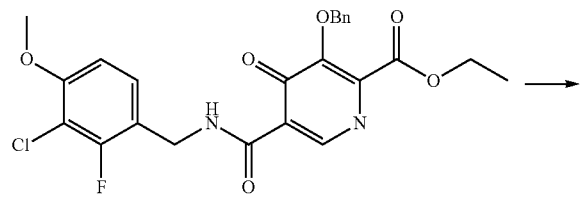
P7

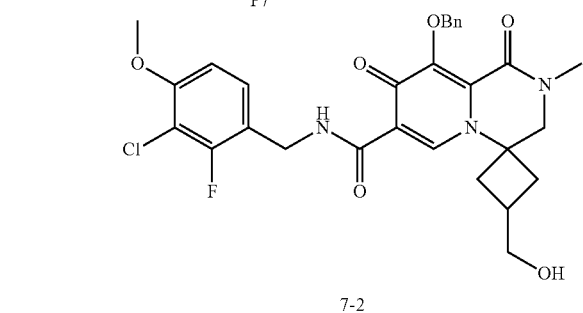
7-2

From the crude product of compound 7-1 obtained in the above-mentioned step and compound P7 (170 mg) obtained in below-mentioned Preliminary step 7-9, and in the same manner as in Example 5, step 9, compound 7-2 (165 mg) was obtained.

Step 3

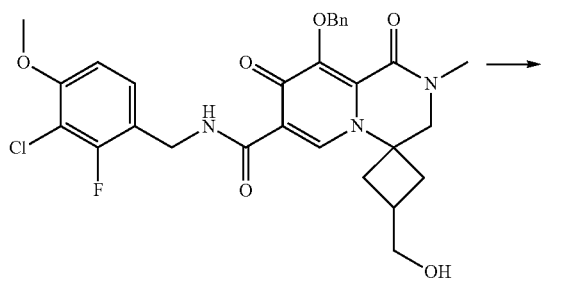
7-2

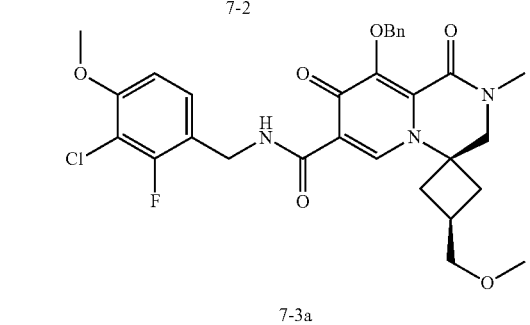
7-3a

-continued

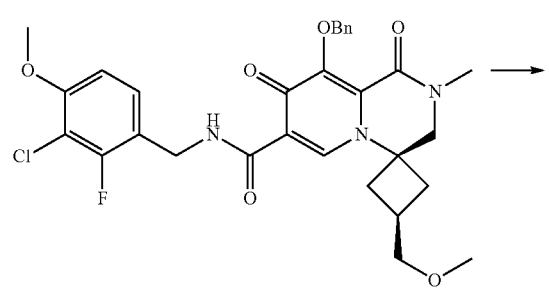
7-3b

From compound 7-2 (80 mg) obtained in the above-mentioned step, and in the same manner as in Example 5, step 10, compound 7-3a (23 mg) and 7-3b (51 mg) were obtained.

Step 4

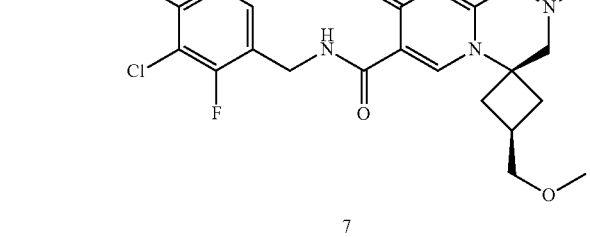
7-3a

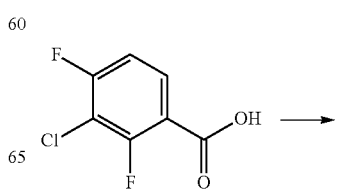
7

From compound 7-3a (23 mg) obtained in the above-mentioned step, and in the same manner as in Example 1, step 11, the title compound (19 mg) was obtained.

$^1$H-NMR (DMSO-$d_6$) δ: 12.93 (br s, 1H), 10.39 (t, 1H, J=5.6 Hz), 8.58 (s, 1H), 7.32 (t, 1H, J=8.9 Hz), 6.99 (dd, 1H, J=8.8, 1.2 Hz), 4.54 (d, 2H, J=5.6 Hz), 3.87 (s, 3H), 3.82 (s, 2H), 3.43 (d, 2H, J=6.0 Hz), 3.28 (s, 3H), 3.10 (s, 3H), 2.73-2.63 (m, 1H), 2.57-2.51 (m, 2H), 2.25-2.20 (m, 2H).

Preliminary Step 7-1

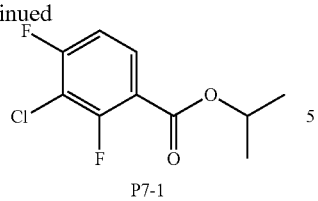
P7-1

To a solution of commercially available 3-chloro-2,4-difluorobenzoic acid (10 g) in DMF (30 mL) was added cesium carbonate (17.8 g), and the mixture was heated to 70° C. To the reaction mixture was added dropwise 2-iodopropane (5.96 mL), and the mixture was stirred at the same temperature for 3.5 hr. The reaction mixture was ice-cooled, and water (50 mL), ethyl acetate (200 mL) and hexane (20 mL) were added to partition the mixture. The organic layer was washed twice with water and with saturated brine, dried over sodium sulfate and concentrated to give compound P7-1 (11 g).

$^{1}$H-NMR (CDCl$_3$) δ: 7.86 (ddd, 1H, J=8.9, 7.7, 6.4 Hz), 7.03 (ddd, 1H, J=8.9, 7.7, 1.6 Hz), 5.27 (sep, 1H, J=6.0 Hz), 1.39 (d, 6H, J=6.0 Hz).

Preliminary Step 7-2

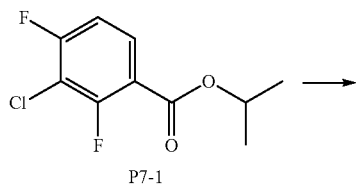
P7-1

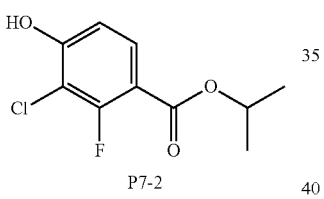
P7-2

To a solution of compound P7-1 (11 g) obtained in the above-mentioned step in DMF (22 mL) was added cesium carbonate (33.6 g), and the mixture was heated to 60° C. A solution of 2-(methylsulfonyl)ethanol (10.9 mL) in DMF (6 mL) was added dropwise over 20 min, and the mixture was stirred at the same temperature for 6 hr. The reaction mixture was ice-cooled, 6N hydrochloric acid (38 mL) and water (60 mL) were successively added, and the mixture was extracted with ethyl acetate. The organic layer was washed twice with water, and with saturated brine, dried over sodium sulfate and concentrated. Crystallization from hexane-ethyl acetate (1:3) gave compound P7-2 (2.3 g).

$^{1}$H-NMR (DMSO-d$_6$) δ: 11.61 (br s, 1H), 7.69 (t, 1H, J=8.7 Hz), 6.90 (dd, 1H, J=8.7, 1.2 Hz), 5.10 (sep, 1H, J=6.4 Hz), 1.29 (d, 6H, J=6.4 Hz).

Preliminary Step 7-3

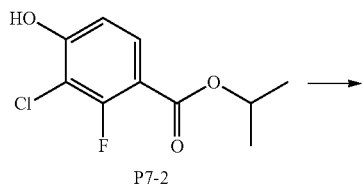
P7-2

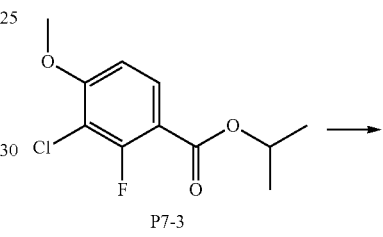
P7-3

To a solution of compound P7-2 (690 mg) obtained in the above-mentioned step in DMF (7 mL) were added potassium carbonate (820 mg) and iodomethane (280 μL), and the mixture was stirred at 50° C. for 30 min. The reaction mixture was ice-cooled, water was added and the mixture was extracted with an ethyl acetate-hexane mixed solvent. The organic layer was washed with saturated brine, dried over sodium sulfate and concentrated to give compound P7-3 (840 mg).

Preliminary Step 7-4

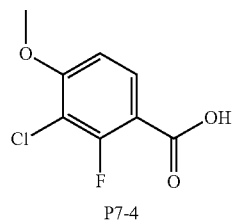
P7-3

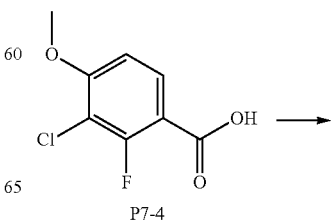
P7-4

To a solution of compound P7-3 (840 mg) obtained in the above-mentioned step in THF (5 mL) were added methanol (5 mL) and 2N aqueous sodium hydroxide solution (2.3 mL), and the mixture was stirred at 55° C. for 45 min. The reaction mixture was concentrated, water (10 mL) and 2N hydrochloric acid (2.5 mL) were added, and the mixture was stirred at room temperature for a while. The solid was filtered off, and the filtrate was dried under reduced pressure to give compound P7-4 (587 mg).

Preliminary Step 7-5

-continued

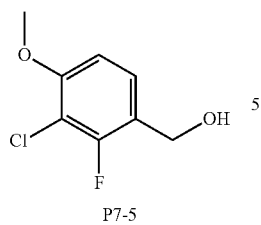

P7-5

To a solution of compound P7-4 (587 mg) obtained in the above-mentioned step in THF (6 mL) were successively added triethylamine (520 μL) and isobutyl chloroformate (484 μL) under ice-cooling, and the mixture was stirred at the same temperature for 30 min. The reaction mixture was filtered to give filtrate P7-5.

To a solution of sodium borohydride (326 mg) in water (1.3 mL) was added dropwise filtrate P7-5 under ice-cooling, and the mixture was stirred at the same temperature for 1.5 hr. To the reaction mixture was added saturated aqueous ammonium chloride solution, and the mixture was extracted with ethyl acetate. The organic layer was washed with saturated brine, dried over sodium sulfate and concentrated. The residue was purified by silica gel column chromatography (hexane:ethyl acetate=4:1 to 2:1) to give compound P7-5 (500 mg).

$^1$H-NMR (CDCl$_3$) δ: 7.26 (t, 1H, J=8.5 Hz), 6.73 (dd, 1H, J=8.5, 1.6 Hz), 4.71 (d, 2H, J=6.0 Hz), 3.92 (s, 3H), 1.77 (t, 1H, J=6.0 Hz).

Preliminary Step 7-6

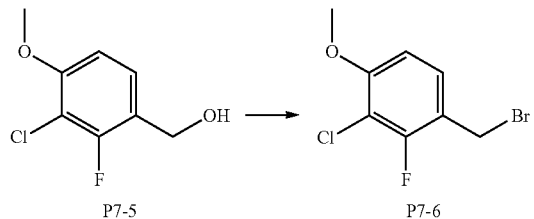

To a solution of compound P7-5 (500 mg) obtained in the above-mentioned step in THF (6 mL) were successively added triethylamine (550 μL) and methanesulfonyl chloride (305 μL) under ice-cooling, and the mixture was stirred at room temperature for 30 min. The mixture was ice-cooled again, lithium bromide (2.2 g) was added and the mixture was stirred at the same temperature for 30 min. To the reaction mixture was added water under ice-cooling, and the mixture was extracted with ethyl acetate. The organic layer was washed with saturated brine, dried over sodium sulfate and concentrated to give compound P7-6 (690 mg). The obtained compound P7-6 was directly used in the next step.

Preliminary Step 7-7

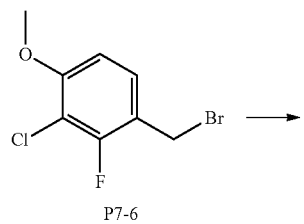

P7-6

-continued

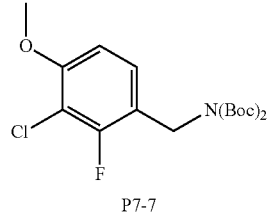

P7-7

To a solution of compound P7-6 (690 mg) obtained in the above-mentioned step in DMF (7 mL) were added cesium carbonate (1.42 g) and di-tert-butyl iminodicarboxylate (867 mg), and the mixture was stirred at 60° C. for 1 hr. The reaction mixture was cooled to room temperature, water was added, and the mixture was extracted with ethyl acetate. The organic layer was washed with saturated brine, dried over sodium sulfate and concentrated. The residue was purified by silica gel column chromatography (hexane:ethyl acetate=8:1 to 6:1) to give compound P7-7 (1.06 g).

$^1$H-NMR (CDCl$_3$) δ: 7.13 (t, 1H, J=8.5 Hz), 6.69 (dd, 1H, J=8.5, 1.6 Hz), 4.80 (s, 2H), 3.90 (s, 3H), 1.48-1.46 (m, 18H).

Preliminary Step 7-8

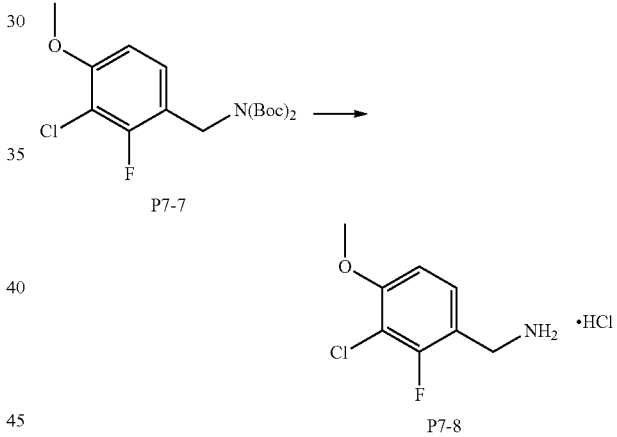

To a solution of compound P7-7 (1.06 g) obtained in the above-mentioned step in chloroform (5 mL) was added TFA (5 mL), and the mixture was stirred at room temperature for 30 min. The reaction mixture was concentrated, 4N hydrochloric acid/dioxane (5 mL) was added and the mixture was concentrated again. Crystallization from diisopropyl ether gave compound P7-8 (515 mg).

Preliminary Step 7-9

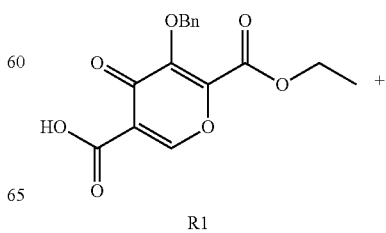

R1

-continued

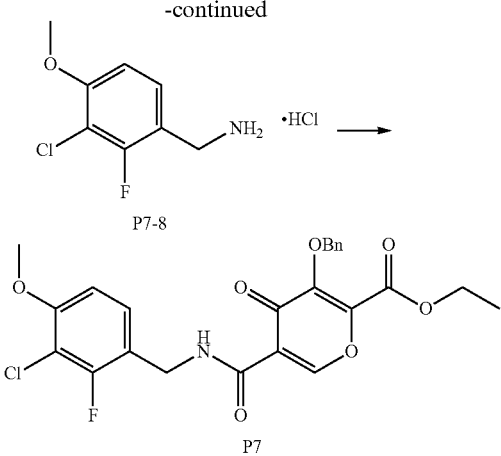

From compound R1 (870 mg) obtained in Reference Example 1, step R1-4 and compound P7-8 (515 mg) obtained in the above-mentioned step, and by a method similar to that in Example 1, Preliminary step 1-1, compound P7 (700 mg) was obtained.

$^1$H-NMR (CDCl$_3$) δ: 9.49 (t, 1H, J=5.8 Hz), 8.78 (s, 1H), 7.48-7.45 (m, 2H), 7.39-7.31 (m, 3H), 7.27 (t, 1H, J=8.5 Hz), 6.72-6.69 (m, 1H), 5.27 (s, 2H), 4.61 (d, 2H, J=5.8 Hz), 4.36 (q, 2H, J=7.1 Hz), 3.90 (s, 3H), 1.33 (t, 3H, J=7.1 Hz).

Example 8

Production of N-(3-chloro-2-fluoro-4-methoxybenzyl)-9'-hydroxy-cis-3-(methoxymethyl)-2'-methyl-1',8'-dioxo-1',2',3',8'-tetrahydrospiro[cyclobutane-1,4'-pyrido[1,2-a]pyrazine]-7'-carboxamide hydrochloride Step 1

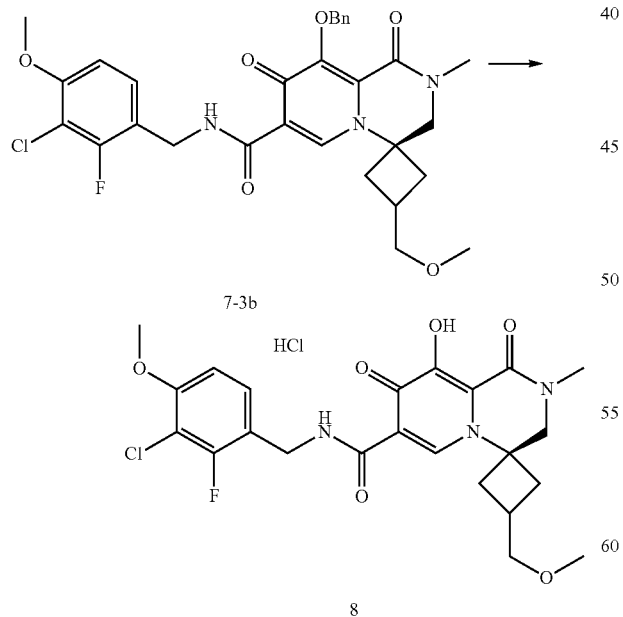

From compound 7-3b (51 mg) obtained in Example 7, step 3, and in the same manner as in Example 1, step 11, the title compound (40 mg) was obtained.

$^1$H-NMR (DMSO-d$_6$) δ: 12.81 (br s, 1H), 10.38 (t, 1H, J=6.0 Hz), 8.53 (s, 1H), 7.32 (t, 1H, J=8.5 Hz), 7.02-6.96 (m, 1H), 4.54 (d, 2H, J=6.0 Hz), 3.90 (s, 2H), 3.87 (s, 3H), 3.39 (d, 2H, J=5.2 Hz), 3.28 (s, 3H), 3.14 (s, 3H), 2.64-2.47 (m, 1H), 2.40-2.23 (m, 4H).

Example 9

Production of (1S,2S)—N-(2,4-difluorobenzyl)-9'-hydroxy-2-(hydroxymethyl)-2'-isopropyl-1',8'-dioxo-1',2',3',8'-tetrahydrospiro[cyclopropane-1,4'-pyrido[1,2-a]pyrazine]-7'-carboxamide hydrochloride Step 1

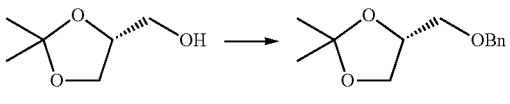

To a solution of ((R)-2,2-dimethyl-[1,3]dioxolan-4-yl)-methanol (15.4 g) in DMF (850 mL) was added sodium hydride (60% dispersion, 7 g) under ice-cooling, and the mixture was stirred at room temperature for 45 min. The mixture was ice-cooled again, benzyl bromide (16.6 mL) was added, and the mixture was stirred at room temperature overnight. To the reaction mixture was added water (150 mL) under ice-cooling, and the solvent was evaporated under reduced pressure. Water (600 mL) was added, and the mixture was extracted 3 times with chloroform (200 mL) and washed with saturated brine. The mixture was dried, and concentrated to give a crude product of compound 9-1. The obtained crude product of compound 9-1 was directly used in the next step.

$^1$H-NMR (CDCl$_3$) δ: 7.38-7.26 (m, 5H), 4.60 (d, 1H, J=12.1 Hz), 4.55 (d, 1H, J=12.1 Hz), 4.34-4.27 (m, 1H), 4.06 (dd, 1H, J=8.4, 6.5 Hz), 3.75 (dd, 1H, J=8.4, 6.5 Hz), 3.56 (dd, 1H, J=9.8, 5.8 Hz), 3.48 (dd, 1H, J=9.8, 5.6 Hz), 1.42 (s, 3H), 1.36 (s, 3H).

Step 2

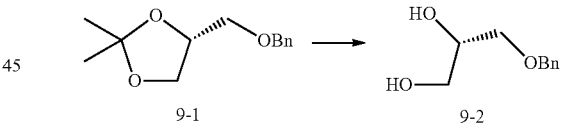

To a crude product of compound 9-1 obtained in the above-mentioned step was added an acetic acid-water (400 mL-100 mL) mixed solution, and the mixture was stirred at 55° C. for 1.5 hr. The mixture was concentrated and purified by silica gel column chromatography (hexane:ethyl acetate=1:1 to 1:2) to give compound 9-2 (15.87 g).

$^1$H-NMR (CDCl$_3$) δ: 7.39-7.27 (m, 5H), 4.56 (s, 2H), 3.94-3.86 (m, 1H), 3.76-3.53 (m, 4H), 2.56 (d, 1H, J=5.1 Hz), 2.07-2.02 (m, 1H).

Step 3

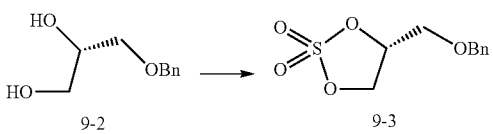 [SMILES: OC[C@H](O)COCc1ccccc1 ; O=S1(=O)OC[C@@H](COCc2ccccc2)O1]

To a solution of compound 9-2 (13.87 g) obtained in the above-mentioned step in carbon tetrachloride (76 mL) was added dropwise a solution of thionyl chloride (6.7 mL) in carbon tetrachloride (10 mL) at room temperature, and the mixture was heated under reflux for 30 min. Acetonitrile (80 mL), ruthenium(III) chloride n-hydrate (20 mg), sodium periodate (24.4 g) and water (120 mL) were successively added, and the mixture was stirred at room temperature for 1.5 hr. Diisopropyl ether (600 mL) was added and, after partitioning, the organic layer was washed successively with water, saturated aqueous sodium hydrogen carbonate solution and saturated brine, dried and purified by silica gel column chromatography (hexane:ethyl acetate=2:1) to give compound 9-3 (14.9 g).

$^{1}$H-NMR (CDCl$_3$) δ: 7.41-7.29 (m, 5H), 5.08-5.00 (m, 1H), 4.71 (dd, 1H, J=8.8, 6.5 Hz), 4.66-4.57 (m, 3H), 3.83-3.67 (m, 2H).

Step 4

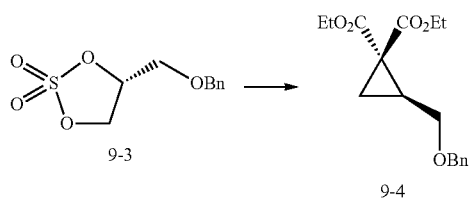

To a suspension of sodium hydride (60% dispersion, 5.1 g) in DME (450 mL) was added dropwise a solution of diethyl malonate (9.26 mL) in DME (25 mL), and the mixture was stirred at room temperature for 10 min. A solution of compound 9-3 (14.9 g) obtained in the above-mentioned step in DME (25 mL) was added, and the mixture was stirred at overnight. After concentration, water was added, and the mixture was extracted 3 times with ethyl acetate. The organic layer was washed successively with saturated aqueous sodium hydrogen carbonate solution and saturated brine, dried, concentrated and purified by silica gel column chromatography (hexane:ethyl acetate=20:1 to 10:1) to give compound 9-4 (16.6 g).

$^{1}$H-NMR (CDCl$_3$) δ: 7.37-7.24 (m, 5H), 4.48 (s, 2H), 4.26-4.07 (m, 4H), 3.57-3.46 (m, 2H), 2.30-2.20 (m, 1H), 1.57-1.52 (m, 1H), 1.42 (dd, 1H, J=9.1, 4.7 Hz), 1.31-1.20 (m, 6H).

Step 5

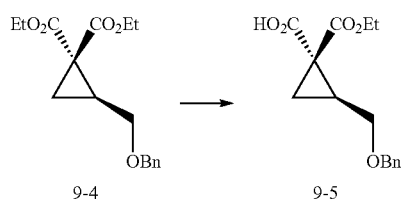

To a solution of compound 9-4 (7.59 g) obtained in the above-mentioned step in ethanol (24 mL) was added a solution of sodium carbonate (5.8 g) in water (70 mL), and the mixture was stirred at 60° C. overnight. Ethanol (20 mL) was added, and the mixture was stirred at 60° C. for 9 hr. After concentration, water was added, and the mixture was washed twice with diisopropyl ether. The aqueous layer was acidified with 5% aqueous potassium hydrogen sulfate solution, and the mixture was extracted 3 times with ethyl acetate, dried and concentrated to give compound 9-5 (6.09 g).

$^{1}$H-NMR (CDCl$_3$) δ: 7.38-7.25 (m, 5H), 4.51 (d, 1H, J=12.1 Hz), 4.42 (d, 1H, J=12.1 Hz), 4.28-4.18 (m, 1H), 4.15-4.05 (m, 1H), 3.87 (dd, 1H, J=10.9, 5.8 Hz), 3.50 (dd, 1H, J=10.7, 9.3 Hz), 2.53-2.42 (m, 1H), 2.08-2.02 (m, 1H), 1.82 (dd, 1H, J=8.4, 4.2 Hz), 1.21 (t, 3H, J=7.2 Hz).

Step 6

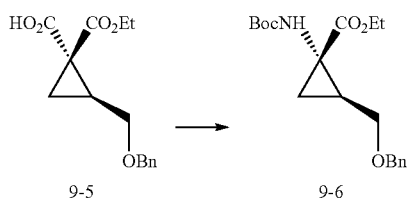 [SMILES: CCOC(=O)[C@]1(C(=O)O)C[C@@H]1COCc1ccccc1 ; CCOC(=O)[C@]1(NC(=O)OC(C)(C)C)C[C@@H]1COCc1ccccc1]

To a solution of compound 9-5 (6.09 g) obtained in the above-mentioned step in tert-butanol (100 mL) were successively added dropwise triethylamine (3.6 mL) and DPPA (5.2 mL), and the mixture was heated under reflux overnight. After concentration, the residue was dissolved in ethyl acetate, and the mixture was washed successively with saturated aqueous sodium hydrogen carbonate solution and saturated brine. The mixture was dried, concentrated, and purified by silica gel column chromatography (hexane:ethyl acetate=10:1 to 5:1) to give compound 9-6 (3.87 g).

$^{1}$H-NMR (CDCl$_3$) δ: 7.37-7.24 (m, 5H), 5.18 (br s, 1H), 4.45 (s, 2H), 4.22-4.07 (m, 2H), 3.79 (dd, 1H, J=10.2, 5.8 Hz), 3.53 (t, 1H, J=9.3 Hz), 1.83-1.73 (m, 1H), 1.70-1.58 (m, 1H), 1.46-1.31 (m, 1H), 1.44 (s, 9H), 1.23 (t, 3H, J=7.0 Hz).

Step 7

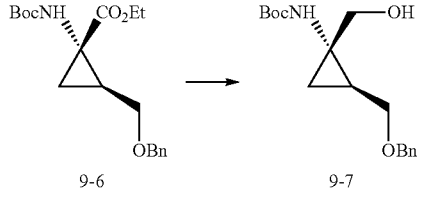 [SMILES: CCOC(=O)[C@]1(NC(=O)OC(C)(C)C)C[C@@H]1COCc1ccccc1 ; CC(C)(C)OC(=O)N[C@@]1(CO)C[C@@H]1COCc1ccccc1]

To a suspension of lithium aluminum hydride (70 mg) in THF (2 mL) was added dropwise under ice-cooling a solution of compound 9-6 (431 mg) obtained in the above-mentioned step in THF (2 mL), and the mixture was stirred at room temperature for 1 hr. Under ice-cooling, water (70 μL), 15% aqueous sodium hydroxide solution (70 μL), and water (210 μL) were successively added dropwise, the mixture was stirred at room temperature for 30 min, and the insoluble material was filtered off. The filtrate was dried, and concentrated to give compound 9-7 (377 mg).

$^{1}$H-NMR (CDCl$_3$) δ: 7.39-7.26 (m, 5H), 5.22 (br s, 1H), 4.54 (dd, 2H, J=18.4, 11.6 Hz), 3.98 (t, 1H, J=11.2 Hz), 3.85 (dd, 1H, J=10.7, 6.0 Hz), 3.46-3.28 (m, 2H), 3.16 (t, 1H, J=10.5 Hz), 1.43 (s, 9H), 1.28-1.11 (m, 1H), 0.82-0.70 (m, 1H).

Step 8

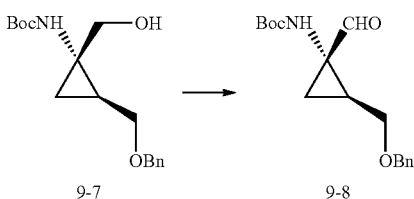 [SMILES: CC(C)(C)OC(=O)N[C@@]1(CO)C[C@@H]1COCc1ccccc1 ; CC(C)(C)OC(=O)N[C@@]1(C=O)C[C@@H]1COCc1ccccc1]

To a solution of oxalyl chloride (120 μL) in chloroform (3 mL) was added dropwise a solution of DMSO (191 μL) in chloroform (1 mL) at an inside temperature of −50 to −60° C., and the mixture was stirred at the same temperature for 2 min. A solution of compound 9-7 (377 mg) obtained in the above-mentioned step in chloroform (1 mL) was added dropwise, and the mixture was stirred at the same temperature for 15 min. Triethylamine (850 μL) was added, and the mixture was further stirred at the same temperature for 5 min. The mixture was allowed to warm to room temperature, water was added, and the mixture was extracted with chloroform. The organic layer was washed with saturated brine, dried, concentrated, and purified by silica gel column chromatography (hexane:ethyl acetate=10:1 to 5:1) to give compound 9-8 (293 mg).

$^1$H-NMR (CDCl$_3$) δ: 9.44 (s, 1H), 7.35-7.25 (m, 5H), 5.18-5.18 (m, 1H), 4.43 (s, 2H), 3.84-3.72 (m, 1H), 3.51-3.37 (m, 1H), 2.00-1.87 (m, 1H), 1.75-1.63 (m, 1H), 1.45-1.40 (m, 10H).

Step 9

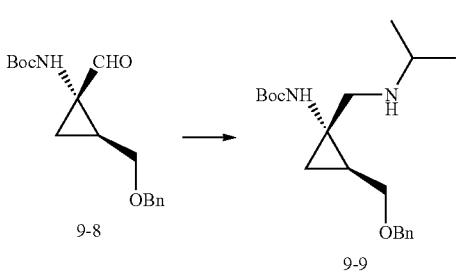 [SMILES: CC(C)(C)OC(=O)N[C@@]1(C=O)C[C@@H]1COCc1ccccc1 ; CC(C)NC[C@]1(NC(=O)OC(C)(C)C)C[C@@H]1COCc1ccccc1]

To a solution of compound 9-8 (293 mg) obtained in the above-mentioned step in chloroform (10 mL) were successively added isopropylamine (106 μL), acetic acid (55 μL) and sodium triacetoxyborohydride (204 mg) under ice-cooling, and the mixture was stirred at room temperature overnight. To the reaction mixture was added saturated aqueous sodium hydrogen carbonate solution and, after partitioning, the organic layer was washed with saturated brine, dried, concentrated, and purified by silica gel column chromatography (chloroform:methanol=10:1) to give compound 9-9 (228 mg).

$^1$H-NMR (CDCl$_3$) δ: 7.37-7.25 (m, 5H), 5.41 (br s, 1H), 4.56 (d, 1H, J=11.9 Hz), 4.49 (d, 1H, J=11.9 Hz), 3.73-3.61 (m, 1H), 3.35-3.24 (m, 1H), 3.10-2.91 (m, 1H), 2.81-2.70 (m, 1H), 2.61-2.45 (m, 1H), 1.43 (s, 10H), 1.19-1.08 (m, 1H), 0.99 (t, 6H, J=6.3 Hz), 0.77-0.57 (m, 1H).

Step 10

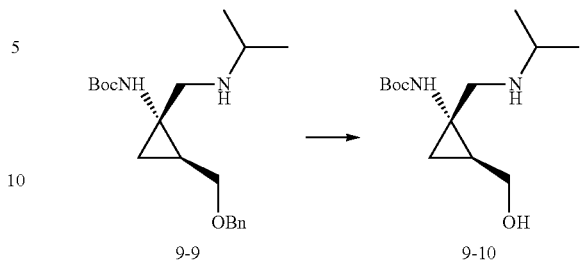

To a suspension of palladium-platinum/carbon (ASCA2, manufactured by N.E. CHEMCAT Corporation, 200 mg) in ethanol (6 mL) was added a solution of acetic acid (45 μL) and compound 9-9 (228 mg) obtained in the above-mentioned step in ethanol (1 mL), and the mixture was stirred under a hydrogen atmosphere at room temperature for 3 hr. The catalyst was filtered off, and the same, fresh catalyst (200 mg) was added, and the mixture was stirred under a hydrogen atmosphere at room temperature overnight. The insoluble material was filtered off, and the filtrate was concentrated to give a crude product of compound 9-10. The obtained crude product of compound 9-10 was directly used in the next step.

$^1$H-NMR (CDCl$_3$) δ: 6.24 (br's, 1H), 4.31-4.21 (m, 1H), 3.71-3.62 (m, 1H), 3.26-3.14 (m, 1H), 3.00 (t, 1H, J=12.1 Hz), 2.61 (d, 1H, J=12.8 Hz), 1.69-1.58 (m, 1H), 1.46-1.32 (m, 1H), 1.43 (s, 9H), 1.32 (t, 6H, J=6.7 Hz), 0.88-0.79 (m, 1H).

Step 11

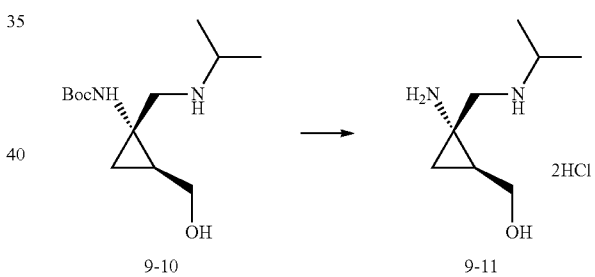

To the crude product of compound 9-10 obtained in the above-mentioned step was added 4N hydrochloric acid/dioxane (10 mL), and the mixture was stirred for 1 hr, and concentrated to give a crude product of compound 9-11 (125 mg). The obtained crude product of compound 9-11 was directly used in the next step.

$^1$H-NMR (DMSO-d$_6$) δ: 9.41-9.23 (m, 1H), 9.20-9.04 (m, 1H), 3.81 (dd, 1H, J=12.4, 5.5 Hz), 3.52-3.21 (m, 4H), 1.75-1.64 (m, 1H), 1.32-1.26 (m, 6H), 1.24-1.15 (m, 2H).

Step 12

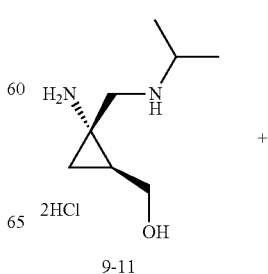

157

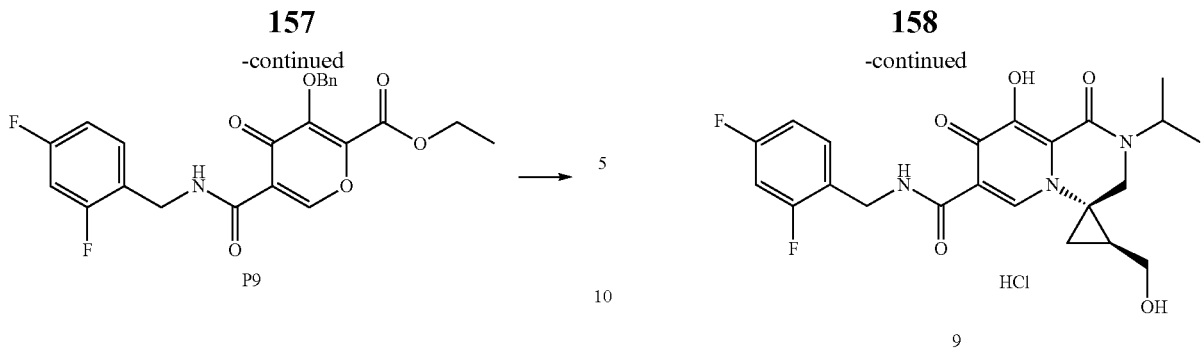

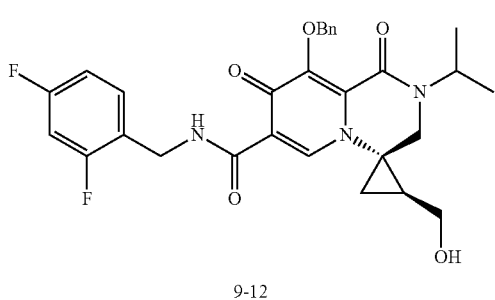

To a solution of the crude product (40 mg) of compound 9-11 obtained in the above-mentioned step in THF (1.5 mL) were successively added ethanol (300 μL), triethylamine (96 μL) and compound P9 (65 mg) obtained in below-mentioned Preliminary step 9-1, and the mixture was stirred at room temperature for 1 hr. DBU (104 μL) was added, and the mixture was further stirred for 1 hr. After concentration, toluene (5 mL), ethanol (500 μL), and acetic acid (80 μL) were successively added, and the mixture was stirred at 100° C. for 1 hr. Acetic acid (120 μL) was added, and the mixture was stirred at 100° C. overnight. To the reaction mixture was added saturated aqueous sodium hydrogen carbonate solution, and the mixture was extracted 3 times with chloroform. The organic layer was washed with saturated brine, dried, concentrated, and purified by silica gel column chromatography (ethyl acetate:methanol=100:4) to give compound 9-12 (70 mg).

$^1$H-NMR (CDCl$_3$) δ: 10.51 (t, 1H, J=6.0 Hz), 8.34 (s, 1H), 7.62-7.58 (m, 2H), 7.40-7.25 (m, 4H), 6.84-6.75 (m, 2H), 5.32 (d, 1H, J=10.0 Hz), 5.25 (d, 1H, J=10.0 Hz), 4.92-4.82 (m, 1H), 4.61 (d, 2H, J=6.0 Hz), 4.11-4.02 (m, 1H), 3.80-3.70 (m, 1H), 3.59 (d, 1H, J=14.2 Hz), 3.41 (d, 1H, J=14.2 Hz), 2.23-2.13 (m, 1H), 1.90-1.81 (m, 1H), 1.60-1.42 (m, 1H), 1.18-1.13 (m, 6H).

Step 13

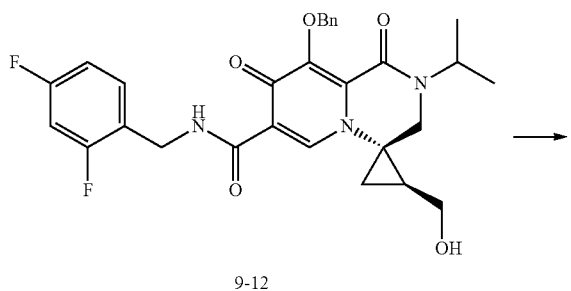

158

To compound 9-12 (20 mg) obtained in the above-mentioned step was added TFA (1.5 mL) and the mixture was stirred for 30 min. After concentration, the residue was azeotropically distilled 4 times with methanol. The residue was dissolved in methanol (1 mL), 4N hydrochloric acid/ethyl acetate was added, and the mixture was concentrated. Hexane was added and the supernatant liquid was removed by decantation. The resulting residue was crystallized from ethyl acetate-hexane to give the title compound (9 mg).

$^1$H-NMR (DMSO-d$_6$) δ: 12.89-12.73 (m, 1H), 10.38 (t, 1H, J=6.0 Hz), 8.14 (s, 1H), 7.43-7.35 (m, 1H), 7.26-7.19 (m, 1H), 7.10-7.02 (m, 1H), 4.78-4.68 (m, 1H), 4.53 (d, 2H, J=6.0 Hz), 4.42-3.99 (m, 1H), 3.80-3.67 (m, 3H), 3.51 (dd, 1H, J=12.1, 7.7 Hz), 1.94-1.84 (m, 1H), 1.74-1.67 (m, 1H), 1.19 (d, 3H, J=7.0 Hz), 1.17 (d, 3H, J=7.0 Hz), 1.03 (t, 1H, J=7.2 Hz).

Preliminary Step 9-1

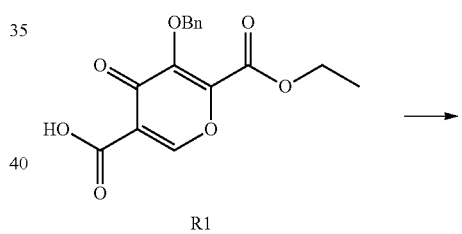

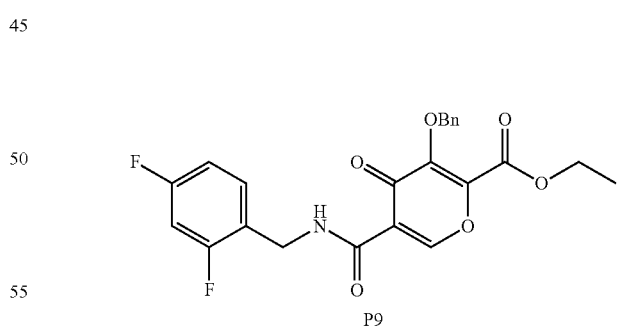

From compound R1 (12.15 g) obtained in Reference Example 1, step R1-4, and commercially available 2,4-difluorobenzylamine (3.6 mL) and by a method similar to that in Example 1, Preliminary step 1-1, compound P9 (11.7 g) was obtained.

$^1$H-NMR (CDCl$_3$) δ: 9.54-9.45 (m, 1H), 8.79 (s, 1H), 7.48-7.43 (m, 2H), 7.42-7.30 (m, 4H), 6.89-6.79 (m, 2H), 5.27 (s, 2H), 4.62 (d, 2H, J=6.3 Hz), 4.37 (q, 2H, J=7.2 Hz), 1.33 (t, 3H, J=7.2 Hz).

Example 10

Production of (1S,2S)—N-(2,4-difluorobenzyl)-9'-hydroxy-2'-isopropyl-2-(methoxymethyl)-1',8'-dioxo-1',2',3',8'-tetrahydrospiro[cyclopropane-1,4'-pyrido[1,2-a]pyrazine]-7'-carboxamide hydrochloride

Step 1

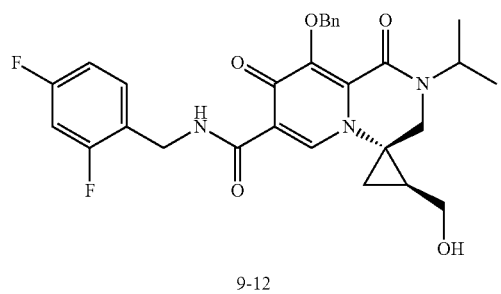

9-12

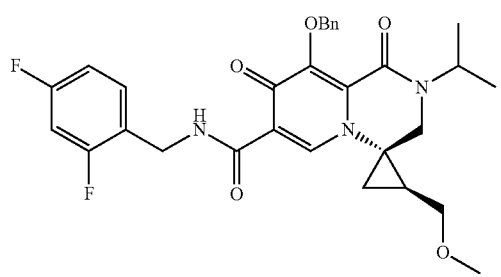

10-1

To a solution of compound 9-12 (29 mg) obtained in Example 9, step 12, in toluene (1 mL) were successively added tetrabutylammonium hydrogen sulfate (2 mg), 50% aqueous sodium hydroxide solution (17 μL) and dimethyl sulfate (10 μL) under ice-cooling, and the mixture was stirred at room temperature for 20 min. 50% Aqueous sodium hydroxide solution (8 μL) and dimethyl sulfate (5 μL) were successively added, and the mixture was further stirred at room temperature for 20 min. To the reaction mixture was added saturated aqueous sodium hydrogen carbonate solution, and the mixture was extracted 3 times with chloroform and washed with saturated brine, dried, concentrated, and purified by silica gel thin layer chromatography (ethyl acetate:methanol=100:5) to give compound 10-1 (23 mg).

$^1$H-NMR (CDCl$_3$) δ: 10.51 (t, 1H, J=6.3 Hz), 8.34 (s, 1H), 7.64-7.60 (m, 2H), 7.40-7.24 (m, 4H), 6.85-6.77 (m, 2H), 5.34 (d, 1H, J=9.8 Hz), 5.27 (d, 1H, J=9.8 Hz), 4.92-4.84 (m, 1H), 4.63 (d, 2H, J=5.8 Hz), 3.78 (dd, 1H, J=10.7, 3.7 Hz), 3.58-3.45 (m, 2H), 3.38 (d, 1H, J=14.0 Hz), 3.35 (s, 3H), 2.21-2.11 (m, 1H), 1.58-1.44 (m, 1H), 1.18-1.11 (m, 7H).

Step 2

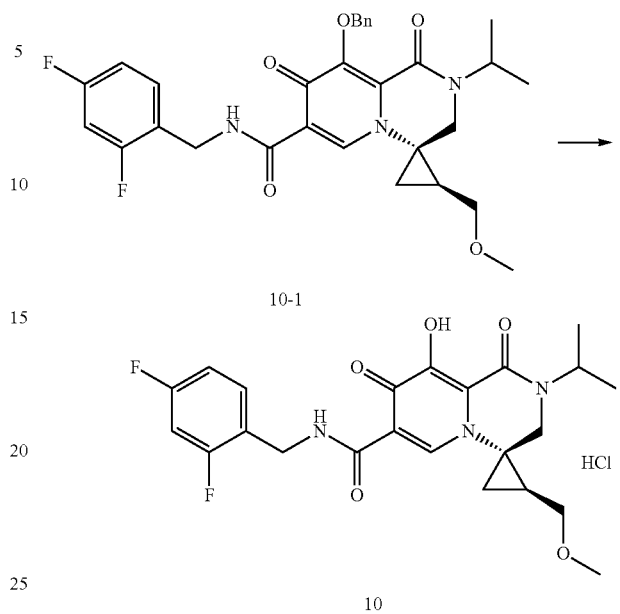

To compound 10-1 (23 mg) obtained in the above-mentioned step was added TFA (1.5 mL), and the mixture was stirred at room temperature for 30 min. After concentration, the residue was azeotropically distilled twice with ethyl acetate, and dissolved in ethyl acetate (1 mL), and 4N hydrochloric acid/ethyl acetate was added. After concentration, hexane was added and the supernatant liquid was removed by decantation. Crystallization from ethyl acetate-hexane gave the title compound (8 mg).

$^1$H-NMR (DMSO-d$_6$) δ: 12.83 (s, 1H), 10.36 (t, 1H, J=6.0 Hz), 8.10 (s, 1H), 7.43-7.35 (m, 1H), 7.27-7.19 (m, 1H), 7.09-7.02 (m, 1H), 4.77-4.68 (m, 1H), 4.52 (d, 2H, J=6.0 Hz), 3.80 (d, 1H, J=14.2 Hz), 3.66 (d, 1H, J=14.2 Hz), 3.61-3.40 (m, 2H), 3.23 (s, 3H), 1.93-1.84 (m, 2H), 1.17 (dd, 6H, J=6.5, 1.4 Hz), 1.10-1.06 (m, 1H).

Example 11

Production of (1R,2R)—N-(2,4-difluorobenzyl)-9'-hydroxy-2'-(hydroxymethyl)-2'-isopropyl-1',8'-dioxo-1',2',3',8'-tetrahydrospiro[cyclopropane-1,4'-pyrido[1,2-a]pyrazine]-7'-carboxamide hydrochloride

Step 1

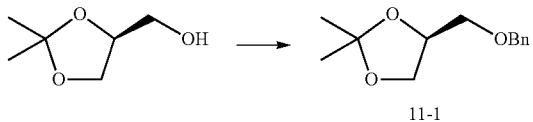

11-1

From ((S)-2,2-dimethyl-[1,3]dioxolan-4-yl)-methanol (15.29 g) and by an operation similar to that in Example 9-1, a crude product of compound 11-1 was obtained.

$^1$H-NMR (CDCl$_3$) δ: 7.38-7.26 (m, 5H), 4.60 (d, 1H, J=12.1 Hz), 4.55 (d, 1H, J=12.1 Hz), 4.34-4.27 (m, 1H), 4.06 (dd, 1H, J=8.4, 6.5 Hz), 3.75 (dd, 1H, J=8.4, 6.5 Hz), 3.56 (dd, 1H, J=9.8, 5.8 Hz), 3.48 (dd, 1H, J=9.8, 5.6 Hz), 1.42 (s, 3H), 1.36 (s, 3H).

Step 2

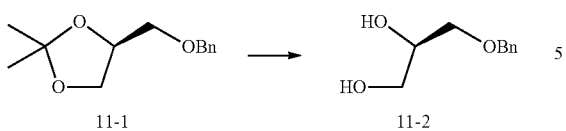

From crude product of compound 11-1 obtained in the above-mentioned step and by a method similar to that in Example 9, step 2, compound 11-2 (21.42 g) was obtained.

$^1$H-NMR (CDCl$_3$) δ: 7.39-7.27 (m, 5H), 4.56 (s, 2H), 3.94-3.86 (m, 1H), 3.76-3.53 (m, 4H), 2.56 (d, 1H, J=5.1 Hz), 2.07-2.02 (m, 1H).

Step 3

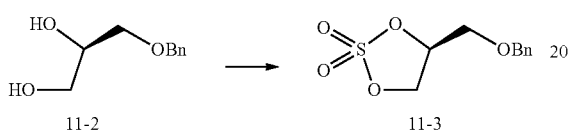

From compound 11-2 (21.42 g) obtained in the above-mentioned step and by a method similar to that in Example 9, step 3, compound 11-3 (26.2 g) was obtained.

$^1$H-NMR (CDCl$_3$) δ: 7.41-7.29 (m, 5H), 5.08-5.00 (m, 1H), 4.71 (dd, 1H, J=8.8, 6.5 Hz), 4.66-4.57 (m, 3H), 3.83-3.67 (m, 2H).

Step 4

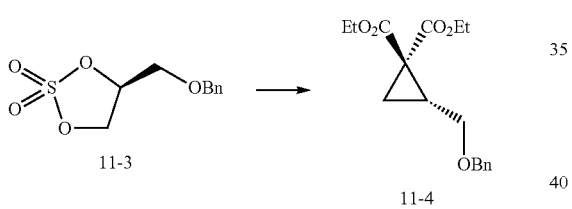

From compound 11-3 (26.2 g) obtained in the above-mentioned step and by a method similar to that in Example 9, step 4, compound 11-4 (31.6 g) was obtained.

$^1$H-NMR (CDCl$_3$) δ: 7.37-7.24 (m, 5H), 4.48 (s, 2H), 4.26-4.07 (m, 4H), 3.57-3.46 (m, 2H), 2.30-2.20 (m, 1H), 1.57-1.52 (m, 1H), 1.42 (dd, 1H, J=9.1, 4.7 Hz), 1.31-1.20 (m, 6H).

Step 5

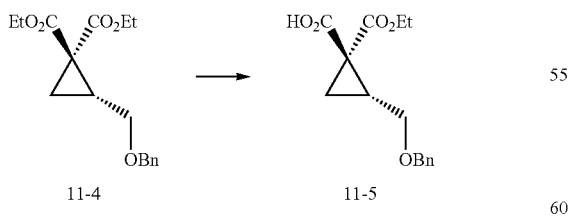

From compound 11-4 (13.09 g) obtained in the above-mentioned step and by a method similar to that in Example 9, step 5, compound 11-5 (9.01 g) was obtained.

$^1$H-NMR (CDCl$_3$) δ: 7.38-7.25 (m, 5H), 4.51 (d, 1H, J=12.1 Hz), 4.42 (d, 1H, J=12.1 Hz), 4.28-4.18 (m, 1H), 4.15-4.05 (m, 1H), 3.87 (dd, 1H, J=10.9, 5.8 Hz), 3.50 (dd, 1H, J=10.7, 9.3 Hz), 2.53-2.42 (m, 1H), 2.08-2.02 (m, 1H), 1.82 (dd, 1H, J=8.4, 4.2 Hz), 1.21 (t, 3H, J=7.2 Hz).

Step 6

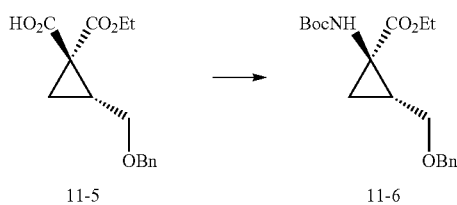 [SMILES: CCOC(=O)[C@@]1(C(=O)O)C[C@H]1COCc1ccccc1 ; CCOC(=O)[C@@]1(NC(=O)OC(C)(C)C)C[C@H]1COCc1ccccc1]

From compound 11-5 (9.01 g) obtained in the above-mentioned step and by a method similar to that in Example 9, step 6, compound 11-6 (8.56 g) was obtained.

$^1$H-NMR (CDCl$_3$) δ: 7.37-7.24 (m, 5H), 5.18 (br s, 1H), 4.45 (s, 2H), 4.22-4.07 (m, 2H), 3.79 (dd, 1H, J=10.2, 5.8 Hz), 3.53 (t, 1H, J=9.3 Hz), 1.83-1.73 (m, 1H), 1.70-1.58 (m, 1H), 1.46-1.31 (m, 1H), 1.44 (s, 9H), 1.23 (t, 3H, J=7.0 Hz).

Step 7

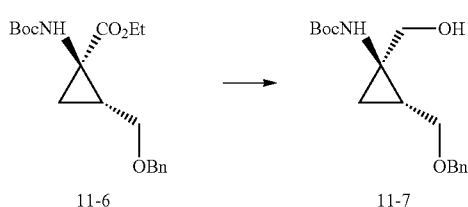 [SMILES: CCOC(=O)[C@@]1(NC(=O)OC(C)(C)C)C[C@H]1COCc1ccccc1 ; CC(C)(C)OC(=O)N[C@]1(CO)C[C@H]1COCc1ccccc1]

From compound 11-6 (8.56 g) obtained in the above-mentioned step and by a method similar to that in Example 9, step 7, compound 11-7 was obtained. The obtained compound 11-7 was directly used in the next step.

$^1$H-NMR (CDCl$_3$) δ: 7.39-7.26 (m, 5H), 5.22 (br s, 1H), 4.54 (dd, 2H, J=18.4, 11.6 Hz), 3.98 (t, 1H, J=11.2 Hz), 3.85 (dd, 1H, J=10.7, 6.0 Hz), 3.46-3.28 (m, 2H), 3.16 (t, 1H, J=10.5 Hz), 1.43 (s, 9H), 1.28-1.11 (m, 1H), 0.82-0.70 (m, 1H).

Step 8

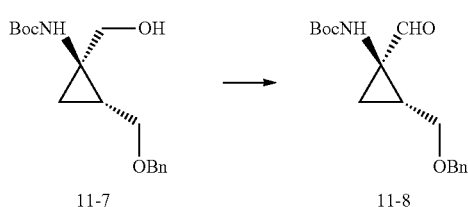 [SMILES: CC(C)(C)OC(=O)N[C@]1(CO)C[C@H]1COCc1ccccc1 ; CC(C)(C)OC(=O)N[C@]1(C=O)C[C@H]1COCc1ccccc1]

From compound 11-7 obtained in the above-mentioned step and by a method similar to that in Example 1, step 4, a crude product of compound 11-8 was obtained. The crude product of compound 11-8 was purified by silica gel column chromatography (hexane:ethyl acetate=3:1) to give compound 11-8 (2.78 g).

$^1$H-NMR (CDCl$_3$) δ: 9.44 (s, 1H), 7.35-7.25 (m, 5H), 5.18-5.18 (m, 1H), 4.43 (s, 2H), 3.84-3.72 (m, 1H), 3.51-3.37 (m, 1H), 2.00-1.87 (m, 1H), 1.75-1.63 (m, 1H), 1.45-1.40 (m, 10H).

Step 9

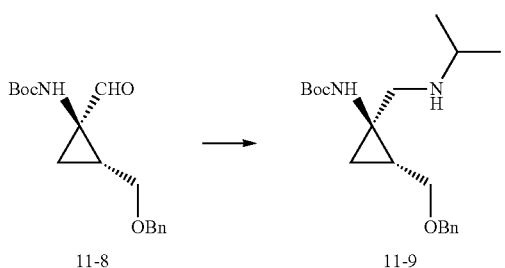 [SMILES: CC(C)(C)OC(=O)N[C@]1(C=O)C[C@H]1COCc1ccccc1 ; CC(C)NC[C@@]1(NC(=O)OC(C)(C)C)C[C@H]1COCc1ccccc1]

From compound 11-8 (950 mg) obtained in the above-mentioned step and by a method similar to that in Example 9, step 9, compound 11-9 (510 mg) was obtained.

¹H-NMR (CDCl₃) δ: 7.37-7.25 (m, 5H), 5.41 (br s, 1H), 4.56 (d, 1H, J=11.9 Hz), 4.49 (d, 1H, J=11.9 Hz), 3.73-3.61 (m, 1H), 3.35-3.24 (m, 1H), 3.10-2.91 (m, 1H), 2.81-2.70 (m, 1H), 2.61-2.45 (m, 1H), 1.43 (s, 10H), 1.19-1.08 (m, 1H), 0.99 (t, 6H, J=6.3 Hz), 0.77-0.57 (m, 1H).

Step 10

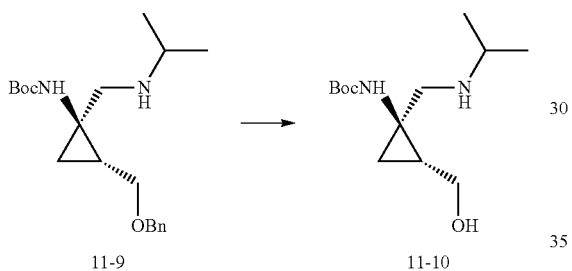

From compound 11-9 (510 mg) obtained in the above-mentioned step and by a method similar to that in Example 9, step 10, a crude product of compound 11-10 was obtained. The obtained crude product of compound 11-10 was directly used in the next step.

¹H-NMR (CDCl₃) δ: 6.24 (br s, 1H), 4.31-4.21 (m, 1H), 3.71-3.62 (m, 1H), 3.26-3.14 (m, 1H), 3.00 (t, 1H, J=12.1 Hz), 2.61 (d, 1H, J=12.8 Hz), 1.69-1.58 (m, 1H), 1.46-1.32 (m, 1H), 1.43 (s, 9H), 1.32 (t, 6H, J=6.7 Hz), 0.88-0.79 (m, 1H).

Step 11

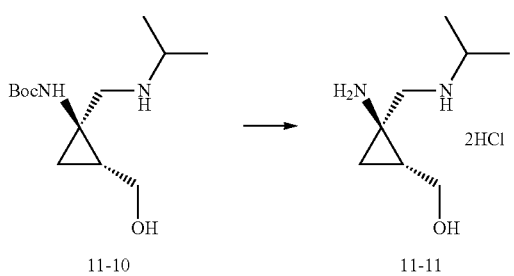 [SMILES: CC(C)NC[C@@]1(NC(=O)OC(C)(C)C)C[C@H]1CO ; CC(C)NC[C@@]1(N)C[C@H]1CO]

From the crude product of compound 11-10 obtained in the above-mentioned step and by a method similar to that in Example 9, step 11, a crude product of compound 11-11 (163 mg) was obtained. The obtained crude product of compound 11-11 was directly used in the next step.

¹H-NMR (DMSO-d₆) δ: 9.41-9.23 (m, 1H), 9.20-9.04 (m, 1H), 3.81 (dd, 1H, J=12.4, 5.5 Hz), 3.52-3.21 (m, 4H), 1.75-1.64 (m, 1H), 1.32-1.26 (m, 6H), 1.24-1.15 (m, 2H).

Step 12

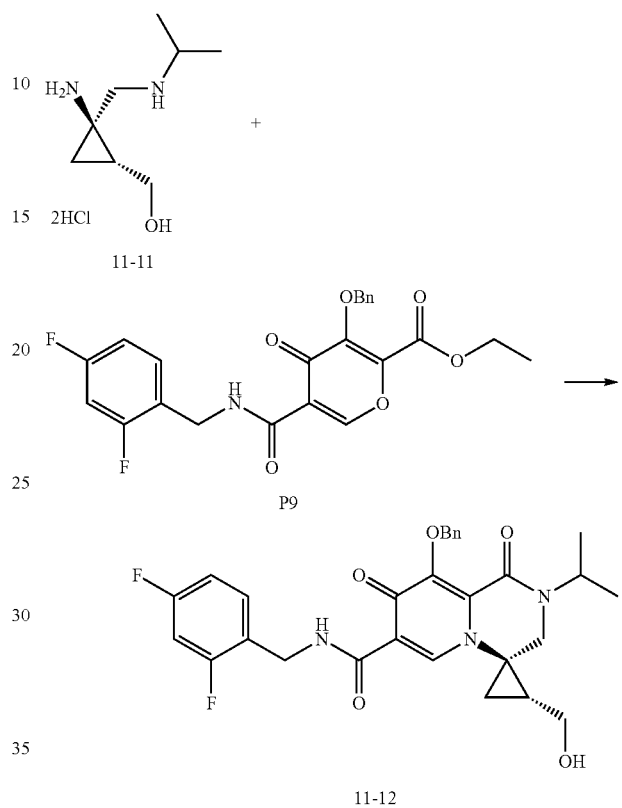

From the crude product of compound 11-11 obtained in the above-mentioned step (140 mg) and compound P9 obtained in Example 9, Preliminary step 9-1, and by a method similar to that in Example 9, step 12, compound 11-12 (190 mg) was obtained.

¹H-NMR (CDCl₃) δ: 10.51 (t, 1H, J=6.0 Hz), 8.34 (s, 1H), 7.62-7.58 (m, 2H), 7.40-7.25 (m, 4H), 6.84-6.75 (m, 2H), 5.32 (d, 1H, J=10.0 Hz), 5.25 (d, 1H, J=10.0 Hz), 4.92-4.82 (m, 1H), 4.61 (d, 2H, J=6.0 Hz), 4.11-4.02 (m, 1H), 3.80-3.70 (m, 1H), 3.59 (d, 1H, J=14.2 Hz), 3.41 (d, 1H, J=14.2 Hz), 2.23-2.13 (m, 1H), 1.90-1.81 (m, 1H), 1.60-1.42 (m, 1H), 1.18-1.13 (m, 6H).

Step 13

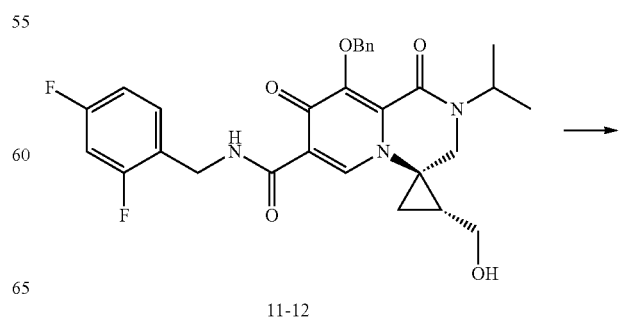

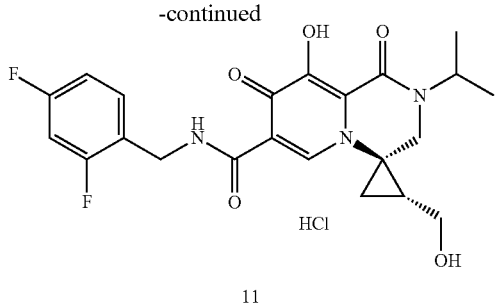

11

From compound 11-12 (15 mg) obtained in the above-mentioned step and by a method similar to that in Example 9, step 13, the title compound (7 mg) was obtained.
$^1$H-NMR (DMSO-d$_6$) δ: 12.82 (s, 1H), 10.38 (t, 1H, J=6.0 Hz), 8.14 (s, 1H), 7.44-7.35 (m, 1H), 7.27-7.19 (m, 1H), 7.10-7.02 (m, 1H), 4.98-4.80 (m, 1H), 4.78-4.69 (m, 1H), 4.53 (d, 2H, J=6.0 Hz), 3.86-3.58 (m, 3H), 3.56-3.47 (m, 1H), 1.95-1.83 (m, 1H), 1.72 (dd, 1H, J=10.6, 6.6 Hz), 1.19 (d, 3H, J=6.8 Hz), 1.17 (d, 3H, J=6.8 Hz), 1.03 (t, 1H, J=7.1 Hz).

Example 12

Production of (1R,2R)—N-(2,4-difluorobenzyl)-9'-hydroxy-2'-isopropyl-2-(methoxymethyl)-1',8'-dioxo-1',2',3',8'-tetrahydrospiro[cyclopropane-1,4'-pyrido[1,2-a]pyrazine]-7'-carboxamide hydrochloride
Step 1

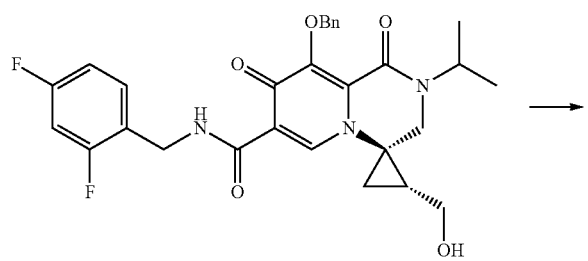

11-12

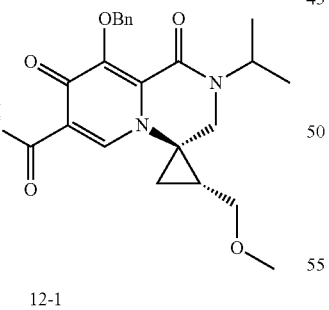

12-1

From compound 11-12 (130 mg) obtained in Example 11, step 12 and by a method similar to that in Example 10, step 1, compound 12-1 (118 mg) was obtained.
$^1$H-NMR (CDCl$_3$) δ: 10.51 (t, 1H, J=6.3 Hz), 8.34 (s, 1H), 7.64-7.60 (m, 2H), 7.40-7.24 (m, 4H), 6.85-6.77 (m, 2H), 5.34 (d, 1H, J=9.8 Hz), 5.27 (d, 1H, J=9.8 Hz), 4.92-4.84 (m, 1H), 4.63 (d, 2H, J=5.8 Hz), 3.78 (dd, 1H, J=10.7, 3.7 Hz), 3.58-3.45 (m, 2H), 3.38 (d, 1H, J=14.0 Hz), 3.35 (s, 3H), 2.21-2.11 (m, 1H), 1.58-1.44 (m, 1H), 1.18-1.11 (m, 7H).

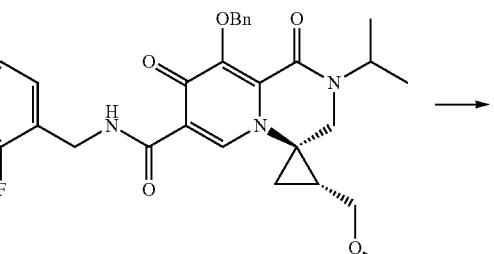

12-1

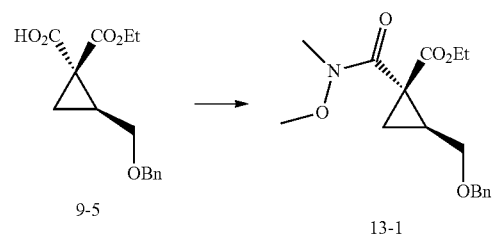 [SMILES: CCOC(=O)[C@]1(C(=O)O)C[C@@H]1COCc1ccccc1 ; CCOC(=O)[C@]1(C(=O)N(C)OC)C[C@@H]1COCc1ccccc1]

12

From compound 12-1 (118 mg) obtained in the above-mentioned step and by a method similar to that in Example 10, step 2, the title compound (53 mg) was obtained.
$^1$H-NMR (DMSO-d$_6$) δ: 12.96-12.71 (m, 1H), 10.36 (t, 1H, J=6.2 Hz), 8.10 (s, 1H), 7.43-7.35 (m, 1H), 7.27-7.19 (m, 1H), 7.09-7.02 (m, 1H), 4.78-4.68 (m, 1H), 4.52 (d, 2H, J=6.0 Hz), 3.80 (d, 1H, J=14.1 Hz), 3.67 (d, 1H, J=14.1 Hz), 3.61-3.53 (m, 1H), 3.50-3.42 (m, 1H), 3.23 (s, 3H), 1.94-1.84 (m, 2H), 1.17 (dd, 6H, J=6.6, 1.5 Hz), 1.11-1.05 (m, 1H).

Example 13

Production of (1R,2S)—N-(2,4-difluorobenzyl)-9'-hydroxy-2-(hydroxymethyl)-2'-isopropyl-1',8'-dioxo-1',2',3',8'-tetrahydrospiro[cyclopropane-1,4'-pyrido[1,2-a]pyrazine]-7'-carboxamide hydrochloride
Step 1

To a solution of compound 9-5 (1.5 g) obtained in the same manner as in Example 9, step 5, in DMF (10 mL) were added N,O-dimethylhydroxylamine hydrochloride (1.1 g), triethylamine (1.6 mL), HOBt.H$_2$O (1.1 g) and EDC (1.55 g) under ice-cooling, and the mixture was stirred at room temperature for 3 hr. To the reaction mixture were added under ice-cooling a saturated aqueous sodium hydrogen carbonate solution and ethyl acetate to allow for partitioning, and the organic layer was washed with saturated brine. The mixture was dried, concentrated and purified by silica gel column chromatography (hexane:ethyl acetate=2:1) to give compound 13-1 (1.38 g).

$^1$H-NMR (CDCl$_3$) δ: 7.36-7.22 (m, 5H), 4.51 (dd, 2H, J=14.1, 11.7 Hz), 4.20-4.05 (m, 2H), 3.72-3.61 (m, 1H), 3.66 (s, 3H), 3.53 (dd, 1H, J=10.5, 8.1 Hz), 3.24 (s, 3H), 2.38-2.20 (m, 1H), 1.60-1.55 (m, 1H), 1.39-1.27 (m, 1H), 1.21 (t, 3H, J=7.3 Hz).

Step 2

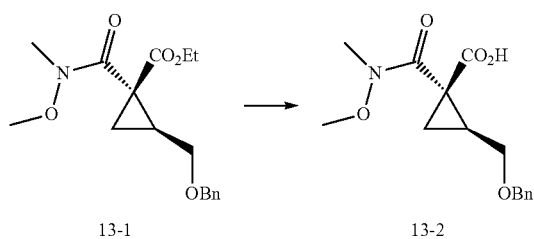 [SMILES: CCOC(=O)[C@]1(C(=O)N(C)OC)C[C@@H]1COCc1ccccc1 ; CON(C)C(=O)[C@@]1(C(=O)O)C[C@@H]1COCc1ccccc1]

To a solution of compound 13-1 (1.38 g) obtained in the above-mentioned step in methanol (14 mL) was added 2N aqueous sodium hydroxide solution (4.6 mL), and the mixture was stirred for 2 hr. 2N Aqueous sodium hydroxide solution (4.6 mL) was added, and the mixture was further stirred overnight. The mixture was neutralized with 2N hydrochloric acid, and extracted with ethyl acetate. The organic layer was washed with saturated brine, dried, and concentrated to give residue 13-2 (1 g). The obtained residue 13-2 was directly used in the next step.

Step 3

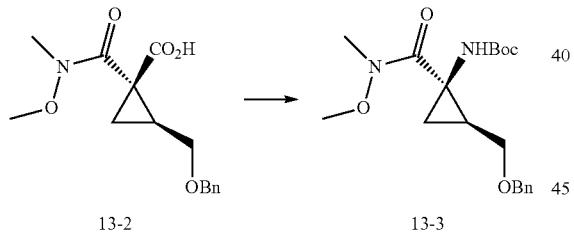

To a solution of residue 13-2 (1 g) obtained in the above-mentioned step in toluene (10 mL) were added triethylamine (1.43 mL) and DPPA (1.84 mL), and the mixture was stirred at 90° C. for 40 min. tert-Butanol (15 mL) was added, and the mixture was stirred at 100° C. overnight. The reaction mixture was concentrated, and saturated aqueous sodium hydrogen carbonate solution and ethyl acetate were added to allow for partitioning. The organic layer was washed with saturated brine, dried, concentrated, and purified by silica gel column chromatography (hexane:ethyl acetate=5:1 to 1:1) to give compound 13-3 (350 mg).

$^1$H-NMR (CDCl$_3$) δ: 7.39-7.24 (m, 5H), 5.52-5.30 (m, 1H), 4.64-4.52 (m, 1H), 4.52-4.41 (m, 1H), 3.85 (dd, 1H, J=10.9, 5.2 Hz), 3.65 (s, 3H), 3.38 (t, 1H, J=10.1 Hz), 3.17 (s, 3H), 1.96-1.86 (m, 1H), 1.81-1.70 (m, 1H), 1.43 (s, 9H), 1.02-0.85 (m, 1H).

Step 4

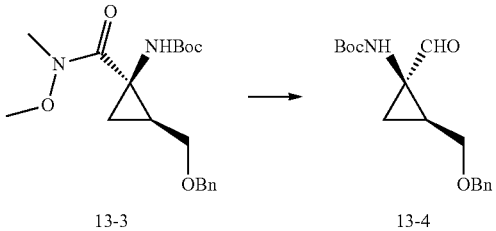 [SMILES: CON(C)C(=O)[C@@]1(NC(=O)OC(C)(C)C)C[C@@H]1COCc1ccccc1 ; CC(C)(C)OC(=O)N[C@]1(C=O)C[C@@H]1COCc1ccccc1]

To a suspension of lithium aluminum hydride (73 mg) in THF (2 mL) was added dropwise a solution of compound 13-3 (350 mg) obtained in the above-mentioned step in THF (3 mL) under ice-cooling, and the mixture was stirred at the same temperature for 15 min. To the reaction mixture were successively added water (73 μL), 4N aqueous sodium hydroxide solution (73 μL), and water (219 μL), and the mixture was stirred for 45 min. Anhydrous sodium sulfate and ethyl acetate were added, the insoluble material was filtered off through Celite and the filtrate was concentrated and purified by silica gel column chromatography (hexane:ethyl acetate=5:1 to 4:1) to give compound 13-4 (170 mg).

$^1$H-NMR (CDCl$_3$) δ: 9.30 (s, 1H), 7.39-7.26 (m, 5H), 5.43-5.10 (m, 1H), 4.59-4.44 (m, 2H), 3.83 (dd, 1H, J=10.9, 5.6 Hz), 3.38 (t, 1H, J=9.7 Hz), 2.04-1.92 (m, 1H), 1.82-1.68 (m, 1H), 1.45 (s, 9H), 1.31-1.21 (m, 1H).

Step 5

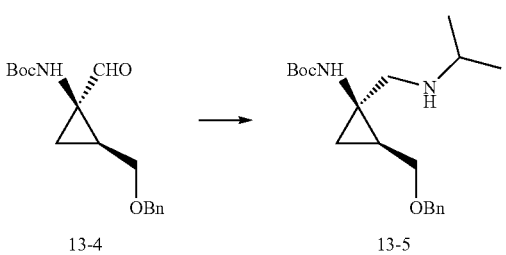 [SMILES: CC(C)(C)OC(=O)N[C@]1(C=O)C[C@@H]1COCc1ccccc1 ; CC(C)NC[C@@]1(NC(=O)OC(C)(C)C)C[C@@H]1COCc1ccccc1]

To a solution of compound 13-4 (85 mg) obtained in the above-mentioned step in chloroform (1 mL) were successively added isopropylamine (31 μL), acetic acid (20 μL) and sodium triacetoxyborohydride (71 mg) under ice-cooling, and the mixture was stirred at room temperature for 2 hr 20 min. Under ice-cooling, isopropylamine (31 μL), acetic acid (20 μL), and sodium triacetoxyborohydride (71 mg) were added, and the mixture was further stirred at room temperature for 1 hr. To the reaction mixture was added saturated aqueous sodium hydrogen carbonate solution and ethyl acetate to allow for partitioning, and the organic layer was washed with saturated brine, dried, concentrated, and purified by silica gel column chromatography (chloroform:methanol=15:1 to 10:1) to give compound 13-5 (93 mg).

$^1$H-NMR (CDCl$_3$) δ: 7.39-7.25 (m, 5H), 5.43-5.24 (m, 1H), 4.56 (d, 1H, J=12.1 Hz), 4.49 (d, 1H, J=12.1 Hz), 3.67 (dd, 1H, J=10.5, 6.0 Hz), 3.43-3.30 (m, 1H), 2.98-2.81 (m, 2H), 2.75-2.27 (m, 1H), 1.43 (s, 9H), 1.36-0.99 (m, 2H), 1.08 (d, 6H, J=6.0 Hz), 0.84-0.70 (m, 1H).

Step 6

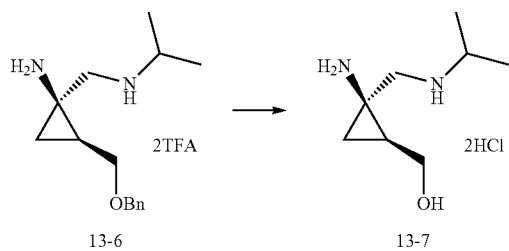 [SMILES: CC(C)NC[C@@]1(N)C[C@@H]1COCc1ccccc1 ; CC(C)NC[C@@]1(N)C[C@@H]1CO]

To compound 13-5 (93 mg) obtained in the above-mentioned step was added TFA (1 mL), and the mixture was stirred at room temperature for 1 hr 40 min. After concentration, the residue was azeotropically distilled 3 times with methanol to give a crude product of compound 13-6. The obtained crude product of compound 13-6 was directly used in the next step.

Step 7

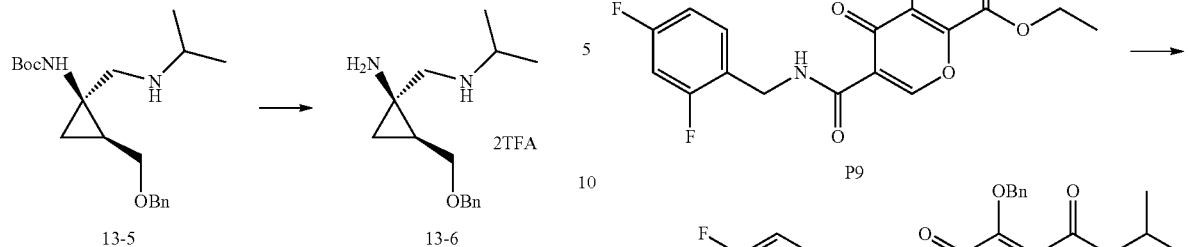

The crude product of compound 13-6 obtained in the above-mentioned step was dissolved in an acetic acid-ethanol (1 mL-1 mL) mixed solution, palladium-platinum/carbon (ASCA2, manufactured by N.E. CHEMCAT Corporation, 100 mg) was added, and the mixture was stirred under a hydrogen atmosphere at room temperature overnight. The insoluble material was filtered off, and the filtrate was concentrated and azeotropically distilled 3 times with methanol. 4N Hydrochloric acid/dioxane was added, and the mixture was concentrated to give a crude product of compound 13-7 (70 mg). The obtained crude product of compound 13-7 was directly used in the next step.

$^1$H-NMR (DMSO-$d_6$) δ: 9.39-9.04 (m, 1H), 8.92-8.72 (m, 2H), 3.75 (dd, 1H, J=12.1, 4.8 Hz), 3.64-3.56 (m, 1H), 3.38-3.22 (m, 3H), 1.64-1.54 (m, 1H), 1.33-1.21 (m, 7H), 1.03 (t, 1H, J=6.9 Hz).

Step 8

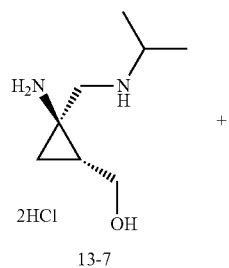

+

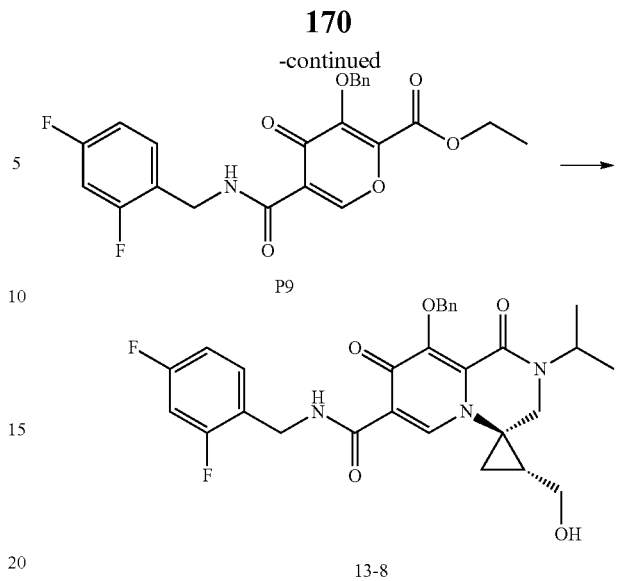

To a solution of crude product of compound 13-7 (70 mg) obtained in the above-mentioned step in THF (1 mL) were successively added chloroform (1 mL), ethanol (500 μL), triethylamine (211 μL) and compound P9 (111 mg) obtained in Example 9, Preliminary step 9-1, and the mixture was stirred at room temperature for 25 min and concentrated. Toluene (2.5 mL), ethanol (250 μL), and DBU (250 μL) were added, and the mixture was stirred at 80° C. for 2 hr. Toluene (5 mL) and acetic acid (1.5 mL) were further added, and the mixture was stirred at 110° C. overnight. To the reaction mixture were added ethyl acetate and 5% aqueous potassium hydrogen sulfate solution to allow for partitioning, and the organic layer was washed successively with saturated aqueous sodium hydrogen carbonate solution and saturated brine, dried and concentrated to give residue 13-8.

The residue 13-8 was dissolved in methanol (3 mL), potassium carbonate (160 mg) was added, and the mixture was stirred at room temperature for 20 min. Ethyl acetate and saturated brine were added to allow for partitioning. The organic layer was dried, concentrated, and purified by silica gel thin layer chromatography (ethyl acetate:methanol=15:1) to give compound 13-8 (66 mg).

$^1$H-NMR (CDCl$_3$) δ: 10.56 (t, 1H, J=85.8 Hz), 8.29 (s, 1H), 7.59-7.53 (m, 2H), 7.41-7.24 (m, 4H), 6.86-6.76 (m, 2H), 5.35 (d, 1H, J=10.1 Hz), 5.22 (d, 1H, J=10.1 Hz), 4.89-4.76 (m, 1H), 4.61 (d, 2H, J=6.0 Hz), 3.77 (d, 1H, J=13.7 Hz), 3.69 (dd, 1H, J=12.1, 4.8 Hz), 3.09 (dd, 1H, J=12.1, 8.5 Hz), 2.60 (d, 1H, J=13.7 Hz), 1.94-1.87 (m, 1H), 1.49-1.38 (m, 1H), 1.37-1.29 (m, 1H), 1.15 (d, 3H, J=6.9 Hz), 1.08 (d, 3H, J=6.9 Hz).

Step 9

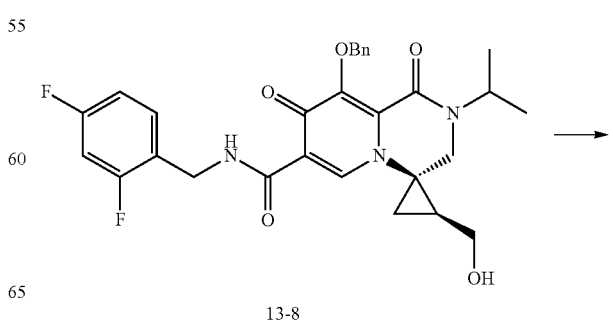

-continued

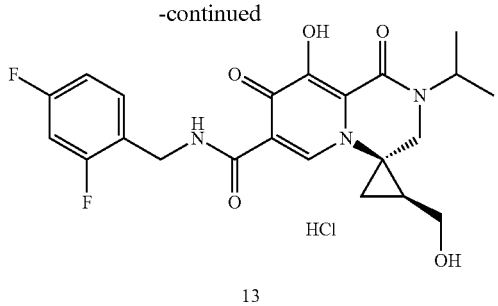

13

From compound 13-8 (33 mg) obtained in the above-mentioned step, and by a method similar to that in Example 9, step 13, the title compound (18 mg) was obtained.

$^1$H-NMR (DMSO-d$_6$) δ: 12.61 (s, 1H), 10.43-10.36 (m, 1H), 8.15 (s, 1H), 7.45-7.35 (m, 1H), 7.27-7.20 (m, 1H), 7.10-7.02 (m, 1H), 4.79-4.69 (m, 1H), 4.57-4.49 (m, 2H), 4.04 (d, 1H, J=13.6 Hz), 3.55-3.48 (m, 1H), 3.18 (d, 1H, J=13.6 Hz), 2.69-2.51 (m, 1H), 1.95-1.90 (m, 1H), 1.44-1.37 (m, 2H), 1.18 (d, 3H, J=6.7 Hz), 1.12 (d, 3H, J=6.7 Hz).

Example 14

Production of (1R,2S)—N-(2,4-difluorobenzyl)-9'-hydroxy-2'-isopropyl-2-(methoxymethyl)-1',8'-dioxo-1',2',3',8'-tetrahydrospiro[cyclopropane-1,4'-pyrido[1,2-a]pyrazine]-7'-carboxamide Step 1

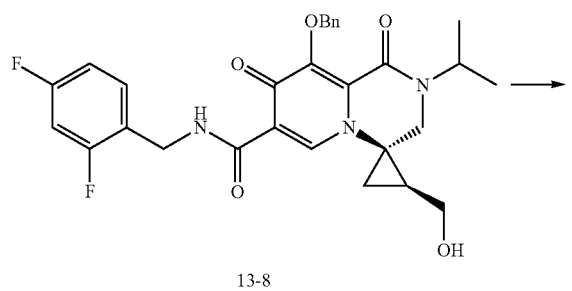

13-8

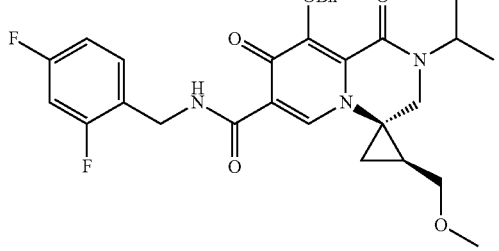

14-1

From compound 13-8 (34 mg) obtained in Example 13, step 8, and by a method similar to that in Example 10, step 1, compound 14-1 was obtained. The obtained compound 14-1 was directly used in the next step.

$^1$H-NMR (CDCl$_3$) δ: 10.56-10.49 (m, 1H), 8.35 (s, 1H), 7.65-7.61 (m, 2H), 7.41-7.25 (m, 4H), 6.87-6.77 (m, 2H), 5.36 (d, 1H, J=9.9 Hz), 5.24 (d, 1H, J=9.9 Hz), 4.94-4.85 (m, 1H), 4.69-4.58 (m, 2H), 3.84 (d, 1H, J=13.6 Hz), 3.51-3.42 (m, 1H), 3.08 (s, 3H), 2.78 (dd, 1H, J=10.9, 8.6 Hz), 2.63 (d, 1H, J=13.6 Hz), 1.94-1.88 (m, 1H), 1.55-1.36 (m, 2H), 1.18 (d, 3H, J=6.7 Hz), 1.10 (d, 3H, J=6.9 Hz).

Step 2

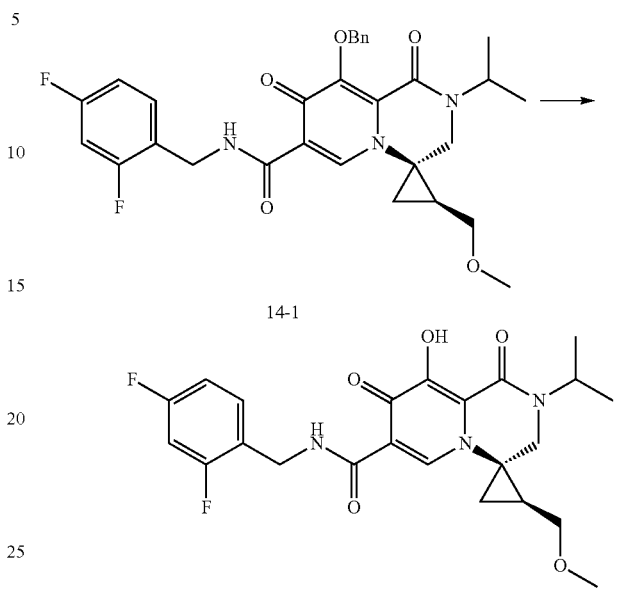

14-1

14

To compound 14-1 obtained in the above-mentioned step was added TFA (1 mL), and the mixture was stirred for 1 hr. After concentration, the residue was dissolved in ethyl acetate (300 μL), 4N hydrochloric acid/ethyl acetate (100 μL), and hexane (1 mL) were added, and the mixture was concentrated. Saturated aqueous sodium hydrogen carbonate solution was added, and the mixture was extracted twice with chloroform, dried, concentrated and crystallized from ethyl acetate:hexane to give the title compound (17 mg).

$^1$H-NMR (DMSO-d$_6$) δ: 12.58 (s, 1H), 10.40-10.30 (m, 1H), 8.18 (s, 1H), 7.47-7.35 (m, 1H), 7.29-7.18 (m, 1H), 7.12-6.99 (m, 1H), 4.80-4.67 (m, 1H), 4.53 (d, 2H, J=5.6 Hz), 4.05 (d, 1H, J=13.7 Hz), 3.45 (d, 1H, J=11.3 Hz), 3.21 (d, 1H, J=13.7 Hz), 2.92 (s, 3H), 2.61-2.42 (m, 1H), 2.11-1.98 (m, 1H), 1.58-1.44 (m, 2H), 1.16 (d, 3H, J=6.4 Hz), 1.12 (d, 3H, J=6.9 Hz).

Example 15

Production of (1S,2R)—N-(2,4-difluorobenzyl)-9'-hydroxy-2-(hydroxymethyl)-2'-isopropyl-1',8'-dioxo-1',2',3',8'-tetrahydrospiro[cyclopropane-1,4'-pyrido[1,2-a]pyrazine]-7'-carboxamide hydrochloride Step 1

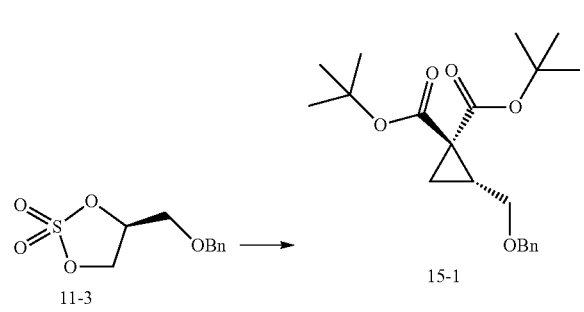

11-3          15-1

To a suspension of sodium hydride (60% dispersion, 1.2 g) in DME (50 mL) was added dropwise under water-cooling a solution of di-tert-butyl malonate (3.1 mL) in DME (10 mL) and the mixture was stirred at room temperature for 10 min. A solution of compound 11-3 (3.4 g) obtained in the same manner as in Example 11, step 3, in DME (30 mL) was added, and the mixture was stirred at an outer temperature of 85° C. overnight (reaction 1). In reaction 1, DME (30 mL) was added to the reaction mixture during the overnight stirring mentioned above and the stirring was continued. In the same manner as above, separately, to a suspension of sodium hydride (60% dispersion, 2.86 g) in DME (120 mL) was added dropwise a solution of di-tert-butyl malonate (7.7 mL) in DME (45 mL) under water-cooling, and the mixture was stirred at room temperature for 10 min. A solution of compound 11-3 (8.37 g) obtained in the same manner as in Example 11, step 3, in DME (40 mL) was added, and the mixture was stirred at an outer temperature of 85° C. overnight (reaction 2). The reaction mixture of reaction 1 and that of reaction 2 were combined (reaction mixture 3). To the reaction mixture 3 was added water, and the mixture was extracted 3 times with ethyl acetate. The organic layer was washed successively with saturated aqueous sodium hydrogen carbonate solution and saturated brine, dried, concentrated, and purified by silica gel column chromatography (hexane:ethyl acetate=20:1 to 10:1) to give compound 15-1 (17.37 g).

$^1$H-NMR (CDCl$_3$) δ: 7.36-7.25 (m, 5H), 4.53 (d, 1H, J=11.9 Hz), 4.48 (d, 1H, J=11.9 Hz), 3.54 (dd, 1H, J=10.6, 6.8 Hz), 3.41 (dd, 1H, J=10.6, 7.1 Hz), 2.19-2.10 (m, 1H), 1.46 (s, 9H), 1.44 (s, 9H), 1.37 (dd, 1H, J=7.3, 4.6 Hz), 1.27 (dd, 1H, J=9.0, 4.6 Hz).

Step 2

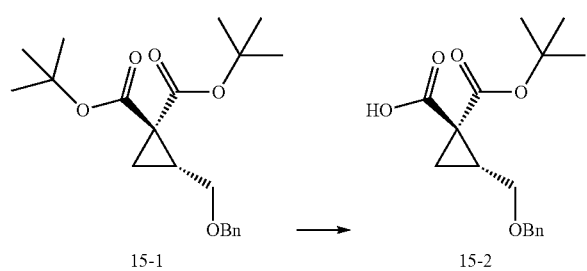

To a solution of compound 15-1 (3.3 g) obtained in the above-mentioned step in THF (50 mL) were added potassium tert-butoxide (2.04 g) and water (164 μL) under ice-cooling, and the mixture was stirred at room temperature overnight. To the reaction mixture was added water, and the mixture was washed twice with diisopropyl ether. The aqueous layer was acidified with a 5% aqueous potassium hydrogen sulfate solution, and extracted 3 times with ethyl acetate. The organic layer was washed with saturated brine, dried, and concentrated to give a crude product of compound 15-2 (2.24 g). The obtained crude product of compound 15-2 was directly used in the next step.

Step 3

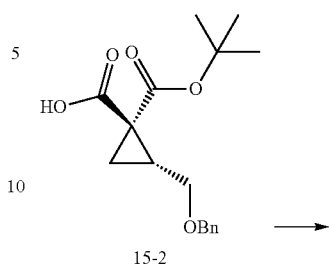

From the crude product of compound 15-2 obtained in the above-mentioned step (2.24 g) and by a method similar to that in Example 13, step 1, compound 15-3 (1.86 g) was obtained.

$^1$H-NMR (CDCl$_3$) δ: 7.37-7.24 (m, 5H), 4.54 (d, 1H, J=11.8 Hz), 4.50 (d, 1H, J=11.8 Hz), 3.70-3.54 (m, 2H), 3.67 (s, 3H), 3.24 (s, 3H), 2.30-2.14 (m, 1H), 1.53-1.47 (m, 1H), 1.45-1.22 (m, 1H), 1.40 (s, 9H).

Step 4

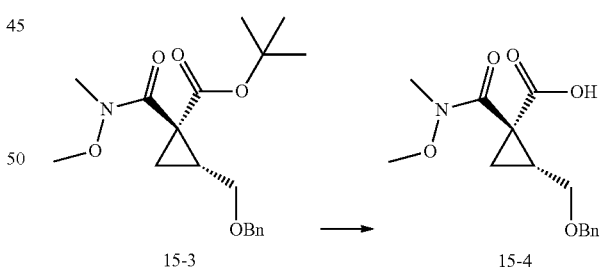

To compound 15-3 (2.29 g) obtained in the above-mentioned step was added TFA (40 mL), and the mixture was stirred for 30 min. After concentration, the residue was azeotropically distilled 6 times with toluene to give a crude product of compound 15-4 (1.71 g). The obtained crude product of compound 15-4 was directly used in the next step.

$^1$H-NMR (CDCl$_3$) δ: 7.36-7.12 (m, 5H), 4.54 (d, 1H, J=11.8 Hz), 4.49 (d, 1H, J=11.8 Hz), 3.75 (dd, 1H, J=10.9, 6.2 Hz), 3.68 (s, 3H), 3.57 (dd, 1H, J=10.6, 8.3 Hz), 3.26 (s, 3H), 2.37-2.27 (m, 1H), 1.59 (dd, 1H, J=7.6, 4.9 Hz), 1.45 (dd, 1H, J=9.2, 4.9 Hz).

Step 5

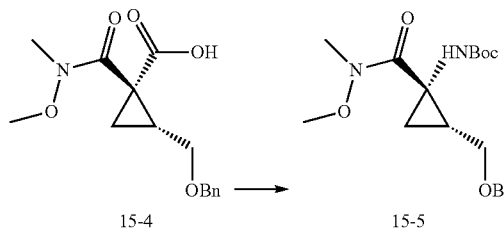

From the crude product of compound 15-4 obtained in the above-mentioned step (1.71 g) and by a method similar to that in Example 13, step 3, compound 15-5 (1.5 g) was obtained.

$^1$H-NMR (CDCl$_3$) δ: 7.39-7.24 (m, 5H), 5.52-5.30 (m, 1H), 4.64-4.52 (m, 1H), 4.52-4.41 (m, 1H), 3.85 (dd, 1H, J=10.9, 5.2 Hz), 3.65 (s, 3H), 3.38 (t, 1H, J=10.1 Hz), 3.17 (s, 3H), 1.96-1.86 (m, 1H), 1.81-1.70 (m, 1H), 1.43 (s, 9H), 1.02-0.85 (m, 1H).

Step 6

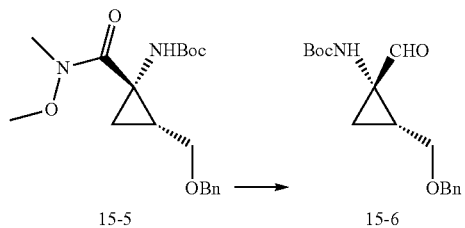 [SMILES: CON(C)C(=O)[C@]1(NC(=O)OC(C)(C)C)C[C@H]1COCc1ccccc1 ; CC(C)(C)OC(=O)N[C@@]1(C=O)C[C@H]1COCc1ccccc1]

From compound 15-5 (1.5 g) obtained in the above-mentioned step and by a method similar to that in Example 13, step 4, a crude product of compound 15-6 (1.05 g) was obtained. The obtained crude product of compound 15-6 was directly used in the next step.

$^1$H-NMR (CDCl$_3$) δ: 9.30 (s, 1H), 7.39-7.26 (m, 5H), 5.43-5.10 (m, 1H), 4.59-4.44 (m, 2H), 3.83 (dd, 1H, J=10.9, 5.6 Hz), 3.38 (t, s1H, J=9.7 Hz), 2.04-1.92 (m, 1H), 1.82-1.68 (m, 1H), 1.45 (s, 9H), 1.31-1.21 (m, 1H).

Step 7

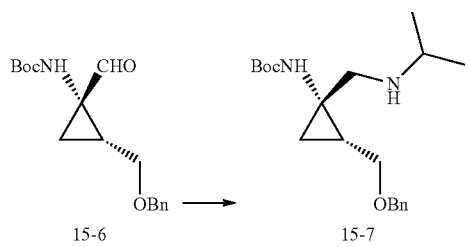 [SMILES: CC(C)(C)OC(=O)N[C@@]1(C=O)C[C@H]1COCc1ccccc1 ; CC(C)NC[C@]1(NC(=O)OC(C)(C)C)C[C@H]1COCc1ccccc1]

From the crude product of compound 15-6 obtained in the above-mentioned step (510 mg) and by a method similar to that in Example 13, step 5, compound 15-7 (361 mg) was obtained.

$^1$H-NMR (CDCl$_3$) δ: 7.39-7.25 (m, 5H), 5.43-5.24 (m, 1H), 4.56 (d, 1H, J=12.1 Hz), 4.49 (d, 1H, J=12.1 Hz), 3.67 (dd, 1H, J=10.5, 6.0 Hz), 3.43-3.30 (m, 1H), 2.98-2.81 (m, 2H), 2.75-2.27 (m, 1H), 1.43 (s, 9H), 1.36-0.99 (m, 2H), 1.08 (d, 6H, J=6.0 Hz), 0.84-0.70 (m, 1H).

Step 8

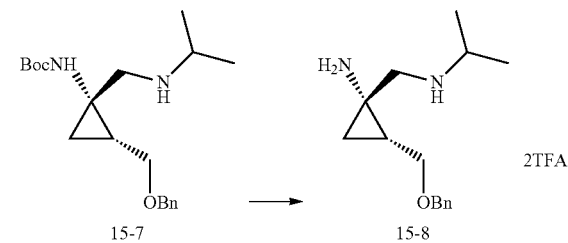 [SMILES: CC(C)NC[C@]1(NC(=O)OC(C)(C)C)C[C@H]1COCc1ccccc1 ; CC(C)NC[C@]1(N)C[C@H]1COCc1ccccc1]

From compound 15-7 (52 mg) obtained in the above-mentioned step and by a method similar to that in Example 13, step 6, a crude product of compound 15-8 was obtained. The obtained crude product of compound 15-8 was directly used in the next step.

Step 9

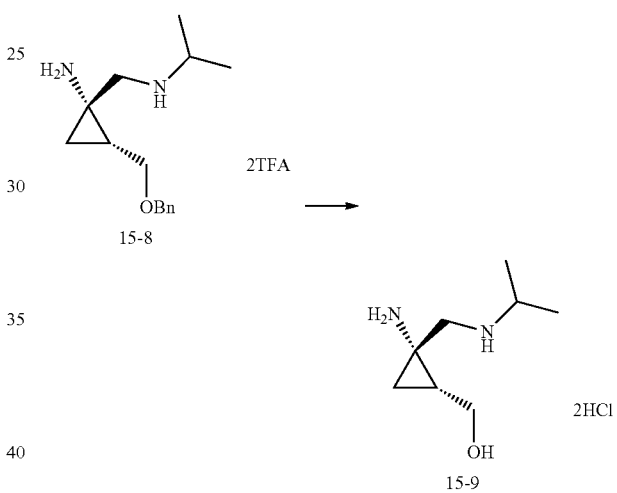

From the crude product of compound 15-8 obtained in the above-mentioned step and by a method similar to that in Example 13, step 7, a crude product of compound 15-9 (62 mg) was obtained. The obtained crude product of compound 15-9 was directly used in the next step.

$^1$H-NMR (DMSO-d$_6$) δ: 9.39-9.04 (m, 1H), 8.92-8.72 (m, 2H), 3.75 (dd, 1H, J=12.1, 4.8 Hz), 3.64-3.56 (m, 1H), 3.38-3.22 (m, 3H), 1.64-1.54 (m, 1H), 1.33-1.21 (m, 7H), 1.03 (t, 1H, J=6.9 Hz).

Step 10

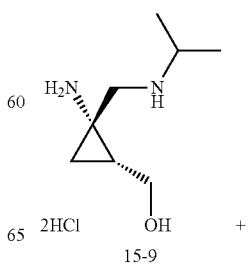

-continued

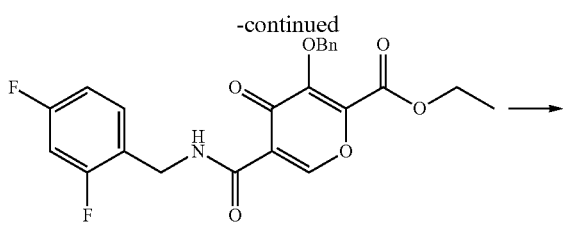
P9

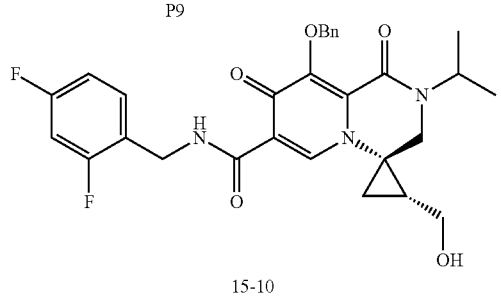
15-10

From the crude product of compound 15-9 obtained in the above-mentioned step (62 mg) and compound P9 (66 mg) obtained in Example 9, Preliminary step 9-1, and by a method similar to that in Example 13, step 8, compound 15-10 (42 mg) was obtained.

¹H-NMR (CDCl₃) δ: 10.56 (t, 1H, J=85.8 Hz), 8.29 (s, 1H), 7.59-7.53 (m, 2H), 7.41-7.24 (m, 4H), 6.86-6.76 (m, 2H), 5.35 (d, 1H, J=10.1 Hz), 5.22 (d, 1H, J=10.1 Hz), 4.89-4.76 (m, 1H), 4.61 (d, 2H, J=6.0 Hz), 3.77 (d, 1H, J=13.7 Hz), 3.69 (dd, 1H, J s=12.1, 4.8 Hz), 3.09 (dd, 1H, J=12.1, 8.5 Hz), 2.60 (d, 1H, J=13.7 Hz), 1.94-1.87 (m, 1H), 1.49-1.38 (m, 1H), 1.37-1.29 (m, 1H), 1.15 (d, 3H, J=6.9 Hz), 1.08 (d, 3H, J=6.9 Hz).

Step 11

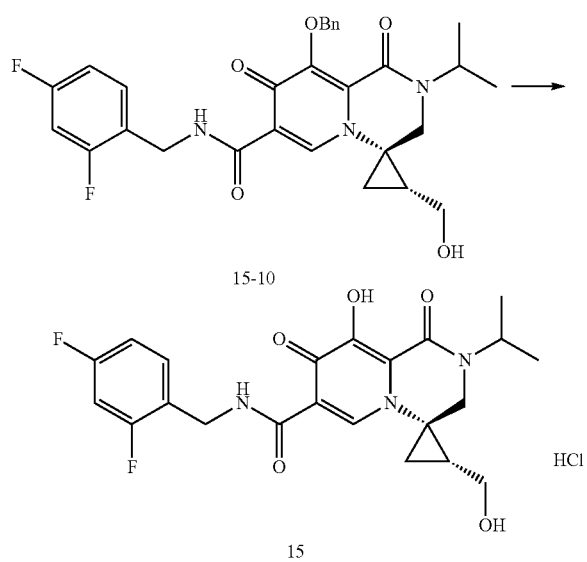

From compound 15-10 (10 mg) obtained in the above-mentioned step and by a method similar to that in Example 9, step 13, the title compound (6 mg) was obtained.

¹H-NMR (DMSO-d₆) δ: 12.61 (s, 1H), 10.43-10.36 (m, 1H), 8.15 (s, 1H), 7.45-7.35 (m, 1H), 7.27-7.20 (m, 1H), 7.10-7.02 (m, 1H), 4.79-4.69 (m, 1H), 4.57-4.49 (m, 2H), 4.04 (d, 1H, J=13.6 Hz), 3.55-3.48 (m, 1H), 3.18 (d, 1H, J=13.6 Hz), 2.69-2.51 (m, 1H), 1.95-1.90 (m, 1H), 1.44-1.37 (m, 2H), 1.18 (d, 3H, J=6.7 Hz), 1.12 (d, 3H, J=6.7 Hz).

Example 16

Production of (1S,2R)—N-(2,4-difluorobenzyl)-9'-hydroxy-2'-isopropyl-2-(methoxymethyl)-1',8'-di-oxo-1',2',3',8'-tetrahydrospiro[cyclopropane-1,4'-pyrido[1,2-a]pyrazine]-7'-carboxamide Step 1

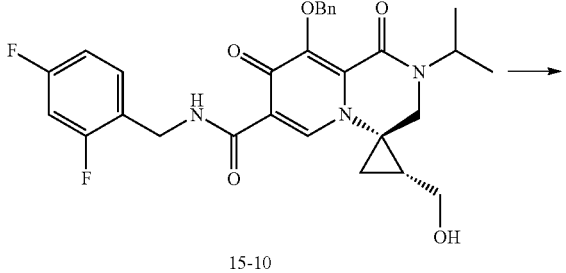
15-10

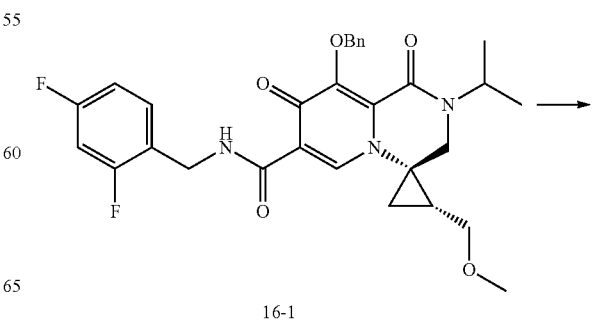
16-1

From compound 15-10 (30 mg) obtained in Example 15, step 10, and by a method similar to that in Example 10, step 1, compound 16-1 (22 mg) was obtained.

¹H-NMR (CDCl₃) δ: 10.56-10.49 (m, 1H), 8.35 (s, 1H), 7.65-7.61 (m, 2H), 7.41-7.25 (m, 4H), 6.87-6.77 (m, 2H), 5.36 (d, 1H, J=9.9 Hz), 5.24 (d, 1H, J=9.9 Hz), 4.94-4.85 (m, 1H), 4.69-4.58 (m, 2H), 3.84 (d, 1H, J=13.6 Hz), 3.51-3.42 (m, 1H), 3.08 (s, 3H), 2.78 (dd, 1H, J=10.9, 8.6 Hz), 2.63 (d, 1H, J=13.6 Hz), 1.94-1.88 (m, 1H), 1.55-1.36 (m, 2H), 1.18 (d, 3H, J=6.7 Hz), 1.10 (d, 3H, J=6.9 Hz).

Step 2

16-1

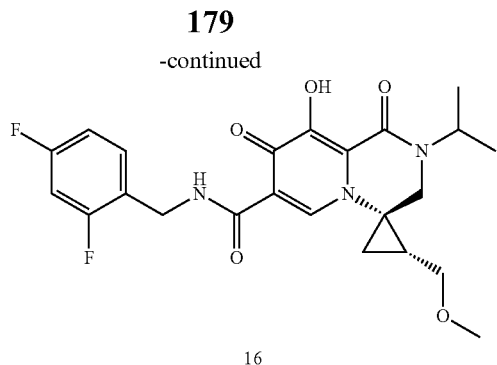

16

From compound 16-1 (22 mg) obtained in the above-mentioned step and by a method similar to that in Example 14, step 2, the title compound (9 mg) was obtained.

$^1$H-NMR (DMSO-d$_6$) δ: 12.58 (s, 1H), 10.36 (t, 1H, J=5.8 Hz), 8.18 (s, 1H), 7.45-7.37 (m, 1H), 7.27-7.20 (m, 1H), 7.10-7.03 (m, 1H), 4.78-4.69 (m, 1H), 4.53 (d, 2H, J=5.8 Hz), 4.05 (d, 1H, J=13.6 Hz), 3.45 (dd, 1H, J=11.1, 3.7 Hz), 3.21 (d, 1H, J=13.6 Hz), 2.92 (s, 3H), 2.61-2.42 (m, 1H), 2.07-2.01 (m, 1H), 1.55-1.45 (m, 2H), 1.16 (d, 3H, J=6.7 Hz), 1.12 (d, 3H, J=6.9 Hz).

Example 17

Production of (1S,2S)—N-(3-chloro-2-fluorobenzyl)-2'-ethyl-9'-hydroxy-2-(methoxymethyl)-1',8'-dioxo-1',2',4',8'-tetrahydrospiro[cyclopropane-1,3'-pyrido[1,2-a]pyrazine]-7'-carboxamide Step 1

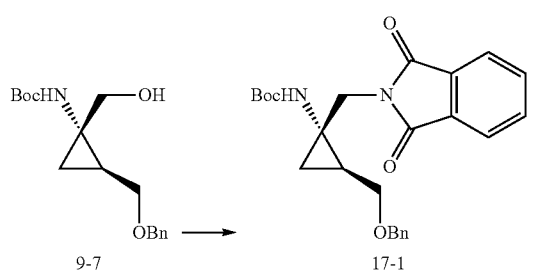 [SMILES: CC(C)(C)OC(=O)N[C@@]1(CO)C[C@@H]1COCc1ccccc1 ; CC(C)(C)OC(=O)N[C@@]1(CN2C(=O)c3ccccc3C2=O)C[C@@H]1COCc1ccccc1]

To a solution of compound 9-7 (800 mg) obtained in the same manner as in Example 9, step 7, in THF (20 mL) were added triphenylphosphine (2.8 g), phthalimide (2 g) and DIAD (2.1 mL), and the mixture was stirred at room temperature overnight. After concentration, the residue was purified by silica gel column chromatography (hexane:ethyl acetate=5:1 to 2:1) to give compound 17-1. The obtained compound 17-1 was directly used in the next step.

$^1$H-NMR (CDCl$_3$) δ: 7.89-7.79 (m, 2H), 7.78-7.65 (m, 2H), 7.37-7.25 (m, 5H), 4.56 (d, 1H, J=11.7 Hz), 4.52 (d, 1H, J=11.7 Hz), 4.25 (d, 1H, J=14.6 Hz), 3.85-3.71 (m, 1H), 3.67-3.48 (m, 2H), 1.60-1.05 (m, 12H).

Step 2

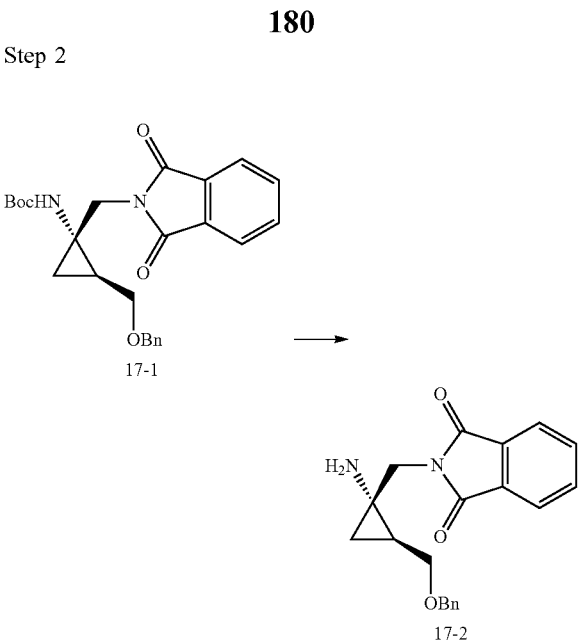

To compound 17-1 obtained in the above-mentioned step was added TFA (15 mL), and the mixture was stirred at room temperature for 1 hr. After concentration, saturated aqueous sodium hydrogen carbonate solution was added, and the mixture was extracted 3 times with chloroform and washed with saturated brine. The mixture was dried, concentrated, and purified by silica gel column chromatography (ethyl acetate to chloroform:methanol=10:1) to give compound 17-2 (659 mg).

$^1$H-NMR (CDCl$_3$) δ: 7.88-7.82 (m, 2H), 7.75-7.69 (m, 2H), 7.35-7.24 (m, 5H), 4.55 (d, 1H, J=12.1 Hz), 4.51 (d, 1H, J=12.1 Hz), 4.14-4.07 (m, 1H), 3.83 (dd, 1H, J=10.7, 6.0 Hz), 3.65 (d, 1H, J=14.4 Hz), 3.39 (dd, 1H, J=10.7, 9.8 Hz), 1.48-1.39 (m, 1H), 0.86-0.80 (m, 1H), 0.72 (dd, 1H, J=6.0, 5.1 Hz).

Step 3

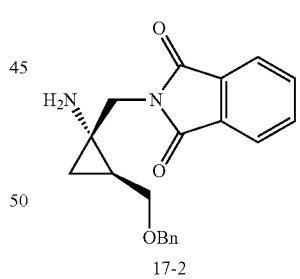

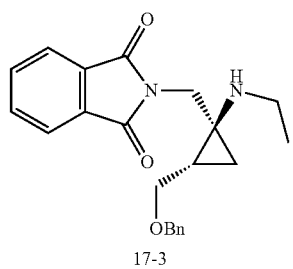

To a solution of compound 17-2 (305 mg) obtained in the above-mentioned step in chloroform (10 mL) were added acetaldehyde (51 μL) and acetic acid (52 μL) under ice-cooling, and the mixture was stirred at room temperature for 1 hr. The mixture was ice-cooled again, sodium triacetoxyborohydride (250 mg) was added, and the mixture was stirred at room temperature overnight. To the reaction mixture was added saturated aqueous sodium hydrogen carbonate solution, and the mixture was extracted with chloroform, washed with saturated brine, dried, concentrated and purified by silica gel column chromatography (chloroform:ethyl acetate=10:1 to ethyl acetate) to give compound 17-3 (127 mg).

Separately, this step was similarly performed with compound 17-2 (396 mg) to give compound 17-3 (106 mg).

¹H-NMR (CDCl₃) δ: 7.87-7.81 (m, 2H), 7.74-7.68 (m, 2H), 7.36-7.22 (m, 5H), 4.58 (d, 1H, J=11.9 Hz), 4.50 (d, 1H, J=11.9 Hz), 4.30 (dd, 1H, J=14.7, 1.4 Hz), 3.84 (dd, 1H, J=10.7, 6.0 Hz), 3.49 (d, 1H, J=14.7 Hz), 3.40-3.33 (m, 1H), 3.11-3.01 (m, 1H), 2.77-2.65 (m, 1H), 1.47-1.37 (m, 1H), 1.08 (t, 3H, J=7.2 Hz), 0.86-0.80 (m, 1H), 0.79-0.73 (m, 1H).

Step 4

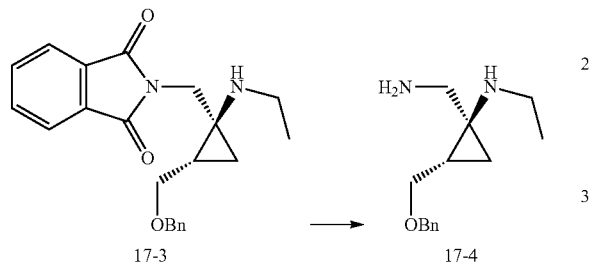

To a solution of compound 17-3 (233 mg) obtained in the above-mentioned step in ethanol (10 mL) was added hydrazine monohydrate (124 μL), and the mixture was stirred at 100° C. for 1 hr. After concentration, toluene (10 mL) was added, the insoluble material was filtered off and the filtrate was concentrated. This operation was performed twice to give a crude product of compound 17-4 (136 mg). The obtained crude product of compound 17-4 was directly used in the next step.

¹H-NMR (CDCl₃) δ: 7.38-7.25 (m, 5H), 4.55 (d, 1H, J=11.9 Hz), 4.48 (d, 1H, J=11.9 Hz), 3.73 (dd, 1H, J=10.6, 5.7 Hz), 3.14 (t, 1H, J=10.6 Hz), 2.95 (d, 1H, J=13.7 Hz), 2.79-2.69 (m, 1H), 2.63-2.53 (m, 1H), 2.49 (d, 1H, J=13.7 Hz), 1.36-1.22 (m, 1H), 1.07 (t, 3H, J=7.1 Hz), 0.83 (dd, 1H, J=9.5, 5.1 Hz), 0.24 (t, 1H, J=5.1 Hz).

Step 5

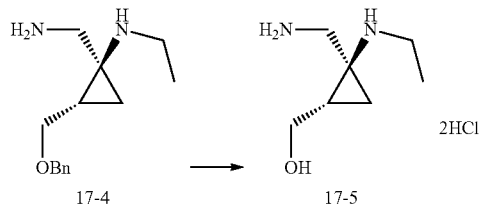

To a suspension of palladium-platinum/carbon (ASCA2, manufactured by N.E. CHEMCAT Corporation, 200 mg) in acetic acid (4 mL) was added a solution of crude product of compound 17-4 (136 mg) obtained in the above-mentioned step in ethanol (5 mL), and the mixture was stirred under a hydrogen atmosphere at room temperature overnight. The insoluble material was filtered off, the filtrate was concentrated, dissolved in methanol (5 mL), 4N hydrochloric acid/ethyl acetate (5 mL) was added, and the mixture was concentrated again to give a crude product of compound 17-5 (152 mg). The obtained crude product of compound 17-5 was directly used in the next step.

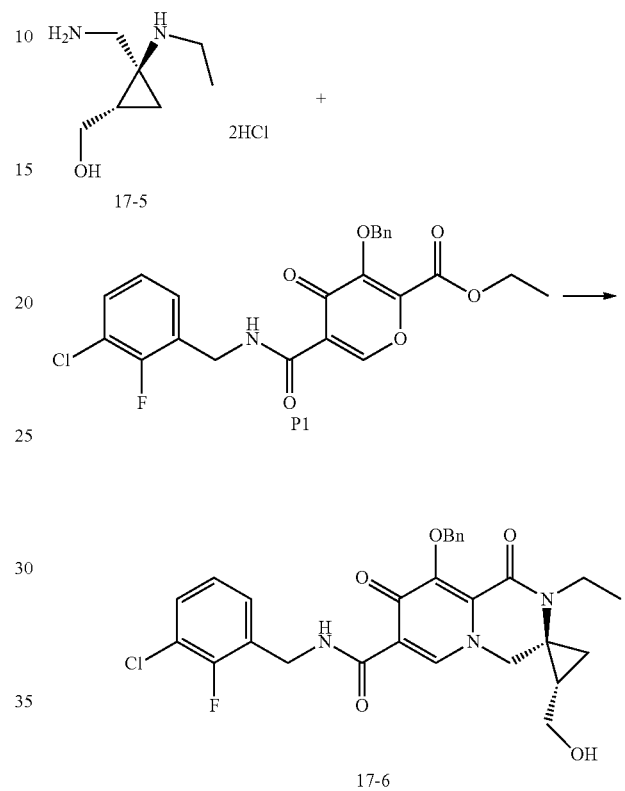

From the crude product of compound 17-5 obtained in the above-mentioned step (70 mg) and compound P1 (114 mg) obtained in Example 1, Preliminary step 1-1, and by a method similar to that in Example 13, step 8, compound 17-6 (100 mg) was obtained.

¹H-NMR (CDCl₃) δ: 10.68-10.60 (m, 1H), 8.29 (s, 1H), 7.60-7.55 (m, 2H), 7.37-7.24 (m, 5H), 7.04 (t, 1H, J=7.9 Hz), 5.42 (d, 1H, J=10.4 Hz), 5.30 (d, 1H, J=10.4 Hz), 4.70 (d, 2H, J=6.0 Hz), 4.24 (d, 1H, J=12.9 Hz), 4.18-4.09 (m, 1H), 3.82-3.72 (m, 1H), 3.66-3.54 (m, 1H), 3.51-3.38 (m, 1H), 3.37-3.23 (m, 1H), 1.94-1.74 (m, 1H), 1.44-1.21 (m, 2H), 1.17 (t, 3H, J=7.2 Hz), 1.04 (t, 1H, J=6.9 Hz).

Step 7

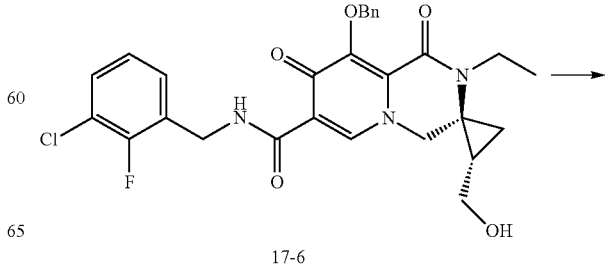

183
-continued

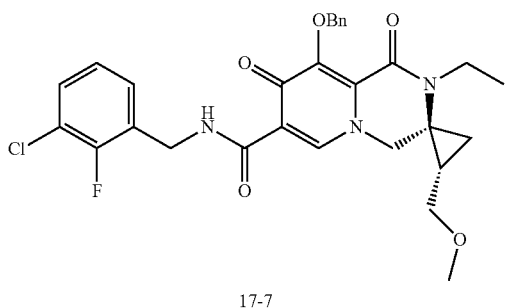

17-7

From compound 17-6 (50 mg) obtained in the above-mentioned step and by a method similar to that in Example 10, step 1, compound 17-7 (40 mg) was obtained.

$^1$H-NMR (CDCl$_3$) δ: 10.60 (t, 1H, J=6.0 Hz), 8.29 (s, 1H), 7.61-7.56 (m, 2H), 7.36-7.25 (m, 5H), 7.07-6.99 (m, 1H), 5.39 (d, 1H, J=10.1 Hz), 5.31 (d, 1H, J=10.1 Hz), 4.79-4.64 (m, 2H), 4.19-4.05 (m, 2H), 3.60-3.44 (m, 2H), 3.41-3.28 (m, 1H), 3.21 (s, 3H), 3.16 (dd, 1H, J=10.6, 7.3 Hz), 1.60-1.45 (m, 1H), 1.30-1.23 (m, 1H), 1.19-1.13 (m, 3H), 0.99 (t, 1H, J=7.1 Hz).

Step 8

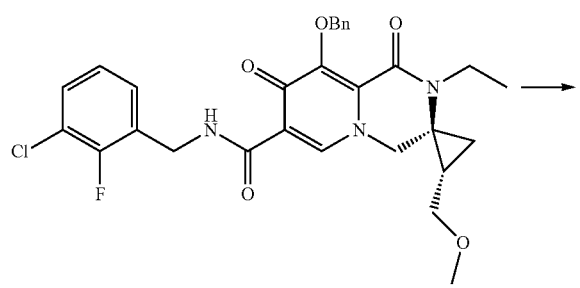

17-7

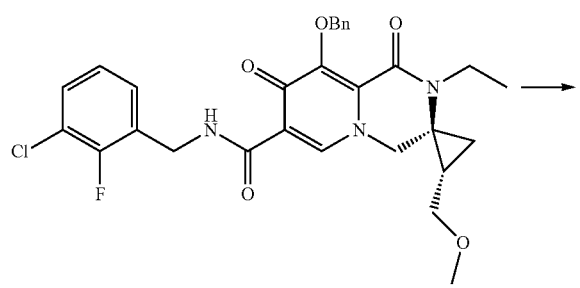

17-8

From compound 17-7 (40 mg) obtained in the above-mentioned step and by a method similar to that in Example 14, step 2, the title compound (6 mg) was obtained.

$^1$H-NMR (DMSO-d$_6$) δ: 11.97 (s, 1H), 10.49 (t, 1H, J=6.0 Hz), 8.41 (s, 1H), 7.52-7.47 (m, 1H), 7.35-7.29 (m, 1H), 7.20 (t, 1H, J=7.9 Hz), 4.65-4.58 (m, 2H), 4.49 (d, 1H, J=13.6 Hz), 4.41 (d, 1H, J=13.6 Hz), 3.63 (dd, 1H, J=10.9, 6.0 Hz), 3.52-3.40 (m, 1H), 3.39-3.21 (m, 2H), 3.13 (s, 3H), 1.85-1.74 (m, 1H), 1.44 (dd, 1H, J=10.2, 6.7 Hz), 1.08 (t, 3H, J=7.2 Hz), 0.98 (t, 1H, J=7.2 Hz).

184

Example 18

Production of (1R,2R)—N-(3-chloro-2-fluorobenzyl)-2'-ethyl-9'-hydroxy-2-(methoxymethyl)-1',8'-dioxo-1',2',4',8'-tetrahydrospiro[cyclopropane-1,3'-pyrido[1,2-a]pyrazine]-7'-carboxamide Step 1

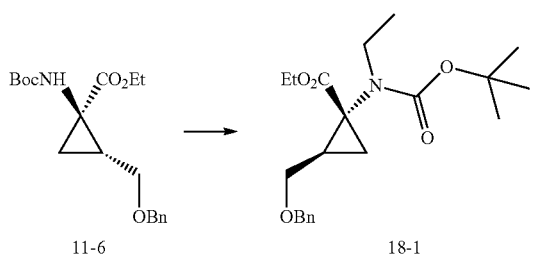 [SMILES: CCOC(=O)[C@@]1(NC(=O)OC(C)(C)C)C[C@H]1COCc1ccccc1 ; CCOC(=O)[C@@]1(N(CC)C(=O)OC(C)(C)C)C[C@H]1COCc1ccccc1]

11-6     18-1

To a solution of compound 11-6 (1.09 g) obtained in the same manner as in Example 11, step 6, in DMF (20 mL) was added sodium hydride (60% dispersion, 162 mg) under ice-cooling, and the mixture was stirred at room temperature for 30 min. Ethyl iodide (39 μL) was added, and the mixture was stirred at room temperature overnight. To the reaction mixture was added water, and the mixture was extracted 3 times with ethyl acetate. The organic layer was washed successively with saturated aqueous sodium hydrogen carbonate solution (twice) and saturated brine (twice), dried, concentrated, and purified by silica gel column chromatography (hexane:ethyl acetate=20:1 to 10:1) to give compound 18-1 (399 mg).

$^1$H-NMR (CDCl$_3$) δ: 7.37-7.25 (m, 5H), 4.60-4.40 (m, 2H), 4.21-4.03 (m, 2H), 3.93-3.10 (m, 4H), 2.03-1.85 (m, 1H), 1.80-1.01 (m, 17H).

Step 2

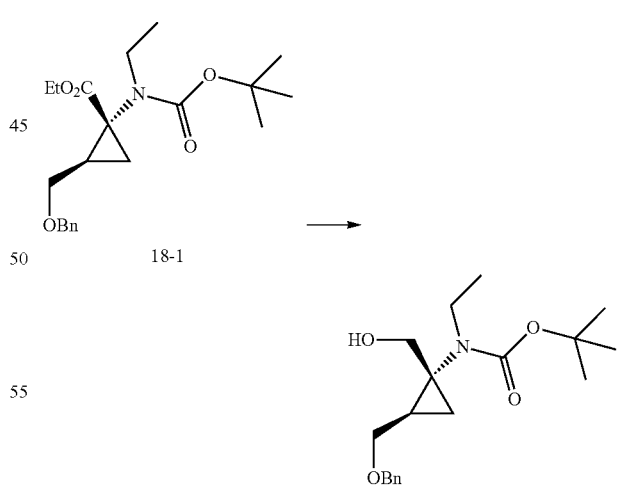

18-1

18-2

From compound 18-1 (399 mg) obtained in the above-mentioned step and by a method similar to that in Example 9, step 7, compound 18-2 (304 mg) was obtained.

$^1$H-NMR (CDCl$_3$) δ: 7.39-7.24 (m, 5H), 4.59 (d, 1H, J=12.0 Hz), 4.53 (d, 1H, J=12.0 Hz), 3.99-3.66 (m, 3H), 3.50-3.20 (m, 3H), 1.75-0.65 (m, 6H), 1.45-1.45 (m, 9H).

Step 3

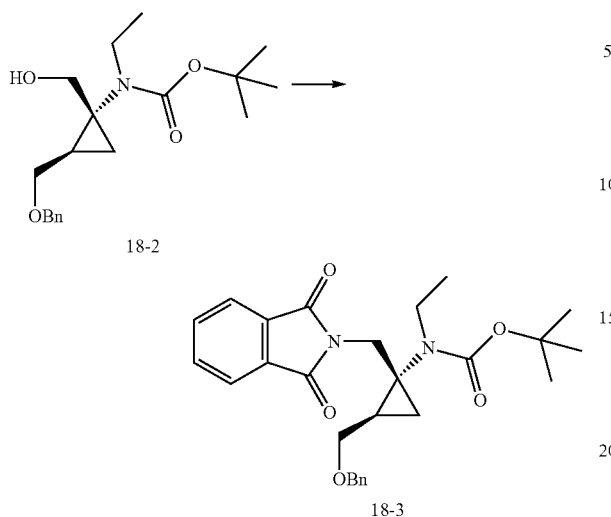

From compound 18-2 (304 mg) obtained in the above-mentioned step and by a method similar to that in Example 17, step 1, compound 18-3 (243 mg) was obtained.

$^1$H-NMR (CDCl$_3$) δ: 7.88-7.76 (m, 2H), 7.75-7.60 (m, 2H), 7.40-7.25 (m, 5H), 4.65-4.50 (m, 2H), 4.37-2.76 (m, 6H), 1.68-0.90 (m, 15H).

Step 4

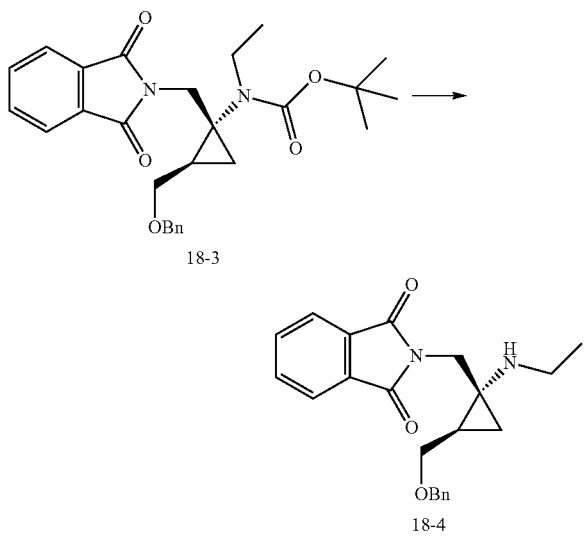

From compound 18-3 (243 mg) obtained in the above-mentioned step and by a method similar to that in Example 17, step 2, a crude product of compound 18-4 (219 mg) was obtained. The obtained crude product of compound 18-4 was directly used in the next step.

$^1$H-NMR (CDCl$_3$) δ: 7.87-7.81 (m, 2H), 7.74-7.68 (m, 2H), 7.36-7.22 (m, 5H), 4.58 (d, 1H, J=11.9 Hz), 4.50 (d, 1H, J=11.9 Hz), 4.30 (dd, 1H, J=14.7, 1.4 Hz), 3.84 (dd, 1H, J=10.7, 6.0 Hz), 3.49 (d, 1H, J=14.7 Hz), 3.40-3.33 (m, 1H), 3.11-3.01 (m, 1H), 2.77-2.65 (m, 1H), 1.47-1.37 (m, 1H), 1.08 (t, 3H, J=7.2 Hz), 0.86-0.80 (m, 1H), 0.79-0.73 (m, 1H).

Step 5

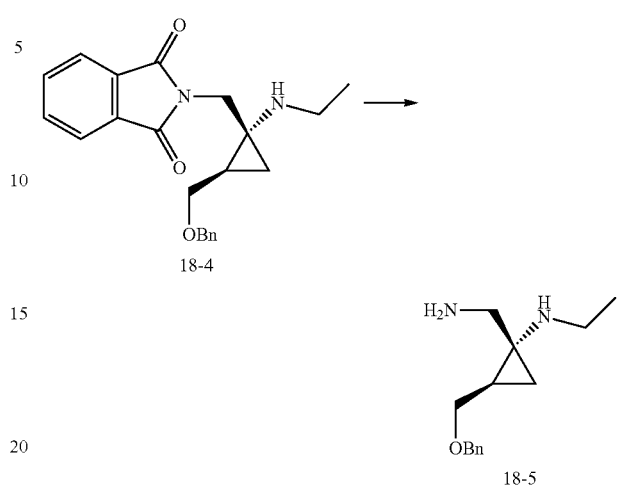

From crude product of compound 18-4 (219 mg) obtained in the above-mentioned step and by a method similar to that in Example 17, step 4, a crude product of compound 18-5 (96 mg) was obtained. The obtained crude product of compound 18-5 was directly used in the next step.

$^1$H-NMR (CDCl$_3$) δ: 7.38-7.25 (m, 5H), 4.55 (d, 1H, J=11.9 Hz), 4.48 (d, 1H, J=11.9 Hz), 3.73 (dd, 1H, J=10.6, 5.7 Hz), 3.14 (t, 1H, J=10.6 Hz), 2.95 (d, 1H, J=13.7 Hz), 2.79-2.69 (m, 1H), 2.63-2.53 (m, 1H), 2.49 (d, 1H, J=13.7 Hz), 1.36-1.22 (m, 1H), 1.07 (t, 3H, J=7.1 Hz), 0.83 (dd, 1H, J=9.5, 5.1 Hz), 0.24 (t, 1H, J=5.1 Hz).

Step 6

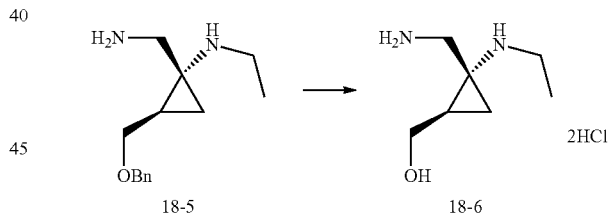

From crude product of compound 18-5 (96 mg) obtained in the above-mentioned step and by a method similar to that in Example 17, step 5, a crude product of compound 18-6 (97 mg) was obtained. The obtained crude product of compound 18-6 was directly used in the next step.

Step 7

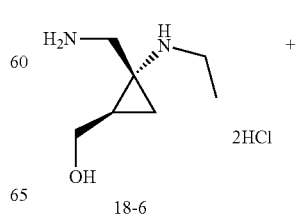

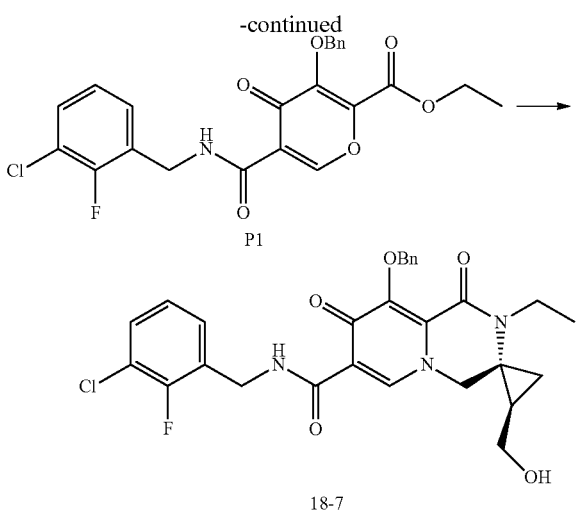

P1

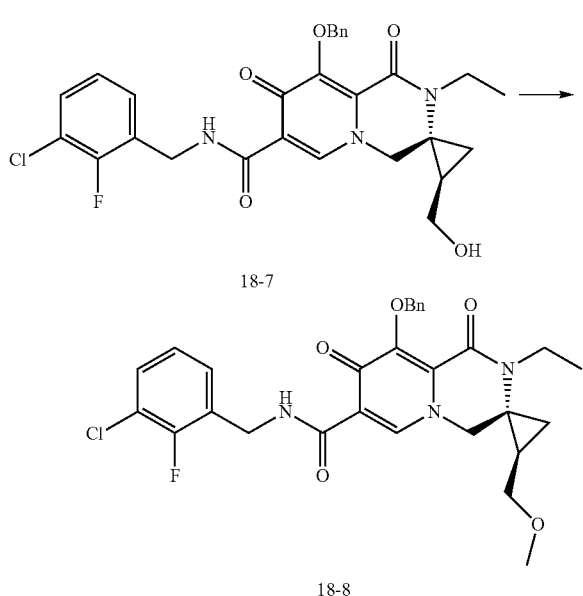

18-7

From crude product of compound 18-6 (97 mg) obtained in the above-mentioned step and compound P1 (120 mg) obtained in Example 1, Preliminary step 1-1, and by a method similar to that in Example 17, step 6, compound 18-7 (100 mg) was obtained.

$^1$H-NMR (CDCl$_3$) δ: 10.68-10.60 (m, 1H), 8.29 (s, 1H), 7.60-7.55 (m, 2H), 7.37-7.24 (m, 5H), 7.04 (t, 1H, J=7.9 Hz), 5.42 (d, 1H, J=10.4 Hz), 5.30 (d, 1H, J=10.4 Hz), 4.70 (d, 2H, J=6.0 Hz), 4.24 (d, 1H, J=12.9 Hz), 4.18-4.09 (m, 1H), 3.82-3.72 (m, 1H), 3.66-3.54 (m, 1H), 3.51-3.38 (m, 1H), 3.37-3.23 (m, 1H), 1.94-1.74 (m, 1H), 1.44-1.21 (m, 2H), 1.17 (t, 3H, J=7.2 Hz), 1.04 (t, 3H, J=6.9 Hz).

Step 8

18-7

18-8

From compound 18-7 (65 mg) obtained in the above-mentioned step and by a method similar to that in Example 10, step 1, compound 18-8 (44 mg) was obtained.

$^1$H-NMR (CDCl$_3$) δ: 10.60 (t, 1H, J=6.0 Hz), 8.29 (s, 1H), 7.61-7.56 (m, 2H), 7.36-7.25 (m, 5H), 7.07-6.99 (m, 1H), 5.39 (d, 1H, J=10.1 Hz), 5.31 (d, 1H, J=10.1 Hz), 4.79-4.64 (m, 2H), 4.19-4.05 (m, 2H), 3.60-3.44 (m, 2H), 3.41-3.28 (m, 1H), 3.21 (s, 3H), 3.16 (dd, 1H, J=10.6, 7.3 Hz), 1.60-1.45 (m, 1H), 1.30-1.23 (m, 1H), 1.19-1.13 (m, 3H), 0.99 (t, 1H, J=7.1 Hz).

Step 9

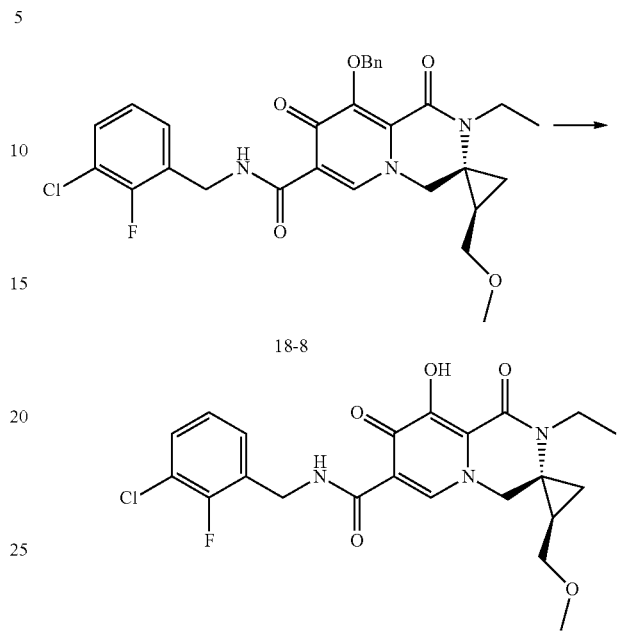

18-8

18

From compound 18-8 (44 mg) obtained in the above-mentioned step and by a method similar to that in Example 14, step 2, the title compound (20 mg) was obtained.

$^1$H-NMR (DMSO-d$_6$) δ: 11.97 (s, 1H), 10.49 (t, 1H, J=6.0 Hz), 8.41 (s, 1H), 7.52-7.47 (m, 1H), 7.35-7.29 (m, 1H), 7.20 (t, 1H, J=7.9 Hz), 4.65-4.58 (m, 2H), 4.49 (d, 1H, J=13.6 Hz), 4.41 (d, 1H, J=13.6 Hz), 3.63 (dd, 1H, J=10.9, 6.0 Hz), 3.52-3.40 (m, 1H), 3.39-3.21 (m, 2H), 3.13 (s, 3H), 1.85-1.74 (m, 1H), 1.44 (dd, 1H, J=10.2, 6.7 Hz), 1.08 (t, 3H, J=7.2 Hz), 0.98 (t, 1H, J=7.2 Hz).

Example 19

Production of (1S,2S)—N$^7$'-(2,4-difluorobenzyl)-2'-ethyl-9'-hydroxy-N$^2$,N$^2$-dimethyl-1',8'-dioxo-1',2',3',8'-tetrahydrospiro[cyclopropane-1,4'-pyrido[1,2-a]pyrazine]-2,7'-dicarboxamide hydrochloride Step 1

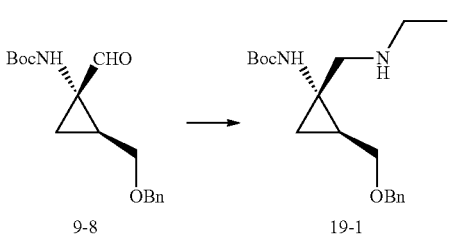 [SMILES: CC(C)(C)OC(=O)N[C@@]1(C=O)C[C@@H]1COCc1ccccc1 ; CCNC[C@]1(NC(=O)OC(C)(C)C)C[C@@H]1COCc1ccccc1]

9-8           19-1

Using compound 9-8 (812 mg) obtained in the same manner as in Example 9, step 8, and ethylamine, and by a method similar to that in Example 9, step 9, compound 19-1 (808 mg) was obtained.

$^1$H-NMR (CDCl$_3$) δ: 7.39-7.26 (m, 5H), 5.87-5.54 (m, 1H), 4.60 (d, 1H, J=11.6 Hz), 4.48 (d, 1H, J=11.6 Hz), 3.82-3.64 (m, 1H), 3.29 (t, 1H, J=10.2 Hz), 3.20-3.01 (m, 1H), 2.77-2.53 (m, 3H), 1.54-1.43 (m, 1H), 1.42 (s, 9H), 1.22-1.07 (m, 1H), 1.04 (t, 3H, J=7.2 Hz), 0.74-0.65 (m, 1H).

Step 2

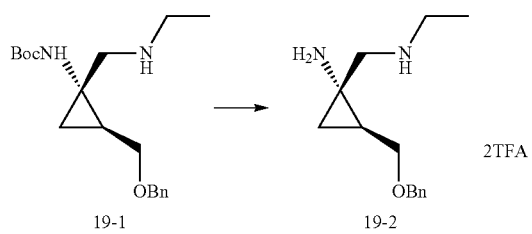 [SMILES: CCNC[C@]1(NC(=O)OC(C)(C)C)C[C@@H]1COCc1ccccc1 ; CCNC[C@]1(N)C[C@@H]1COCc1ccccc1]

To compound 19-1 (808 mg) obtained in the above-mentioned step was added TFA (20 mL), and the mixture was stirred for 1 hr, and concentrated to give a crude product of compound 19-2. The obtained crude product of compound 19-2 was directly used in the next step.

$^1$H-NMR (DMSO-d$_6$) δ: 8.81-8.18 (m, 3H), 7.40-7.27 (m, 5H), 4.53 (d, 1H, J=11.7 Hz), 4.47 (d, 1H, J=11.7 Hz), 3.78 (dd, 1H, J=11.0, 5.7 Hz), 3.49 (d, 1H, J=14.6 Hz), 3.32 (dd, 1H, J=11.0, 9.3 Hz), 3.18-3.09 (m, 1H), 3.08-2.94 (m, 2H), 1.80-1.70 (m, 1H), 1.27 (dd, 1H, J=9.9, 6.6 Hz), 1.17 (t, 3H, J=7.1 Hz), 1.11 (t, 1H, J=6.8 Hz).

Step 3

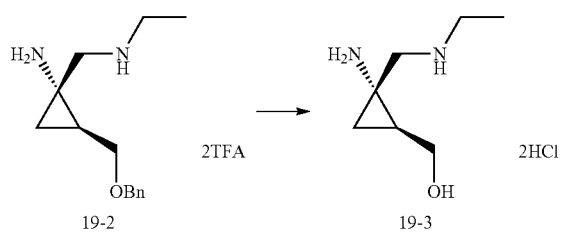

From the crude product of compound 19-2 obtained in the above-mentioned step and by a method similar to that in Example 13, step 7, a crude product of compound 19-3 (447 mg) was obtained. The obtained crude product of compound 19-3 was directly used in the next step.

Step 4

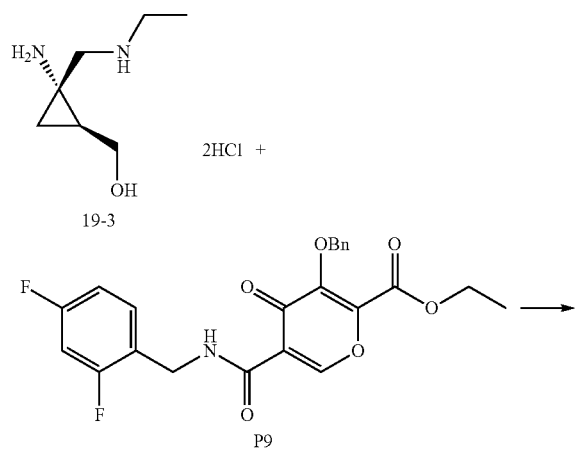

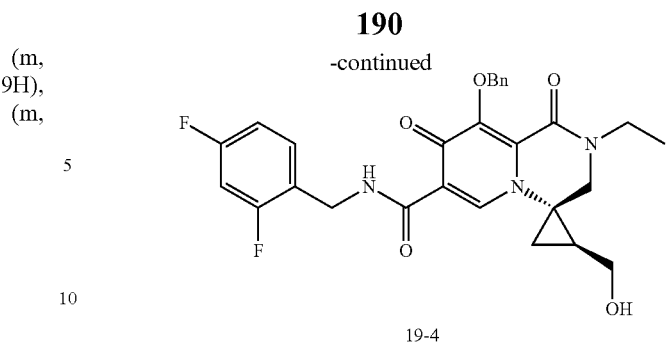

From the crude product of compound 19-3 obtained in the above-mentioned step (290 mg) and compound P9 (503 mg) obtained in Example 9, Preliminary step 9-1, and by a method similar to that in Example 9, step 12, compound 19-4 (356 mg) was obtained.

$^1$H-NMR (CDCl$_3$) δ: 10.51 (t, 1H, J=5.7 Hz), 8.32 (s, 1H), 7.62-7.57 (m, 2H), 7.40-7.25 (m, 4H), 6.86-6.76 (m, 2H), 5.34-5.24 (m, 2H), 4.62 (d, 2H, J=6.2 Hz), 4.08-4.00 (m, 1H), 3.92-3.81 (m, 1H), 3.76-3.55 (m, 3H), 3.37-3.26 (m, 1H), 2.00-1.90 (m, 2H), 1.72 (dd, 1H, J=10.4, 7.5 Hz), 1.27-1.15 (m, 4H).

Step 5

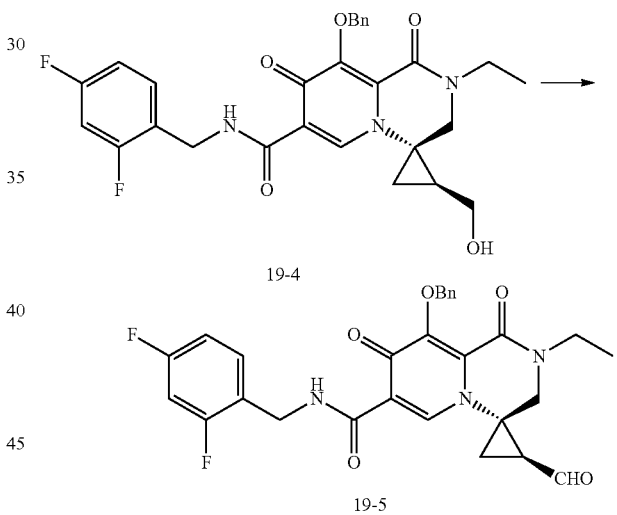

To a solution of compound 19-4 (156 mg) obtained in the above-mentioned step in chloroform (10 mL) was added Dess-Martin reagent (180 mg) under ice-cooling, and the mixture was stirred at room temperature for 1 hr. An aqueous sodium sulfite solution and saturated aqueous sodium hydrogen carbonate solution were added, and the mixture was stirred for 1 hr. After partitioning, the organic layer was washed with saturated brine, and dried. After concentration, the residue was purified by silica gel column chromatography (ethyl acetate) to give compound 19-5 (156 mg).

$^1$H-NMR (CDCl$_3$) δ: 10.38 (t, 1H, J=6.0 Hz), 9.97 (s, 1H), 8.28 (s, 1H), 7.60-7.56 (m, 2H), 7.42-7.27 (m, 4H), 6.86-6.78 (m, 2H), 5.40 (d, 1H, J=10.2 Hz), 5.23 (d, 1H, J=10.2 Hz), 4.63 (d, 2H, J=6.0 Hz), 3.85 (d, 1H, J=14.1 Hz), 3.80-3.69 (m, 1H), 3.50 (d, 1H, J=14.1 Hz), 3.16-3.05 (m, 1H), 2.57 (t, 1H, J=8.6 Hz), 2.43 (t, 1H, J=8.6 Hz), 2.07 (t, 1H, J=7.6 Hz), 1.11 (t, 3H, J=7.2 Hz).

Step 6

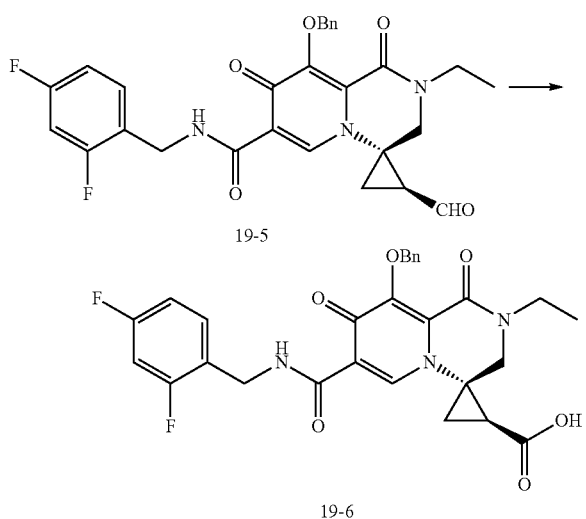

To a solution of compound 19-5 (156 mg) obtained in the above-mentioned step in acetone (6 mL) were successively added water (2 mL), sodium dihydrogen phosphate (35 mg), 2-methylpropene (135 μL) and sodium chlorite (111 mg), and the mixture was stirred at room temperature for 1 hr. An aqueous sodium sulfite solution was added, and the mixture was stirred for 30 min and acidified with 5% aqueous potassium hydrogen sulfate solution. The precipitated solid was collected by filtration and dried to give compound 19-6 (117 mg).

$^1$H-NMR (DMSO-$d_6$) δ: 13.02 (br s, 1H), 10.37 (t, 1H, J=5.8 Hz), 8.22 (s, 1H), 7.56-7.52 (m, 2H), 7.46-7.29 (m, 4H), 7.27-7.19 (m, 1H), 7.10-7.03 (m, 1H), 5.16 (d, 1H, J=10.4 Hz), 5.06 (d, 1H, J=10.4 Hz), 4.57-4.52 (m, 2H), 4.10 (d, 1H, J=14.1 Hz), 3.61-3.52 (m, 2H), 3.24-3.15 (m, 1H), 2.56-2.30 (m, 2H), 1.73-1.67 (m, 1H), 1.07 (t, 3H, J=7.2 Hz).

Step 7

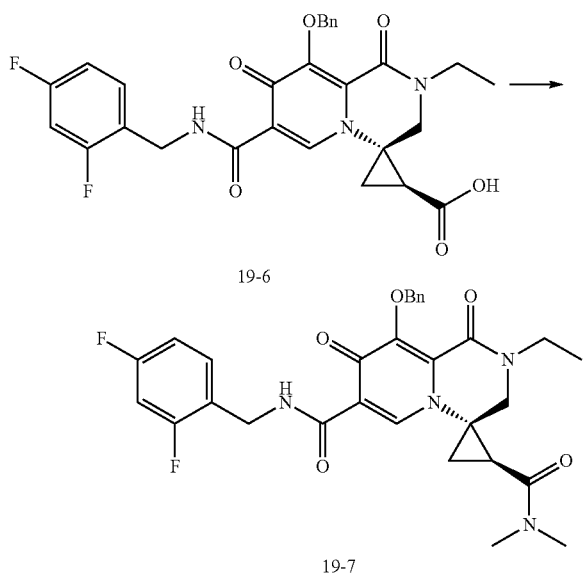

To a solution of compound 19-6 (50 mg) obtained in the above-mentioned step in acetonitrile (4 mL) were successively s0 added dimethylamine hydrochloride (30 mg), diisopropylethylamine (162 μL) and HATU (503 mg), and the mixture was stirred at room temperature for 1 hr. The mixture was concentrated, diluted with ethyl acetate, washed successively with saturated aqueous sodium hydrogen carbonate solution and saturated brine and dried. After concentration, the residue was purified by silica gel column chromatography (ethyl acetate:methanol=50:1 to 10:1) to give compound 19-7 (46 mg).

$^1$H-NMR (CDCl$_3$) δ: 10.42 (t, 1H, J=6.0 Hz), 8.31 (s, 1H), 7.58-7.53 (m, 2H), 7.41-7.26 (m, 4H), 6.87-6.77 (m, 2H), 5.40 (d, 1H, J=10.4 Hz), 5.28 (d, 1H, J=10.4 Hz), 4.69-4.57 (m, 2H), 3.82 (d, 1H, J=13.9 Hz), 3.70-3.59 (m, 1H), 3.51 (d, 1H, J=13.9 Hz), 3.25-3.15 (m, 1H), 3.03 (s, 3H), 2.99 (s, 3H), 2.29-2.18 (m, 2H), 2.07-2.02 (m, 1H), 1.09 (t, 3H, J=7.4 Hz).

Step 8

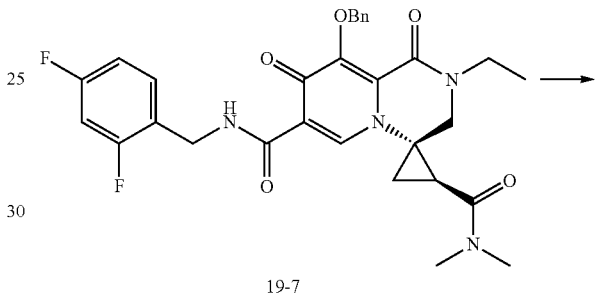

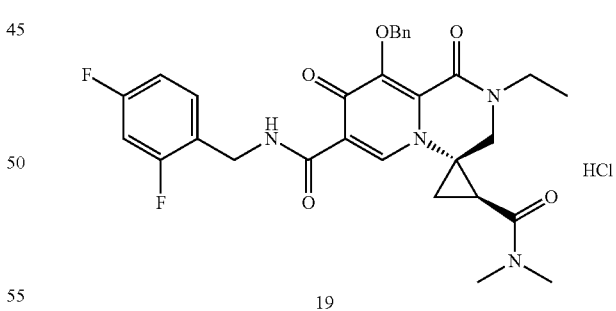

From compound 19-7 (46 mg) obtained in the above-mentioned step and by a method similar to that in Example 10, step 2, the title compound (25 mg) was obtained.

$^1$H-NMR (DMSO-$d_6$) δ: 12.59 (s, 1H), 10.33 (t, 1H, J=5.8 Hz), 8.13 (s, 1H), 7.42-7.35 (m, 1H), 7.25-7.18 (m, 1H), 7.08-7.01 (m, 1H), 4.56 (dd, 1H, J=14.8, 6.2 Hz), 4.47 (dd, 1H, J=14.8, 5.5 Hz), 4.13 (d, 1H, J=13.6 Hz), 3.54-3.43 (m, 1H), 3.36-3.18 (m, 2H), 2.93 (s, 3H), 2.83 (s, 3H), 2.73-2.64 (m, 1H), 2.43-2.35 (m, 1H), 1.71 (t, 1H, J=7.9 Hz), 0.98 (t, 3H, J=7.2 Hz).

Example 20

Production of N-(2,4-difluorobenzyl)-9'-hydroxy-2'-isopropyl-3-(N-methylacetamido)-1',8'-dioxo-1',2',3',8'-tetrahydrospiro[cyclobutane-1,4'-pyrido[1,2-a]pyrazine]-7'-carboxamide hydrochloride

Step 1

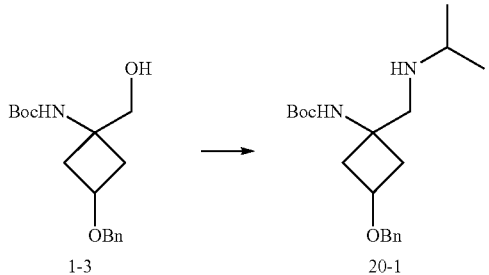 [SMILES: CC(C)(C)OC(=O)NC1(CO)CC(OCc2ccccc2)C1 ; CC(C)NCC1(NC(=O)OC(C)(C)C)CC(OCc2ccccc2)C1]

From compound 1-3 (399 mg) obtained in Example 1, step 3, and in the same manner as in Example 1, step 4, residue 20-1 was obtained.

To a solution of the residue 20-1 in chloroform (4 mL) were successively added isopropylamine (228 μL), acetic acid (228 μL) and sodium triacetoxyborohydride (860 mg), and the mixture was stirred at room temperature for 7 min. Isopropylamine (110 μL) was added, and the mixture was stirred at room temperature for 3 hr. To the reaction mixture was added saturated aqueous sodium hydrogen carbonate solution, and the mixture was extracted 3 times with chloroform. The organic layer was dried over magnesium sulfate and concentrated. Toluene was added and the mixture was concentrated again, and dried under reduced pressure to give a crude product of compound 20-1. The obtained crude product of compound 20-1 was directly used in the next step.

Step 2

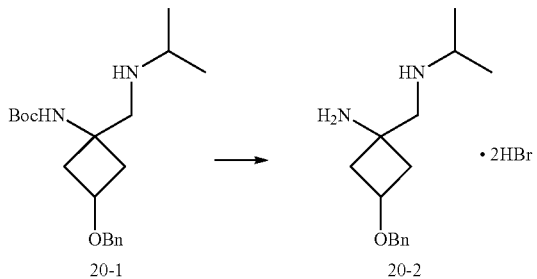 [SMILES: CC(C)NCC1(NC(=O)OC(C)(C)C)CC(OCc2ccccc2)C1 ; CC(C)NCC1(N)CC(OCc2ccccc2)C1]

To the crude product of compound 20-1 obtained in the above-mentioned step was added a 48% aqueous hydrogen bromide solution (15 mL), and the mixture was stirred at room temperature for 10 min, and at 80° C. for 17.5 hr. An operation including adding ethanol to the reaction mixture, concentrating the mixture, adding ethanol and concentrating the mixture, an operation including adding toluene and concentrating the mixture, and an operation including adding ethanol and concentrating the mixture were performed successively. The mixture was dried under reduced pressure to give a crude product of compound 20-2. The obtained crude product of compound 20-2 was directly used in the next step.

Step 3

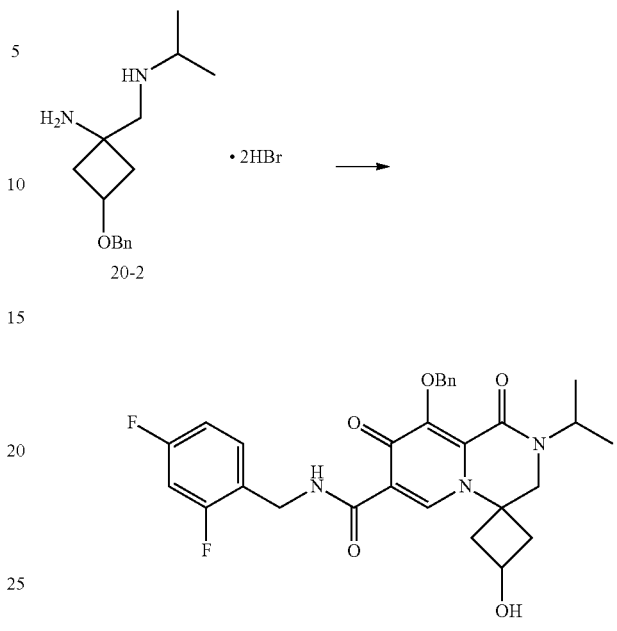

To a mixed solution of the crude product of compound 20-2 obtained in the above-mentioned step in THF-ethanol (8 mL-4 mL) were added triethylamine (4 mL) and compound P9 (525 mg) obtained in Preliminary step 9-1. After stirring at room temperature for 30 min, the mixture was concentrated, dried under reduced pressure, toluene (30 mL) and DBU (3 mL) were added and the mixture was stirred at 80° C. for 30 min. To the reaction mixture were added acetic acid (6 mL) and ethanol (5 mL), and the mixture was stirred at 100° C. for 50 min and stood at room temperature overnight. To the reaction mixture were added toluene and a 10% aqueous potassium hydrogen sulfate solution, and the mixture was extracted with toluene to give an organic layer 20-3-1 and an aqueous layer 20-3-1. The aqueous layer 20-3-1 was extracted twice with chloroform to give an organic layer 20-3-2.

The organic layer 20-3-1 and the organic layer 20-3-2 were combined, washed with saturated brine to give an organic layer 20-3-3 and an aqueous layer 20-3-2. The organic layer 20-3-3 was washed twice with a saturated aqueous sodium hydrogen carbonate solution to give an organic layer 20-3-4 and an aqueous layer 20-3-3. The aqueous layer 20-3-3 was extracted twice with chloroform to give an organic layer 20-3-5. The organic layer 20-3-4 and the organic layer 20-3-5 were combined, and the mixture was dried over magnesium sulfate, concentrated and purified by silica gel column chromatography (chloroform:acetone=4:1 to 2:3) to give compound 20-3 (457 mg).

$^1$H-NMR (CDCl$_3$) δ: 10.58-10.52 (m, 1.0H), 8.80 (s, 0.5H), 8.66 (s, 0.5H), 7.63-7.60 (m, 2.0H), 7.41-7.27 (m, 4.0H), 6.85-6.79 (m, 2.0H), 5.30 (s, 2.0H), 4.97-4.90 (m, 1.0H), 4.77-4.69 (m, 0.5H), 4.66-4.64 (m, 2.0H), 4.34-4.25 (m, 0.5H), 3.66 (s, 1.0H), 3.28 (s, 1.0H), 2.96-2.85 (m, 1.0H), 2.75-2.69 (m, 1.5H), 2.65-2.59 (m, 1.0H), 2.34-2.28 (m, 1.0H), 2.24-2.22 (m, 0.5H), 1.22 (d, 3.0H, J=6.9 Hz), 1.19 (d, 3.0H, J 6.9 Hz).

Step 4

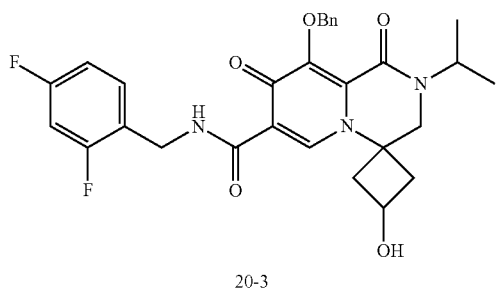

20-3

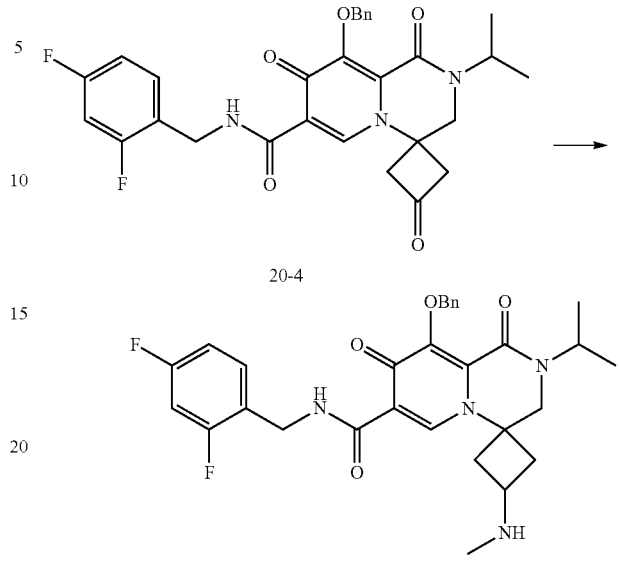

To a solution of compound 20-3 (60 mg) obtained in the above-mentioned step in chloroform (1.8 mL) was added Dess-Martin reagent (96 mg), and the mixture was stirred at room temperature for 40 min. Chloroform (1 mL) and Dess-Martin reagent (47 mg) were added, and the mixture was stirred at room temperature for 1 hr. To the reaction mixture were added a saturated aqueous sodium hydrogen carbonate solution and sodium sulfite, and the mixture was extracted twice with ethyl acetate. The organic layer was washed with saturated brine, dried over magnesium sulfate, concentrated and dried under reduced pressure to give residue 20-4-1.

To a solution of compound 20-3 (180 mg) obtained in the above-mentioned step in chloroform (5 mL) was added Dess-Martin reagent (444 mg), and the mixture was stirred at room temperature for 1 hr. To the reaction mixture were added a saturated aqueous sodium hydrogen carbonate solution and sodium sulfite, and the mixture was extracted twice with ethyl acetate. The organic layer was washed with saturated brine, dried over magnesium sulfate and concentrated to give residue 20-4-2.

The residue 20-4-1 (19 mg was removed from the total amount) and the residue 20-4-2 were combined and the mixture was dissolved in chloroform and concentrated. Hexane was added, and the mixture was concentrated, and dried under reduced pressure to give compound 20-4 (235 mg).

$^1$H-NMR (CDCl$_3$) δ: 10.43 (t, 1H, J=6.0 Hz), 8.74 (s, 1H), 7.63-7.60 (m, 2H), 7.40-7.29 (m, 4H), 6.86-6.78 (m, 2H), 5.32 (s, 2H), 4.97 (sep, 1H, J=6.7 Hz), 4.64 (d, 2H, J=6.0 Hz), 3.81-3.75 (m, 2H), 3.54 (s, 2H), 3.32-3.27 (m, 2H), 1.21 (d, 6H, J=6.7 Hz).

Step 5

From compound 20-4 (103 mg) obtained in the above-mentioned step, and by an operation similar to that in Example 1, step 5, a crude product of compound 20-5 (97 mg) was obtained. The obtained crude product of compound 20-5 was directly used in the next step.

Step 6

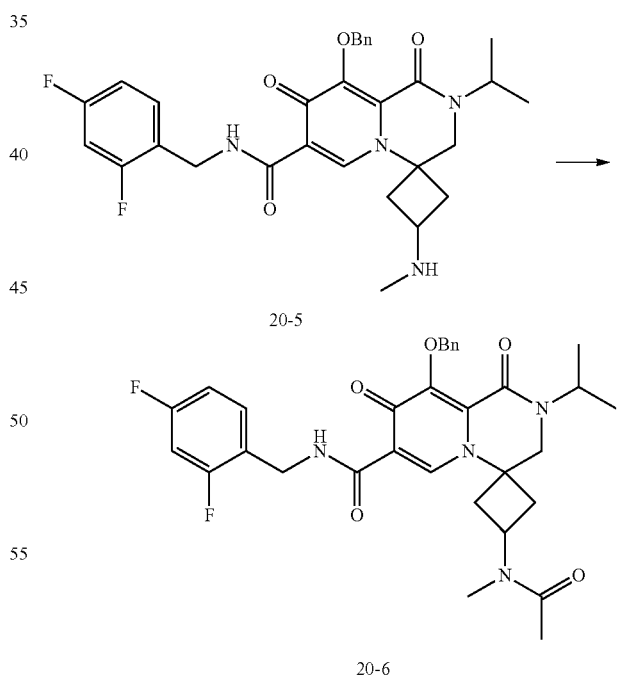

To a solution of crude product of compound 20-5 (43 mg) obtained in the above-mentioned step in deuterated chloroform (600 μL) were added 4-dimethylaminopyridine (14.3 mg), triethylamine (60 μL) and acetic anhydride (25 μL), and the mixture was stirred at room temperature for 1.5 hr. To the reaction mixture was added a 10% aqueous potassium hydrogen sulfate solution, and the mixture was extracted 3 times with chloroform. The organic layer was washed with saturated brine, dried over magnesium sulfate, concentrated, and purified by silica gel thin layer chromatography (ethyl acetate:methanol=12:1) to give compound 20-6 (36 mg).

Step 7

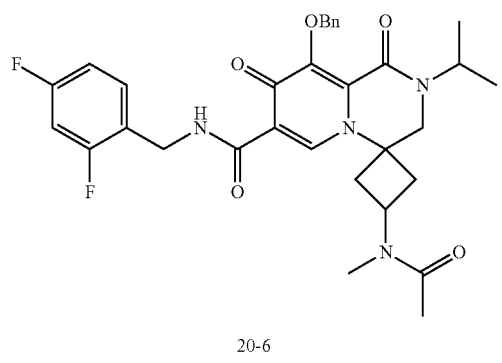

To compound 20-6 (36 mg) obtained in the above-mentioned step was added TFA (1 mL), and the mixture was stood at room temperature for 20 min. The reaction mixture was concentrated, ethyl acetate was added and the mixture was concentrated to give residue 20-7.

To the residue 20-7 were successively added ethyl acetate (400 μL), 4N hydrochloric acid/ethyl acetate (100 μL), and ethyl acetate (4.5 mL), and the mixture was stirred at room temperature for 10 min. Ethyl acetate (5 mL) was added and the mixture was further stirred at room temperature for 10 min. The precipitated solid was collected by filtration, and dried under reduced pressure to give the title compound (4.5 mg).

$^1$H-NMR (DMSO-$d_6$) δ: 10.43-10.39 (br m, 1H), 8.56-8.53 (m, 1H), 7.46-7.38 (m, 1H), 7.27-7.21 (m, 1H), 7.09-7.04 (m, 1H), 4.81-4.63 (m, 1H), 4.55 (d, 2H, J=5.3 Hz), 3.83-3.76 (m, 2H), 2.98-2.92 (m, 2H), 2.87-2.79 (m, 3H), 2.67-2.60 (m, 1H), 2.50-2.45 (m, 2H), 2.08-1.99 (m, 3H), 1.25-1.19 (m, 6H).

Example 21

Production of (1R,2R)—N-(3-chloro-2-fluorobenzyl)-9'-hydroxy-2'-isopropyl-2-(methylsulfonylmethyl)-1',8'-dioxo-1',2',3',8'-tetrahydrospiro[cyclopropane-1,4'-pyrido[1,2-a]pyrazine]-7'-carboxamide hydrochloride Step 1

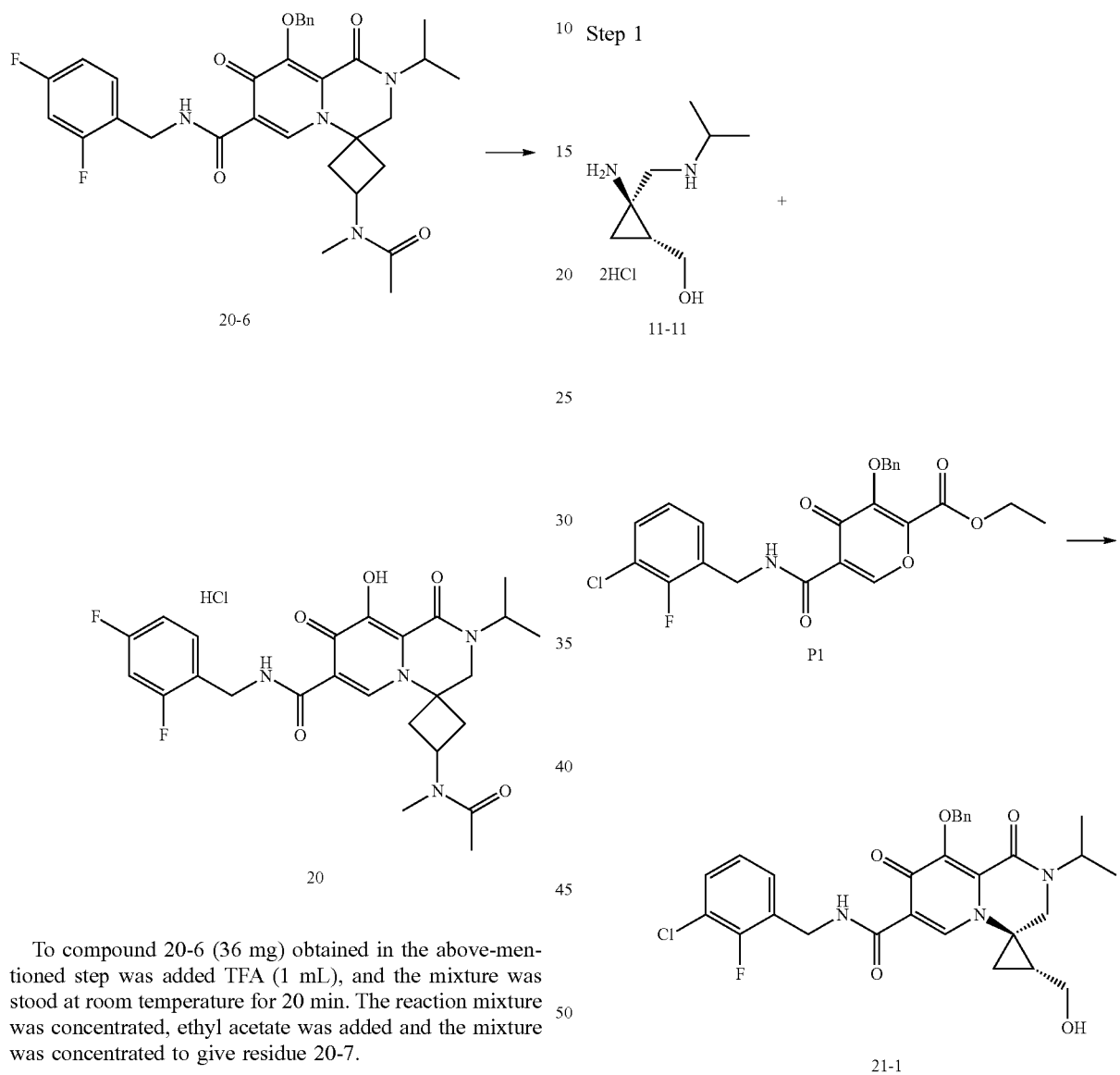

From the crude product of compound 11-11 (122 mg) obtained in the same manner as in Example 11, step 11, and compound P1 (206 mg) obtained in Example 1, Preliminary step 1-1, and in the same manner as in Example 9, step 12, compound 21-1 (210 mg) was obtained.

$^1$H-NMR (CDCl$_3$) δ: 10.66 (t, 1H, J=6.0 Hz), 8.38 (s, 1H), 7.67-7.54 (m, 2H), 7.45-7.20 (m, 5H), 7.05-6.99 (m, 1H), 5.33 (d, 1H, J=10.1 Hz), 5.25 (d, 1H, J=10.1 Hz), 4.92-4.80 (m, 1H), 4.67 (d, 2H, J=6.0 Hz), 4.10-4.03 (m, 1H), 3.68 (d, 1H, J=14.1 Hz), 3.67-3.60 (m, 1H), 3.34 (d, 1H, J=14.1 Hz), 2.37-2.25 (m, 1H), 1.51-1.42 (m, 1H), 1.19-1.13 (m, 6H), 1.10-1.03 (m, 1H).

Step 2

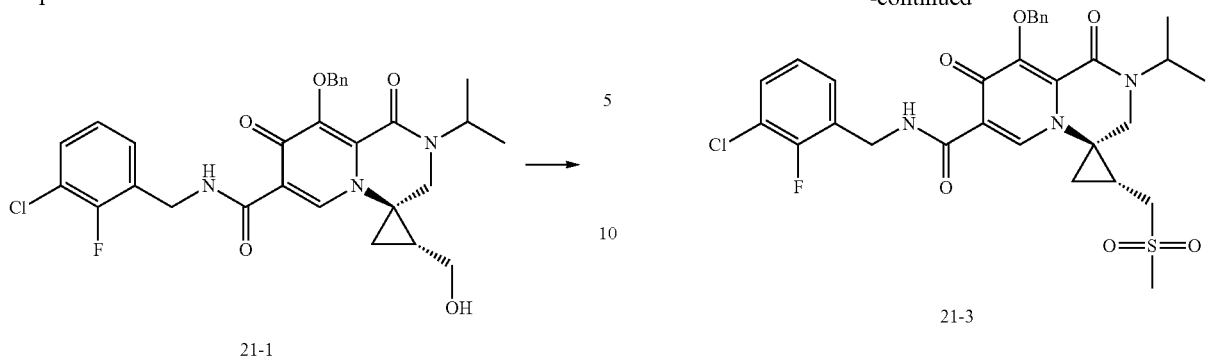

21-1

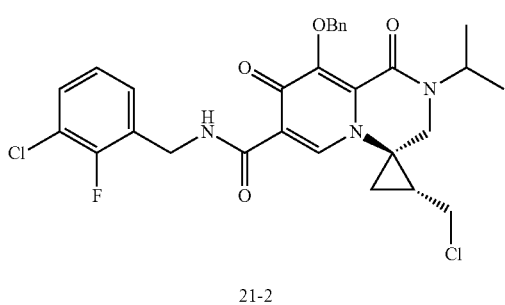

21-2

To a solution of compound 21-1 (71 mg) obtained in the above-mentioned step in chloroform (3 mL) was added thionyl chloride (19 μL), and the mixture was stirred at room temperature overnight. A saturated aqueous sodium hydrogen carbonate solution was added and, after partitioning, the aqueous layer was extracted with chloroform. The organic layers were combined, washed with saturated brine, and dried. After concentration, the residue was purified by silica gel column chromatography (ethyl acetate) to give compound 21-2 (69 mg).

$^1$H-NMR (CDCl$_3$) δ: 10.49 (t, 1H, J=6.0 Hz), 8.34 (s, 1H), 7.64-7.60 (m, 2H), 7.42 (s, 2H), 7.39-7.26 (m, 3H), 7.06-7.00 (m, 1H), 5.35 (d, 1H, J=9.9 Hz), 5.28 (d, 1H, J=9.9 Hz), 4.96-4.87 (m, 1H), 4.69 (d, 2H, J=6.0 Hz), 3.83 (dd, 1H, J=12.0, 6.2 Hz), 3.60-3.50 (m, 2H), 3.31 (d, 1H, J=14.1 Hz), 2.45-2.35 (m, 1H), 1.78-1.70 (m, 1H), 1.19 (t, 6H, J=6.7 Hz), 1.10 (t, 1H, J=7.2 Hz).

Step 3

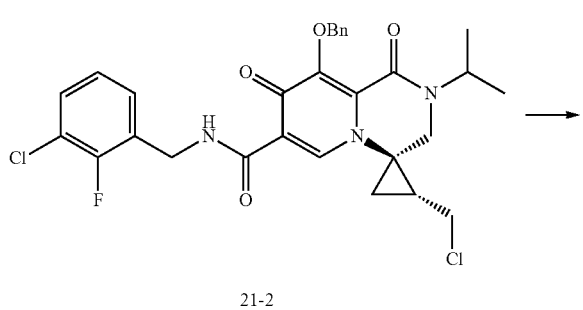

21-2

To a solution of compound 21-2 (69 mg) obtained in the above-mentioned step in DMF (3 mL) was added sodium methanesulfinate (44 mg), and the mixture was stirred at 80° C. for 3 hr. Water was added, and the mixture was extracted 3 times with ethyl acetate, and the organic layer was washed 4 times with saturated brine. The mixture was dried, concentrated, and purified by silica gel column chromatography (ethyl acetate to ethyl acetate:methanol=20:1), and successively by silica gel thin layer chromatography (ethyl acetate: acetone=4:1) to give compound 21-3 (18 mg).

$^1$H-NMR (CDCl$_3$) δ: 10.49-10.42 (m, 1H), 8.34 (s, 1H), 7.63-7.58 (m, 2H), 7.39-7.13 (m, 5H), 7.07-6.99 (m, 1H), 5.31 (s, 2H), 4.95-4.87 (m, 1H), 4.69 (d, 2H, J=6.0 Hz), 3.52-3.30 (m, 3H), 3.08-2.99 (m, 1H), 3.03 (s, 3H), 2.23-2.13 (m, 1H), 1.99-1.91 (m, 1H), 1.32-1.24 (m, 1H), 1.21-1.16 (m, 6H).

Step 4

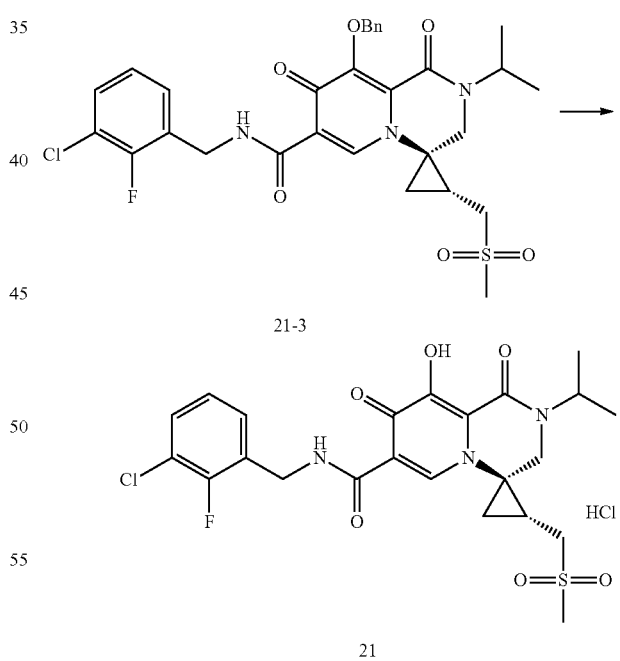

From compound 21-3 (18 mg) obtained in the above-mentioned step and by a method similar to that in Example 10, step 2, the title compound (13 mg) was obtained.

$^1$H-NMR (DMSO-d$_6$) δ: 12.90-12.80 (m, 1H), 10.41 (t, 1H, J=6.0 Hz), 8.13 (s, 1H), 7.51-7.46 (m, 1H), 7.34-7.28 (m, 1H), 7.22-7.16 (m, 1H), 4.79-4.70 (m, 1H), 4.64-4.55 (m, 2H), 3.85 (d, 1H, J=14.3 Hz), 3.73-3.55 (m, 2H), 3.41-3.32 (m, 1H), 3.01 (s, 3H), 2.15-2.08 (m, 1H), 2.01-1.90 (m, 1H), 1.27-1.15 (m, 1H), 1.18 (dd, 6H, J=9.2, 6.9 Hz).

Example 22

Production of 7'-(3-chloro-2-fluorobenzylcarbamoyl)-9'-hydroxy-2'-methyl-1',8'-dioxo-1',2',3',8'-tetrahydrospiro[cyclobutane-1,4'-pyrido[1,2-a]pyrazine]-cis-3-carboxylic acid hydrochloride Step 1

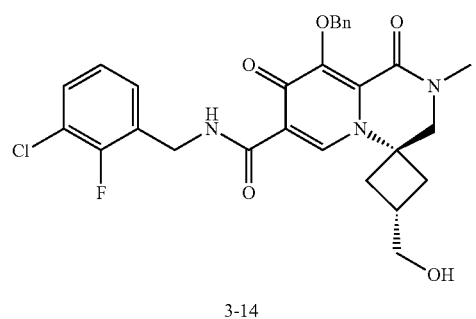

3-14

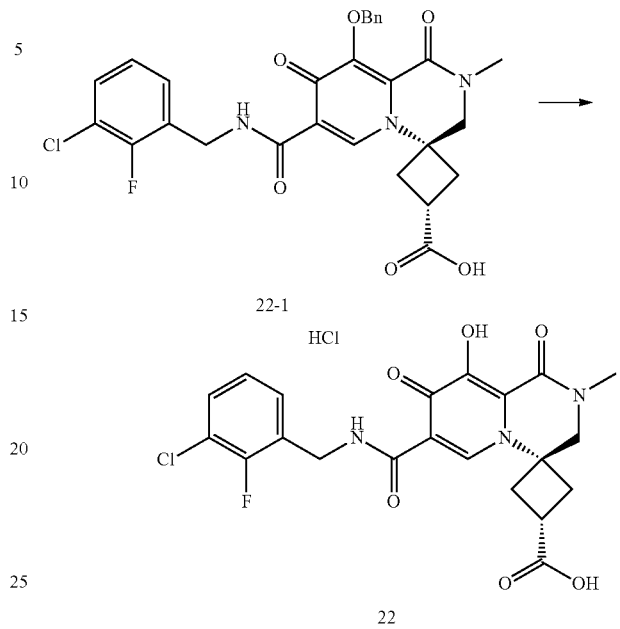

To a suspension of compound 3-14 (135 mg) obtained by the operation of Example 3, step 14, in acetonitrile (2 mL) were successively added water (45 μL), N-methylmorpholine (293 mg) and tetrapropylammonium perruthenate (8.8 mg), and the mixture was stirred for 2.5 hr. Water (1 mL) and 5% aqueous potassium hydrogen sulfate solution (4.5 mL) were successively added, and the mixture was extracted twice with chloroform. The organic layers were combined and washed with saturated brine. The mixture was dried, concentrated, and purified by silica gel thin layer chromatography (chloroform:methanol:acetic acid=100:10:5) to give compound 22-1 (103 mg).

$^1$H-NMR (DMSO-$d_6$) δ: 12.73-12.40 (m, 1H), 10.49 (t, 1H, J=6.0 Hz), 8.64 (s, 1H), 7.57-7.46 (m, 3H), 7.40-7.28 (m, 4H), 7.25-7.15 (m, 1H), 5.11 (s, 2H), 4.63 (d, 2H, J=6.0 Hz), 3.83 (s, 2H), 3.23-3.11 (m, 1H), 3.12 (s, 3H), 2.79-2.68 (m, 2H), 2.52-2.48 (m, 2H).

Step 2

To compound 22-1 (50 mg) obtained in the above-mentioned step were added 2N hydrochloric acid (100 μL) and trifluoroacetic acid (1 mL), and the mixture was stirred for 20 min. After concentration, toluene was added and the mixture was concentrated. To the residue were added dioxane (5 mL) and 4N hydrochloric acid/dioxane (2 mL) and the mixture was stirred at room temperature for 1 hr. Hexane (3.5 mL) was added, and the mixture was further stirred at room temperature for 1 hr. The solid was collected by filtration, washed with hexane-dioxane (1:1) and dried to give the title compound (40 mg).

$^1$H-NMR (DMSO-$d_6$) δ: 12.90-12.77 (m, 1H), 10.43 (t, 1H, J=6.0 Hz), 8.52 (s, 1H), 7.52-7.46 (m, 1H), 7.36-7.30 (m, 1H), 7.23-7.17 (m, 1H), 4.62 (d, 2H, J=6.0 Hz), 3.92 (s, 2H), 3.23-3.12 (m, 1H), 3.14 (s, 3H), 2.75-2.65 (m, 2H), 2.56-2.45 (m, 2H).

Example 23

Production of N-(3-chloro-2-fluorobenzyl)-9'-hydroxy-cis-3-methoxy-2'-methyl-1',8'-dioxo-1',2',3',8'-tetrahydrospiro[cyclobutane-1,4'-pyrido[, 2-a]pyrazine]-7'-carboxamide

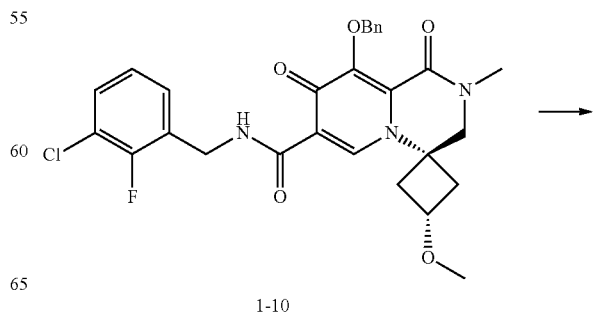

1-10

-continued

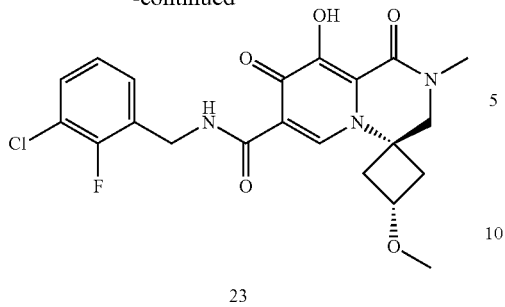

23

To compound 1-10 (100 mg) obtained by the operation of Example 1, step 10 were successively added 4N hydrochloric acid/ethyl acetate (0.5 mL) and trifluoroacetic acid (1.5 mL), and the mixture was stood at room temperature for 45 min. After concentration, a saturated aqueous sodium hydrogen carbonate solution was added, and the mixture was extracted 3 times with chloroform. The organic layers were combined, dried over magnesium sulfate, and concentrated. Ethyl acetate was added and the mixture was concentrated and crystallized from ethyl acetate-hexane to give the title compound (62 mg).

As other crystallization conditions, the title compound (450 mg) was dissolved in acetonitrile (10 mL), the solution was stood at room temperature to give a single crystal. The steric configuration of compound 23 was determined by X-ray structural analysis of the obtained single crystal.

$^1$H-NMR (DMSO-$d_6$) δ: 12.83 (s, 1H), 10.43 (t, 1H, J=6.0 Hz), 8.48 (s, 1H), 7.52-7.46 (m, 1H), 7.36-7.30 (m, 1H), 7.23-7.17 (m, 1H), 4.62 (d, 2H, J=6.0 Hz), 4.01-3.93 (m, 1H), 3.78 (s, 2H), 3.20 (s, 3H), 3.12 (s, 3H), 2.73-2.63 (m, 2H), 2.44-2.34 (m, 2H).

Elemental analysis: calcd. C, 56.07; H, 4.71; N, 9.34. found C, 56.05; H, 4.68; N, 9.37.

Example 24

Production of Monosodium 7'-(3-chloro-2-fluorobenzylcarbamoyl)-cis-3-methoxy-2'-methyl-1',8'-dioxo-1',2',3',8'-tetrahydrospiro[cyclobutane-1,4'-pyrido[1,2-a]pyrazin]-9'-olate

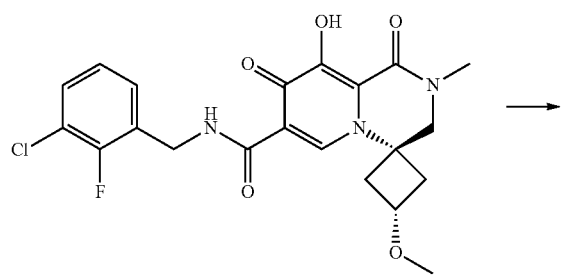

23

-continued

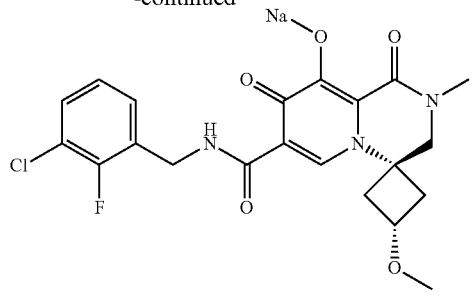

24

To a suspension of compound 23 (0.31 g) obtained by the operation of Example 23 in methanol (15 mL) was added dropwise a 1N aqueous sodium hydroxide solution (0.68 mL). After stirring at 70° C. for 3 hr, the mixture was allowed to cool and stirred at room temperature for 6 hr. The solid was collected by filtration, washed with methanol and dried at 60° C. to give the title compound (0.22 g).

$^1$H-NMR (DMSO-$d_6$) δ: 10.81 (t, 1H, J=6.0 Hz), 8.02 (s, 1H), 7.50-7.44 (m, 1H), 7.32-7.26 (m, 1H), 7.20-7.14 (m, 1H), 4.59 (d, 2H, J=6.0 Hz), 4.02-3.93 (m, 1H), 3.54 (s, 2H), 3.20 (s, 3H), 3.02 (s, 3H), 2.66-2.54 (m, 2H), 2.28-2.17 (m, 2H).

Example 25

Production of Monopotassium 7'-(3-chloro-2-fluorobenzylcarbamoyl)-cis-3-methoxy-2'-methyl-1',8'-dioxo-1',2',3',8'-tetrahydrospiro[cyclobutane-1,4'-pyrido[1,2-a]pyrazin]-9'-olate

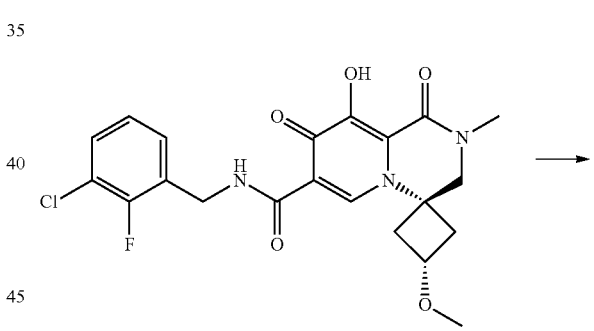

23

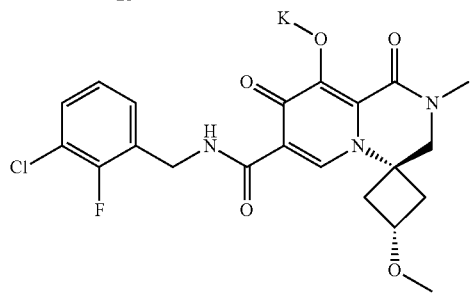

25

To a suspension of compound 23 (10 g) obtained by the operation of Example 23 in methanol (40 mL) was added dropwise a 1N aqueous potassium hydroxide solution (22.4 mL). After stirring at room temperature for 67 min, the mixture was concentrated and dried at 60° C. to give the title compound (10.9 g).

¹H-NMR (DMSO-d₆) δ: 11.11-11.04 (m, 1H), 7.92 (s, 1H), 7.50-7.44 (m, 1H), 7.32-7.25 (m, 1H), 7.21-7.14 (m, 1H), 4.56 (d, 2H, J=6.0 Hz), 4.00-3.91 (m, 1H), 3.46 (s, 2H), 3.20 (s, 3H), 2.98 (s, 3H), 2.63-2.53 (m, 2H), 2.25-2.14 (m, 2H).

Example 26

Production of N-(3-chloro-2-fluorobenzyl)-9'-hydroxy-cis-3-(methoxymethyl)-2'-methyl-1',8'-dioxo-1',2',3',8'-tetrahydrospiro[cyclobutane-1,4'-pyrido[1,2-a]pyrazine]-7'-carboxamide

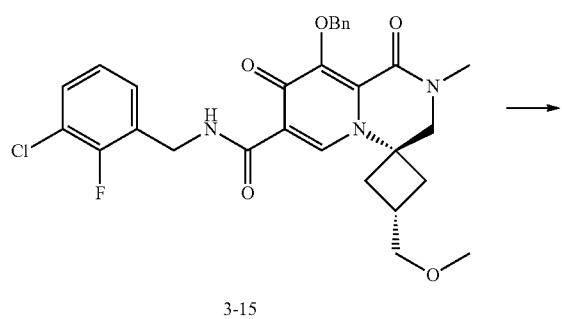

3-15

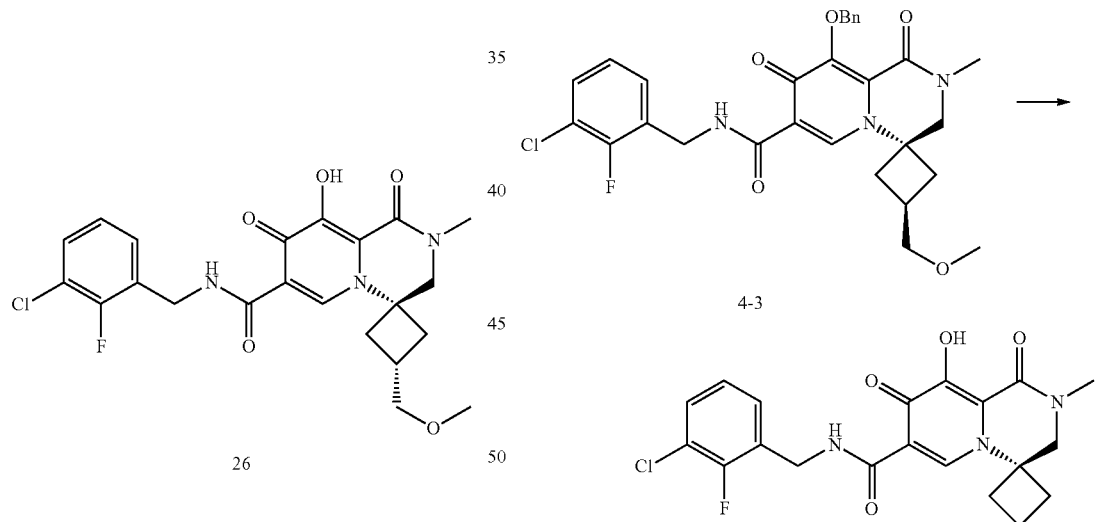

26

To a solution of compound 3-15 (227 g) obtained by the operation of Example 3, step 15, in chloroform (450 mL) were successively added 4N hydrochloric acid/ethyl acetate (113 mL) and trifluoroacetic acid (225 mL) under ice-cooling, and the mixture was stirred at room temperature for 3 hr. Under ice-cooling, water (500 mL) was added, and the mixture was stirred at room temperature. After separating an organic layer and an aqueous layer, the aqueous layer was extracted with chloroform (400 mL). The combined organic layers were washed successively with saturated brine (500 mL: twice), saturated aqueous sodium hydrogen carbonate solution (500 mL), a mixed solution of saturated aqueous sodium hydrogen carbonate solution (250 mL) and saturated brine (250 mL), and saturated brine (300 mL), and dried over magnesium sulfate. After concentration, ethanol (500 mL) was added to the residue, and the mixture was concentrated. The operation of concentration with ethanol was performed twice. Ethanol (1 L) was added, and the mixture was stirred at 90° C. for 1 hr, allowed to cool, and stirred at room temperature overnight. The solid was collected by filtration, and washed with ethanol (500 mL) and dried under reduced pressure to give the title compound (181 g).

As other crystallization conditions, the title compound (5 mg) was dissolved in acetonitrile (0.6 mL), the solution was stood at room temperature to give a single crystal. The steric configuration of compound 26 was determined by X-ray structural analysis of the obtained single crystal.

¹H-NMR (DMSO-d₆) δ: 12.83 (s, 1H), 10.46 (t, 1H, J=6.0 Hz), 8.53 (s, 1H), 7.53-7.47 (m, 1H), 7.36-7.30 (m, 1H), 7.23-7.17 (m, 1H), 4.62 (d, 2H, J=6.0 Hz), 3.90 (s, 2H), 3.39 (d, 2H, J=5.3 Hz), 3.27 (s, 3H), 3.14 (s, 3H), 2.68-2.47 (m, 1H), 2.40-2.23 (m, 4H).

Elemental analysis: calcd. C, 56.96; H, 5.00; N, 9.06. found C, 57.01; H, 4.93; N, 9.01.

Example 27

Production of N-(3-chloro-2-fluorobenzyl)-9'-hydroxy-trans-3-(methoxymethyl)-2'-methyl-1',8'-dioxo-1',2',3',8'-tetrahydrospiro[cyclobutane-1,4'-pyrido[1,2-a]pyrazine]-7'-carboxamide From compound 4-3 (13.4 g) obtained by the operation of Example 4, step 3, and by a method similar to that in Example 26 to give the title compound (10.7 g).

¹H-NMR (DMSO-d₆) δ: 12.94-12.94 (m, 1H), 10.46 (t, 1H, J=6.0 Hz), 8.58 (s, 1H), 7.53-7.46 (m, 1H), 7.37-7.31 (m, 1H), 7.23-7.17 (m, 1H), 4.62 (d, 2H, J=6.0 Hz), 3.82 (s, 2H), 3.42 (d, 2H, J=6.0 Hz), 3.28 (s, 3H), 3.10 (s, 3H), 2.76-2.62 (m, 1H), 2.59-2.51 (m, 2H), 2.27-2.18 (m, 2H).

Example 28

Production of Monosodium 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-olate

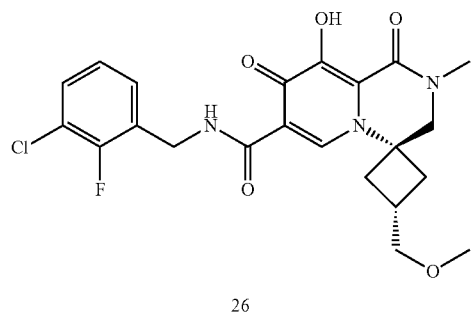
26

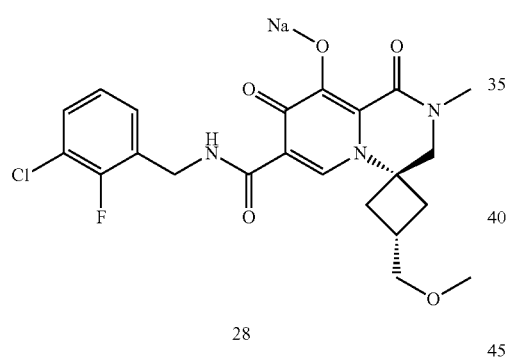
28

To compound 26 (180 g) obtained in Example 26 was added a mixture of ethanol (1980 mL) and water (330 mL), and a 1N aqueous sodium hydroxide solution (390 mL) was added dropwise at room temperature. After stirring at 70° C. for 6 hr, the mixture was allowed to cool, and stirred at room temperature overnight. Under ice-cooling, the mixture was stirred for 5 hr, and the solid was collected by filtration, and washed with a mixture of ethanol (430 mL) and water (160 mL). The solid was dried at 50° C. under reduced pressure, and stood in an environment of temperature: 24.2 to 26.8° C., humidity: 58.5-73.9% for 3 days to give the title compound (170.1 g).

$^1$H-NMR (DMSO-$d_6$) δ: 10.82 (t, 1H, J=6.0 Hz), 8.05 (s, 1H), 7.50-7.44 (m, 1H), 7.33-7.27 (m, 1H), 7.20-7.14 (m, 1H), 4.59 (d, 2H, J=6.0 Hz), 3.65 (s, 2H), 3.38 (d, 2H, J=5.5 Hz), 3.27 (s, 3H), 3.05 (s, 3H), 2.61-2.49 (m, 1H), 2.28-2.15 (m, 4H).

Water by Karl Fischer: 2.20%

Elemental analysis: calcd. (calculated as with 2.20% of water) C, 53.19; H, 4.71; N, 8.46. found C, 53.40; H, 4.68; N, 8.31.

Example 29

Production of Monopotassium 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-olate

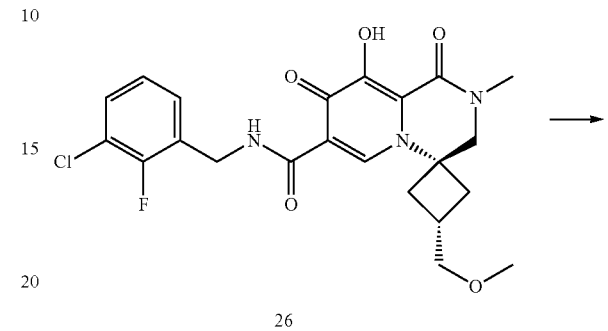
26

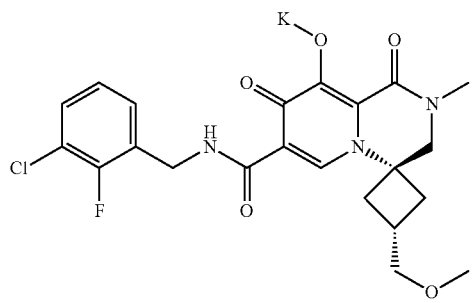
29

To a suspension of compound 26 (8.63 g) obtained by the operation of Example 26 in ethanol (40 mL) was added a 1N aqueous potassium hydroxide solution (18.5 mL) at room temperature. The mixture was concentrated, and dried at 50° C. to give a crude product 29-1 (9.27 g). To the crude product 29-1 (2.16 g) was added acetonitrile (10 mL), and the mixture was stirred at room temperature overnight. The solid was collected by filtration, and dried at 50° C. under reduced pressure to give the title compound (2.08 g).

$^1$H-NMR (DMSO-$d_6$) δ: 11.07 (t, 1H, J=6.2 Hz), 7.95 (s, 1H), 7.48-7.44 (m, 1H), 7.31-7.27 (m, 1H), 7.19-7.15 (m, 1H), 4.56 (d, 2H, J=6.2 Hz), 3.57 (s, 2H), 3.38 (d, 2H, J=5.5 Hz), 3.27 (s, 3H), 3.00 (s, 3H), 2.59-2.50 (m, 1H), 2.20-2.16 (m, 4H).

Example 30

Production of Monocalcium bis[7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-olate]

Step 1

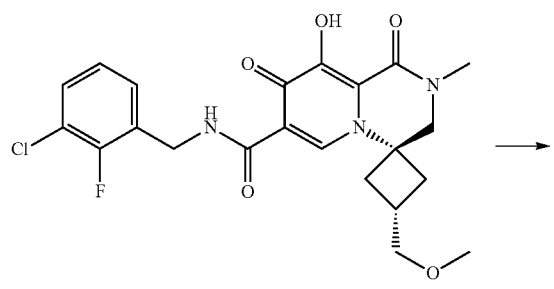

26

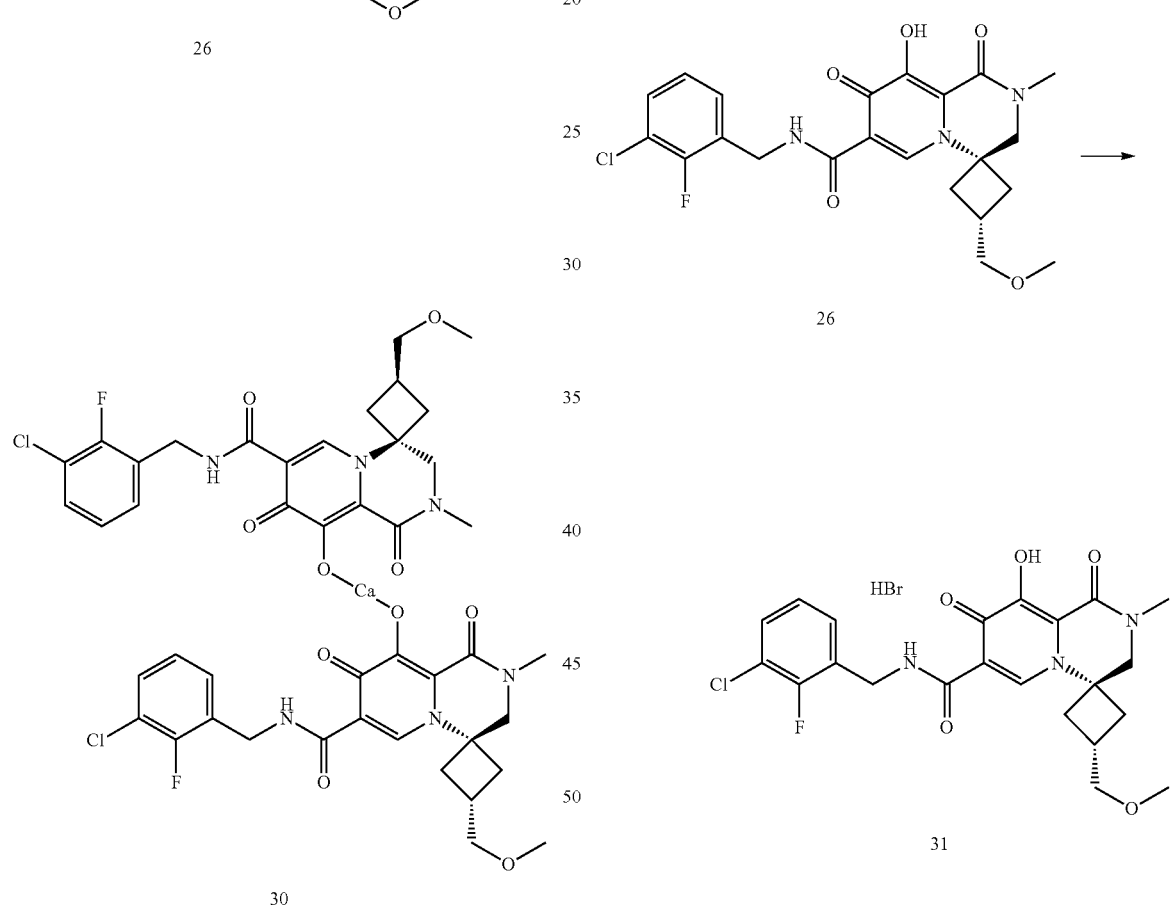

To a suspension of compound 26 (22.6 g) obtained by the operation of Example 26 in methanol (200 mL) was added dropwise a 1N aqueous potassium hydroxide solution (48.5 mL) at room temperature, and the mixture was stirred at room temperature for 30 min and concentrated. Acetonitrile was added and the mixture was concentrated, and acetonitrile (100 mL) was added. A solution of calcium chloride dihydrate (4.08 g) in water (20 mL) was added dropwise, and water (480 mL) was added. The mixture was refluxed for 13 hr and stirred at 55° C. for 3 hr under reduced pressure at 300 hPa while evaporating the solvent. The mixture was allowed to cool and stirred at room temperature for 3 hr and the solid was collected by filtration. The solid was washed with water (800 mL) and dried under reduced pressure to give the title compound (23.54 g).

$^1$H-NMR (DMSO-d$_6$, 120° C.) δ: 10.43 (br a, 2H), 8.22 (s, 2H), 7.40-7.30 (m, 2H), 7.23-7.13 (m, 2H), 7.05-6.94 (m, 2H), 4.53-4.37 (m, 4H), 3.59 (s, 4H), 3.37 (d, 4H, J=5.3 Hz), 3.28 (s, 6H), 2.91 (s, 6H), 2.63-2.43 (m, 2H), 2.20 (d, 8H, J=8.2 Hz).

Example 31

Production of N-(3-chloro-2-fluorobenzyl)-9'-hydroxy-cis-3-(methoxymethyl)-2'-methyl-1',8'-dioxo-1',2',3',8'-tetrahydrospiro[cyclobutane-1,4'-pyrido[1,2-a]pyrazine]-7'-carboxamide hydrobromide To compound 26 (331 mg) obtained by the operation of Example 26 were added acetic acid (1 mL) and 25% hydrobromic acid in acetic acid (0.5 mL) at room temperature. The reaction mixture was concentrated, toluene was added and the mixture was concentrated. After crystallization from ethyl acetate (24 mL), the solid was collected by filtration, and dried at room temperature under reduced pressure to give the title compound (320 mg).

$^1$H-NMR (DMSO-d$_6$) δ: 10.45 (t, 1H, J=6.0 Hz), 8.53 (s, 1H), 7.52-7.48 (m, 1H), 7.35-7.31 (m, 1H), 7.22-7.18 (m, 1H), 4.62 (d, 2H, J=6.0 Hz), 3.90 (6, 2H), 3.39 (d, 2H, J=5.3 Hz), 3.27 (s, 3H), 3.14 (s, 3H), 2.61-2.53 (m, 1H), 2.37-2.25 (m, 4H).

Example 32

Production of N-(3-chloro-2-fluorobenzyl)-9'-hydroxy-cis-3-(methoxymethyl)-2'-methyl-1',8'-dioxo-1',2',3',8'-tetrahydrospiro[cyclobutane-1,4'-pyrido[1,2-a]pyrazine]-7'-carboxamide monosulfate

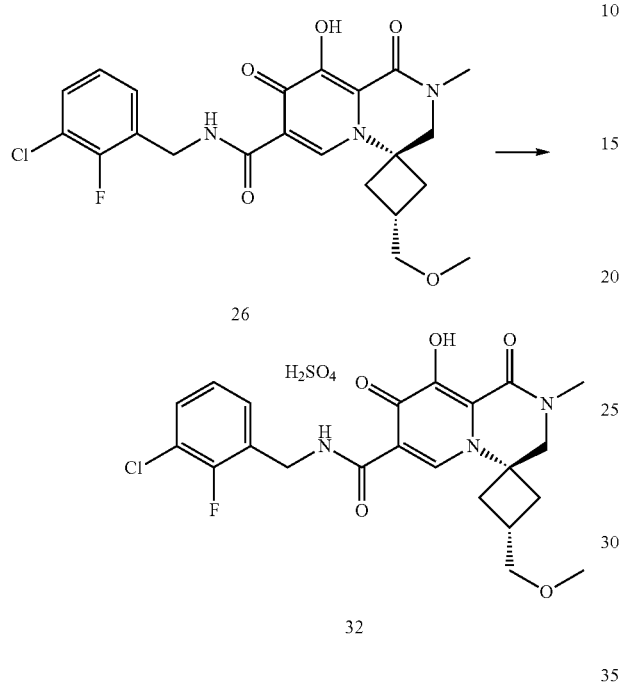

To a suspension of compound 26 (90 mg) obtained by the operation of Example 26 in ethyl acetate (4 mL) was added concentrated sulfuric acid (10.6 μL) at room temperature. Toluene and chloroform were added and the mixture was concentrated. Methanol-chloroform was added and the mixture was concentrated. Ethyl acetate (2 mL) was added, compound 31 obtained in Example 31 was seeded, ethyl acetate (2 mL) and chloroform (6 mL) were added and the mixture was stirred at room temperature for 3 days. The solid was collected by filtration and dried at 50° C. under reduced pressure to give compound 32-1 (34 mg), which is a crystal of the title compound.

To a solution of compound 26 (644 mg) obtained by the operation of Example 26 in chloroform (4 mL) was added concentrated sulfuric acid (77.7 μL) at room temperature, and compound 32-1 was seeded. Chloroform (4 mL) was added, and the mixture was stirred at 60° C. for 2.5 hr. The mixture was cooled to room temperature, and the solid was collected by filtration and dried under reduced pressure to give a crude product 32-2 (633 mg). To the crude product 32-2 (367 mg) was added ethyl acetate (3.6 mL), and the mixture was stirred at room temperature overnight. The solid was collected by filtration, and dried at 50° C. under reduced pressure to give the title compound (320 mg).

$^1$H-NMR (DMSO-$d_6$) δ: 10.46 (t, 1H, J=6.0 Hz), 8.53 (s, 1H), 7.52-7.48 (m, 1H), 7.35-7.31 (m, 1H), 7.22-7.18 (m, 1H), 4.62 (d, 2H, J=6.0 Hz), 3.90 (s, 2H), 3.39 (d, 2H, J=5.2 Hz), 3.27 (s, 3H), 3.14 (s, 3H), 2.60-2.52 (m, 1H), 2.37-2.25 (m, 4H).

Elemental analysis: calcd. C, 47.02; H, 4.48; N, 7.48. found C, 46.85; H, 4.49; N, 7.36.

Example 33

Production of N-(3-chloro-2-fluorobenzyl)-9'-hydroxy-cis-3-(methoxymethyl)-2'-methyl-1',8'-dioxo-1',2',3',8'-tetrahydrospiro[cyclobutane-1,4'-pyrido[1,2-a]pyrazine]-7'-carboxamide 4-methylbenzenesulfonate To a solution of compound 26 (63 mg) obtained in Example 26 in chloroform (2 mL) was added p-toluenesulfonic acid monohydrate (27 mg) at room temperature, and the mixture was concentrated. Toluene was added and the mixture was concentrated. Ethyl acetate (1 mL) was added, and the mixture was stirred at room temperature for 3 days and concentrated. Crystallization from chloroform-hexane (1:1) gave compound 33-1 (74 mg), which is a crystal of the title compound. To a solution of compound 26 (621 mg) obtained by the operation of Example 26 in chloroform (4 mL) was added a solution of p-toluenesulfonic acid monohydrate (255 mg) in dioxane (4 mL) at room temperature, and the mixture was concentrated. Toluene was added, and the mixture was concentrated. Chloroform (4 mL) was added, and the mixture was concentrated. Chloroform-hexane (1:1, 18 mL) was added, compound 33-1 was seeded, and the mixture was stirred at room temperature overnight. The solid was collected by filtration, and dried at 50° C. under reduced pressure to give the title compound (756 mg).

$^1$H-NMR (DMSO-$d_6$) δ: 10.46 (t, 1H, J=6.0 Hz), 8.53 (s, 1H), 7.52-7.46 (m, 1H), 7.35-7.31 (m, 1H), 7.22-7.18 (m, 1H), 7.11 (d, 2H, J=7.9 Hz), 4.62 (d, 2H, J=6.0 Hz), 3.90 (s, 2H), 3.39 (d, 2H, J=5.5 Hz), 3.27 (s, 3H), 3.14 (s, 3H), 2.62-2.51 (m, 1H), 2.29 (s, 3H), 2.37-2.25 (m, 4H).

Example 34

Production of N-(3-chloro-2-fluorobenzyl)-2'-ethyl-9'-hydroxy-trans-3-methoxy-1',8'-dioxo-1',2',4',8'-tetrahydrospiro[cyclobutane-1,3'-pyrido[1,2-a]pyrazine]-7'-carboxamide

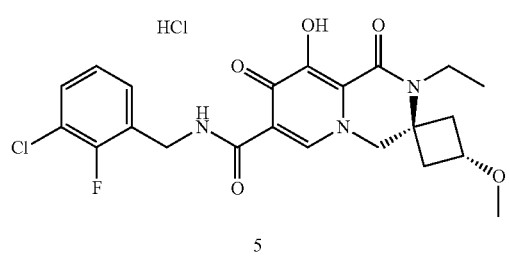

5

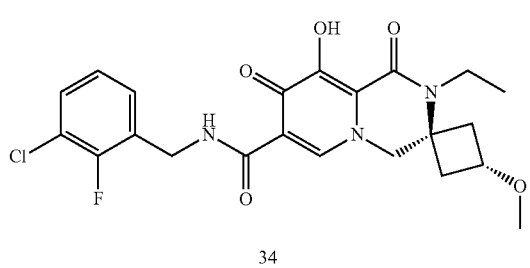

34

To compound 5 (3.87 g) obtained by the operation of Example 5, step 11, was added saturated aqueous sodium hydrogen carbonate solution, and the mixture was extracted with chloroform-methanol. The organic layer was washed with saturated brine, dried over magnesium sulfate and concentrated. Methanol (290 mL) was added and dissolved by stirring with heating. Under stirring, the mixture was cooled to room temperature, and the obtained solid was collected by filtration, and dried under reduced pressure to give the title compound (2.94 g).

As other crystallization conditions, the title compound (5 mg) was dissolved in acetonitrile (0.6 mL), the solution was stood at room temperature to give a single crystal. The steric configuration of compound 34 was determined by X-ray structural analysis of the obtained single crystal.

$^1$H-NMR (DMSO-$d_6$) δ: 12.39 (s, 1H), 10.47 (t, 1H, J=6.0 Hz), 8.45 (s, 1H), 7.52-7.48 (m, 1H), 7.35-7.31 (m, 1H), 7.22-7.18 (m, 1H), 4.61 (d, 2H, J=6.0 Hz), 4.46 (s, 2H), 4.09-4.04 (m, 1H), 3.65 (q, 2H, J=7.1 Hz), 3.18 (s, 3H), 2.70-2.64 (m, 2H), 2.20-2.15 (m, 2H), 1.17 (t, 3H, J=7.1 Hz).

Example 35

Production of Monosodium 7'-(3-chloro-2-fluorobenzylcarbamoyl)-2'-ethyl-trans-3-methoxy-1',8'-dioxo-1',2',4',8'-tetrahydrospiro[cyclobutane-1,3'-pyrido[1,2-a]pyrazin]-9'-olate

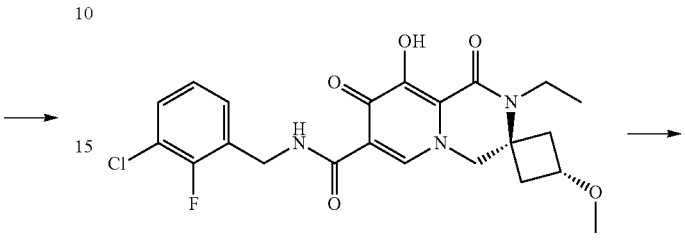

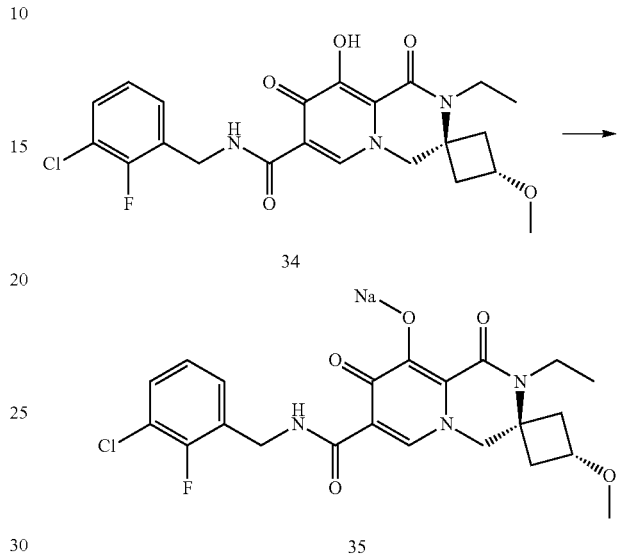

To a suspension of compound 34 (10.1 g) obtained by the operation of Example 34 in ethanol (300 mL) was added dropwise a 1N aqueous sodium hydroxide solution (21.65 mL). The mixture was stirred at 90° C. for 5 hr, allowed to cool and stood at room temperature overnight. The solid was collected by filtration, washed with ethanol (150 mL), and dried under reduced pressure at 60° C. to give the title compound (10.3 g).

$^1$H-NMR (CD$_3$OD) δ: 8.08 (br s, 1H), 7.43-7.31 (m, 2H), 7.19-7.12 (m, 1H), 4.68 (s, 2H), 4.35 (s, 2H), 4.17-4.09 (m, 1H), 3.69 (q, 2H, J=7.1 Hz), 3.30 (s, 3H), 2.76-2.66 (m, 2H), 2.24-2.16 (m, 2H), 1.22 (t, 3H, J=7.1 Hz).

Example 36

Production of Monopotassium 7'-(3-chloro-2-fluorobenzylcarbamoyl)-2'-ethyl-trans-3-methoxy-1',8'-dioxo-1',2',4',8'-tetrahydrospiro[cyclobutane-1,3'-pyrido[1,2-a]pyrazin]-9'-olate

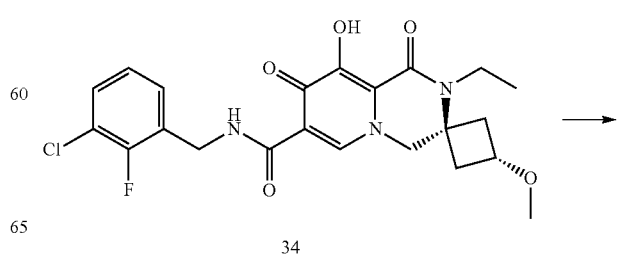

34

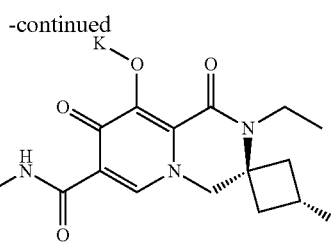

36

To a suspension of compound 34 (814 mg) obtained by the operation of Example 34 in methanol (8 mL) was added a 1N aqueous potassium hydroxide solution (1.75 mL) at room temperature. Methanol (2 mL) was added, and the mixture was stirred at room temperature for 4 days. The solid was collected by filtration, and dried under reduced pressure to give the title compound (796 mg).

$^1$H-NMR (CD$_3$CO$_2$D) δ: 8.71 (s, 1H), 7.35-7.29 (m, 2H), 7.09-7.05 (m, 1H), 4.71 (s, 2H), 4.50 (s, 2H), 4.15-4.10 (m, 1H), 3.72 (q, 2H, J=7.1 Hz), 3.27 (s, 3H), 2.76-2.70 (m, 2H), 2.37-2.32 (m, 2H), 1.24 (t, 3H, J=7.1 Hz).

Example 37

Production of 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yl acetate

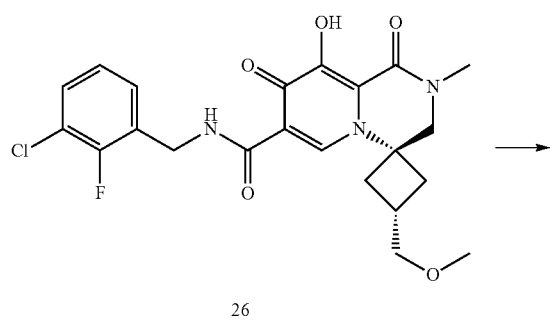

26

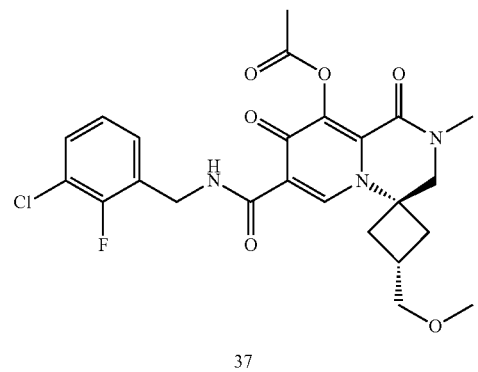

37

To a suspension of compound 26 (500 mg) obtained by the operation of Example 26 and dimethylaminopyridine (50 mg) in chloroform (2 mL) was added triethylamine (0.3 mL), and acetic anhydride (0.16 mL) was added dropwise. The mixture was stirred at room temperature for 1 hr, and purified by silica gel column chromatography (hexane:ethyl acetate=1:1 to ethyl acetate:acetone=6:1). Crystallization from ethyl acetate-hexane gave the title compound (451 mg).

$^1$H-NMR (DMSO-d$_6$) δ: 10.27 (t, 1H, J=6.0 Hz), 8.74 (s, 1H), 7.53-7.47 (m, 1H), 7.36-7.30 (m, 1H), 7.23-7.18 (m, 1H), 4.61 (d, 2H, J=6.0 Hz), 3.87 (br s, 2H), 3.43 (d, 2H, J=4.6 Hz), 3.30 (s, 3H), 3.10 (s, 3H), 2.66-2.14 (m, 5H), 2.22 (s, 3H).

Example 38

Production of 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yl dimethylcarbamate

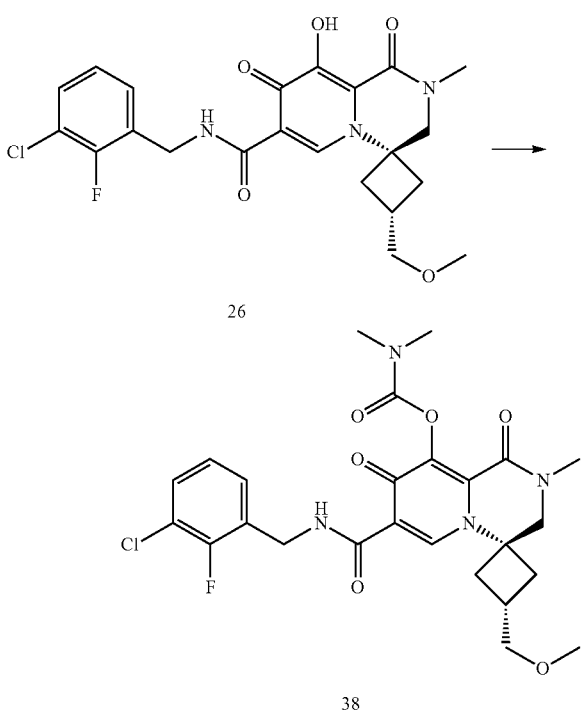

To a solution of compound 26 (420 mg) obtained by the operation of Example 26 in chloroform (4 mL) were successively added triphosgene (94 mg) and pyridine (82 μL) under ice-cooling. The mixture was stirred under ice-cooling for 10 min, 2M dimethylamine/THF (905 μL) was added. The mixture was concentrated, chloroform (4 mL) was added, and triphosgene (94 mg) and pyridine (82 μL) were successively added under ice-cooling. The mixture was stirred under ice-cooling for 10 min, and dimethylamine hydrochloride (148 mg) and pyridine (136 μL) were successively added. The mixture was concentrated, oleic anhydride (500 μL), triethylamine (200 μL), and 4-dimethylaminopyridine (2 mg) were successively added, and the mixture was stirred at room temperature overnight. To the reaction mixture was added a 5% aqueous potassium hydrogen sulfate solution, and the mixture was extracted with ethyl acetate. The organic layer was washed with saturated brine, dried over magnesium sulfate and concentrated. The residue was purified by silica gel column chromatography (ethyl acetate to ethyl acetate:acetone=5:1). Crystallization from methyl isobutyl ketone gave compound 38 (270 mg).

¹H-NMR (DMSO-d₆) δ: 10.32 (t, 1H, J=6.0 Hz), 8.71 (s, 1H), 7.52-7.48 (m, 1H), 7.35-7.31 (m, 1H), 7.23-7.18 (m, 1H), 4.60 (d, 2H, J=6.0 Hz), 3.88-3.82 (br m, 2H), 3.43 (d, 2H, J=4.8 Hz), 3.29 (s, 3H), 3.09 (s, 3H), 2.99 (s, 3H), 2.87 (s, 3H), 2.63-2.51 (m, 2H), 2.35-2.21 (m, 3H).

Example 39

Production of (E)-4-[7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yloxy]-4-oxobut-2-enoic acid

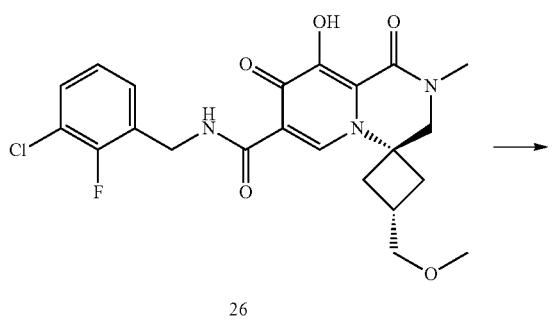

26

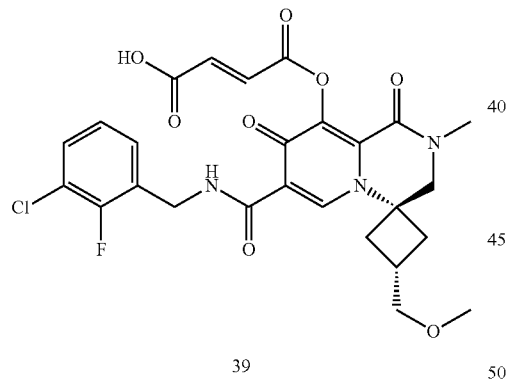

39

To a solution of compound 26 (43.7 mg) obtained by the operation of Example 26 in chloroform (1 mL) was added fumaryl dichloride (54 µL) under ice-cooling. After stirring at room temperature for 1 hr, water (500 µL) was added, and the mixture was further stirred for 10 min. Water and ethyl acetate were added to the reaction mixture, and an organic layer and an aqueous layer were separated. The organic layer was washed with saturated brine, dried, concentrated, and purified by reversed-phase thin layer chromatography (acetonitrile:water=1:1) to give the title compound (35 mg).

¹H-NMR (DMSO-d₆) δ: 10.21 (t, 1H, J=6.0 Hz), 8.77 (s, 1H), 7.52-7.46 (m, 1H), 7.36-7.30 (m, 1H), 7.23-7.17 (m, 1H), 6.85 (s, 2H), 4.61 (d, 2H, J=6.0 Hz), 4.00-3.78 (m, 2H), 3.43 (d, 2H, J=4.6 Hz), 3.30 (s, 3H), 3.09 (s, 3H), 2.71-2.13 (m, 5H).

Example 40

Production of Monosodium 3-{[7'-(3-chloro-2-fluorobenzylcarbamoyl)-cis-3-(methoxymethyl)-2'-methyl-',8'-dioxo-1',2',3',8'-tetrahydrospiro[cyclobutane-1,4'-pyrido[1,2-a]pyrazin]-9'-yloxy]carbonyl}benzoate Step 1

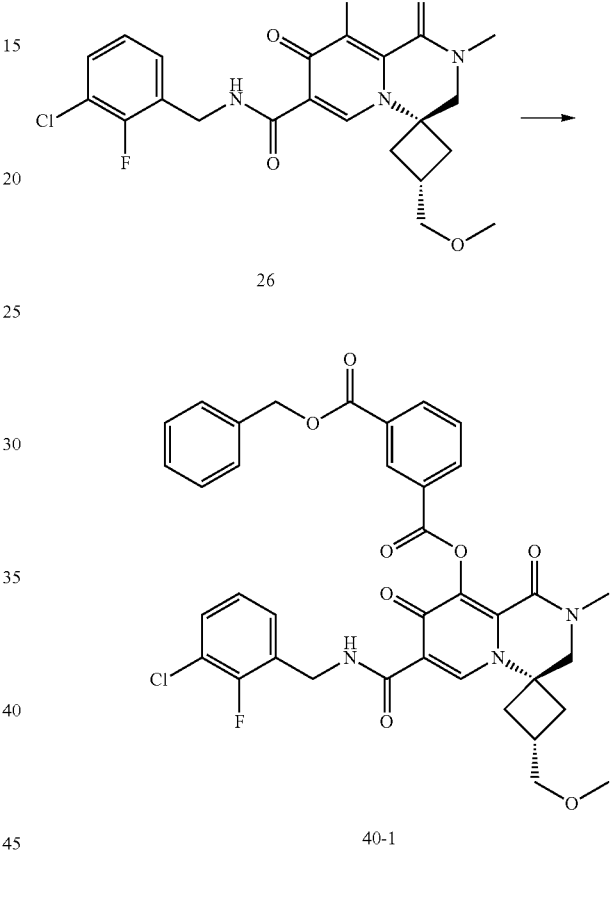

To a solution of isophthaloyl dichloride (4.5 g) in chloroform (30 mL) was added compound 26 (747 mg) obtained by the operation of Example 26. Triethylamine (230 µL) was added dropwise, and the mixture was stirred at room temperature for 30 min. Benzyl alcohol (4.5 mL) and triethylamine (6.2 mL) were successively added dropwise, and the mixture was stirred at room temperature for 30 min. To the reaction mixture was added a 10% aqueous potassium hydrogen sulfate solution, and an organic layer and an aqueous layer were separated. The organic layer was washed with saturated brine, and purified by silica gel column chromatography (hexane:ethyl acetate=2:1 to ethyl acetate) to give compound 40-1 (950 mg).

¹H-NMR (DMSO-d₆) δ: 10.21 (t, 1H, J=6.1 Hz), 8.80 (s, 1H), 8.58 (t, 1H, J=1.7 Hz), 8.36-8.28 (m, 2H), 7.79 (t, 1H, J=7.9 Hz), 7.52-7.46 (m, 3H), 7.44-7.30 (m, 4H), 7.29-7.11 (m, 2H), 5.41 (s, 2H), 4.67-4.54 (m, 2H), 3.96 (d, 1H, J=13.9 Hz), 3.85 (d, 1H, J=13.9 Hz), 3.44 (d, 2H, J=5.1 Hz), 3.31 (s, 3H), 3.06 (s, 3H), 2.73-2.19 (m, 5H).

Step 2

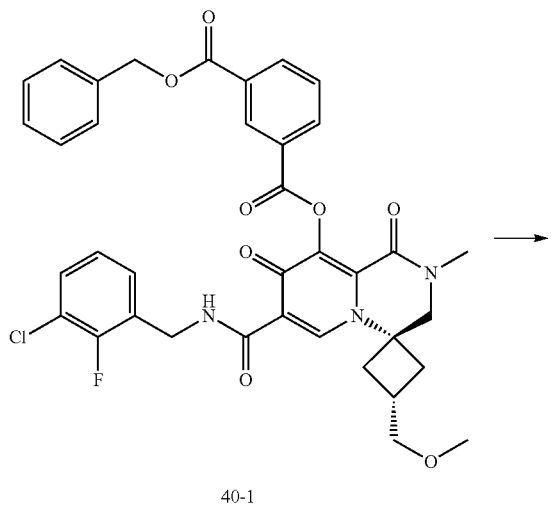

40-1

40-2

A suspension of compound 40-1 (778 mg) obtained in the above-mentioned step and palladium-platinum/carbon (ASCA2, manufactured by N.E. CHEMCAT Corporation, 525 mg) in tetrahydrofuran (18 mL) was stirred at room temperature for 50 min under a hydrogen atmosphere. To the reaction mixture were added chloroform and celite, and the insoluble material was filtered off and washed with chloroform. After concentration, methyl isobutyl ketone was added and the mixture was concentrated again and crystallized from methyl isobutyl ketone-hexane to give compound 40-2 (488 mg).

$^1$H-NMR (DMSO-d$_6$) δ: 13.39 (br s, 1H), 10.23 (t, 1H, J=6.0 Hz), 8.81 (s, 1H), 8.59-8.56 (m, 1H), 8.30-8.23 (m, 2H), 7.74 (t, 1H, J=7.9 Hz), 7.52-7.46 (m, 1H), 7.36-7.30 (m, 1H), 7.23-7.17 (m, 1H), 4.66-4.55 (m, 2H), 3.97 (d, 1H, J=13.9 Hz), 3.86 (d, 1H, J=13.9 Hz), 3.45 (d, 2H, J=4.9 Hz), 3.31 (s, 3H), 3.07 (s, 3H), 2.73-2.54 (m, 2H), 2.47-2.17 (m, 3H).

Step 3

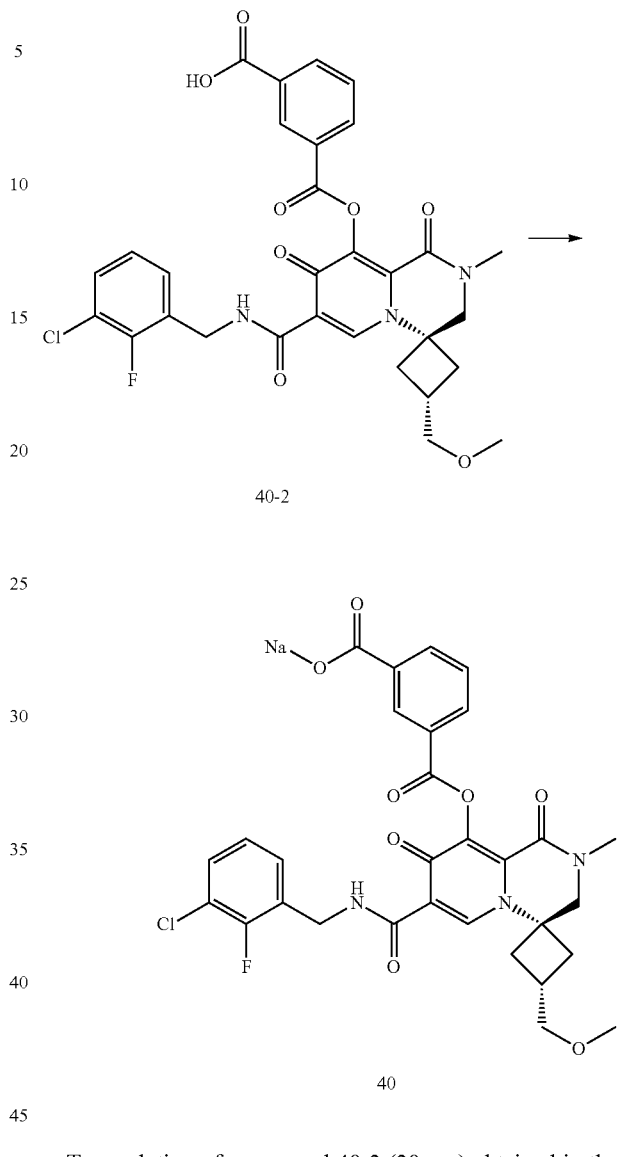

40-2

40

To a solution of compound 40-2 (20 mg) obtained in the above-mentioned step in tetrahydrofuran (0.8 mL) was added dropwise a 1N aqueous sodium hydroxide solution (32 µL). Hexane (0.4 mL) was added, and the mixture was concentrated and crystallized from methyl isobutyl ketone-hexane to give the title compound (18 mg).

$^1$H-NMR (DMSO-d$_6$) δ: 10.27 (t, 1H, J=6.0 Hz), 8.80 (s, 1H), 8.55 (s, 1H), 8.18-8.10 (m, 1H), 7.96-7.89 (m, 1H), 7.52-7.41 (m, 2H), 7.37-7.29 (m, 1H), 7.23-7.16 (m, 1H), 4.68-4.53 (m, 2H), 3.96 (d, 1H, J=13.9 Hz), 3.85 (d, 1H, J=13.9 Hz), 3.45 (d, 2H, J=4.9 Hz), 3.31 (s, 3H), 3.07 (s, 3H), 2.74-2.18 (m, 5H).

By a method similar to the above-mentioned Examples 1 to 40, or using other conventional method as necessary, the compounds of Examples S1 to S73 and Examples T1 to T50 shown in the following Tables were produced. The structural formulas and property data of the compounds of Examples S1 to S73 and Examples T1 to T50 are shown in the following Tables. The compound obtained in Example S1 is sometimes also referred to as compound S1.

TABLE 1-1

| Example No. | structural formula | salt | compound name |
|---|---|---|---|
| S1 | | HCl | trans-3-(benzyloxy)-N-(2,4-difluorobenzyl)-9'-hydroxy-2'-isopropyl-1',8-dioxo-1',2',3',8'-tetrahydrospiro[cyclobutane-1,4'-pyrido[1,2-a]pyrazine]-7'-carboxamide hydrochloride |
| S2 | | HCl | cis-3-(benzyloxy)-N-(2,4-difluorobenzyl)-9'-hydroxy-2'-isopropyl-1',8-dioxo-1',2',3',8'-tetrahydrospiro[cyclobutane-1,4'-pyrido[1,2-a]pyrazine]-7'-carboxamide hydrochloride |
| S3 | | HBr | N-(2,4-difluorobenzyl)-trans-3,9'-dihydroxy-2'-isopropyl-1',8'-dioxo-1',2',3',8'-tetrahydrospiro[cyclobutane-1,4'-pyrido[1,2-a]pyrazine]-7'-carboxamide hydrobromide |
| S4 | | | N-(2,4-difluorobenzyl)-cis-3,9'-dihydroxy-2'-isopropyl-1',8'-dioxo-1',2',3',8'-tetrahydrospiro[cyclobutane-1,4'-pyrido[1,2-a]pyrazine]-7'-carboxamide |
| S5 | | HCl | N-(2,4-difluorobenzyl)-9'-hydroxy-2'-isopropyl-trans-3-methoxy-1',8'-dioxo-1',2',3',8'-tetrahydrospiro[cyclobutane-1,4'-pyrido[1,2-a]pyrazine]-7'-carboxamide hydrochloride |

TABLE 1-2

| Example No. | structural formula | salt | compound name |
|---|---|---|---|
| S6 | | HCl | N-(2,4-difluorobenzyl)-9'-hydroxy-2'-isopropyl-cis-3-methoxy-1',8'-dioxo-1',2',3',8'-tetrahydrospiro[cyclobutane-1,4'-pyrido[1,2-a]pyrazine]-7'-carboxamide hydrochloride |
| S7 | | HCl | N-(2,4-difluorobenzyl)-trans-3-ethoxy-9'-hydroxy-2'-isopropyl-1',8'-dioxo-1',2',3',8'-tetrahydrospiro[cyclobutane-1,4'-pyrido[1,2-a]pyrazine]-7'-carboxamide hydrochloride |
| S8 | | HCl | N-(2,4-difluorobenzyl)-9'-hydroxy-2'-isopropyl-trans-3-(2-methoxyethoxy)-1',8'-dioxo-1',2'-3',8'-tetrahydrospiro[cyclobutane-1,4'-pyrido[1,2-a]pyrazine]-7'-carboxamide hydrochloride |
| S9 | | HCl | trans-3-(benzyloxy)-N-(2,4-difluorobenzyl)-9'-hydroxy-2'-methyl-1',8'-dioxo-1',2',3',8'-tetrahydrospiro[cyclobutane-1,4'-pyrido[1,2-a]pyrazine]-7'-carboxamide hydrochloride |
| S10 | | HCl | cis-3-(benzyloxy)-N-(2,4-difluorobenzyl)-9'-hydroxy-2'-methyl-1',8'-dioxo-1',2',3',8'-tetrahydrospiro[cyclobutane-1,4'-pyrido[1,2-a]pyrazine]-7'-carboxamide hydrochloride |

TABLE 1-3

| Example No. | structural formula | salt | compound name |
|---|---|---|---|
| S11 | | HBr | N-(2,4-difluorobenzyl)-trans-3,9'-dihydroxy-2'-methyl-1',8'-dioxo-1',2',3',8'-tetrahydrospiro[cyclobutane-1,4'-pyrido[1,2-a]pyrazine]-7'-carboxamide hydrobromide |
| S12 | | HBr | N-(2,4-difluorobenzyl)-cis-3,9'-dihydroxy-2'-methyl-1',8'-dioxo-1',2',3',8'-tetrahydrospiro[cyclobutane-1,4'-pyrido[1,2-a]pyrazine]-7'-carboxamide hydrobromide |
| S13 | | HCl | N-(2,4-difluorobenzyl)-9'-hydroxy-trans-3-methoxy-2'-methyl-1',8'-dioxo-1',2',3',8'-tetrahydrospiro[1,2-a]pyrazine]-1,4'-pyrido[1,2-a]pyrazine]-7'-carboxamide hydrochloride |
| S14 | | HCl | N-(2,4-difluorobenzyl)-9'-hydroxy-cis-3-methoxy-2'-methyl-1',8'-dioxo-1',2',3',8'-tetrahydrospiro[cyclobutane-1,4'-pyrido[1,2-a]pyrazine]-7'-carboxamide hydrochloride |
| S15 | | HCl | trans-3-(benzyloxy)-N-(2,4-difluorobenzyl)-2'-ethyl-9'-hydroxy-1',8'-dioxo-1',2',3',8'-tetrahydrospiro[cyclobutane-1,4'-pyrido[1,2-a]pyrazine]-7'-carboxamide hydrochloride |

TABLE 1-4

| Example No. | structural formula | salt | compound name |
|---|---|---|---|
| S16 | | HCl | cis-3-(benzyloxy)-N-(2,4-difluorobenzyl)-2'-ethyl-9'-hydroxy-1',8'-dioxo-1',2',3',8'-tetrahydrospiro[cyclobutane-1,4'-pyrido[1,2-a]pyrazine]-7'-carboxamide hydrochloride |
| S17 | | HBr | N-(2,4-difluorobenzyl)-2'-ethyl-trans-3,9'-dihydroxy-1',8'-dioxo-1',2',3',8'-tetrahydrospiro[cyclobutane-1,4'-pyrido[1,2-a]pyrazine]-7'-carboxamide hydrobromide |
| S18 | | HBr | N-(2,4-difluorobenzyl)-2'-ethyl-cis-3,9'-dihydroxy-1',8'-dioxo-1',2',3',8'-tetrahydrospiro[cyclobutane-1,4'-pyrido[1,2-a]pyrazine]-7'-carboxamide hydrobromide |
| S19 | | HCl | N-(2,4-difluorobenzyl)-2'-ethyl-9'-hydroxy-trans-3-methoxy-1',8'-dioxo-1',2',3',8'-tetrahydrospiro[cyclobutane-1,4'-pyrido[1,2-a]pyrazine]-7'-carboxamide hydrochloride |
| S20 | | HCl | N-(2,4-difluorobenzyl)-2'-ethyl-9'-hydroxy-cis-3-methoxy-1',8'-dioxo-1',2',3',8'-tetrahydrospiro[cyclobutane-1,4'-pyrido[1,2-a]pyrazine]-7'-carboxamide hydrochloride |

TABLE 1-5

| Example No. | structural formula | salt | compound name |
| --- | --- | --- | --- |
| S21 | | HCl | N-(2,4-difluorobenzyl)-cis-3-ethoxy-2'-ethyl-9'-hydroxy-1',8'-dioxo-1',2',3',8'-tetrahydrospiro[cyclobutane-1,4'-pyrido[1,2-a]pyrazine]-7'-carboxamide hydrochloride |
| S22 | | HBr | N-(2,4-difluorobenzyl)-9'-hydroxy-cis-3-(hydroxymethyl)-2'-isopropyl-1',8'-dioxo-1',2',3',8'-tetrahydrospiro[cyclobutane-1,4'-pyrido[1,2-a]pyrazine]-7'-carboxamide hydrobromide |
| S23 | | HCl | N-(2,4-difluorobenzyl)-9'-hydroxy-2'-isopropyl-cis-3-(methoxymethyl)-1',8'-dioxo-1',2',3',8'-tetrahydrospiro[cyclobutane-1,4'-pyrido[1,2-a]pyrazine]-7'-carboxamide hydrochloride |
| S24 | | HBr | N-(2,4-difluorobenzyl)-9'-hydroxy-trans-3-(hydroxymethyl)-2'-isopropyl-1',8'-dioxo-1',2',3',8'-tetrahydrospiro[cyclobutane-1,4'-pyrido[1,2-a]pyrazine]-7'-carboxamide hydrobromide |
| S25 | | HCl | N-(2,4-difluorobenzyl)-9'-hydroxy-2'-isopropyl-trans-3-(methoxymethyl)-1',8'-dioxo-1',2',3',8'-tetrahydrospiro[cyclobutane-1,4'-pyrido[1,2-a]pyrazine]-7'-carboxamide hydrochloride |

TABLE 1-6

| Example No. | structure formula | salt | compound name |
|---|---|---|---|
| S26 | | HCl | N-(3-chloro-2-fluorobenzyl)-trans-3,9'-dihydroxy-2'-methyl-1',8'-dioxo-1',2',3',8'-tetrahydrospiro[cyclobutane-1,4'-pyrido[1,2-a]pyrazine]-7'-carboxamide hydrochloride |
| S27 | | HCl | N-(3-chloro-2-fluorobenzyl)-cis-3,9'-dihydroxy-2'-methyl-1',8'-dioxo-1',2',3',8'-tetrahydrospiro[cyclobutane-1,4'-pyrido[1,2-a]pyrazine]-7'-carboxamide hydrochloride |
| S28 | | HCl | N-(3-chloro-2-fluorobenzyl)-trans-3-ethoxy-9'-hydroxy-2'-methyl-1',8'-dioxo-1',2',3',8'-tetrahydrospiro[cyclobutane-1,4'-pyrido[1,2-a]pyrazine]-7'-carboxamide hydrochloride |
| S29 | | HCl | N-(3-chloro-2-fluorobenzyl)-cis-3-ethoxy-9'-hydroxy-2'-methyl-1',8'-dioxo-1',2',3',8'-tetrahydrospiro[cyclobutane-1,4'-pyrido[1,2-a]pyrazine]-7'-carboxamide hydrochloride |
| S30 | | HCl | $N^{7'}$-(2,4-difluorobenzyl)-9'-hydroxy-2'-isopropyl-$N^3$-methyl-1',8'-dioxo-1',2',3',8'-tetrahydrospiro[cyclobutane-1,4'-pyrido[1,2-a]pyrazine]-cis-3,7'-dicarboxamide hydrochloride |

TABLE 1-7

| Example No. | structural formula | salt | compound name |
|---|---|---|---|
| S31 | | HCl | $N^{7'}$-(2,4-difluorobenzyl)-9'-hydroxy-2'-isopropyl-$N^3$-$N^3$-dimethyl-1',8'-dioxo-1',2',3',8'-tetrahydrospiro[cyclobutane-1,4'-pyrido[1,2-a]pyrazine]-cis-3,7'-dicarboxamide hydrochloride |
| S32 | | HCl | N-(2,4-difluorobenzyl)-9'-hydroxy-trans-3-isopropoxy-2'-isopropyl-1',8'-dioxo-1',2',3',8'-tetrahydrospiro[cyclobutane-1,4'-pyrido[1,2-a]pyrazine]-7'-carboxamide hydrochloride |
| S33 | | HCl | N-(2,4-difluorobenzyl)-9'-hydroxy-cis-3-isopropoxy-2'-isopropyl-1',8'-dioxo-1',2',3',8'-tetrahydrospiro[cyclobutane-1,4'-pyrido[1,2-a]pyrazine]-7'-carboxamide hydrochloride |
| S34 | | HCl | 7'-(2,4-difluorobenzylcarbamoyl)-9'-hydroxy-2'-isopropyl-1',8'-dioxo-1',2',3',8'-tetrahydrospiro[cyclobutane-1,4'-pyrido[1,2-a]pyrazine]-trans-3-yl methanesulfonate hydrochloride |

TABLE 1-8

| Example No. | structural formula | salt | compound name |
|---|---|---|---|
| S35 | | HCl | 7'-(2,4-difluorobenzylcarbamoyl)-9'-hydroxy-2'-isopropyl-1',8'-dioxo-1',2',3',8'-tetrahydrospiro[cyclobutane-1,4'-pyrido[1,2-a]pyrazine]-cis-3-yl methanesulfonate hydrochloride |
| S36 | | | N-(3-chloro-2-fluorobenzyl)-9'-hydroxy-trans-3-(hydroxymethyl)-2'-methyl-1',8'-dioxo-1',2',3',8'-tetrahydrospiro[cyclobutane-1,4'-pyrido[1,2-a]pyrazine]-7'-carboxamide |
| S37 | | HCl | N-(3-chloro-2-fluorobenzyl)-9'-hydroxy-cis-3-(hydroxymethyl)-2'-methyl-1',8'-dioxo-1',2',3',8'-tetrahydrospiro[cyclobutane-1,4'-pyrido[1,2-a]pyrazine]-7'-carboxamide hydrochloride |
| S38 | | HCl | cis-3-(acetamidomethyl)-N-(2,4-difluorobenzyl)-9'-hydroxy-2'-isopropyl-1',8'-dioxo-1',2',3',8'-tetrahydrospiro[cyclobutane-1,4'-pyrido[1,2-a]pyrazine]-7'-carboxamide hydrochloride |

TABLE 1-9

| Example No. | structural formula | salt | compound name |
| --- | --- | --- | --- |
| S39 | | HCl | N-(3-chloro-2-fluorobenzyl)-cis-3-(ethoxymethyl)-9'-hydroxy-2'-methyl-1',8'-dioxo-1',2',3',8'-tetrahydrospiro[cyclobutane-1,4'-pyrido[1,2-a]pyrazine]-7'-carboxamide hydrochloride |
| S40 | | HCl | N-(3-chloro-2-fluorobenzyl)-9'-hydroxy-trans-3-isopropoxy-2'-methyl-1'-8'-dioxo-1',2',3',8'-tetrahydrospiro[cyclobutane-1,4'-pyrido[1,2-a]pyrazine]-7'-carboxamide hydrochloride |
| S41 | | HCl | N-(3-chloro-2-fluorobenzyl)-9'-hydroxy-cis-3-isopropoxy-2'-methyl-1',8'-dioxo-1',2',3',8'-tetrahydrospiro[cyclobutane-1,4'-pyrido[1,2-a]pyrazine]-7'-carboxamide hydrochloride |
| S42 | | HCl | N-(3-chloro-2-fluorobenzyl)-9'-hydroxy-2'-methyl-1',8'-dioxo-trans-3-propoxy-1',2',3',8'-tetrahydrospiro[cyclobutane-1,4'-pyrido[1,2-a]pyrazine]-7'-carboxamide hydrochloride |

TABLE 1-10

| Example No. | structural formula | salt | compound name |
|---|---|---|---|
| S43 | | HCl | N-(3-chloro-2-fluorobenzyl)-9'-hydroxy-2'-methyl-1'-8'-dioxo-cis-3-propoxy-1',2',3',8'-tetrahydrospiro[cyclobutane-1,4'-pyrido[1,2-a]pyrazine]-7'-carboxamide hydrochloride |
| S44 | | HCl | N-(3-chloro-2-fluorobenzyl)-2'-ethyl-9'-hydroxy-trans-3-(hydroxymethyl)-1',8'-dioxo-1',2',3',8'-tetrahydrospiro[cyclobutane-1,4'-pyrido[1,2-a]pyrazine]-7'-carboxamide hydrochloride |
| S45 | | HCl | N-(3-chloro-2-fluorobenzyl)-2'-ethyl-9'-hydroxy-trans-3-(methoxymethyl)-1',8'-dioxo-1',2',3',8'-tetrahydrospiro[cyclobutane-1,4'-pyrido[1,2-a]pyrazine]-7'-carboxamide hydrochloride |
| S46 | | HCl | N-(3-chloro-2-fluorobenzyl)-2'-ethyl-9'-hydroxy-cis-3-(hydroxymethyl)-1',8'-dioxo-1',2',3',8'-tetrahydrospiro[cyclobutane-1,4'-pyrido[1,2-a]pyrazine]-7'-carboxamide hydrochloride |
| S47 | | HCl | N-(3-chloro-2-fluorobenzyl)-2'-ethyl-9'-hydroxy-cis-3-(methoxymethyl)-1',8'-dioxo-1',2',3',8'-tetrahydrospiro[cyclobutane-1,4'-pyrido[1,2-a]pyrazine]-7'-carboxamide hydrochloride |

TABLE 1-11

| Example No. | structural formula | salt | compound name |
|---|---|---|---|
| S48 | | HCl | N-(3-chloro-2-fluorobenzyl)-cis-3-(ethoxymethyl)-2'-ethyl-9'-hydroxy-1',8'-dioxo-1',2',3',8'-tetrahydrospiro[cyclobutane-1,4'-pyrido[1,2-a]pyrazine]-7'-carboxamide hydrochloride |
| S49 | | | N-(3-chloro-2-fluoro-4-methoxyphenyl)-9'-hydroxy-trans-3-(hydroxymethyl)-2'-methyl-1',8'-dioxo-1',2',3',8'-tetrahydrospiro[cyclobutane-1,4'-pyrido[1,2-a]pyrazine]-7'-carboxamide |
| S50 | | | N-(3-chloro-2-fluoro-4-methoxybenzyl)-9'-hydroxy-cis-3-(hydroxymethyl)-2'-methyl-1',8'-dioxo-1',2',3',8'-tetrahydrospiro[cyclobutane-1,4'-pyrido[1,2-a]pyrazine]-7'-carboxamide |
| S51 | | HCl | N-(2,4-difluorobenzyl)-cis-3-ethoxy-9'-hydroxy-2'-methyl-1',8'-dioxo-1',2',3',8'-tetrahydrospiro[cyclobutane-1,4'-pyrido[1,2-a]pyrazine]-7'-carboxamide hydrochloride |

TABLE 1-12

| Example No. | structural formula | salt | compound name |
|---|---|---|---|
| S52 | | HCl | N-(2,4-difluorobenzyl)-9'-hydroxy-2'-isopropyl-trans-3-methoxy-1',8'-dioxo-1',2',4',8'-tetrahydrospiro[cyclobutane-1,3'-pyrido[1,2-a]pyrazine]-7'-carboxamide hydrochloride |

TABLE 1-12-continued

| Example No. | structural formula | salt | compound name |
|---|---|---|---|
| S53 | | HCl | N-(2,4-difluorobenzyl)-9'-hydroxy-2'-isopropyl-cis-3-methoxy-1',8'-dioxo-1',2',4',8'-tetrahydrospiro[cyclobutane-1,3'-pyrido[1,2-a]pyrazine]-7'-carboxamide hydrochloride |
| S54 | | HCl | N-(2,4-difluorobenzyl)-trans-3,9'-dihydroxy-2'-isopropyl-1',8'-dioxo-1',2',4',8'-tetrahydrospiro[cyclobutane-1,3'-pyrido[1,2-a]pyrazine]-7'-carboxamide hydrochloride |
| S55 | | HCl | N-(2,4-difluorobenzyl)-cis-3,9'-dihydroxy-2'-isopropyl-1',8'-dioxo-1',2',4',8'-tetrahydrospiro[cyclobutane-1,3'-pyrido[1,2-a]pyrazine]-7'-carboxamide hydrochloride |
| S56 | | HCl | N-(3-chloro-2-fluorobenzyl)-trans-3-ethoxy-2'-ethyl-9'-hydroxy-1',8'-dioxo-1',2',4',8'-tetrahydrospiro[cyclobutane-1,3'-pyrido[1,2-a]pyrazine]-7'-carboxamide hydrochloride |

TABLE 1-13

| Example No. | structural formula | salt | compound name |
|---|---|---|---|
| S57 | | HCl | N-(3-chloro-2-fluorobenzyl)-cis-3-ethoxy-2'-ethyl-9'-hydroxy-1',8'-dioxo-1',2',4',8'-tetrahydrospiro[cyclobutane-1,3'-pyrido[1,2-a]pyrazine]-7'-carboxamide hydrochloride |
| S58 | | HCl | N-(3-chloro-2-fluorobenzyl)-2'-ethyl-9'-hydroxy-trans-3-(hydroxymethyl)-1',8'-dioxo-1',2',4',8'-tetrahydrospiro[cyclobutane-1,3'-pyrido[1,2-a]pyrazine]-7'-carboxamide hydrochloride |

TABLE 1-13-continued

| Example No. | structural formula | salt | compound name |
| --- | --- | --- | --- |
| S59 | | HCl | N-(3-chloro-2-fluorobenzyl)-2'-ethyl-9'-hydroxy-trans-3-(methoxymethyl)-1',8'-dioxo-1',2',4',8'-tetrahydrospiro[cyclobutane-1,3'-pyrido[1,2-a]pyrazine]-7'-carboxamide hydrochloride |
| S60 | | HCl | N-(3-chloro-2-fluorobenzyl)-2'-ethyl-9'-hydroxy-cis-3-(hydroxymethyl)-1',8'-dioxo-1',2',4',8'-tetrahydrospiro[cyclobutane-1,3'-pyrido[1,2-a]pyrazine]-7'-carboxamide hydrochloride |

TABLE 1-14

| Example No. | structural formula | salt | compound name |
| --- | --- | --- | --- |
| S61 | | HCl | N-(3-chloro-2-fluorobenzyl)-2'-ethyl-9'-hydroxy-cis-3-(methoxymethyl)-1',8'-dioxo-1',2',4',8'-tetrahydrospiro[cyclobutane-1,3'-pyrido[1,2-a]pyrazine]-7'-carboxamide hydrochloride |
| S62 | | HCl | N-(3-chloro-2-fluorobenzyl)-9'-hydroxy-trans-3-methoxy-2'-methyl-1',8'-dioxo-1',2',4',8'-tetrahydrospiro[cyclobutane-1,3'-pyrido[1,2-a]pyrazine]-7'-carboxamide hydrochloride |
| S63 | | HCl | N-(3-chloro-2-fluorobenzyl)-9'-hydroxy-cis-3-methoxy-2'-methyl-1',8'-dioxo-1',2',4',8'-tetrahydrospiro[cyclobutane-1,3'-pyrido[1,2-a]pyrazine]-7'-carboxamide hydrochloride |

TABLE 1-15

| Example No. | structural formula | salt | compound name |
|---|---|---|---|
| S64 | | | 7'-(3-chloro-2-fluorobenzylcarbamoyl)-cis-3-methoxy-2'-methyl-1',8'-dioxo-1',2',3',8'-tetrahydrospiro[cyclobutane-1,4'-pyrido[1,2-a]pyrazin]-9'-yl acetate |
| S65 | | | 7'-(3-chloro-2-fluorobenzylcarbamoyl)-cis-3-methoxy-2'-methyl-1',8'-dioxo-1',2',3',8'-tetrahydrospiro[cyclobutane-1,4'-pyrido[1,2-a]pyrazin]-9'-yl propionate |
| S66 | | | 7'-(3-chloro-2-fluorobenzylcarbamoyl)-cis-3-methoxy-2'-methyl-1',8'-dioxo-1',2',3',8'-tetrahydrospiro[cyclobutane-1,4'-pyrido[1,2-a]pyrazin]-9'-yl isobutyrate |
| S67 | | | 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yl propionate |

TABLE 1-16

| Example No. | structural formula | salt compound name |
|---|---|---|
| S68 | | 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yl isobutyrate |
| S69 | | 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yl palmitate |
| S70 | | 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yl benzoate |
| S71 | | 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yl pivalate |

TABLE 1-17

| Example No. | structural formula | salt | compound name |
|---|---|---|---|
| S72 | | | 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yl 4-methylbenzoate |
| S73 | | 2HCl | 7'-(3-chloro-2-fluorobenzylcarbamoyl)-cis-3-(methoxymethyl)-2'-methyl-1',8'-dioxo-1',2',3',8'-tetrahydrospiro[cyclobutane-1,4'-pyrido[1,2-a]pyrazin]-9'-yl 2-(dimethylamino)acetate dihydrochloride |

TABLE 1-18

| Example No. | 1H-NMR (DMSO-d6) δ (peak, integ., J) |
|---|---|
| S1 | 1H-NMR (DMSO-d6) δ: 12.89 (s, 1H), 10.40 (t, 1H, J = 6.0 Hz), 8.49 (s, 1H), 7.44-7.21 (m, 7H), 7.09-7.04 (m, 1H), 4.75 (sep, 1H, J = 6.7 Hz), 4.55 (d, 2H, J = 6.0 Hz), 4.45 (s, 2H), 4.32-4.26 (m, 1H), 3.83 (s, 2H), 2.90-2.84 (m, 2H), 2.35-2.31 (m, 2H), 1.15 (d, 6H, J = 6.7 Hz). |
| S2 | 1H-NMR (DMSO-d6) δ: 12.86 (br s, 1H), 10.39 (t, 1H, J = 6.0 Hz), 8.53 (s, 1H), 7.44-7.21 (m, 7H), 7.08-7.03 (m, 1H), 4.75 (sep, 1H, J = 6.7 Hz), 4.55 (d, 2H, J = 6.0 Hz), 4.46 (s, 2H), 4.22 (quint, 1H, J = 6.3 Hz), 3.68 (s, 2H), 2.64-2.59 (m, 2H), 2.51-2.45 (m, 2H), 1.19 (d, 6H, J = 6.7 Hz). |
| S3 | 1H-NMR (DMSO-d6) δ: 10.40 (t, 1H, J = 5.8 Hz), 8.46 (s, 1H), 7.41 (dt, 1H, J = 6.5, 8.6 Hz), 7.24 (ddd, 1H, J = 10.5, 9.3, 2.6 Hz), 7.09-7.04 (m, 1H), 4.77 (sep, 1H, J = 6.7 Hz), 4.54 (d, 2H, J = 5.8 Hz), 4.40-4.34 (m, 1H), 3.83 (s, 2H), 2.83-2.78 (m, 2H), 2.21-2.16 (m, 2H), 1.19 (d, 6H, J = 6.7 Hz). |
| S4 | 1H-NMR (DMSO-d6) δ: 10.42 (t, 1H, J = 5.8 Hz), 8.57 (s, 1H), 7.44-7.38 (m, 1H), 7.26-7.21 (m, 1H), 7.09-7.04 (m, 1H), 5.51 (d, 1H, J = 7.9 Hz), 4.76 (sep, 1H, J = 6.7 Hz), 4.55 (d, 2H, J = 5.8 Hz), 4.26-4.17 (m, 1H), 3.63 (s, 2H), 2.59-2.52 (m, 2H), 2.41-2.35 (m, 2H), 1.19 (d, 6H, J = 6.7 Hz). |
| S5 | 1H-NMR (DMSO-d6) δ: 10.40 (t, 1H, J = 5.9 Hz), 8.48 (s, 1H), 7.44-7.38 (m, 1H), 7.24 (ddd, 1H, J = 10.7, 9.5, 2.8 Hz), 7.09-7.04 (m, 1H), 4.77 (sep, 1H, J = 6.7 Hz), 4.55 (d, 2H, J = 5.9 Hz), 4.10-4.04 (m, 1H), 3.79 (s, 2H), 3.21 (s, 3H), 2.85-2.80 (m, 2H), 2.28-2.23 (m, 2H), 1.18 (d, 6H, J = 6.7 Hz). |
| S6 | 1H-NMR (DMSO-d6) δ: 12.87 (br s, 1H), 10.38 (t, 1H, J = 5.8 Hz), 8.49 (s, 1H), 7.41 (dt, 1H, J = 6.5, 8.6 Hz), 7.24 (ddd, 1H, J = 10.7, 9.3, 2.6 Hz), 7.09-7.04 (m, 1H), 4.76 (sep, 1H, J = 6.7 Hz), 4.55 (d, 2H, J = 5.8 Hz), 4.03 (quint, 1H, J = 6.3 Hz), 3.67 (s, 2H), 3.21 (s, 3H), 2.63-2.58 (m, 2H), 2.43-2.38 (m, 2H), 1.20 (d, 6H, J = 6.7 Hz). |
| S7 | 1H-NMR (DMSO-d6) δ: 12.90 (br s, 1H), 10.40 (t, 1H, J = 5.9 Hz), 8.48 (s, 1H), 7.44-7.38 (m, 1H), 7.26-7.21 (m, 1H), 7.09-7.04 (m, 1H), 4.77 (sep, 1H, J = 6.7 Hz), 4.55 (d, 2H, J = 5.9 Hz), 4.18-4.12 (m, 1H), 3.82 (s, 2H), 3.39 (q, 2H, J = 7.1 Hz), 2.86-2.80 (m, 2H), 2.28-2.23 (m, 2H), 1.18 (d, 6H, J = 6.7 Hz), 1.14 (t, 3H, J = 7.1 Hz). |
| S8 | 1H-NMR (DMSO-d6) δ: 12.89 (br s, 1H), 10.40 (t, 1H, J = 5.9 Hz), 8.48 (s, 1H), 7.44-7.38 (m, 1H), 7.24 (ddd, 1H, J = 10.5, 9.3, 2.3 Hz), 7.09-7.04 (m, 1H), 4.76 (sep, 1H, J = 6.7 Hz), 4.55 (d, 2H, J = 5.9 Hz), 4.22-4.14 (m, 1H), 3.83 (s, 2H), 3.49-3.46 (m, 4H), 3.27 (s, 3H), 2.86-2.60 (m, 4H), 2.28-2.23 (m, 2H), 1.19 (d, 6H, J = 6.7 Hz). |
| S9 | 1H-NMR (DMSO-d6) δ: 12.87 (br s, 1H), 10.39 (t, 1H, J = 6.0 Hz), 8.48 (s, 1H), 7.44-7.21 (m, 7H), 7.09-7.04 (m, 1H), 4.55 (d, 2H, J = 6.0 Hz), 4.44 (s, 2H), 4.32-4.26 (m, 1H), 3.92 (s, 2H), 3.10 (s, 3H), 2.89-2.84 (m, 2H), 2.42-2.37 (m, 2H). |

TABLE 1-19

| Example No. | 1H-NMR (DMSO-d6) δ (peak, integ., J) |
|---|---|
| S10 | 1H-NMR (DMSO-d6) δ: 12.83 (br s, 1H), 10.38 (t, 1H, J = 6.0 Hz), 8.53 (s, 1H), 7.44-7.21 (m, 7H), 7.08-7.03 (m, 1H), 4.55 (d, 2H, J = 6.0 Hz), 4.45 (s, 2H), 4.16 (quint, 1H, J = 6.5 Hz), 3.79 (s, 2H), 3.11 (s, 3H). 2.72-2.66 (m, 2H), 2.51-2.45 (m, 2H). |
| S11 | 1H-NMR (DMSO-d6) δ: 10.39 (t, 1H, J = 6.0 Hz), 8.46 (s, 1H), 7.44-7.38 (m, 1H), 7.26-7.21 (m, 1H), 7.09-7.04 (m, 1H), 4.54 (d, 2H, J = 6.0 Hz), 4.40-4.34 (m, 1H), 3.92 (s, 2H), 3.11 (s, 3H), 2.84-2.78 (m, 2H), 2.26-2.21 (m, 2H). |
| S12 | 1H-NMR (DMSO-d6) δ: 10.41 (t, 1H, J = 6.0 Hz), 8.57 (s, 1H), 7.44-7.38 (m, 1H), 7.26-7.20 (m, 1H), 7.09-7.04 (m, 1H), 4.55 (d, 2H, J = 6.0 Hz), 4.16 (quint, 1H, J = 6.7 Hz), 3.75 (s, 2H), 3.11 (s, 3H), 2.65-2.59 (m, 2H), 2.40-2.34 (m, 2H). |
| S13 | 1H-NMR (DMSO-d6) δ: 13.03-12.71 (m, 1H), 10.39 (t, 1H, J = 6.0 Hz), 8.48 (s, 1H), 7.46-7.37 (m, 1H), 7.27-7.20 (m, 1H), 7.10-7.03 (m, 1H), 4.55 (d, 2H, J = 6.0 Hz), 4.12-4.02 (m, 1H), 3.88 (s, 2H), 3.20 (s, 3H), 3.11 (s, 3H), 2.90-2.79 (m, 2H), 2.37-2.29 (m, 2H). |
| S14 | 1H-NMR (DMSO-d6) δ: 12.83 (br s, 1H), 10.37 (t, 1H, J = 6.0 Hz), 8.49 (s, 1H), 7.44-7.38 (m, 1H), 7.26-7.21 (m, 1H), 7.09-7.04 (m, 1H), 4.55 (d, 2H, J = 6.0 Hz), 3.97 (quint, 1H, J = 6.4 Hz), 3.79 (s, 2H), 3.20 (s, 3H), 3.12 (s, 3H), 2.70-2.65 (m, 2H), 2.42-2.37 (m, 2H). |
| S15 | 1H-NMR (DMSO-d6) δ: 12.85 (s, 1H), 10.39 (t, 1H, J = 6.0 Hz), 8.48 (s, 1H), 7.44-7.21 (m, 7H), 7.09-7.04 (m, 1H), 4.54 (d, 2H, J = 6.0 Hz), 4.45 (s, 2H), 4.32-4.26 (m, 1H), 3.92 (s, 2H), 3.54 (q, 2H, J = 7.1 Hz), 2.90-2.85 (m, 2H), 2.37-2.32 (m, 2H), 1.15 (t, 3H, J = 7.1 Hz). |
| S16 | 1H-NMR (DMSO-d6) δ: 12.82 (s, 1H), 10.38 (t, 1H, J = 6.0 Hz), 8.53 (s, 1H), 7.44-7.21 (m, 7H), 7.09-7.04 (m, 1H), 4.55 (d, 2H, J = 6.0 Hz), 4.45 (s, 2H), 4.19 (quint, 1H, J = 6.4 Hz), 3.79 (s, 2H), 3.56 (q, 2H, J = 7.1 Hz), 2.67-2.62 (m, 2H), 2.51-2.45 (m, 2H), 1.17 (t, 3H, J = 7.1 Hz). |
| S17 | 1H-NMR (DMSO-d6) δ: 10.39 (t, 1H, J = 6.0 Hz), 8.45 (s, 1H), 7.41 (td, 1H, J = 8.6, 6.6 Hz), 7.24 (ddd, 1H, J = 10.6, 9.5, 2.6 Hz), 7.09-7.04 (m, 1H), 4.54 (d, 2H, J = 6.0 Hz), 4.40-4.34 (m, 1H), 3.93 (s, 2H), 3.55 (q, 2H, J = 7.2 Hz), 2.84-2.79 (m, 2H), 2.23-2.18 (m, 2H), 1.17 (t, 3H, J = 7.2 Hz). |
| S18 | 1H-NMR (DMSO-d6) δ: 10.41 (t, 1H, J = 6.0 Hz), 8.57 (s, 1H), 7.44-7.38 (m, 1H), 7.26-7.21 (m, 1H), 7.09-7.04 (m, 1H), 4.55 (d, 2H, J = 6.0 Hz), 4.19 (quint, 1H, J = 6.7 Hz), 3.75 (s, 2H), 3.56 (q, 2H, J = 7.1 Hz), 2.61-2.56 (m, 2H), 2.41-2.36 (m, 2H), 1.17 (t, 3H, J = 7.1 Hz). |

TABLE 1-20

| Example No. | 1H-NMR (DMSO-d6) δ (peak, integ., J) |
|---|---|
| S19 | 1H-NMR (DMSO-d6) δ: 12.85 (s, 1H), 10.39 (t, 1H, J = 6.0 Hz), 8.48 (s, 1H), 7.44-7.38 (m, 1H), 7.26-7.21 (m, 1H), 7.09-7.04 (m, 1H), 4.55 (d, 2H, J = 6.0 Hz), 4.11-4.05 (m, 1H), 3.89 (s, 2H), 3.55 (q, 2H, J = 7.2 Hz), 3.21 (s, 3H), 2.86-2.61 (m, 2H), 2.30-2.25 (m, 2H), 1.16 (t, 3H, J = 7.2 Hz). |
| S20 | 1H-NMR (DMSO-d6) δ: 10.37 (t, 1H, J = 5.8 Hz), 8.49 (s, 1H), 7.44-7.38 (m, 1H), 7.26-7.21 (m, 1H), 7.09-7.03 (m, 1H), 4.55 (d, 2H, J = 5.8 Hz), 4.00 (quint, 1H, J = 6.2 Hz), 3.79 (s, 2H), 3.57 (q, 2H, J = 7.1 Hz), 3.20 (s, 3H), 2.67-2.61 (m, 2H), 2.43-2.38 (m, 2H), 1.18 (t, 3H, J = 7.1 Hz). |
| S21 | 1H-NMR (DMSO-d6) δ: 12.83 (br s, 1H), 10.38 (t, 1H, J = 5.9 Hz), 8.50 (s, 1H), 7.44-7.38 (m, 1H), 7.23 (ddd, 1H, J = 10.4, 9.5, 2.5 Hz), 7.09-7.03 (m, 1H), 4.55 (d, 2H, J = 5.9 Hz), 4.08 (quint, 1H, J = 6.4 Hz), 3.79 (s, 2H), 3.57 (q, 2H, J = 7.2 Hz), 3.41 (q, 2H, J = 7.0 Hz), 2.67-2.61 (m, 2H), 2.42-2.37 (m, 2H), 1.17 (t, 3H, J = 7.2 Hz), 1.13 (t, 3H, J = 7.0 Hz). |
| S22 | 1H-NMR (DMSO-d6) δ: 10.41 (t, 1H, J = 6.0 Hz), 8.54 (s, 1H), 7.45-7.37 (m, 1H), 7.27-7.20 (m, 1H), 7.10-7.03 (m, 1H), 4.83-4.72 (m, 1H), 4.54 (d, 2H, J = 6.0 Hz), 3.93-3.54 (m, 2H), 3.44 (d, 2H, J = 4.6 Hz), 2.54-2.47 (m, 1H), 2.45-2.33 (m, 2H), 2.19-2.10 (m, 2H), 1.22 (d, 6H, J = 6.9 Hz). |
| S23 | 1H-NMR (DMSO-d6) δ: 12.98-12.72 (m, 1H), 10.41 (t, 1H, J = 6.0 Hz), 8.54 (s, 1H), 7.46-7.38 (m, 1H), 7.28-7.20 (m, 1H), 7.10-7.03 (m, 1H), 4.82-4.73 (m, 1H), 4.55 (d, 2H, J = 6.0 Hz), 3.78 (s, 2H), 3.50-3.33 (m, 2H), 3.28 (s, 3H), 2.70-2.56 (m, 1H), 2.41-2.31 (m, 2H), 2.27-2.18 (m, 2H), 1.22 (d, 6H, J = 6.7 Hz). |
| S24 | 1H-NMR (DMSO-d6) δ: 10.45-10.39 (m, 1H), 8.60 (s, 1H), 7.46-7.38 (m, 1H), 7.27-7.20 (m, 1H), 7.10-7.03 (m, 1H), 4.79-4.70 (m, 1H), 4.55 (d, 2H, J = 6.0 Hz), 3.74 (s, 2H), 3.64-3.30 (m, 2H), 2.53-2.45 (m, 3H), 2.25-2.14 (m, 2H), 1.19 (d, 6H, J = 6.7 Hz). |
| S25 | 1H-NMR (DMSO-d6) δ: 13.13-12.80 (m, 1H), 10.42 (t, 1H, J = 6.0 Hz), 8.59 (s, 1H), 7.46-7.38 (m, 1H), 7.27-7.20 (m, 1H), 7.10-7.03 (m, 1H), 4.80-4.70 (m, 1H), 4.55 (d, 2H, J = 6.0 Hz), 3.74 (s, 2H), 3.48-3.33 (m, 2H), 3.30 (s, 3H), 2.76-2.48 (m, 3H), 2.22-2.13 (m, 2H), 1.19 (d, 6H, J = 6.9 Hz). |
| S26 | 1H-NMR (DMSO-d6) δ: 13.06-12.73 (m, 1H), 10.45 (t, 1H, J = 6.0 Hz), 8.46 (s, 1H), 7.52-7.46 (m, 1H), 7.36-7.30 (m, 1H), 7.23-7.17 (m, 1H), 4.61 (d, 2H, J = 6.0 Hz), 4.41-4.33 (m, 1H), 3.92 (s, 2H), 3.12 (s, 3H), 2.86-2.77 (m, 2H), 2.29-2.20 (m, 2H). |
| S27 | 1H-NMR (DMSO-d6) δ: 12.92-12.78 (m, 1H), 10.49-10.43 (m, 1H), 8.57 (s, 1H), 7.52-7.46 (m, 1H), 7.36-7.30 (m, 1H), 7.23-7.17 (m, 1H), 4.62 (d, 2H, J = 6.0 Hz), 4.20-4.12 (m, 1H), 3.75 (s, 2H), 3.11 (s, 3H), 2.69-2.56 (m, 2H), 2.41-2.30 (m, 2H). |

TABLE 1-21

| Example No. | 1H-NMR (DMSO-d6) δ (peak, integ., J) |
|---|---|
| S28 | 1H-NMR (DMSO-d6) δ: 13.14-12.59 (m, 1H), 10.45 (t, 1H, J = 6.0 Hz), 8.47 (s, 1H), 7.52-7.46 (m, 1H), 7.36-7.30 (m, 1H), 7.23-7.17 (m, 1H), 4.62 (d, 2H, J = 6.0 Hz), 4.20-4.12 (m, 1H), 3.90 (s, 2H), 3.39 (q, 2H, J = 6.9 Hz), 3.11 (s, 3H), 2.88-2.79 (m, 2H), 2.37-2.29 (m, 2H), 1.13 (t, 3H, J = 6.9 Hz). |
| S29 | 1H-NMR (DMSO-d6) δ: 12.94-12.70 (m, 1H), 10.43 (t, 1H, J = 6.0 Hz), 8.49 (s, 1H), 7.52-7.47 (m, 1H), 7.35-7.30 (m, 1H), 7.23-7.17 (m, 1H), 4.62-4.62 (m, 2H), 4.09-4.01 (m, 1H), 3.79 (s, 2H), 3.40 (q, 2H, J = 6.9 Hz), 3.12 (s, 3H), 2.72-2.63 (m, 2H), 2.43-2.31 (m, 2H), 1.13 (t, 3H, J = 6.9 Hz). |
| S30 | 1H-NMR (DMSO-d6) δ: 13.06-12.60 (m, 1H), 10.39 (t, 1H, J = 5.8 Hz), 8.57 (s, 1H), 7.95-7.85 (m, 1H), 7.46-7.38 (m, 1H), 7.28-7.19 (m, 1H), 7.10-7.03 (m, 1H), 4.83-4.73 (m, 1H), 4.55 (d, 2H, J = 5.8 Hz), 3.79 (s, 2H), 3.72-3.03 (m, 1H), 2.72-2.61 (m, 2H), 2.60 (d, 3H, J = 4.6 Hz), 2.40-2.30 (m, 2H), 1.22 (d, 6H, J = 6.9 Hz). |
| S31 | 1H-NMR (DMSO-d6) δ: 12.97-12.80 (m, 1H), 10.38 (t, 1H, J = 5.8 Hz), 8.50 (s, 1H), 7.46-7. 37 (m, 1H), 7.27-7.19 (m, 1H), 7.10-7.02 (m, 1H), 4.84-4.73 (m, 1H), 4.54 (d, 2H, J = 5.8 Hz), 3.85 (s, 2H), 3.62-3.49 (m, 1H), 2.93 (s, 3H), 2.84 (s, 3H), 2.76-2.65 (m, 2H), 2.43-2.31 (m, 2H), 1.24 (d, 6H, J = 6.7 Hz). |
| S32 | 1H-NMR (DMSO-d6) δ: 12.89 (s, 1H) 10.41 (t, 1H, J = 6.0 Hz), 8.48 (s, 1H), 7.45-7.38 (m, 1H), 7.27-7.20 (m, 1H), 7.10-7.03 (m, 1H), 4.80-4.72 (m, 1H), 4.55 (d, 2H, J = 6.0 Hz), 4.28-4.20 (m, 1H), 3.81 (s, 2H), 3.65-3.58 (m, 1H), 2.89-2.80 (m, 2H), 2.28-2.20 |

TABLE 1-21-continued

| Example No. | 1H-NMR (DMSO-d6) δ (peak, integ., J) |
|---|---|
|  | (m, 2H), 1.19 (d, 6H, J = 6.9 Hz), 1.10 (d, 6H, J = 6.2 Hz). |
| S33 | 1H-NMR (DMSO-d6) δ: 12.86 (s, 1H), 10.38 (t, 1H, J = 6.2 Hz), 8.49 (s, 1H), 7.45-7.37 (m, 1H), 7.27-7.20 (m, 1H), 7.09-7.03 (m, 1H), 4.80-4.72 (m, 1H), 4.55 (d, 2H, J = 6.0 Hz), 4.24-4.15 (m, 1H), 3.68 (s, 2H), 3.68-3.58 (m, 1H), 2.68-2.56 (m, 2H), 2.42-2.31 (m, 2H), 1.20 (d, 6H, J = 6.7 Hz), 1.11 (d, 6H, J = 6.2 Hz). |
| S34 | 1H-NMR (DMSO-d6) δ: 12.93-12.84 (m, 1H), 10.40 (t, 1H, J = 6.0 Hz), 8.49 (s, 1H), 7.46-7.38 (m, 1H), 7.27-7.20 (m, 1H), 7.10-7.03 (m, 1H), 5.28-5.20 (m, 1H), 4.80-4.71 (m, 1H), 4.55 (d, 2H, J = 6.0 Hz), 3.85 (s, 2H), 3.24 (s, 3H), 3.18-3.09 (m, 2H), 2.71-2.62 (m, 2H), 1.20 (d, 6H, J = 6.9 Hz). |
| S35 | 1H-NMR (DMSO-d6) δ: 12.90-12.79 (m, 1H), 10.37 (t, 1H, J = 6.0 Hz), 8.52 (s, 1H), 7.45-7.38 (m, 1H), 7.27-7.19 (m, 1H), 7.10-7.03 (m, 1H), 5.29-5.20 (m, 1H), 4.79-4.70 (m, 1H), 4.55 (d, 2H, J = 6.0 Hz), 3.75 (s, 2H), 3.24 (s, 3H), 2.96-2.87 (m, 2H), 2.85-2.76 (m, 2H), 1.21 (d, 6H, J = 6.9 Hz). |
| S36 | 1H-NMR (CDCl3) δ: 12.83-12.68 (m, 1H), 10.57 (s, 1H), 8.77 (s, 1H), 7.33-7.24 (m, 1H), 7.07-6.98 (m, 1H), 4.77-4.67 (m, 2H), 3.79 (s, 2H), 3.73 (br s, 2H), 3.20 (s, 3H), 2.91-2.77 (m, 1H), 2.64-2.52 (m, 2H), 2.50-2.39 (m, 2H). |

TABLE 1-22

| Example No. | 1H-NMR (DMSO-d6) δ (peak, integ., J) |
|---|---|
| S37 | 1H-NMR (DMSO-d6) δ: 10.46 (t, 1H, J = 6.0 Hz), 8.54 (s, 1H), 7.53-7.46 (m, 1H), 7.36-7.30 (m, 1H), 7.24-7.17 (m, 1H), 4.61 (d, 2H, J = 6.0 Hz), 3.89 (s, 2H), 3.57 (s, 2H), 3.15 (s, 3H), 2.27-2.13 (m, 2H), 2.53-2.29 (m, 3H). |
| S38 | 1H-NMR (DMSO-d6) δ: 13.08-12.60 (m, 1H), 10.40 (t, 1H, J = 6.0 Hz), 8.49 (s, 1H), 8.08-7.96 (m, 1H), 7.46-7.37 (m, 1H), 7.27-7.19 (m, 1H), 7.10-7.02 (m, 1H), 4.82-4.71 (m, 1H), 4.55 (d, 2H, J = 6.0 Hz), 3.75 (s, 2H), 3.17 (t, 2H, J = 6.2 Hz), 2.55-2.37 (m, 1H), 2.35-2.14 (m, 4H), 1.83 (s, 3H), 1.21 (d, 6H, J = 6.9 Hz). |
| S39 | 1H-NMR (DMSO-d6) δ: 12.83 (s, 1H), 10.44 (t, 1H, J = 6.0 Hz), 8.57 (s, 1H), 7.53-7.46 (m, 1H), 7.36-7.30 (m, 1H), 7.23-7.17 (m, 1H), 4.61 (d, 2H, J = 6.0 Hz), 3.89 (s, 2H), 3.52-3.40 (m, 4H), 3.14 (s, 3H), 2.71-2.48 (m, 1H), 2.44-2.19 (m, 4H), 1.09 (t, 3H, J = 6.9 Hz). |
| S40 | 1H-NMR (DMSO-d6) δ: 13.08-12.69 (m, 1H), 10.45 (t, 1H, J = 6.0 Hz), 8.48 (s, 1H), 7.52-7.46 (m, 1H), 7.36-7.31 (m, 1H), 7.23-7.18 (m, 1H), 4.62 (d, 2H, J = 6.0 Hz), 4.28-4.20 (m, 1H), 3.89 (s, 2H), 3.66-3.55 (m, 1H), 3.11 (s, 3H), 2.90-2.80 (m, 2H), 2.37-2.28 (m, 2H), 1.09 (d, 6H, J = 6.9 Hz). |
| S41 | 1H-NMR (DMSO-d6) δ: 12.99-12.65 (m, 1H), 10.43 (t, 1H, J = 6.0 Hz), 8.48 (s, 1H), 7.52-7.46 (m, 1H), 7.35-7.30 (m, 1H), 7.23-7.17 (m, 1H), 4.62 (d, 2H, J = 6.0 Hz), 4.18-4.09 (m, 1H), 3.79 (s, 2H), 3.67-3.57 (m, 1H), 3.12 (s, 3H), 2.73-2.64 (m, 2H), 2.41-2.31 (m, 2H), 1.10 (d, 6H, J = 6.0 Hz). |
| S42 | 1H-NMR (DMSO-d6) δ: 12.92-12.83 (m, 1H), 10.45 (t, 1H, J = 6.0 Hz), 8.47 (s, 1H), 7.52-7.46 (m, 1H), 7.36-7.30 (m, 1H), 7.23-7.17 (m, 1H), 4.62 (d, 2H, J = 6.0 Hz), 4.19-4.11 (m, 1H), 3.90 (s, 2H), 3.29 (t, 2H, J = 6.7 Hz), 3.11 (s, 3H), 2.88-2.79 (m, 2H), 2.37-2.28 (m, 2H), 1.58-1.47 (m, 2H), 0.89 (t, 3H, J = 7.4 Hz). |
| S43 | 1H-NMR (DMSO-d6) δ: 12.83 (s, 1H), 10.43 (t, 1H, J = 6.0 Hz), 8.49 (s, 1H), 7.52-7.46 (m, 1H), 7.36-7.30 (m, 1H), 7.23-7.17 (m, 1H), 4.62 (d, 2H, J = 6.0 Hz), 4.09-4.00 (m, 1H), 3.79 (s, 2H), 3.35-3.27 (m, |

TABLE 1-22-continued

| Example No. | 1H-NMR (DMSO-d6) δ (peak, integ., J) |
|---|---|
|  | 2H), 3.12 (s, 3H), 2.73-2.63 (m, 2H), 2.43-2.31 (m, 2H), 1.57-1.46 (m, 2H), 0.86 (t, 3H J = 7.4 Hz). |
| S44 | 1H-NMR (DMSO-d6) δ: 12.93 (s, 1H), 10.47 (t, 1H, J = 6.0 Hz), 8.59 (s, 1H), 7.53-7.46 (m, 1H), 7.37-7.31 (m, 1H), 7,21 (t, 1H, J = 7.9 Hz), 4.62 (d, 2H, J = 6.0 Hz), 3.83 (s, 2H), 3.58-3.44 (m, 4H), 2.71-2.44 (m, 3H), 2.26-2.16 (m, 2H), 1.17 (t, 3H, J = 7.2 Hz). |
| S45 | 1H-NMR (DMSO-d6) δ: 13.09-12.70 (m, 1H), 10.46 (t, 1H, J = 6.0 Hz), 8.58 (s, 1H), 7.52-7.46 (m, 1H), 7.37-7.30 (m, 1H), 7.23-7.17 (m, 1H), 4.62 (d, 2H, J = 6.0 Hz), 3.83 (s, 2H), 3.55 (q, 2H, J = 7.2 Hz), 3.43 (d, 2H, J = 5.8 Hz), 3.29 (s, 3H), 2.76-2.49 (m, 3H), 2.23-2.14 (m, 2H), 1.17 (t, 3H, J = 7.2 Hz). |

TABLE 1-23

| Example No. | 1H-NMR (DMSO-d6) δ (peak, inteq., J) |
|---|---|
| S46 | 1H-NMR (DMSO-d6) δ: 12.84 (s, 1H), 10.46 (t, 1H, J = 6.0 Hz), 8.54 (s, 1H), 7.53-7.46 (m, 1H), 7.36-7.30 (m, 1H), 7.23-7.17 (m, 1H), 4.81 (t, 1H, J = 5.3 Hz), 4.61 (d, 2H, J = 6.0 Hz), 3.89 (s, 2H), 3.59 (q, 2H, J = 7.2 Hz), 3.47-3.40 (m, 2H), 2.60-2.31 (m, 3H), 2.21-2.12 (m, 2H), 1.19 (t, 3H, J = 7.2 Hz). |
| S47 | 1H-NMR (DMSO-d6) δ: 12.81 (br s, 1H), 10.46 (t, 1H, J = 6.0 Hz), 8.53 (s, 1H), 7.53-7.47 (m, 1H), 7.36-7.30 (m, 1H), 7.23-7.18 (m, 1H), 4.62 (d, 2H, J = 6.0 Hz), 3.89 (s, 2H), 3.59 (q, 2H, J = 7.2 Hz), 3.42-3.35 (m, 2H); 3.27 (s, 3H), 2.69-2.51 (m, 1H), 2.42-2.30 (m, 2H), 2.29-2.19 (m, 2H), 1.19 (t, 3H, J = 7.2 Hz). |
| S48 | 1H-NMR (DMSO-d6) δ: 12.83 (s, 1H), 10.45 (t, 1H, J = 6.0 Hz), 8.54 (s, 1H), 7.52-7.46 (m, 1H), 7.36-7.29 (m, 1H), 7.23-7.16 (m, 1H), 4.61 (d, 2H, J = 6.0 Hz), 3.89 (s, 2H), 3.59 (q, 2H, J = 7.2 Hz), 3.48-3.36 (m, 4H), 2.70-2.51 (m, 1H), 2.41-2.31 (m, 2H), 2.30-2.20 (m, 2H), 1.19 (t, 3H, J = 7.4 Hz), 1.10 (t, 3H, J = 7.2 Hz). |
| S49 | 1H-NMR (DMSO-d6) δ: 12.93 (s, 1H), 10.43-10.36 (m, 1H), 8.58 (s, 1H), 7.32 (t, 1H, J = 8.5 Hz), 7.02-6.97 (m, 1H); 4,77 (t, 1H, J = 5.2 Hz), 4.54 (d, 2H, J = 6.0 Hz), 3.87 (s, 3H), 3.82 (s, 2H), 3.47 (t, 2H, J = 5.2 Hz), 3.10 (s, 3H), 2.69-2.40 (m, 3H), 2.28-2.19 (m, 2H). |
| S50 | 1H-NMR (DMSO-d6) δ: 12.80 (br s, 1H), 10.39 (t, 1H, J = 6.0 Hz), 8.53 (s, 1H), 7.32 (t, 1H, J = 8.5 Hz), 7.01-6.97 (m, 1H), 4.82 (t, 1H, J = 5.2 Hz), 4.53 (d, 2H, J = 6.0 Hz), 3.89 (s, 2H), 3.87 (s, 3H), 3.43 (t, 2H, J = 4.8 Hz), 3.14 (s, 3H), 2.55-2.30 (m, 3H), 2.25-2.15 (m, 2H). |
| S51 | 1H-NMR (DMSO-d6) δ: 12.83 (br s, 1H), 10.38 (t, 1H, J = 6.0 Hz), 8.49 (s, 1H), 7.45-7.37 (m, 1H), 7.28-7.19 (m, 1H), 7.10-7.02 (m, 1H), 4.55 (d, 2H, J = 6.0 Hz), 4.10-4.01 (m, 1H), 3.79 (s, 2H), 3.41 (q, 2H, J = 6.9 Hz), 3.12 (s, 3H), 2.72-2.63 (m, 2H), 2.44-2.31 (m, 2H), 1.13 (t, 3H, J = 6.9 Hz). |
| S52 | 1H-NMR (DMSO-d6) δ: 12.40 (s, 1H), 10.41 (t, 1H, J = 6.0 Hz), 8.43 (s, 1H), 7.44-7.36 (m, 1H), 7.27-7.20 (m, 1H), 7.09-7.03 (m, 1H), 4.54 (d, 2H, J = 6.0 Hz), 4.44 (s, 2H), 4.15-4.01 (m, 2H), 3.18 (s, 3H), 2.76-2.65 (m, 2H), 2.23-2.15 (m, 2H), 1.46 (d, 6H, J = 6.7 Hz). |
| S53 | 1H-NMR (DMSO-d6) δ: 10.41 (t, 1H, J = 6.0 Hz), 8.45 (s, 1H), 7.44-7.36 (m, 1H), 7.27-7.20 (m, 1H), 7.10-7.02 (m, 1H), 4.54 (d, 2H, J = 6.0 Hz), 4.37 (s, 2H), 4.32-4.14 (m, 1H), 3.91-3.83 (m, 1H), 3.18 (s, 3H), 2.56-2.42 (m, 2H), 2.40-2.30 (m, 2H), 1.43 (d, 6H, J = 6.9 Hz). |
| S54 | 1H-NMR (DMSO-d6) δ: 12.58-12.27 (m, 1H), 10.42 (t, 1H, J = 6.0 Hz), 8.40 (s, 1H), 7.44-7.36 (m, 1H), 7.27-7.20 (m, 1H), 7.10-7.02 (m, 1H), 5.01-3.98 (m, |

TABLE 1-23-continued

| Example No. | 1H-NMR (DMSO-d6) δ (peak, integ., J) |
|---|---|
| | 2H), 4.54 (d, 2H, J = 6.0 Hz), 4.49 (s, 2H), 2.80-2.68 (m, 2H), 2.13-2.04 (m, 2H), 1.45 (d, 6H, J = 6.9 Hz). |

TABLE 1-24

| Example No. | 1H-NMR (DMSO-d6) δ (peak, integ., J) |
|---|---|
| S55 | 1H-NMR (DMSO-d6) δ: 12.54-12.20 (m, 1H), 10.43 (t, 1H, J = 6.0 Hz), 8.46 (s, 1H), 7.44-7.36 (m, 1H), 7.33-7.18 (m, 1H), 7.10-7.03 (m, 1H), 4.54 (d, 2H, J = 6.0 Hz), 4.43-3.77 (m, 2H), 4.35 (s, 2H), 2.47-2.37 (m, 2H), 2.37-2.28 (m, 2H), 1.44 (d, 6H, J = 6.7 Hz). |
| S56 | 1H-NMR (DMSO-d6) δ: 12.39 (br s, 1H), 10.47 (t, 1H, J = 6.0 Hz), 8.45 (s, 1H), 7.52-7.46 (m, 1H), 7.35-7.29 (m, 1H), 7.23-7.17 (m, 1H), 4.61 (d, 2H, J = 6.0 Hz), 4.46 (s, 2H), 4.20-4.12 (m, 1H), 3.64 (q, 2H, J = 7.2 Hz), 3.36 (q, 2H, J = 6.9 Hz), 2.72-2.63 (m, 2H), 2.22-2.13 (m, 2H), 1.21-1.12 (m, 6H). |
| S57 | 1H-NMR (DMSO-d6) δ: 12.38-12.24 (m, 1H), 10.46 (t, 1H, J = 5.8 Hz), 8.45 (s, 1H), 7.52-7.47 (m, 1H), 7.35-7.29 (m, 1H), 7.23-7.17 (m, 1H), 4.62 (d, 2H, J = 5.8 Hz), 4.39 (s, 2H), 4.02-3.93 (m, 1H), 3.65 (q, 2H, J = 7.2 Hz), 3.45-3.32 (m, 2H), 2.54-2.46 (m, 2H), 2.34-2.23 (m, 2H), 1.19-1.09 (m, 6H). |
| S58 | 1H-NMR (DMSO-d6) δ: 12.58-12.31 (m, 1H), 10.47 (t, 1H, J = 6.0 Hz), 8.49 (s, 1H), 7.52-7.46 (m, 1H), 7.35-7.29 (m, 1H), 7.23-7.17 (m, 1H), 4.61 (d, 2H, J = 6.0 Hz), 4.42 (s, 2H), 3.72 (q, 2H, J = 7.2 Hz), 3.52-3.47 (m, 2H), 2.59-2.40 (m, 3H), 2.08-1.98 (m, 2H), 1.22 (t, 3H, J = 7.2 Hz). |
| S59 | 1H-NMR (DMSO-d6) δ: 12.45 (s, 1H), 10.47 (t, 1H, J = 6.0 Hz), 8.53 (s, 1H), 7.53-7.46 (m, 1H), 7.36-7.29 (m, 1H), 7.24-7.16 (m, 1H), 4.62 (d, 2H, J = 6.0 Hz), 4.42 (s, 2H), 3.72 (q, 2H, J = 6.9 Hz), 3.46 (d, 2H, J = 6.9 Hz), 3.28 (s, 3H), 2.74-2.60 (m, 1H), 2.59-2.46 (m, 2H), 2.05-1.96 (m, 2H), 1.22 (t, 3H, J = 6.9 Hz). |
| S60 | 1H-NMR (DMSO-d6) δ: 12.40 (br s, 1H), 10.48 (t, 1H, J = 6.0 Hz), 8.53 (s, 1H), 7.54-7.46 (m, 1H), 7.36-7.29 (m, 1H), 7.20 (t, 1H, J = 7.9 Hz), 4.62 (d, 2H, J = 6.0 Hz), 4.50 (s, 2H), 3.67 (q, 2H, J = 6.9 Hz), 3.46-3.41 (m, 2H), 2.70-2.24 (m, 3H), 2.06-1.96 (m, 2H), 1.16 (t, 3H, J = 6.9 Hz). |
| S61 | 1H-NMR (DMSO-d6) δ: 12.83-11.92 (m, 1H), 10.47 (t, 1H, J = 6.0 Hz), 8.52 (s, 1H), 7.53-7.46 (m, 1H), 7.36-7.29 (m, 1H), 7.23-7.17 (m, 1H), 4.62 (d, 2H, J = 6.0 Hz), 4.50 (s, 2H), 3.66 (q, 2H, J = 7.2 Hz), 3.43-3.35 (m, 2H), 3.27 (s, 3H), 2.61-2.38 (m, 1H), 2.29-2.20 (m, 2H), 2.13-2.03 (m, 2H), 1.15 (t, 3H, J = 7.2 Hz). |
| S62 | 1H-NMR (DMSO-d6) δ: 12.43 (s, 1H), 10.46 (t, 1H, J = 6.0 Hz), 8.46 (s, 1H), 7.52-7.46 (m, 1H), 7.35-7.29 (m, 1H), 7.23-7.16 (m, 1H), 4.61 (d, 2H, J = 6.0 Hz), 4.47 (s, 2H), 4.11-4.01 (m, 1H), 3.18 (s, 3H), 3.14 (s, 3H), 2.79-2.70 (m, 2H), 2.20-2.11 (m, 2H). |
| S63 | 1H-NMR (DMSO-d6) δ: 12.64-12.00 (m, 1H), 10.46 (t, 1H, J = 6.0 Hz), 8.46 (s, 1H), 7.53-7.47 (m, 1H), 7.35-7.29 (m, 1H), 7.23-7.17 (m, 1H), 4.62 (d, 2H, J = 6.0 Hz), 4.41 (s, 2H), 3.91-3.83 (m, 1H), 3.17 (s, 3H), 3.11 (s, 3H), 2.47-2.31 (m, 4H). |

TABLE 1-25

| Example No. | 1H-NMR (DMSO-d6) δ (peak, integ., J) |
|---|---|
| S64 | 1H-NMR (DMSO-d6) δ: 10.25 (t, 1H, J = 6.0 Hz), 8.66 (s, 1H), 7.53-7.47 (m, 1H), 7.36-7.30 (m, 1H), 7.23-7.17 (m, 1H), 4.61 (d, 2H, J = 6.0 Hz), 4.02-3.50 (m, 3H), 3.22 (s, 3H), 3.08 (s, 3H), 2.78-2.15 (m, 4H), 2.23 (s, 3H). |
| S65 | 1H-NMR (DMSO-d6) δ: 10.25 (t, 1H, J = 5.9 Hz), 8.66 (s, 1H), 7.54-7.45 (m, 1H), 7.37-7.29 (m, 1H), 7.23-7.15 (m, 1H), 4.60 (d, 2H, J = 5.9 Hz), 4.04-3.53 (m, 3H), 3.22 (s, 3H), 3.07 (s, 3H), 2.78-2.19 (m, 6H), 1.13 (t, 3H, J = 7.5 Hz). |
| S66 | 1H-NMR (DMSO-d6) δ: 10.23 (t, 1H, J = 6.0 Hz), 8.65 (s, 1H), 7.53-7.46 (m, 1H), 7.35-7.29 (m, 1H), 7.23-7.17 (m, 1H), 4.67-4.55 (m, 2H), 4.02-3.53 (m, 3H), 3.22 (s, 3H), 3.07 (s, 3H), 2.83-2.18 (m, 5H), 1.23 (d, 6H, J = 6.9 Hz). |
| S67 | 1H-NMR (DMSO-d6) δ: 10.26 (t, 1H, J = 6.0 Hz), 8.74 (s, 1H), 7.53-7.47 (m, 1H), 7.36-7.30 (m, 1H), 7.23-7.17 (m, 1H), 4.61 (d, 2H, J = 6.0 Hz), 3.87 (br s, 2H), 3.43 (d, 2H, J = 4.4 Hz); 3.29 (s, 3H), 3.09 (s; 3H), 2.73-2.13 (m, 7H), 1.13 (t, 3H, J = 7.4 Hz). |
| S68 | 1H-NMR (DMSO-d6) δ: 10.25 (t, 1H, J = 6.0 Hz), 8.73 (s, 1H), 7.52-7.46 (m, 1H), 7.36-7.30 (m, 1H), 7.23-7.17 (m, 1H), 4.60 (d, 2H, J = 6.0 Hz), 4.00-3.75 (m, 2H), 3.43 (d, 2H, J = 4.4 Hz), 3.29 (s, 3H), 3.09 (s, 3H), 2.83-2.71 (m, 1H), 2.69-2.09 (m, 5H), 1.23 (d, 6H, J = 6.9 Hz). |
| S69 | 1H-NMR (DMSO-d6) δ: 10.26 (t, 1H, J = 6.0 Hz), 8.73 (s, 1H), 7.53-7.46 (m, 1H), 7.36-7.29 (m, 1H), 7.24-7.17 (m, 1H), 4.60 (d, 2H, J = 6.0 Hz), 3.86 (br s, 2H), 3.43 (d, 2H, J = 4.4 Hz), 3.29 (s, 3H), 3.09 (s, 3H), 2.70-2.07 (m, 7H), 1.69-1.55 (m, 2H), 1.46-1.16 (m, 24H), 0.85 (t, 3H, J = 6.8 Hz). |
| S70 | 1H-NMR (DMSO-d6) δ: 10.25 (t, 1H, J = 5.8 Hz), 8.80 (s, 1H), 8.07-8.02 (m, 1H), 7.77-7.71 (m, 1H), 7.63-7.57 (m, 2H), 7.52-7.46 (m, 1H), 7.36-7.30 (m, 1H), 7.20 (t, 1H, J = 8.1 Hz), 4.55-4.57 (m, 2H), 3.96 (d, 1H, J = 13.9 Hz), 3.86 (d, 1H, J = 13.9 Hz), 3.45 (d, 2H, J = 4.9 Hz), 3.31 (s, 3H), 3.07 (s, 3H), 2.71-2.55 (m, 2H), 2.43-2.17 (m, 3H). |
| S71 | 1H-NMR (DMSO-d6) δ: 10.23 (t, 1H, J = 6.0 Hz), 8.72 (s, 1H), 7.52-7.45 (m, 1H), 7.35-7.28 (m, 1H), 7.22-7.17 (m, 1H), 4.67-4.54 (m, 2H), 3.92 (3H, J = 13.7 Hz), 3.81 (d, 1H, J = 13.7 Hz), 3.43 (d, 2H, J = 4.8 Hz), 3.29 (s, 3H), 3.09 (s, 3H), 2.68-2.52 (m, 2H), 2.39-2.27 (m, 1H), 2.27-2.14 (m, 3H), 1.29 (s, 9H). |
| S72 | 1H-NMR (DMSO-d6) δ: 10.25 (t, 1H, J = 6.0 Hz), 8.79 (s, 1H), 7.93 (d, 2H, J = 8.1 Hz), 7.52-7.46 (m, 1H), 7.39 (d, 2H, J = 8.1 Hz), 7.36-7.30 (m, 1H), 7.23-7.16 (m, 1H), 4.64-4.57 (m, 2H), 3.95 (d, 1H, J = 13.9 Hz), 3.85 (d, 1H, J = 13.9 Hz), 3.44 (d, 2H, J = 4.9 Hz), 3.31 (s, 3H), 3.06 (s, 3H), 2.70-2.55 (m, 2H), 2.42 (s, 3H), 2.40-2.17 (m, 3H). |
| S73 | 1H-NMR (DMSO-d6) δ: 10.62-10.39 (m, 1H), 10.17 (t, 1H, J = 6.0 Hz), 8.80 (s, 1H), 7.54-7.46 (m, 1H), 7.36-7.31 (m, 1H), 7.24-7.18 (m, 1H), 4.66-4.45 (n, 2H), 4.62 (d, 2H, J = 6.0 Hz), 3.99-3.84 (m, 2H), 3.43 (d, 2H, J = 4.8 Hz), 3.30 (s, 3H), 3.12 (s, 3H), 2.92 (s, 6H) 2.70-2.11 (m, 5H). |

TABLE 2-1

| Example No. | structural formula | salt | compound name |
|---|---|---|---|
| T1 | | HCl | (1S,2S)-N-(2,4-difluorobenzyl)-2'-ethyl-9'-hydroxy-2-(hydroxymethyl)-1',8'-dioxo-1',2',3',8'-tetrahydrospiro[cyclopropane-1,4'-pyrido[1,2-a]pyrazine]-7'-carboxamide hydrochloride |
| T2 | | HCl | (1S,2S)-N-(2,4-difluoorobenzyl)-2'-ethyl-9'-hydroxy-2-(methoxymethyl)-1',8'-dioxo-1',2',3',8'-tetrahydrospiro[cyclopropane-1,4'-pyrido[1,2-a]pyrazine]-7'-carboxamide hydrochloride |
| T3 | | HCl | (1S,2S)-N-(2,4-difluorobenzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide hydrochloride |
| T4 | | HCl | (1S,2S)-N-(2,4-difluorobenzyl)-9'-hydroxy-2-(hydroxymethyl)-2'-methyl-1',8'-dioxo-1',2',3',8'-tetrahydrospiro[cyclopropane-1,4'-pyrido[1,2-a]pyrazine]-7'-carboxamide hydrochloride |
| T5 | | HCl | (1R,2R)-N-(3-chloro-2-fluorobenzyl)-9'-hydroxy-2-(hydroxymethyl)-2'-isopropyl-1',8'-dioxo-1',2',3',8'-tetrahydrospiro[cyclopropane-1,4'-pyrido[1,2-a]pyrazine]-7'-carboxamide hydrochloride |

TABLE 2-2

| Example No. | structural formula | salt | compound name |
|---|---|---|---|
| T6 | | HCl | (1R,2R)-N-(3-chloro-2-fluorobenzyl)-9'-hydroxy-2'-isopropyl-2-(methoxymethyl)-1',8'-dioxo-1',2',3',8'-tetrahydrospiro[cyclopropane-1,4'-pyrido[1,2-a]pyrazine]-7'-carboxamide hydrochloride |
| T7 | | HCl | (1S,2S)-7'-(2,4-difluorobenzylcarbamoyl)-2'-ethyl-9'-hydroxy-1',8'-dioxo-1',2',3',8'-tetrahydrospiro[cyclopropane-1,4'-pyrido[1,2-a]pyrazine]-2-carboxylic acid hydrochloride |
| T8 | | HCl | (1S,2S)-$N^{7'}$-(2,4-difluorobenzyl)-2'-ethyl-9'-hydroxy-$N^2$-methyl-1',8'-dioxo-1',2',3',8'-tetrahydrospiro[cylcopropane-1,4'-pyrido[1,2-a]pyrazine]-2,7'-dicarboxamide hydrochloride |
| T9 | | HCl | (1R,2R)-N-(2,4-difluorobenzyl)-2'-ethyl-9'-hydroxy-2-(methoxymethyl)-1',8'-dioxo-1',2',3',8'-tetrahydrospiro[cyclopropane-1,4'-pyrido[1,2-a]pyrazine]-7'-carboxamide hydrochloride |
| T10 | | HCl | (1R,2R)-N-(2,4-difluorobenzyl)-2'-ethyl-9'-hydroxy-2-(hydroxymethyl)-1',8'-dioxo-1',2',3',8'-tetrahydrospiro[cyclopropane-1,4'-pyrido[1,2-a]pyrazine]-7'-carboxamide hydrochloride |

TABLE 2-3

| Example No. | structural formula | salt | compound name |
|---|---|---|---|
| T11 | | HCl | (1S,2S)-N-(3-chloro-2-fluorobenzyl)-9'-hydroxy-2-(hydroxymethyl)-2'-isopropyl-1',8'-dioxo-1',2',3',8'-tetrahydrospiro[cyclopropane-1,4'-pyrido[1,2-a]pyrazine]-7'-carboxamide hydrochloride |
| T12 | | HCl | (1S,2S)-N-(3-chloro-2-fluorobenzyl)-9'-hydroxy-2'-isopropyl-2-(methoxymethyl)-1',8'-dioxo-1',2',3',8'-tetrahydrospiro[cylcopropane-1,4'-pyrido[1,2-a]pyrazine]-7'-carboxamide hydrochloride |
| T13 | | HCl | (1S,2S)-$N^{7'}$-(3-chloro-2-fluorobenzyl)-9'-hydroxy-2'-isopropyl-$N^2,N^2$-dimethyl-1',8'-dioxo-1',2',3',8'-tetrahydrospiro[cyclopropane-1,4'-pyrido[1,2-a]pyrazine]-2,7'-dicarboxamide hydrochloride |
| T14 | | HCl | (1R,2R)-$N^{7'}$-(3-chloro-2-fluorobenzyl)-9'-hydroxy-2'-isopropyl-$N^2,N^2$-dimethyl-1',8'-dioxo-1',2',3',8'-tetrahydrospiro[cyclopropane-1,4'-pyrido[1,2-a]pyrazine]-2,7'-dicarboxamide hydrochloride |
| T15 | | HCl | (1S,2S)-N-(3-chloro-2-fluorobenzyl)-9'-hydroxy-2-(hydroxymethyl)-2'-methyl-1',8'-dioxo-1',2',3',8'-tetrahydrospiro[cyclopropane-1,4'-pyrido[1,2-a]pyrazine]-7'-carboxamide hydrochloride |

TABLE 2-4

| Example No. | structural formula | salt | compound name |
|---|---|---|---|
| T16 | | HCl | (1S,2S)-N-(3-chloro-2-fluorobenzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide hydrochloride |
| T17 | | HCl | (1R,2R)-N-(3-chloro-2-fluorobenzyl)-2'-ethyl-9'-hydroxy-2-(hydroxymethyl)-1',8'-dioxo-1',2',3',8'-tetrahydrospiro[cyclopropane-1,4'-pyrido[1,2-a]pyrazine]-7'-carboxamide hydrochloride |
| T18 | | HCl | (1S,2S)-N-(3-chloro-2-fluorobenzyl)-2'-ethyl-9'-hydroxy-2-(hydroxymethyl)-1',8'-dioxo-1',2',3',8'-tetrahydrospiro[cyclopropane-1,4'-pyrido[1,2-a]pyrazine]-7'-carboxamide hydrochloride |
| T19 | | | (1S,2S)-N-(3-chloro-2-fluorobenzyl)-2'-ethyl-9'-hydroxy-2-(methoxymethyl)-1',8'-dioxo-1',2',3',8'-tetrahydrospiro[cyclopropane-1,4'-pyrido[1,2-a]pyrazine]-7'-carboxamide |
| T20 | | HCl | (1R,2R)-N-(3-chloro-2-fluorobenzyl)-2'-ethyl-9'-hydroxy-2-(methoxymethyl)-1',8'-dioxo-1',2',3',8'-tetrahydrospiro[cyclopropane-1,4'-pyrido[1,2-a]pyrazine]-7'-carboxamide hydrochloride |

TABLE 2-5

| Example No. | structural formula | salt | compound name |
|---|---|---|---|
| T21 | | | (1S,2S)-N-(3-chloro-2-fluoro-5-methoxybenzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide |
| T22 | | HCl | (1S,2S)-N-(3-chloro-2-fluoro-4-methoxybenzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide hydrochloride |
| T23 | | HCl | (1R,2R)-N-(3-chloro-2-fluorobenzyl)-9'-hydroxy-2-(hydroxymethyl)-2'-methyl-1',8'-dioxo-1',2',3',8'-tetrahydrospiro[cyclopropane-1,4'-pyrido[1,2-a]pyrazine]-7'-carboxamide hydrochloride |
| T24 | | HCl | (1R,2R)-N-(3-chloro-2-fluorobenzyl)-9'-hydroxy-2-(methoxymethyl)-2'-methyl-1',8'-dioxo-1',2',3',8'-tetrahydrospiro[cyclopropane-1,4 -pyrido[1,2-a]pyrazine]-7'-carboxamide hydrochloride |
| T25 | | HCl | (1S,2S)-N-(3-chloro-5-ethoxy-2-fluorobenzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide hydrochloride |

TABLE 2-6

| Example No. | structural formula | salt | compound name |
|---|---|---|---|
| T26 | | HCl | (1S,2S)-N-(3-chloro-2-fluoro-5-isopropoxybenzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide hydrochloride |
| T27 | | | (1S,2S)-2'-ethyl-N-(2-fluoro-3-(trifluoromethyl)benzyl)-9'-hydroxy-2-(methoxymethyl)-1',8'-dioxo-1',2',3',8'-tetrahydrospiro[cyclopropane-1,4'-pyrido[1,2-a]pyrazine]-7'-carboxamide |
| T28 | | HCl | (1S,2R)-N-(3-chloro-2-fluorobenzyl)-9'-hydroxy-2-(hydroxymethyl)-2'-isopropyl-1',8'-dioxo-1',2',3',8'-tetrahydrospiro[cyclopropane-1,4'-pyrido[1,2-a]pyrazine]-7'-carboxamide hydrochloride |
| T29 | | HCl | (1S,2R)-N-(3-chloro-2-fluorobenzyl)-2'-ethyl-9'-hydroxy-2-(hydroxymethyl)-1',8'-dioxo-1',2',3',8'-tetrahydrospiro[cyclopropane-1,4'-pyrido[1,2-a]pyrazine]-7'-carboxamide hydrochloride |
| T30 | | | (1S,2R)-N-(3-chloro-2-fluorobenzyl)-2'-ethyl-9'-hydroxy-2-(methoxymethyl)-1',8'-dioxo-1',2',3',8'-tetrahydrospiro[cyclopropane-1,4'-pyrido[1,2-a]pyrazine]-7'-carboxamide |

TABLE 2-7

| Example No. | structural formula | salt | compound name |
|---|---|---|---|
| T31 | | | (1S,2S)-N-(3-chloro-2-fluoro-4-methoxybenzyl)-2-(ethoxymethyl)-9'-hydroxy-2'-methyl-1',8'-dioxo-1',2',3',8'-tetrahydrospiro[cyclopropane-1,4'-pyrido[1,2-a]pyrazine]-7'-carboxamide |
| T32 | | | (1S,2S)-N⁷'-(3-chloro-2-fluorobenzyl)-2'-cyclopropyl-9'-hydroxy-N²,N²-dimethyl-1',8'-dioxo-1',2',3',8'-tetrahydrospiro[cyclopropane-1,4'-pyrido[1,2-a]pyrazine]-2,7'-dicarboxamide |
| T33 | | | (1R,2R)-N⁷'-(3-chloro-2-fluorobenzyl)-2'-cyclopropyl-9'-hydroxy-N²,N²-dimethyl-1',8'-dioxo-1',2',3',8'-tetrahydrospiro[cyclopropane-1,4'-pyrido[1,2-a]pyrazine]-2,7'-dicarboxamide |
| T34 | | | (1S,2S)-N-(3-chloro-2-fluoro-5-(2-oxopyrrolidin-1-yl)benzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide |
| T35 | | HCl | (1R,2R)-N-(3-chloro-2-fluoro-4-methoxybenzyl)-2-(ethoxymethyl)-9'-hydroxy-2'-methyl-1',8'-dioxo-1',2',3',8'-tetrahydrospiro[cyclopropane-1,4'-pyrido[1,2-a]pyrazine]-7'-carboxamide hydrochloride |

TABLE 2-8

| Example No. | structural formula | salt | compound name |
|---|---|---|---|
| T36 | | HCl | (1R,2R)-N-(3-chloro-2-fluoro-4-methoxybenzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide hydrochloride |
| T37 | | HCl | (1S,2S)-N-(3-chloro-4-ethoxy-2-fluorobenzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide hydrochloride |
| T38 | | HCl | (1R,2R)-N-(3-chloro-4-ethoxy-2-fluorobenzyl)-9'-hydroxy-2-(methoxymethyl)-2'-methyl-1',8'-dioxo-1',2',3',8'-tetrahydrospiro[cyclopropane-1,4'-pyrido[1,2-a]pyrazine]-7'-carboxamide hydrochloride |
| T39 | | HCl | (1S,2S)-N-(2,4-difluorobenzyl)-2'-ethyl-9'-hydroxy-2-(hydroxymethyl)-1',8'-dioxo-1',2',4',8'-tetrahydrospiro[cyclopropane-1,3'-pyrido[1,2-a]pyrazine]-7'-carboxamide hydrochloride |
| T40 | | HCl | (1S,2S)-N-(2,4-difluorobenzyl)-2'-ethyl-9'-hydroxy-2-(methoxymethyl)-1',8'-dioxo-1',2',4',8'-tetrahydrospiro[cylcopropane-1,3'-pyrido[1,2-a]pyrazine]-7'-carboxamide hydrochloride |

TABLE 2-9

| Example No. | structural formula | salt | compound name |
|---|---|---|---|
| T41 | | | (1S,2S)-N-(2,4-difluorobenzyl)-9'-hydroxy-2'-isopropyl-2-(methoxymethyl)-1',8'-dioxo-1',2',4',8'-tetrahydrospiro[cyclopropane-1,3'-pyrido[1,2-a]pyrazine]-7'-carboxamide |
| T42 | | | (1S,2S)-N-(2,4-difluorobenzyl)-9'-hydroxy-2-(hydroxymethyl)-2'-isopropyl-1',8'-dioxo-1',2',4',8'-tetrahydrospiro[cyclopropane-1,3'-pyrido[1,2-a]pyrazine]-7'-carboxamide |
| T43 | | | (1S,2S)-N-(2,4-difluorobenzyl)-2-(ethoxymethyl)-9'-hydroxy-2'-isopropyl-1',8'-dioxo-1',2',4',8'-tetrahydrospiro[cyclopropane-1,3'-pyrido[1,2-a]pyrazine]-7'-carboxamide |
| T44 | | HCl | (1S,2S)-N-(3-chloro-2-fluorobenzyl)-2'-ethyl-9'-hydroxy-2-(hydroxymethyl)-1',8'-dioxo-1',2',4',8'-tetrahydrospiro[cyclopropane-1,3'-pyrido[1,2-a]pyrazine]-7'-carboxamide hydrochloride |
| T45 | | | (1S,2S)-N-(3-chloro-2-fluorobenzyl)-2-(ethoxymethyl)-2'-ethyl-9'-hydroxy-1',8'-dioxo-1',2',4',8'-tetrahydrospiro[cyclopropane-1,3'-pyrido[1,2-a]pyrazine]-7'-carboxamide |

TABLE 2-10

| Example No. | structural formula | salt | compound name |
|---|---|---|---|
| T46 | | HCl | (1R,2R)-N-(3-chloro-2-fluorobenzyl)-2'-ethyl-9'-hydroxy-2-(hydroxymethyl)-1',8'-dioxo-1',2',4',8'-tetrahydrospiro[cyclopropane-1,3'-pyrido[1,2-a]pyrazine]-7'-carboxamide hydrochloride |
| T47 | | | (1S,2S)-N-(3-chloro-2-fluorobenzyl)-9'-hydroxy-2-(hydroxymethyl)-2'-isopropyl-1',8'-dioxo-1',2',4',8'-tetrahydrospiro[cyclopropane-1,3'-pyrido[1,2-a]pyrazine]-7'-carboxamide |
| T48 | | HCl | (1S,2S)-N-(3-chloro-2-fluoro-4-methoxybenzyl)-2'-ethyl-9'-hydroxy-2-(hydroxymethyl)-1',8'-dioxo-1',2',4',8'-tetrahydrospiro[cyclopropane-1,3'-pyrido[1,2-a]pyrazine]-7'-carboxamide hydrochloride |
| T49 | | | (1R,2R)-N-(3-chloro-2-fluorobenzyl)-9'-hydroxy-2-(hydroxymethyl)-2'-methyl-1',8'-dioxo-1',2',4',8'-tetrahydrospiro[cyclopropane-1,3'-pyrido[1,2-a]pyrazine]-7'-carboxamide |
| T50 | | HCl | (1R,2R)-N-(3-chloro-2-fluorobenzyl)-9'-hydroxy-2-(methoxymethyl)-2'-methyl-1',8'-dioxo-1',2',4',8'-tetrahydrospiro[cyclopropane-1,3'-pyrido[1,2-a]pyrazine]-7'-carboxamide hydrochloride |

TABLE 2-11

| Example No. | 1H-NMR (DMSO-d6) δ (peak, integ., J) |
|---|---|
| T1 | 1H-NMR (DMSO-d6) δ: 12.86-12.61 (m, 1H), 10.37 (t, 1H, J = 6.0 Hz), 8.14 (s, 1H), 7.43-7.35 (m, 1H), 7.27-7.19 (m, 1H), 7.09-7.02 (m, 1H), 4.52 (d, 2H, J = 6.0 Hz), 3.35 (s, 2H), 3.76 (dd, 1H, J = 12.1, 5.3 Hz), 3.65-3.54 (m, 1H), 3.54-3.42 (m, 2H), 1.95-1.86 (m, 1H), 1.69 (dd, 1H, J = 10.6, 6.6 Hz), 1.30-1.21 (m, 1H), 1.16 (t, 3H, J = 7.3 Hz), 1.07 (t, 1H, J = 7.1 Hz). |
| T2 | 1H-NMR (DMSO-d6) δ: 12.73 (s, 1H), 10.35 (t, 1H, J = 6.0 Hz), 8.10 (s, 1H), 7.43-7.35 (m, 1H), 7.27-7.19 (m, 1H), 7.09-7.02 (m, 1H), 4.52 (d, 2H, J = 6.0 Hz), 3.96 (d, 1H, J = 13.9 Hz), 3.71 (d, 1H, J = 13.9 Hz), 3.67-3.57 (m, 2H), 3.50-3.38 (m, 2H), 3.24 (s, 3H), 1.95-1.85 (m, 2H), 1.15 (t, 3H, J = 7.3 Hz), 1.14-1.08 (m, 1H). |
| T3 | 1H-NMR (DMSO-d6) δ: 12.67 (s, 1H), 10.35 (t, 1H, J = 5.8 Hz), 8.10 (s, 1H), 7.44-7.35 (m, 1H), 7.26-7.19 |

TABLE 2-11-continued

| Example No. | 1H-NMR (DMSO-d6) δ (peak, integ., J) |
|---|---|
| | (m, 1H), 7.09-7.02 (m, 1H), 4.52 (d, 2H, J = 6.0 Hz), 4.02 (d, 1H, J = 13.9 Hz), 3.67-3.59 (m, 2H), 3.45-3.33 (m, 1H), 3.25 (s, 3H), 3.06 (s, 3H), 1.95-1.81 (m, 2H), 1.20-1.13 (m, 1H). |
| T4 | 1H-NMR (DMSO-d6) δ: 12.81-12.59 (m, 1H), 10.36 (t, 1H, J = 6.0 Hz), 8.14 (s, 1H), 7.43-7.35 (m, 1H), 7.26-7.19 (m, 1H), 7.09-7.02 (m, 1H), 4.52 (d, 2H, J = 6.0 Hz), 3.91 (d, 1H, J = 14.1 Hz), 3.80-3.73 (m, 2H), 3.40 (dd, 1H, J = 12.0, 8.6 Hz), 3.08 (s, 3H), 1.94-1.82 (m, 1H), 1.74-1.58 (m, 1H), 1.18 (t, 1H, J = 7.2 Hz). |
| T5 | 1H-NMR (DMSO-d6) δ: 12.90-12.74 (m, 1H), 10.43 (t, 1H, J = 5.6 Hz), 8.14 (s, 1H), 7.49 (t, 1H, J = 7.3 Hz), 7.31 (t, 1H, J = 6.9 Hz), 7.19 (t, 1H, J = 8.1 Hz), 4.80-4.68 (m, 1H), 4.59 (d, 2H, J = 6.0 Hz), 3.80-3.68 (m, 3H), 3.57-3.47 (m, 1H), 1.95-1.84 (m, 1H), 1.76-1.66 (m, 1H), 1.31-1.22 (m, 1H), 1.19 (d, 3H, J = 6.9 Hz), 1.17 (d, 3H, J = 6.9 Hz), 1.03 (t, 1H, J = 7.3 Hz). |
| T6 | 1H-NMR (DMSO-d6) δ: 12.89-12.76 (m, 1H), 10.46-10.35 (m, 1H), 8.10 (s, 1H), 7.49 (t, 1H, J = 7.7 Hz), 7.31 (t, 1H, J = 7.3 Hz), 7.19 (t, 1H, J = 7.7 Hz), 4.79-4.68 (m, 1H), 4.59 (d, 2H, J = 6.0 Hz), 3.80 (d, 1H, J = 14.1 Hz), 3.67 (d, 1H, J = 14.1 Hz), 3.61-3.53 (m, 1H), 3.51-3.42 (m, 1H), 3.23 (s, 3H), 1.95-1.83 (m, 2H), 1.18 (d, 6H, J = 6.9 Hz), 1.11-1.03 (m, 1H). |
| T7 | 1H-NMR (DMSO-d6) δ: 13.09-12.95 (m, 1H), 12.62-12.57 (m, 1H), 10.34-10.26 (m, 1H), 8.12 (s, 1H), 7.44-7.36 (m, 1H), 7.27-7.19 (m, 1H), 7.09-7.02 (m, 1H), 4.60-4.45 (m, 1H), 4.29-4.19 (m, 1H), 3.71-3.60 (m, 1H), 3.55-3.44 (m, 1H), 3.42-3.30 (m, 1H), 2.69-2.40 (m, 1H), 2.34-2.22 (m, 1H), 1.81-1.65 (m, 1H), 1.12-1.01 (m, 3H). |
| T8 | 1H-NMR (DMSO-d6) δ: 12.68 (s, 1H), 10.30 (t, 1H, J = 6.0 Hz), 8.32-8.25 (m, 1H), 8.15 (s, 1H), 7.42-7.34 (m, 1H), 7.25-7.18 (m, 1H), 7.08-7.01 (m, 1H), 4.55-4.49 (m, 2H), 4.11 (d, 1H, J = 13.6 Hz), 3.68 (d, 1H, J = 13.6 Hz), 3.56-3.46 (m, 1H), 3.34-3.20 (m, 1H), 2.60 (d, 3H, J = 4.6 Hz), 2.40-2.30 (m, 1H), 2.14 (t, 1H, J = 8.6 Hz), 1.62 (t, 1H, J = 7.6 Hz), 1.03 (t, 3H, J = 7.2 Hz). |
| T9 | 1H-NMR (DMSO-d6) δ: 12.73 (s, 1H), 10.35 (t, 1H, J = 5.0 Hz), 8.10 (s, 1H), 7.43-7.35 (m, 1H), 7.27-7.19 (m, 1H), 7.09-7.02 (m, 1H), 4.52 (d, 2H, J = 6.0 Hz), 3.97 (d, 1H, J = 14.1 Hz), 3.71 (d, 1H, J = 14.1 Hz), 3.66-3.57 (m, 2H), 3.49-3.35 (m, 2H), 3.24 (s, 3H), 1.96-1.85 (m, 2H), 1.15 (t, 3H, J = 7.3 Hz), 1.14-1.08 (m, 1H). |

TABLE 2-12

| Example No. | 1H-NMR (DMSO-d6) δ (peak, integ., J) |
|---|---|
| T10 | 1H-NMR (DMSO-d6) δ: 12.82-12.64 (m, 1H), 10.37 (t, 1H, J = 6.0 Hz), 8.14 (s, 1H), 7.43-7.35 (m, 3H), 7.27-7.19 (m, 1H), 7.10-7.02 (m, 1H), 4.52 (d, 2H, J = 6.0 Hz), 3.85 (s, 2H), 3.76 (dd, 1H, J = 11.7, 5.1 Hz), 3.65-3.55 (m, 1H), 3.54-3.42 (m, 2H), 1.96-1.86 (m, 1H), 1.69 (dd, 1H, J = 10.8, 6.8 Hz), 1.29-1.21 (m, 1H), 1.16 (t, 3H, J = 7.3 Hz), 1.07 (t, 1H, J = 7.3 Hz). |
| T11 | 1H-NMR (DMSO-d6) δ: 12.90-12.74 (m, 1H), 10.43 (t, 1H, J = 5.6 Hz), 8.14 (s, 1H), 7.49 (t, 1H, J = 7.3 Hz), 7.31 (t, 1H, J = 6.9 Hz), 7.19 (t, 1H, J = 8.1 Hz), 4.80-4.68 (m, 1H), 4.59 (d, 2H, J = 6.0 Hz), 3.80-3.68 (m, 3H), 3.57-3.47 (m, 1H), 1.95-1.84 (m, 1H), 1.76-1.66 (m, 1H), 1.31-1.22 (m, 1H), 1.19 (d, 3H, J = 6.9 Hz), 1.17 (d, 3H, J = 6.9 Hz), 1.03 (t, 1H, J = 7.3 Hz). |
| T12 | 1H-NMR (DMSO-d6) δ: 12.89-12.76 (m, 1H), 10.46-10.35 (m, 1H), 8.10 (s, 1H), 7.49 (t, 1H, J = 7.7 Hz), 7.31 (t, 1H, J = 7.3 Hz), 7.19 (t, 1H, J = 7.7 Hz), |

TABLE 2-12-continued

| Example No. | 1H-NMR (DMSO-d6) δ (peak, integ., J) |
|---|---|
| | 4.79-4.68 (m, 1H), 4.59 (d, 2H, J = 6.0 Hz), 3.80 (d, 1H, J = 14.1 Hz), 3.67 (d, 1H, J = 14.1 Hz), 3.61-3.53 (m, 1H), 3.51-3.42 (m, 1H), 3.23 (s, 3H), 1.95-1.83 (m, 2H), 1.18 (d, 6H, J = 6.9 Hz), 1.11-1.03 (m, 1H). |
| T13 | 1H-NMR (DMSO-d6) δ: 12.84-12.65 (m, 1H), 10.41 (t, 1H, J = 6.0 Hz), 8.15 (s, 1H), 7.51-7.46 (m, 1H), 7.35-7.29 (m, 1H), 7.22-7.16 (m, 1H), 4.71-4.61 (m, 2H), 4.59-4.51 (m, 1H), 3.99 (d, 1H, J = 13.7 Hz), 3.30 (d, 1H, J = 13.7 Hz), 2.94 (s, 3H), 2.81 (s, 3H), 2.73-2.65 (m, 1H), 2.45-2.36 (m, 1H), 1.75 (t, 1H, J = 7.3 Hz), 1.09 (d, 3H, J = 6.9 Hz), 0.95 (d, 3H, J = 6.4 Hz). |
| T14 | 1H-NMR (DMSO-d6) δ: 12.84-12.65 (m, 1H), 10.41 (t, 1H, J = 6.0 Hz), 8.15 (s, 1H), 7.51-7.46 (m, 1H), 7.35-7.29 (m, 1H), 7.22-7.16 (m, 1H), 4.71-4.61 (m, 2H), 4.59-4.51 (m, 1H), 3.99 (d, 1H, J = 13.7 Hz), 3.30 (d, 1H, J = 13.7 Hz), 2.94 (s, 3H), 2.81 (s, 3H), 2.73-2.65 (m, 1H), 2.45-2.36 (m, 1H), 1.75 (t, 1H, J = 7.3 Hz), 1.09 (d, 3H, J = 6.9 Hz), 0.95 (d, 3H, J = 6.4 Hz). |
| T15 | 1H-NMR (DMSO-d6) δ: 12.70 (s, 1H), 10.42 (t, 1H, J = 6.0 Hz), 8.14 (s, 1H), 7.52-7.46 (m, 1H), 7.34-7.28 (m, 1H), 7.22-7.16 (m, 1H), 4.94-4.79 (m, 1H), 4.59 (d, 2H, J = 5.0 Hz), 3.91 (d, 1H, J = 13.9 Hz), 3.81-3.72 (m, 2H), 3.44-3.26 (m, 1H), 3.08 (s, 3H), 1.94-1.83 (m, 1H), 1.75-1.68 (m, 1H), 1.12 (t, 1H, J = 6.9 Hz). |
| T16 | 1H-NMR (DMSO-d6) δ: 12.68 (s, 1H), 10.44-10.38 (m, 1H), 8.10 (s, 1H), 7.52-7.45 (m, 1H), 7.34-7.28 (m, 1H), 7.22-7.16 (m, 1H), 4.59 (d, 2H, J = 6.0 Hz), 4.02 (d, 1H, J = 14.1 Hz), 3.67-3.59 (m, 2H), 3.41-3.31 (m, 1H), 3.25 (s, 3H), 3.05 (s, 3H), 1.95-1.84 (m, 2H), 1.20-1.13 (m, 1H). |
| T17 | 1H-NMR (DMSO-d6) δ: 12.74 (s, 1H), 10.42 (t, 1H, J = 6.0 Hz), 8.14 (s, 1H), 7.52-7.46 (m, 1H), 7.34-7.28 (m, 1H), 7.22-7.16 (m, 1H), 4.90-4.84 (m, 1H), 4.59 (d, 2H, J = 6.0 Hz), 3.85 (s, 2H), 3.79-3.72 (m, 1H), 3.67-3.54 (m, 1H), 3.54-3.41 (m, 2H), 1.97-1.86 (m, 1H), 1.73-1.66 (m, 1H), 1.16 (t, 3H, J = 7.2 Hz), 1.07 (t, 1H, J = 6.9 Hz). |
| T18 | 1H-NMR (DMSO-d6) δ: 12.74 (s, 1H), 10.42 (t, 1H, J = 5.0 Hz), 8.14 (s, 1H), 7.52-7.46 (m, 1H), 7.34-7.28 (m, 1H), 7.22-7.16 (m, 1H), 4.90-4.84 (m, 1H), 4.59 (d, 2H, J = 6.0 Hz), 3.85 (s, 2H), 3.79-3.72 (m, 1H), 3.67-3.54 (m, 1H), 3.54-3.41 (m, 2H), 1.97-1.86 (m, 1H), 1.73-1.66 (m, 1H), 1.16 (t, 3H, J = 7.2 Hz), 1.07 (t, 1H, J = 6.9 Hz). |

TABLE 2-13

| Example No. | 1H-NMR (DMSO-d6) δ (peak, integ., J) |
|---|---|
| T19 | 1H-NMR (DMSO-d6) δ: 12.81-12.64 (m, 1H), 10.52-10.30 (m, 1H), 8.21-8.01 (m, 1H), 7.63-6.98 (m, 3H), 4.74-4.46 (m, 2H), 4.12-3.84 (m, 1H), 3.83-3.05 (m, 8H), 2.00-1.79 (m, 2H), 1.49-0.75 (m, 4H). |
| T20 | 1H-NMR (DMSO-d6) δ: 12.74 (s, 1H), 10.41 (t, 1H, J = 6.0 Hz), 8.10 (s, 1H), 7.51-7.46 (m, 1H), 7.34-7.28 (m, 1H), 7.22-7.16 (m, 1H), 4.59 (d, 2H, J = 6.0 Hz), 3.96 (d, 1H, J = 14.1 Hz), 3.71 (d, 1H, J = 14.1 Hz), 3.66-3.57 (m, 2H), 3.49-3.37 (m, 2H), 3.24 (s, 3H), 1.96-1.84 (m, 2H), 1.15 (t, 3H, J = 7.2 Hz), 1.14-1.09 (m, 1H). |
| T21 | 1H-NMR (DMSO-d6) δ: 12.73-12.63 (m, 1H), 10.38 (t, 1H, J = 6.0 Hz), 8.10 (s, 1H), 7.07 (dd, 1H, J = 5.6, 2.8 Hz), 6.85 (dd, 1H, J = 5.6, 3.2 Hz), 4.54 (d, 2H, J = 6.0 Hz), 4.03 (d, 1H, J = 13.7 Hz), 3.73 (s, 3H), 3.68-3.59 (m, 2H), 3.40-3.33 (m, 1H), 3.25 (s, 3H), 3.06 (s, 3H), 1.96-1.83 (m, 2H), 1.19-1.13 (m, 1H). |
| T22 | 1H-NMR (DMSO-d6) δ: 12.79-12.51 (m, 1H), 10.33 (t, 1H, J = 6.0 Hz), 8.10 (s, 1H), 7.30 (t, 1H, J = 8.9 |

TABLE 2-13-continued

| Example No. | 1H-NMR (DMSO-d6) δ (peak, integ., J) |
|---|---|
|  | Hz), 6.98 (dd, 1H, J = 8.9, 1.6 Hz), 4.51 (d, 2H, J = 6.0 Hz), 4.06-3.99 (m, 1H), 3.87 (s, 3H), 3.67-3.59 (m, 2H), 3.40-3.33 (m, 1H), 3.25 (s, 3H), 3.06 (s, 3H), 1.95-1.82 (m, 2H), 1.21-1.14 (m, 1H). |
| T23 | 1H-NMR (DMSO-d6) δ: 12.70 (br s, 1H), 10.42 (t, 1H, J = 6.0 Hz), 8.14 (s, 1H), 7.52-7.45 (m, 1H), 7.35-7.28 (m, 1H), 7.22-7.16 (m, 1H), 4.59 (d, 2H, J = 6.0 Hz), 3.91 (d, 1H, J = 13.9 Hz), 3.81-3.73 (m, 2H), 3.48-3.32 (m, 1H), 3.08 (s, 3H), 1.92-1.82 (m, 1H), 1.76-1.68 (m, 1H), 1.12 (t, 1H, J = 7.2 Hz). |
| T24 | 1H-NMR (DMSO-d6) δ: 12.68 (br s, 1H), 10.41 (t, 1H, J = 6.0 Hz), 8.10 (s, 1H), 7.52-7.45 (m, 1H), 7.35-7.28 (m, 1H), 7.22-7.16 (m, 1H), 4.59 (d, 2H, J = 6.0 Hz), 4.03 (d, 1H, J = 14.1 Hz), 3.68-3.59 (m, 2H), 3.45-3.32 (m, 1H), 3.25 (s, 3H), 3.06 (s, 3H), 1.95-1.81 (m, 2H), 1.21-1.12 (m, 1H). |
| T25 | 1H-NMR (DMSO-d6) δ: 12.79-12.58 (m, 1H), 10.38 (t, 1H, J = 6.0 Hz), 8.10 (s, 1H), 7.05 (dd, 1H, J = 5.6, 3.2 Hz), 6.82 (dd, 1H, J = 5.6, 3.2 Hz), 4.54 (d, 2H, J = 6.0 Hz), 4.03 (d, 1H, J = 13.7 Hz), 3.99 (q, 2H, J = 6.9 Hz), 3.68-3.59 (m, 2H), 3.41-3.33 (m, 1H), 3.25 (s, 3H), 3.06 (s, 3H), 1.97-1.82 (m, 2H) 1.28 (t, 3H, J = 6.9 Hz), 1.20-1.13 (m, 1H). |
| T26 | 1H-NMR (DMSO-d6) δ: 12.87-12.54 (m, 1H), 10.38 (t, 1H, J = 6.0 Hz), 8.10 (s, 1H), 7.05 (dd, 1H, J = 5.6, 3.2 Hz), 6.80 (dd, 1H, J = 5.6, 3.2 Hz), 4.60-4.51 (m, 1H), 4.54 (d, 2H, J = 6.0 Hz), 4.03 (d, 1H, J = 14.1 Hz), 3.68-3.59 (m, 2H), 3.40-3.33 (m, 1H), 3.25 (s, 3H), 3.06 (s, 3H), 1.98-1.82 (m, 2H), 1.22 (d, 6H, J = 6.0 Hz), 1.20-1.13 (m, 1H). |
| T27 | 1H-NMR (DMSO-d6) δ: 12.74 (s, 1H), 10.44 (t, 1H, J = 6.0 Hz), 8.10 (s, 1H), 7.72-7.63 (m, 2H), 7.38 (t, 1H, J = 7.6 Hz), 4.63 (d, 2H, J = 6.0 Hz), 3.96 (d, 1H, J = 13.9 Hz), 3.71 (d, 1H, J = 13.9 Hz), 3.69-3.57 (m, 2H), 3.50-3.37 (m, 2H), 3.24 (s, 3H), 1.97-1.84 (m, 2H), 1.15 (t, 3H, J = 7.4 Hz), 1.15-1.08 (m, 1H). |

TABLE 2-14

| Example No. | 1H-NMR (DMSO-d6) δ (peak, integ., J) |
|---|---|
| T28 | 1H-NMR (DMSO-d6) δ: 12.89-12.38 (m, 1H), 10.44 (t, 1H, J = 6.0 Hz), 8.15 (s, 1H), 7.52-7.46 (m, 1H), 7.35-7.29 (m, 1H), 7.23-7.17 (m, 1H), 4.79-4.70 (m, 1H), 4.66-4.54 (m, 2H), 4.04 (d, 1H, J = 13.5 Hz), 3.52 (dd, 1H, J = 11.9, 4.0 Hz), 3.18 (d, 1H, J = 13.5 Hz), 2.69-2.55 (m, 1H), 1.98-1.87 (m, 1H), 1.45-1.35 (m, 2H), 1.18 (d, 3H, J = 6.6 Hz), 1.12 (d,3H, J = 6.8 Hz), 0.91-0.81 (m, 1H). |
| T29 | 1H-NMR (DMSO-d6) δ: 12.70-12.47 (m, 1H), 10.43 (t, 1H, J = 5.8 Hz), 8.15 (s, 1H), 7.52-7.46 (m, 1H), 7.35-7.29 (m, 1H), 7.23-7.17 (m, 1H), 4.60 (d, 2H, J = 5.6 Hz), 4.27 (d, 1H, J = 13.4 Hz), 3.66-3.55 (m, 1H), 3.54-3.37 (m, 2H), 3.15 (d, 1H, J = 13.4 Hz), 2.69-2.53 (m, 1H), 1.91 (t, 1H, J = 6.9 Hz), 1.60-1.49 (m, 1H), 1.34 (dd, 1H, J = 9.2, 7.9 Hz), 1.14 (t, 3H, J = 7.4 Hz). |
| T30 | 1H-NMR (DMSO-d6) δ: 12.57 (s, 1H), 10.40 (t, 1H, J = 6.0 Hz), 8.18 (s, 1H), 7.52-7.46 (m, 1H), 7.35-7.29 (m, 1H), 7.23-7.17 (m, 1H), 4.60 (d, 2H, J = 6.0 Hz), 4.27 (d, 1H, J = 13.4 Hz), 3.66-3.56 (m, 1H), 3.48-3.38 (m, 2H), 3.17 (d, 1H, J = 13.4 Hz), 2.93 (s, 3H), 2.03 (t, 1H, J = 6.9 Hz), 1.72-1.62 (m, 1H), 1.43 (dd, 1H, J = 9.9, 8.1 Hz), 1.20-1.11 (m, 4H). |
| T31 | 1H-NMR (DMSO-d6) δ: 12.70-12.63 (m, 1H), 10.34 (t, 1H, J = 6.0 Hz), 8.09 (s, 1H), 7.30 (t, 1H, J = 8.9 Hz), 6.98 (d, 1H, J = 8.9 Hz), 4.51 (d, 2H, J = 5.6 Hz), 4.04 (d, 1H, J = 13.7 Hz), 3.87 (s, 3H), 3.73-3.56 (m, 2H), 3.50-3.32 (m, 3H), 3.06 (s, 3H), 2.00-1.79 (m, 2H), 1.20-1.05 (m, 4H). |

TABLE 2-14-continued

| Example No. | 1H-NMR (DMSO-d6) δ (peak, integ., J) |
|---|---|
| T32 | 1H-NMR (DMSO-d6) δ: 12.67 (s, 1H), 10.45-10.34 (m, 1H), 8.13 (s, 1H), 7.53-7.44 (m, 1H), 7.37-7.27 (m, 1H), 7.25-7.14 (m, 1H), 4.73-4.48 (m, 2H), 4.14 (d, 1H, J = 13.7 Hz), 3.16 (d, 1H, J = 13.7 Hz), 2.90 (s, 3H), 2.85 (s, 3H), 2.84-2.76 (m, 1H), 2.71-2.61 (m, 1H), 2.49-2.30 (m, 1H), 1.74 (t, 1H, J = 7.3 Hz), 0.97-0.81 (m, 1H), 0.73-0.62 (m, 1H), 0.57-0.45 (m, 2H). |
| T33 | 1H-NMR (DMSO-d6) δ: 12.67 (s, 1H), 10.45-10.34 (m, 1H), 8.13 (s, 1H), 7.53-7.44 (m, 1H), 7.37-7.27 (m, 1H), 7.25-7.14 (m, 1H), 4.73-4.48 (m, 2H), 4.14 (d, 1H, J = 13.7 Hz), 3.16 (d, 1H, J = 13.7 Hz), 2.90 (s, 3H), 2.85 (s, 3H), 2.84-2.76 (m, 1H), 2.71-2.61 (m, 1H), 2.49-2.30 (m, 1H), 1.74 (t, 1H, J = 7.3 1Hz), 0.97-0.81 (m, 1H, 0.73-0.62 (m, 1H), 0.57-0.45 |
| T34 | 1H-NMR (DMSO-d6) δ: 12.70-12.64 (m, 1H), 10.39 (t, 1H, J = 6.0 Hz), 8.09 (s, 1H), 7.84-7.79 (m, 1H), 17.62-7.57 (m, 1H), 4.58 (d, 2H, J = 6.0 Hz), 4.06-3.98 (m, 1H), 3.82-3.74 (m, 2H), 3.67-3.58 (m, 2H), 3.40-3.31 (m, 1H), 3.25 (s, 3H), 3.06 (s, 3H), 2.51-2.45 (m, 2H), 2.09-1.97 (m, 2H), 1.95-1.82 (m, 2H), 1.20-1.13 (m, 1H). |
| T35 | 1H-NMR (DMSO-d6) δ: 12.76-12.58 (m, 1H), 10.34 (t, 1H, J = 6.0 Hz), 8.09 (s, 1H), 7.30 (t, 1H, J = 8.9 Hz), 6.98 (dd, 1H, J = 8.9, 1.6 Hz), 4.51 (d, 2H, J = 6.0 Hz), 4.04 (d, 1H, J = 13.7 Hz), 3.87 (s, 3H), 3.72-3.59 (m, 2H), 3.50-3.34 (m, 3H), 3.06 (s, 3H), 1.96-1.80 (m, 2H), 1.20-1.13 (m, 1H), 1.10 (t, 3H), J = 6.9 Hz). |
| T36 | 1H-NMR (DMSO-d6) δ: 12.79-12.51 (m, 1H), 10.33 (t, 1H, J = 6.0 Hz), 8.10 (s, 1H), 7.30 (t, 1H, J = 8.9 Hz), 6.98 (dd, 1H, J = 8.9, 1.6 Hz), 4.51 (d, 2H, J = 6.0 Hz), 4.06-3.99(m, 1H), 3.87 (s, 3H), 3.67-3.59 (m, 2H), 3.40-3.33 (m, 1H), 3.25 (s, 3H), 3.06 (s, 3H, 1.95-1.82 (m, 2H), 1.21-1.14 (m, 1H). |

TABLE 2-15

| Example No. | 1H-NMR (DMSO-d6) δ (peak, integ., J) |
|---|---|
| T37 | 1H-NMR (DMSO-d6) δ: 12.72-12.60 (m, 1H), 10.33 (t, 1H, J = 6.0 Hz), 8.10 (s, 1H), 7.27 (t, 1H, J = 8.6 Hz), 6.96 (dd, 1H, J = 8.6, 1.4 Hz), 4.51 (d, 2H, J = 6.0 Hz), 4.13 (q, 2H, J = 6.9 Hz), 4.02 (d, 1H, J = 14.1 Hz), 3.68-3.59 (m, 2H), 3.41-3.32 (m, 1H), 3.25 (s, 3H), 3.06 (s, 3H), 1.95-1.82 (m, 2H), 1.35 (t, 3H, J = 6.9 Hz), 1.20-1.13 (m, 1H). |
| T38 | 1H-NMR (DMSO-d6) δ: 12.72-12.60 (m, 1H), 10.33 (t, 1H, J = 6.0 Hz), 8.10 (s, 1H), 7.27 (t, 1H, J = 8.6 Hz), 6.96 (dd, 1H, J = 8.6, 1.4 Hz), 4.51 (d, 2H, J = 6.0 Hz), 4.13 (q, 2H, J = 6.9 Hz), 4.02 (d, 1H, J = 14.1 Hz), 3.68-3.59 (m, 2H), 3.41-3.32 (m, 1H), 3.25 (s, 3H), 3.06 (s, 3H), 1.95-1.82 (m, 2H), 1.35 (t, 3H, J = 6.9 Hz), 1.20-1.13 (m, 1H). |
| T39 | 1H-NMR (DMSO-d6) δ: 12.11-11.99 (m, 1H), 10.45 (t, 1H, J = 6.0 Hz), 8.37 (s, 1H), 7.43-7.35 (m, 1H), 7.26-7.19 (m, 1H), 7.08-7.01 (m, 1H), 4.52 (d, 2H, J = 6.0 Hz), 4.43 (s, 2H), 3.72 (dd, 1H, J = 11.8, 5.3 Hz), 3.47-3.19 (m, 3H), 1.76-1.65 (m, 1H), 1.35-1.28 (m, 1H), 1.08 (t, 3H, J = 7.2 Hz), 0,90 (t, 1H, J = 6.9 Hz). |
| T40 | 1H-NMR (DMSO-d6) δ: 11.95 (s, 1H), 10.42 (t, 1H, J = 6.0 Hz), 8.39 (s, 1H), 7.42-7.34 (m, 1H), 7.26-7.19 (m, 1H), 7.09-7.01 (m, 1H), 4.56-4.50 (m, 2H), 4.47 (d, 1H, J = 13.6 Hz), 4.39 (d, 1H, J = 13.6 Hz), 3.62 (dd, 1H, J = 10.9, 5.8 Hz), 3.49-3.22 (m, 3H), 3.11 (s, 3H), 1.83-1.73 (m, 1H), 1.46-1.39 (m, 1H), 1.06 (t, 3H, J = 6.9 Hz), 0.96 (t, 1H, J = 6.9 Hz). |
| T41 | 1H-NMR (DMSO-d6) δ: 11.96 (s, 1H), 10.45 (t, 1H, J = 5.6 Hz), 8.39 (s, 1H), 7.44-7.36 (m, 1H), 7.28-7.20 (m, 1H), 7.10-7.02 (m, 1H), 4.61-4.44 (m, 3H), 4.38 (d, 1H, J = 13.7 Hz), 4.22-4.11 (m, 1H), 3.59 (dd, 1H, J = 10.9, 6.0 Hz), 3.27-3.18 (m, 1H), 3.09 (s, |

TABLE 2-15-continued

| Example No. | 1H-NMR (DMSO-d6) δ (peak, integ., J) |
|---|---|
|  | 3H), 1.85-1.74 (m, 1H), 1.63-1.56 (m, 1H), 1.31 (d, 3H, J = 6.9 Hz), 1.31 (d, 3H, J = 6.9 Hz), 0.96 (t, 1H, J = 7.3 Hz). |
| T42 | 1H-NMR (DMSO-d6) δ: 12.13-12.00 (m, 1H), 10.47 (t, 1H, J = 6.0 Hz), 8.36 (s, 1H), 7.45-7.37 (m, 1H), 7.28-7.20 (m, 1H), 7.10-7.02 (m, 1H), 4.54 (d, 2H, J = 6.0 Hz), 4.42 (s, 2H), 4.22-4.12 (m, 1H), 3.69 (dd, 1H, J = 11.7, 5.6 Hz), 3.32 (dd, 1H, J = 11.7, 8.5 Hz), 1.83-1.72 (m, 1H), 1.45 (dd, 1H, J = 10.1, 6.4 Hz), 1.35-1.29 (m, 6H), 1.29-1.20 (m, 1H), 0.92-0.83 (m, 1H). |
| T43 | 1H-NMR (DMSO-d6) δ: 11.95-11.88 (m, 1H), 10.46 (t, 1H, J = 5.6 Hz), 8.36 (s, 1H), 7.42-7.34 (m, 1H), 7.27-7.20 (m, 1H), 7.09-7.01 (m, 1H), 4.60-4.47 (m, 3H), 4.34 (d, 1H, J = 13.7 Hz), 4.22-4.11 (m, 1H), 3.63 (dd, 1H, J = 10.9, 5.2 Hz), 3.30-3.13 (m, 3H), 1.75-1.59 (m, 2H), 1.31 (t, 6H, J = 6.4 Hz), 0.97 (t, 1H, J = 6.4 Hz), 0.82 (t, 3H, J = 7.3 Hz). |
| T44 | 1H-NMR (DMSO-d6) δ: 12.08 (s, 1H), 10.52 (t, 1H, J = 6.0 Hz), 8.38 (s, 1H), 7.53-7.46 (m, 1H), 7.35-7.29 (m, 1H), 7.23-7.17 (m, 1H), 4.61 (d, 2H, J = 6.0 Hz), 4.44 (s, 2H), 3.74 (dd, 1H, J = 11.8, 5.8 Hz), 3.47-3.26 (m, 3H), 1.78-1.67 (m, 1H), 1.33 (dd, 1H, J = 10.4, 6.5 Hz), 1.09 (t, 3H, J = 7.2 Hz), 0.92 (t, 1H, J = 6.9 Hz). |
| T45 | 1H-NMR (DMSO-d6) δ: 11.97-11.91 (m, 1H), 10.50 (t, 1H, J = 5.6 Hz), 8.39 (s, 1H), 7.52-7.46 (m, 1H), 7.33-7.26 (m, 1H), 7.22-7.16 (m, 1H), 4.64-4.59 (m, 2H), 4.52 (d, 1H, J = 13.7 Hz), 4.38 (d, 1H, J = 13.7 Hz), 3.69 (dd, 1H, J = 10.5, 5.6 Hz), 3.59-3.48 (m, 1H), 3.36-3.19 (m, 4H), 1.76-1.65 (m, 1H), 1.56-1.48 (m, 1H), 1.08 (t, 3H, J = 7.3 Hz), 0.97 (t, 1H, J = 7.3 Hz), 0.86 (t, 3H, J = 7.3 Hz). |

TABLE 2-16

| Example No. | 1H-NMR (DMSO-d6) δ (peak, integ., J) |
|---|---|
| T46 | 1H-NMR (DMSO-d6) δ: 12.08 (s, 1H), 10.52 (t, 1H, J = 6.0 Hz), 8.38 (s, 1H), 7.53-7.46 (m, 1H), 7.35-7.29 (m, 1H), 7.23-7.17 (m, 1H), 4.61 (d, 2H, J = 6.0 Hz), 4.44 (s, 2H), 3.74 (dd, 1H, J = 11.8, 5.8 Hz), 3.47-3.26 (m, 3H), 1.78-1.67 (m, 1H), 1.33 (dd, 1H, J = 10.4, 6.5 Hz), 1.09 (t, 3H, J = 7.2 Hz), 0.92 (t, 1H, J = 6.9 Hz). |
| T47 | 1H-NMR (DMSO-d6) δ: 12.13-12.00 (m, 1H), 10.53 (t, 1H, J = 6.0 Hz), 8.36 (s, 1H), 7.53-7.46 (m, 1H), 7.36-7.29 (m, 1H), 7.24-7.17 (m, 1H), 4.68 (t, 1H, J = 4.8 Hz), 4.61 (d, 2H, J = 5.6 Hz), 4.42 (s, 2H), 4.23-4.12 (m, 1H), 3.73-3.65 (m, 1H), 1.84-1.71 (m, 1H), 1.49-1.40 (m, 1H), 1.33 (d, 3H, J = 6.9 Hz), 1.32 (d, 3H, J = 6.9 Hz), 1.29-1.21 (m, 1H), 0.93-0.83 (m, 1H). |
| T48 | 1H-NMR (DMSO-d6) δ: 12.17-11.93 (m, 1H), 10.44 (t, 1H, J = 6.0 Hz), 8.38 (s, 1H), 7.34-7.23 (m, 1H), 7.01-6.95 (m, 1H), 4.53 (d, 2H, J = 6.0 Hz), 4.44 (s, 2H), 3.87 (s, 3H), 3.77-3.70 (m, 1H), 3.46-3.29 (m, 3H), 1.78-1.67 (m, 1H), 1.33 (dd, 1H, J = 10.1, 6.4 Hz), 1.29-1.21 (m, 1H), 1.09 (t, 3H, J = 7.3 Hz), 0.91 (t, 1H, J = 6.9 Hz). |
| T49 | 1H-NMR (DMSO-d6) δ: 12.22 (br s, 1H), 10.52 (t, J = 6.0 Hz), 8.39 (s, 1H), 7.53-7.47 (m, 1H), 7.35-7.30 (m, 1H), 7.23-7.17 (m, 1H), 4.70-4.65 (m, 1H), 4.61 (d, 1H, J = 6.0 Hz), 4.51 (d, 1H, J = 13.7 Hz), 4.45 (d, 1H, J = 13.7 Hz), 3.79-3.65 (m, 1H), 3.44-3.28 (m, 1H), 2.89 (s, 3M), 1.83-1.70 (m, 1H), 1.45 (dd, 1H, J = 10.1, 6.6 Hz), 0.86 (t, 1H, J = 7.3 Hz). |
| T50 | 1H-NMR (DMSO-d6) δ: 12.13 (s, 1H), 10.49 (t, 1H, J = 6.2 Hz), 8.41 (s, 1H), 7.52-7.47 (m, 1H), 7.34-7.28 (m, 1H), 7.23-7.17 (m, 1H), 4.65-4.59 (m, 2H), 4.55 (d, 1H, J = 13.6 Hz), 4.42 (d, 1H, J = 13.6 Hz), 3.61 (dd, 1H, J = 10.9, 6.0 Hz), 3.33-3.24 (m, 1H), |

TABLE 2-16-continued

| Example No. | 1H-NMR (DMSO-d6) δ (peak, integ., J) |
|---|---|
|  | 3.11 (s, 3H), 2.88 (s, 3H), 1.90-1.79 (m, 1H), 1.55 (dd, 1H, J = 10.2, 6.7 Hz), 0.91 (t, 1H, J = 6.7 Hz). |

TABLE 3-1

| Example No. | Mass (m/z) |
|---|---|
| 1 | 484 (M − 1) |
| 2 | 484 (M − 1) |
| 3 | 498 (M − 1) |
| 4 | 498 (M − 1) |
| 5 | 498 (M − 1) |
| 6 | 498 (M − 1) |
| 7 | 528 (M − 1) |
| 8 | 528 (M − 1) |
| 9 | 448 (as free form, M + 1) |
| 10 | 462 (as free form, M + 1) |
| 11 | 482 (M − 1) |
| 12 | 496 (M − 1) |
| 13 | 482 (M − 1) |
| 14 | 462 (M + 1) |
| 15 | 482 (M − 1) |
| 16 | 462 (M + 1) |
| 17 | 464 (M + 1) |
| 18 | 464 (M + 1) |
| 19 | 509 (M − 1) |
| 20 | 537 (M − 1) |

TABLE 3-2

| Example No. | Mass (m/z) |
|---|---|
| 21 | 560 (M − 1) |
| 22 | 498 (M − 1) |
| 23 | 450 (M + 1) |
| 24 | 472 (M + 1) |
| 25 | 450 (as free form, M + 1) |
| 26 | 464 (M + 1) |
| 27 | 464 (M + 1) |
| 28 | 486 (M + 1) |
| 29 | 502 (M + 1) |
| 30 | 463 (as free form, M + 1) |
| 31 | 542 (M − 1) |
|  | 544 (M − 1) |
| 32 | 560 (M − 1) |
| 33 | 634 (M − 1) |
| 34 | 464 (M + 1) |
| 35 | 486 (M + 1) |
| 36 | 502 (M + 1) |
| 37 | 506 (M + 1) |
| 38 | 535 (M + 1) |
| 39 | 562 (M + 1) |
| 40 | 634 (M + 1) |

TABLE 3-3

| Example No. | Mass (m/z) |
|---|---|
| S1 | 572 (M − 1) |
| S2 | 572 (M − 1) |
| S3 | 526 (M − 1) |
|  | 528 (M − 1) |
| S4 | 448 (M + 1) |
| S5 | 496 (M − 1) |
| S6 | 496 (M − 1) |
| S7 | 476 (as free form, M + 1) |

TABLE 3-3-continued

| Example No. | Mass (m/z) |
| --- | --- |
| S8 | 540 (M − 1) |
| S9 | 510 (as free form, M + 1) |
| S10 | 544 (M − 1) |
| S11 | 498 (M − 1) |
|  | 500 (M − 1) |
| S12 | 498 (M − 1) |
|  | 500 (M − 1) |
| S13 | 468 (M − 1) |
| S14 | 468 (M − 1) |
| S15 | 558 (M − 1) |
| S16 | 558 (M − 1) |
| S17 | 512 (M − 1) |
|  | 514 (M − 1) |
| S18 | 512 (M − 1) |
|  | 514 (M − 1) |
| S19 | 482 (M − 1) |
| S20 | 482 (M − 1) |

TABLE 3-4

| Example No. | Mass (m/z) |
| --- | --- |
| S21 | 496 (M − 1) |
| S22 | 542 (M − 1) |
|  | 540 (M − 1) |
| S23 | 510 (M − 1) |
| S24 | 542 (M − 1) |
|  | 540 (M − 1) |
| S25 | 510 (M − 1) |
| S26 | 470 (M − 1) |
| S27 | 470 (M − 1) |
| S28 | 498 (M − 1) |
| S29 | 498 (M − 1) |
| S30 | 523 (M − 1) |
| S31 | 537 (M − 1) |
| S32 | 524 (M − 1) |
| S33 | 524 (M − 1) |
| S34 | 560 (M − 1) |
| S35 | 560 (M − 1) |
| S36 | 450 (M + 1) |
| S37 | 484 (M − 1) |
| S38 | 537 (M − 1) |
| S39 | 512 (M − 1) |
| S40 | 512 (M − 1) |

TABLE 3-5

| Example No. | Mass (m/z) |
| --- | --- |
| S41 | 512 (M − 1) |
| S42 | 512 (M − 1) |
| S43 | 512 (M − 1) |
| S44 | 498 (M − 1) |
| S45 | 512 (M − 1) |
| S46 | 498 (M − 1) |
| S47 | 478 (as free form, M + 1) |
| S48 | 492 (as free form, M + 1) |
| S49 | 480 (M + 1) |
| S50 | 480 (M + 1) |
| S51 | 482 (M − 1) |
| S52 | 462 (as free form, M + 1) |
| S53 | 496 (M − 1) |
| S54 | 482 (M − 1) |
| S55 | 482 (M − 1) |
| S56 | 478 (as free form, M + 1) |
| S57 | 478 (as free form, M + 1) |
| S58 | 498 (M − 1) |
| S59 | 478 (as free form, M + 1) |
| S60 | 498 (M − 1) |

TABLE 3-6

| Example No. | Mass (m/z) |
| --- | --- |
| S61 | 478 (as free form, M + 1) |
| S62 | 450 (as free form, M + 1) |
| S63 | 484 (M − 1) |
| S64 | 492 (M + 1) |
| S65 | 506 (M + 1) |
| S66 | 520 (M + 1) |
| S67 | 520 (M + 1) |
| S68 | 534 (M + 1) |
| S69 | 702 (M + 1) |
| S70 | 568 (M + 1) |
| S71 | 548 (M + 1) |
| S72 | 582 (M + 1) |
| S73 | 583 (as monohydrochloride, M − 1) |

TABLE 3-7

| Example No | Mass (m/z) |
| --- | --- |
| T1 | 468 (M − 1) |
| T2 | 482 (M − 1) |
| T3 | 468 (M − 1) |
| T4 | 454 (M − 1) |
| T5 | 498 (M − 1) |
| T6 | 478 (as free form, M + 1) |
| T7 | 448 (as free form, M + 1) |
| T8 | 495 (M − 1) |
| T9 | 482 (M − 1) |
| T10 | 468 (M − 1) |
| T11 | 498 (M − 1) |
| T12 | 478 (as free form, M + 1) |
| T13 | 539 (M − 1) |
| T14 | 505 (as free form, M + 1) |
| T15 | 470 (M − 1) |
| T16 | 484 (M − 1) |
| T17 | 484 (M − 1) |
| T18 | 484 (M − 1) |
| T19 | 464 (M + 1) |
| T20 | 498 (M − 1) |

TABLE 3-8

| Example No. | Mass (m/z) |
| --- | --- |
| T21 | 480 (M + 1) |
| T22 | 480 (M + 1) |
| T23 | 470 (M − 1) |
| T24 | 484 (M − 1) |
| T25 | 528 (M − 1) |
| T26 | 542 (M − 1) |
| T27 | 498 (M + 1) |
| T28 | 464 (as free form, M + 1) |
| T29 | 484 (M − 1) |
| T30 | 464 (M + 1) |
| T31 | 494 (M + 1) |
| T32 | 503 (M + 1) |
| T33 | 503 (M + 1) |
| T34 | 533 (M + 1) |
| T35 | 528 (M − 1) |
| T36 | 514 (M − 1) |
| T37 | 528 (M − 1) |
| T38 | 528 (M − 1) |
| T39 | 468 (M − 1) |
| T40 | 482 (M − 1) |

TABLE 3-9

| Example No. | Mass (m/z) |
|---|---|
| T41 | 462 (M + 1) |
| T42 | 448 (M + 1) |
| T43 | 476 (M + 1) |
| T44 | 450 (as free form, M + 1) |
| T45 | 478 (M + 1) |
| T46 | 484 (M − 1) |
| T47 | 464 (M + 1) |
| T48 | 514 (M − 1) |
| T49 | 436 (M + 1) |
| T50 | 450 (as free form, M + 1) |

Experimental Example 1

Evaluation of Antiviral Activity

The antiviral activity of the compound of the present invention was evaluated in an acute infection system of MT-4 cell with HIV-1 NL4-3 strain.
(i) Obtainment of HIV-1 NL4-3 Strain (Subclone AF324493.2)

A $5 \times 10^5$ cells/mL 293T cell suspension (2 mL) prepared using a medium was added to each well of a 6-well plate (manufactured by Corning Incorporated), and cultured at 37° C. for 24 hr. medium composition: D-MEM, 10% FBS (fetal bovine serum).

Then, using Lipofectamine 2000 (manufactured by Invitrogen), plasmid pNL4-3 was transfected at 2 μg/well, and cultured at 37° C. for 4 hr. The medium was exchanged with one containing 100 U/mL penicillin and 100 μg/mL streptomycin and, after culture for 48 hr, the virus in the culture supernatant was recovered.
medium composition: D-MEM, 10% FBS, 100 U/mL penicillin, 100 μg/mL streptomycin.
(ii) Measurement of Antiviral (HIV-1) Activity The medium (40 μL), a test substance (10 μL) diluted with the medium, and a $1 \times 10^5$ cells/mL MT-4 cell suspension (50 μL) wherein HIV-1 NL4-3 strain was infected with MOI (infection multiplicity) 0.05 were added to each well of a 96-well black plate (manufactured by Corning Incorporated), and the mixture was cultured at 37° C. for 5 days.
medium composition: RPMI1640, 10% FBS, 100 U/mL penicillin, 100 μg/mL streptomycin.

Then, Cell Titer-Glo (manufactured by Promega Corporation, 100 μL) was added to each well, and the mixture was stood at room temperature for 10 min, and the luminescence intensity was measured.

The antiviral activity ($EC_{50}$) of the compound of the present invention was calculated from the inhibition rate according to the following formula:

inhibition rate (%)=[(Object−Control)/(Mock control−Control)]×100

Object: (luminescence intensity of well in the presence of test compound and in the presence of infected cells)− [(luminescence intensity of Blank well (in the absence of test compound and in the absence of cells))]
Control: (luminescence intensity of well in the absence of test compound and in the presence of infected cells)− (luminescence intensity of Blank well)
Mock control: (luminescence intensity of well in the absence of test compound and in the presence of uninfected cells)− (luminescence intensity of Blank well)

The results are shown in the following Tables.

TABLE 4

| Example No. | $EC_{50}$ (nM) |
|---|---|
| 1 | 3.1 |
| 2 | 4.2 |
| 3 | 3.2 |
| 4 | 2.9 |
| 5 | 2.9 |
| 6 | 2 |
| 7 | 5 |
| 8 | 8.1 |
| 9 | 5.6 |
| 10 | 3.6 |
| 11 | 5.8 |
| 12 | 5 |
| 13 | 5.4 |
| 14 | 9.1 |
| 15 | 7.2 |
| 16 | 6.1 |
| 17 | 3.4 |
| 18 | 2.6 |
| 19 | 4.2 |
| 20 | 20 |
| 21 | 48 |

TABLE 5-1

| Example No. | $EC_{50}$ (nM) |
|---|---|
| S1 | 7.7 |
| S2 | 10 |
| S3 | 11 |
| S4 | 4.9 |
| S5 | 4.4 |
| S6 | 3.7 |
| S7 | 3.7 |
| S8 | 5.3 |
| S9 | 5.2 |
| S10 | 6.1 |
| S11 | 25 |
| S12 | 23 |
| S13 | 4.5 |
| S14 | 3.9 |
| S15 | 6.9 |
| S16 | 7.8 |
| S17 | 20 |
| S18 | 16 |
| S19 | 4.8 |
| S20 | 3.5 |
| S21 | 3.8 |

TABLE 5-2

| Example No. | $EC_{50}$ (nM) |
|---|---|
| S22 | 5 |
| S23 | 6.3 |
| S24 | 16 |
| S25 | 7 |
| S26 | 3.4 |
| S27 | 14 |
| S28 | 3.6 |
| S29 | 4.3 |
| S30 | 170 |
| S31 | 24 |
| S32 | 6.6 |
| S33 | 6.4 |
| S34 | 5.7 |
| S35 | 7.3 |
| S36 | 15 |
| S37 | 3.8 |
| S38 | 50 |
| S39 | 3.5 |

TABLE 5-2-continued

| Example No. | EC$_{50}$ (nM) |
|---|---|
| S40 | 2.3 |
| S41 | 3.5 |
| S42 | 4.3 |

TABLE 5-3

| Example No. | EC$_{50}$ (nM) |
|---|---|
| S43 | 4.7 |
| S44 | 11 |
| S45 | 3.9 |
| S46 | 4.4 |
| S47 | 3.5 |
| S48 | 4.3 |
| S49 | 65 |
| S50 | 37 |
| S51 | 2.4 |
| S52 | 3.5 |
| S53 | 10 |
| S54 | 27 |
| S55 | 33 |
| S56 | 5.1 |
| S57 | 4.7 |
| S58 | 6.8 |
| S59 | 4 |
| S60 | 13 |
| S61 | 5.1 |
| S62 | 4.6 |
| S63 | 4 |

TABLE 5-4

| Example No. | EC$_{50}$ (nM) |
|---|---|
| 22 | 400 |
| 23 | 1.6 |
| 24 | 0.9 |
| 25 | 2.1 |
| 26 | 1.9 |
| 27 | 1.5 |
| 28 | 2.2 |
| 29 | 2.5 |
| 30 | 1.1 |
| 31 | 1.9 |
| 32 | 0.9 |
| 33 | 0.9 |
| 34 | 3.2 |
| 35 | 3.7 |
| 36 | 2.6 |
| 37 | 0.7 |
| 38 | 110 |
| 39 | 1.4 |
| 40 | 1.0 |

TABLE 5-5

| Example No. | EC$_{50}$ (nM) |
|---|---|
| S64 | 2.8 |
| S65 | 1.0 |
| S66 | 0.9 |
| S67 | 0.9 |
| S68 | 0.7 |
| S69 | 1.0 |
| S70 | 1.4 |
| S71 | 1.9 |

TABLE 5-5-continued

| Example No. | EC$_{50}$ (nM) |
|---|---|
| S72 | 0.9 |
| S73 | 1.1 |

TABLE 6-1

| Example No. | EC$_{50}$ (nM) |
|---|---|
| T1 | 18 |
| T2 | 4.2 |
| T3 | 4.5 |
| T4 | 30 |
| T5 | 4 |
| T6 | 3.8 |
| T7 | 15 |
| T8 | 6.1 |
| T9 | 5.8 |
| T10 | 16 |
| T11 | 6 |
| T12 | 5.7 |
| T13 | 3.4 |
| T14 | 4.8 |
| T15 | 20 |
| T16 | 4.2 |
| T17 | 5.7 |
| T18 | 10 |
| T19 | 3.8 |
| T20 | 3.5 |

TABLE 6-2

| Example No. | EC$_{50}$ (nM) |
|---|---|
| T21 | 6.1 |
| T22 | 4.9 |
| T23 | 9.6 |
| T24 | 3.2 |
| T25 | 7 |
| T26 | 15 |
| T27 | 97 |
| T28 | 5.2 |
| T29 | 4.8 |
| T30 | 4.4 |
| T31 | 12 |
| T32 | 3.3 |
| T33 | 3.3 |
| T34 | 23 |
| T35 | 17 |
| T36 | 10 |
| T37 | 93 |
| T38 | 77 |
| T39 | 2.8 |
| T40 | 1.9 |

TABLE 6-3

| Example No. | EC$_{50}$ (nM) |
|---|---|
| T41 | 2.2 |
| T42 | 3.7 |
| T43 | 5.3 |
| T44 | 5.1 |
| T45 | 4.4 |
| T46 | 3.4 |
| T47 | 4 |
| T48 | 18 |
| T49 | 7.2 |
| T50 | 3.7 |

The pharmacological evaluation of integrase mutant strain (e.g., strain with Q148 mutation plus at least one of integrase inhibitor resistance mutation) can evaluate the antiviral activity by changing the HIV-1 NL4-3 strain (Wild type) to NL4-3 strain (integrase mutant strain) in the above-mentioned Experimental Example 1.

Experimental Example 2

Evaluation of Anti-Integrase Activity

The following explains evaluation methods of the HIV integrase inhibitory activity of the compound of the present invention.
(i) Construction of Recombinant Integrase Gene Expression System
A full-length gene sequence (Accession No.: M19921) of HIV-1 pNL4-3 integrase is inserted into restriction enzyme Nde I and Xho I sites of plasmid pET21a(+) (manufactured by Novagen) to construct an integrase expression vector pET21a-IN-Wild type.
(ii) Production and Purification of Integrase Protein
*Escherichia coli* recombinant BL21(DE3) transformed with plasmid pET21a-IN-Wild type obtained in (i) is shake cultured at 30° C. in a liquid medium containing ampicillin. When the culture reached the logarithmic growth phase, isopropyl-β-D-thiogalactopyranoside is added to promote expression of integrase gene. The culture is continued for 5 hr to promote accumulation of the integrase protein. The recombinant *E. coli* is collected in pellets by centrifugal separation and preserved at −80° C.
This *Escherichia coli* is suspended in Lysis buffer (50 mM Tris-HCl (pH 7.6), 10 mM $MgCl_2$, 5 mM DTT), and disrupted by repeating treatments of pressurization and depressurization, and insoluble fraction is collected by centrifugation at 4° C., 18,000 rpm for 60 min. This is suspended in Lysis buffer containing a protease inhibitor, 1.25 mM sodium chloride and 10 mM CHAPS are added, and the mixture is stirred at 4° C. for 30 min. Water-soluble fraction is collected by centrifugation at 4° C., 9,000 rpm for 30 min. The obtained fraction is diluted with a column buffer (50 mM Tris-HCl (pH 7.6), 1 mM DTT, 10% Glycerol, 10 mM CHAPS) to 5-fold, and the mixture is applied to heparin column (HiPrep 16/10 Heparin FF column: manufactured by GE Healthcare Bio-Sciences). Using a column buffer containing 1M NaCl, a protein is eluted with 0-1M NaCl concentration gradient, and an eluted fraction containing an integrase protein is collected. The obtained fraction is diluted 5-fold with a column buffer (50 mM Tris-HCl (pH 7.6), 1 mM DTT, 10% Glycerol, 10 mM CHAPS), and the mixture is applied to cation exchange column (Mono-S column: manufactured by GE Healthcare Bio-Sciences). Using a column buffer containing 1M NaCl, a protein is eluted with 0-1M NaCl concentration gradient, and an eluted fraction containing an integrase protein is collected. The obtained fractions of the integrase protein are collected, and preserved at −80° C.
(iii) Preparation of DNA Solution
The following DNA synthesized by FASMAC is dissolved in TE buffer (10 mM Tris-hydrochloric acid (pH 8.0), 1 mM EDTA) and mixed with donor DNA, target DNA, and each complementary strand (+ and − strands) to 1 LM. The mixture is heated at 95° C. for 5 min, 80° C. for 10 min, 70° C. for 10 min, 60° C. for 10 min, 50° C. for 10 min and 40° C. for 10 min and kept at 25° C. to give a double stranded DNA, which is used for the test.

Donor DNA (+ strand having biotin attached to the 5' terminus)

```
Donor + strand:
                                        (SEQ ID NO: 1)
5'-Biotin-ACC CTT TTA GTC AGT GTG GAA AAT CTC
TAG CA-3'

Donor - strand:
                                        (SEQ ID NO: 2)
5'-ACT GCT AGA GAT TTT CCA CAC TGA CTA AAA G-3'
```

Target DNA (+, − strands both having digoxigenin attached to the 3' terminus)

```
Target + strand:
                                        (SEQ ID NO: 3)
5'-TGA CCA AGG GCT AAT TCA CT-Dig-3'

Target - strand:
                                        (SEQ ID NO: 4)
5'-AGT GAA TTA GCC CTT GGT CA-Dig-3'
```

(iv) Determination of Enzyme (HIV Integrase) Inhibitory Activity
The donor DNA is diluted with TE buffer to 20 nM, of which 50 μL is added to each well of streptavidin-coated black plate (manufactured by PIAS Corporation) and allowed to adsorb at 37° C. for 20 min. The plate is washed with phosphate buffer (Dulbecco's PBS, Takara) containing 0.1% Tween 20 and phosphate buffer. Then, an enzyme reaction mixture (70 μL), a test substance (10 μL) diluted with the enzyme reaction mixture and 0.75 μM integrase protein (10 μL) are added to each well and the mixture is reacted at 37° C. for 60 min. composition of enzyme reaction mixture: 30 mM MOPS (3-morpholinopropanesulfonic acid), 5 mM magnesium chloride, 3 mM DTT (dithiothreitol), 0.1 mg/mL BSA (bovine serum albumin), 5% glycerol, 10% DMSO (dimethyl sulfoxide), 0.01% Tween 20.

Then, 25 nM target DNA (10 μL) is added, and the mixture is reacted at 37° C. for 20 min and washed with phosphate buffer containing 0.1% Tween 20 to stop the reaction.

Then, 100 mU/mL peroxidase labeled anti-digoxigenin antibody solution (Roche, 100 μL) is added, and the mixture is reacted at 37° C. for 60 min, followed by washing with phosphate buffer containing 0.1% Tween 20.

Then, peroxidase fluorescence substrate solution (manufactured by PIAS Corporation, 100 μL) is added, and the mixture is reacted at room temperature for 20 min to 30 min. A reaction quenching liquid (manufactured by PIAS Corporation, 100 μL) is added to discontinue the reaction, and fluorescence intensity at excitation wavelength 325 nm/fluorescence wavelength 420 nm is measured.

The HIV integrase inhibitory activity ($IC_{50}$) of the compound of the present invention is calculated from the inhibition rate according to the following formula:

inhibition rate (%)=[1−(Object−Blank)/(Control−Blank)]×100

Object: fluorescence intensity of well in the presence of test compound

Control: fluorescence intensity of well in the absence of test compound

Blank: fluorescence intensity of well in the absence of test compound and integrase protein

Experimental Example 3

In Vitro Combined Use Test

The effect of combined use of the compound of the present invention and existent anti-HIV agents can be determined in the following manner.

For example, the effect of combined use of existent nucleoside reverse transcriptase inhibitors (zidovudine, lamivudine), non-nucleoside reverse transcriptase inhibitors (efavirenz, etravirine) or protease inhibitors (atazanavir, darunavir) and test substance A and the like are evaluated using MT-2 cells infected with HIV-1 IIIB by CellTiter-Glo.

Prior to the combined use test, $EC_{50}$ and $CC_{50}$ of each medicament alone are measured. 5 concentrations of medicament A and 7 concentrations of medicament B, determined based on these results, are combined to evaluate the effect of combined use of two agents.

The test results of the test substance and concomitant drug alone or in combination thereof are analyzed based on the programs of Prichard and Shipman MacSynergy II. A three-dimensional plot is drawn from % inhibition at the concentrations of each combined medicament, the obtained from 3 times of tests, with 95% confidence limits, and the effect of the combined use is evaluated based on the numerical values of $\mu M^2 \%$ calculated therefrom. The criteria of evaluation are shown in the following.

| Definition of interaction | $\mu M^2 \%$ |
|---|---|
| Strong synergistic action | >100 |
| Slight synergistic action | +51 to +100 |
| Additive action | +50 to −50 |
| Slight antagonistic action | −50 to −100 |
| Strong antagonistic action | <−100 |

Formulation Example is given below. This example is merely for the exemplification purpose and does not limit the invention.

Formulation Example

| | |
|---|---|
| (a) compound of Example 1 | 10 g |
| (b) lactose | 50 g |
| (c) corn starch | 15 g |
| (d) sodium carboxymethylcellulose | 44 g |
| (e) magnesium stearate | 1 g |

The entire amounts of (a), (b) and (c) and 30 g of (d) are kneaded with water, dried in vacuo and granulated. The obtained granules are mixed with 14 g of (d) and 1 g of (e) and processed into tablets with a tableting machine to give 1000 tablets each containing 10 mg of (a).

INDUSTRIAL APPLICABILITY

The compounds of the present invention show a high inhibitory activity against HIV integrase.

Therefore, these compounds can be medicaments effective for, for example, the prophylaxis or treatment of AIDS, as integrase inhibitors, antiviral agents, anti-HIV agents and the like, having an HIV integrase inhibitory activity. In addition, by a combined use with other anti-HIV agent(s) such as protease inhibitor, reverse transcriptase inhibitor and the like, they can be more effective anti-HIV agents. Furthermore, having high inhibitory activity specific for integrase, they can be medicaments safe for human body with a fewer side effects.

SEQUENCE LISTING FREE TEXT

SEQ ID NO: 1: Donor+ chain for HIV integrase activity measurement
SEQ ID NO: 2: Donor− chain for HIV integrase activity measurement
SEQ ID NO: 3: Target+ chain for HIV integrase activity measurement
SEQ ID NO: 4: Target− chain for HIV integrase activity measurement

We claim:

1. A compound represented by the following formula [I] or [II], or a pharmaceutically acceptable salt thereof:

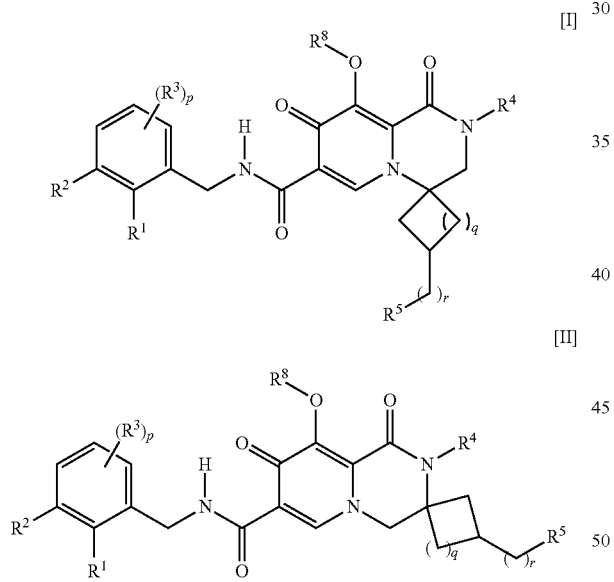

wherein
$R^1$ is halogen atom,
$R^2$ is hydrogen atom, halogen atom or trifluoromethyl group,
$R^3$ is
  (1) halogen atom,
  (2) $C_{1-6}$ alkoxy group, or
  (3) 2-oxopyrrolidinyl group,
when p is 2 or 3, $R^3$ are the same or different,
$R^4$ is $C_{1-6}$ alkyl group or cyclopropyl group,
$R^5$ is
  (1) hydroxy group,
  (2) $C_{1-6}$ alkoxy group,
  (3) benzyloxy group,
  (4) $C_{1-6}$ alkoxy $C_{2-6}$ alkyleneoxy group,
  (5) carboxy group,
  (6) —CO—NR$^{6a}$R$^{6b}$
    wherein $R^{6a}$ and $R^{6b}$ are the same or different and each is
      (i) hydrogen atom, or
      (ii) $C_{1-6}$ alkyl group,
  (7) —NR$^{7a}$COR$^{7b}$
    wherein $R^{7a}$ and $R^{7b}$ are the same or different and each is
      (i) hydrogen atom, or
      (ii) $C_{1-6}$ alkyl group,
  (8) methanesulfonyl group, or
  (9) methanesulfonyloxy group,
$R^8$ is
  (1) hydrogen atom,
  (2) acetyl group,
  (3) propionyl group,
  (4) isobutyryl group,
  (5) pivaloyl group,
  (6) palmitoyl group,
  (7) benzoyl group,
  (8) 4-methylbenzoyl group,
  (9) dimethylcarbamoyl group,
  (10) dimethylaminomethylcarbonyl group,
  (11) fumaryl group, or
  (12) 3-carboxybenzoyl group,
p is an integer of 0 to 3,
q is 0 or 1, and
r is 0 or 1.

2. The compound according to claim 1, wherein q is 1 or a pharmaceutically acceptable salt thereof.

3. The compound according to claim 1, wherein q is 0 or a pharmaceutically acceptable salt thereof.

4. The compound according to claim 1, wherein p is 0 or 1, or a pharmaceutically acceptable salt thereof.

5. The compound according to any one of claims 1 to 4, wherein r is 1, or a pharmaceutically acceptable salt thereof.

6. The compound according to any one of claims 1 to 4, wherein r is 0, or a pharmaceutically acceptable salt thereof.

7. The compound according to any one of claims 1 to 4, wherein $R^2$ is halogen atom, or a pharmaceutically acceptable salt thereof.

8. The compound according to any one of claims 1 to 4, wherein $R^4$ is $C_{1-6}$ alkyl group, or a pharmaceutically acceptable salt thereof.

9. The compound according to any one of claims 1 to 4, wherein $R^5$ is
   (1) hydroxy group,
   (2) $C_{1-6}$ alkoxy group,
   (3) benzyloxy group,
   (4) $C_{1-6}$ alkoxy $C_{2-6}$ alkyleneoxy group, or
   (5) —CO—$NR^{6a}R^{6b}$
      wherein $R^{6a}$ and $R^{6b}$ are the same or different and each is
      (i) hydrogen atom, or
      (ii) $C_{1-6}$ alkyl group,
   or a pharmaceutically acceptable salt thereof.

10. The compound according to any one of claims 1 to 4, wherein $R^5$ is
    (1) hydroxy group,
    (2) $C_{1-6}$ alkoxy group, or
    (3) —CO—$NR^{6a}R^{6b}$
       wherein $R^{6a}$ and $R^{6b}$ are the same or different and each is
       (i) hydrogen atom, or
       (ii) $C_{1-6}$ alkyl group,
    or a pharmaceutically acceptable salt thereof.

11. A compound represented by the formula [I'] or [II'], or a pharmaceutically acceptable salt thereof:

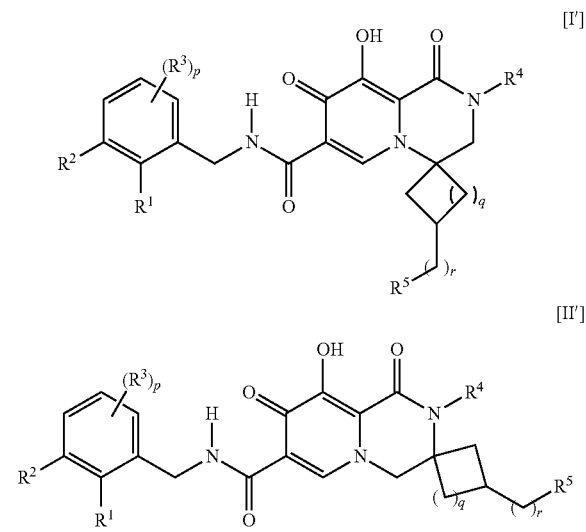

wherein
$R^1$ is halogen atom,
$R^2$ is hydrogen atom, halogen atom or trifluoromethyl group,
$R^3$ is the same or different and each is
   (1) halogen atom,
   (2) $C_{1-6}$ alkoxy group, or
   (3) 2-oxopyrrolidinyl group,
$R^4$ is $C_{1-6}$ alkyl group or cyclopropyl group,
$R^5$ is
   (1) hydroxy group,
   (2) $C_{1-6}$ alkoxy group,
   (3) benzyloxy group,
   (4) $C_{1-6}$ alkoxy $C_{2-6}$ alkyleneoxy group,
   (5) carboxy group,
   (6) —CO—$NR^{6a}R^{6b}$
      wherein $R^{6a}$ and $R^{6b}$ are the same or different and each is
      (i) hydrogen atom, or
      (ii) $C_{1-6}$ alkyl group,
   (7) —$NR^{7a}COR^{7b}$
      wherein $R^{7a}$ and $R^{7b}$ are the same or different and each is
      (i) hydrogen atom, or
      (ii) $C_{1-6}$ alkyl group,
   (8) methanesulfonyl group, or
   (9) methanesulfonyloxy group,
p is an integer of 0 to 3,
q is 0 or 1, and
r is 0 or 1.

12. A pharmaceutical composition comprising the compound according to any one of claims 1 to 4 or a pharmaceutically acceptable salt thereof, and a pharmaceutically acceptable carrier.

13. An anti-HIV agent comprising the compound according to any one of claims 1 to 4 or a pharmaceutically acceptable salt thereof, as an active ingredient.

14. An HIV integrase inhibitor comprising the compound according to any one of claims 1 to 4 or a pharmaceutically acceptable salt thereof, as an active ingredient.

15. An anti-HIV agent comprising the compound according to any one of claims 1 to 4 or a pharmaceutically acceptable salt thereof, in combination with one or more other kinds of anti-HIV active substances.

16. A method for the treatment of an HIV infection in a mammal, comprising administering an effective amount of the compound according to any one of claims 1 to 4 or a pharmaceutically acceptable salt thereof, to the mammal.

17. The method according to claim 16, further comprising administering an effective amount of one or more other kinds of anti-HIV active substances to the mammal.

18. A method for inhibiting HIV integrase in a mammal, comprising administering an effective amount of the compound according to any one of claims 1 to 4 or a pharmaceutically acceptable salt thereof.

19. A compound represented by the formula (6), or a pharmaceutically acceptable salt thereof:

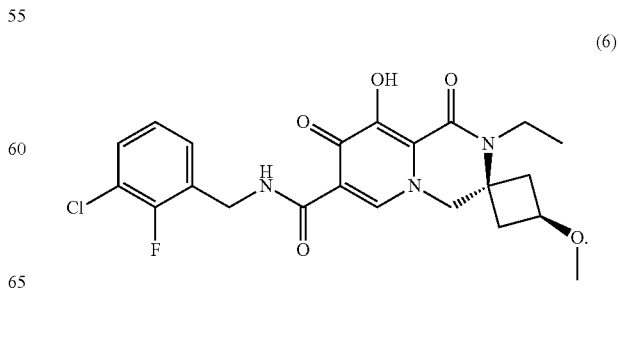

20. A compound represented by the formula (26), or a pharmaceutically acceptable salt thereof:

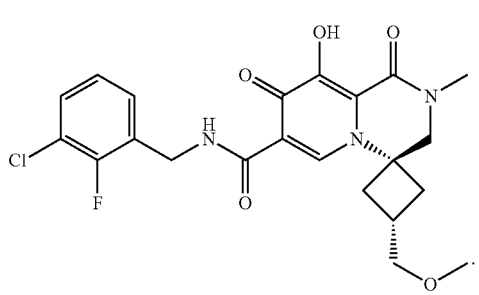
(26)

21. A compound represented by the formula (S20), or a pharmaceutically acceptable salt thereof:

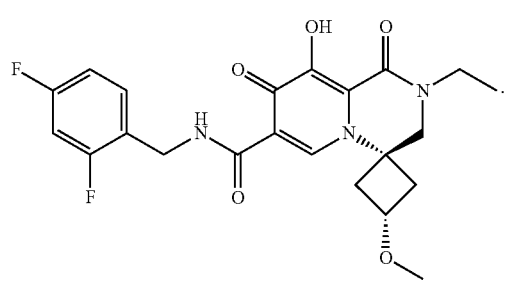
(S20)

22. A compound represented by the formula (S40), or a pharmaceutically acceptable salt thereof:

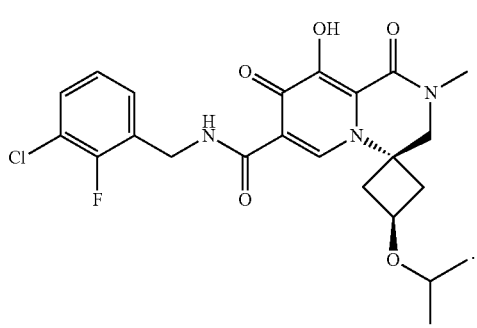
(S40)

23. A compound represented by the formula (S51), or a pharmaceutically acceptable salt thereof:

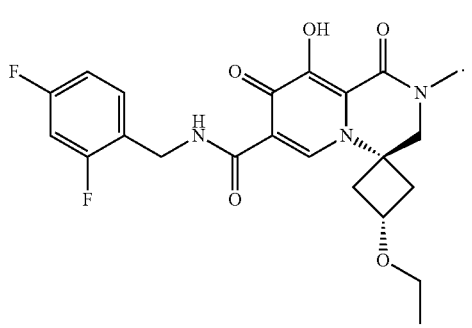
(S51)

24. A compound represented by the formula (S68), or a pharmaceutically acceptable salt thereof:

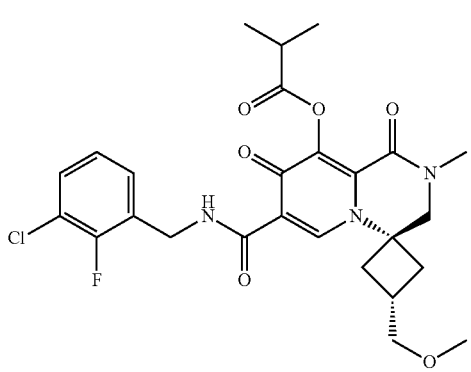 [SMILES: COC[C@H]1C[C@]2(CN(C)C(=O)c3c(OC(=O)C(C)C)c(=O)c(C(=O)NCc4cccc(Cl)c4F)cn32)C1]
(S68)

25. A compound represented by the formula (T13), or a pharmaceutically acceptable salt thereof:

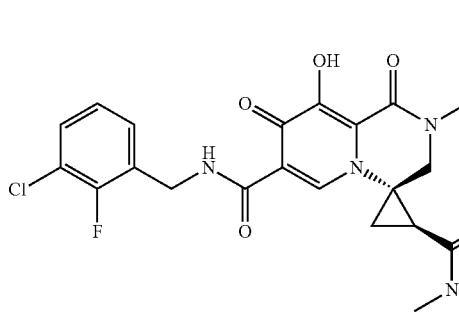
(T13)

26. A compound represented by the formula (T40), or a pharmaceutically acceptable salt thereof:

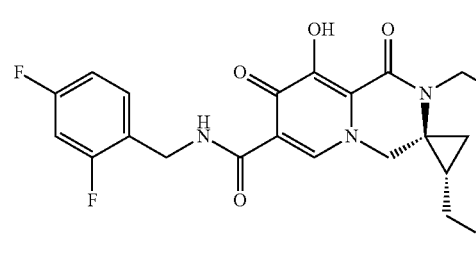
(T40)

27. A compound represented by the formula (T41), or a pharmaceutically acceptable salt thereof:

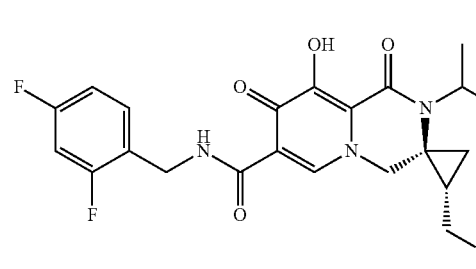
(T41)

28. A pharmaceutical composition comprising the compound according to any one of claims 19-27 or a pharmaceutically acceptable salt thereof, and a pharmaceutically acceptable carrier.

29. An anti-HIV agent comprising the compound according to any one of claims 19-27 or a pharmaceutically acceptable salt thereof, as an active ingredient.

30. An HIV integrase inhibitor comprising the compound according to any one of claims 19-27 or a pharmaceutically acceptable salt thereof, as an active ingredient.

31. An anti-HIV agent comprising the compound according to any one of claims 19-27 or a pharmaceutically acceptable salt thereof, in combination with one or more other kinds of anti-HIV active substances.

32. A method for the treatment of an HIV infection in a mammal, comprising administering an effective amount of the compound according to any one of claims 19-27 or a pharmaceutically acceptable salt thereof, to the mammal.

33. The method according to claim 32, further comprising administering an effective amount of one or more other kinds of anti-HIV active substances to the mammal.

34. A method for inhibiting HIV integrase in a mammal, comprising administering an effective amount of the compound according to any one of claims 19-27 or a pharmaceutically acceptable salt thereof.

\* \* \* \* \*

```
                         SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Donor plus strand for activity determination of
      HIV integrase

<400> SEQUENCE: 1 accctttag tcagtgtgga aaatctctag ca                                   32

<210> SEQ ID NO 2
<211> LENGTH: 31
<212> TYPE: DNA
<213> ORGANISM: Artificial Sequence
<220> FEATURE:
<223> OTHER INFORMATION: Donor minus strand for activity determination
      of HIV integrase

<400> SEQUENCE: 2
actgctagag attttccaca ctgactaaaa g                                   31
```

```
<210> SEQ ID NO 3
<211> LENGTH: 20
<212> TYPE: DNA
<213> ORGANISM: Artificial Sequence
<220> FEATURE:
<223> OTHER INFORMATION: Target plus strand for activity determination
      of HIV integrase

<400> SEQUENCE: 3
tgaccaaggg ctaattcact                                               20

<210> SEQ ID NO 4
<211> LENGTH: 20
<212> TYPE: DNA
<213> ORGANISM: Artificial Sequence
<220> FEATURE:
<223> OTHER INFORMATION: Target minus strand for activity determination
      of HIV integrase

<400> SEQUENCE: 4
agtgaattag cccttggtca                                               20
```